(12) United States Patent
Beck et al.

(10) Patent No.: US 8,993,305 B2
(45) Date of Patent: Mar. 31, 2015

(54) UTILIZATION OF PHOSPHOKETOLASE IN THE PRODUCTION OF MEVALONATE, ISOPRENOID PRECURSORS, AND ISOPRENE

(71) Applicants: Danisco US Inc., Palo Alto, CA (US); The Goodyear Tire & Rubber Company, Akron, OH (US)

(72) Inventors: Zachary Q. Beck, Palo Alto, CA (US); Andrew C. Eliot, Wilmington, DE (US); Caroline M. Peres, Palo Alto, CA (US); Dmitrii V. Vaviline, Palo Alto, CA (US)

(73) Assignees: Danisco US Inc., Palo Alto, CA (US); The Goodyear Tire & Rubber Company, Akron, OH (US)

(*) Notice: Subject to any disclaimer, the term of this patent is extended or adjusted under 35 U.S.C. 154(b) by 0 days.

(21) Appl. No.: 13/646,562

(22) Filed: Oct. 5, 2012

(65) Prior Publication Data

US 2013/0089906 A1    Apr. 11, 2013

Related U.S. Application Data

(60) Provisional application No. 61/545,083, filed on Oct. 7, 2011.

(51) Int. Cl.
  *C12N 1/21* (2006.01)
  *C12P 5/00* (2006.01)
  *C12N 15/70* (2006.01)
  *C12N 9/88* (2006.01)

(52) U.S. Cl.
  CPC ............... *C12P 5/007* (2013.01); *C12N 15/70* (2013.01); *C12N 9/88* (2013.01); *C12Y 401/02009* (2013.01); *C12Y 402/03027* (2013.01)

USPC ............. 435/252.33; 435/252.3; 435/252.31; 435/252.35; 435/254.11; 435/254.2; 435/254.21; 435/254.3; 435/254.6; 435/257.2; 435/167

(58) Field of Classification Search
None
See application file for complete search history.

(56) References Cited

U.S. PATENT DOCUMENTS

| 6,689,593 | B2 * | 2/2004 | Millis et al. ................. 435/155 |
| 7,172,886 | B2 * | 2/2007 | Keasling et al. ............ 435/132 |
| 7,371,558 | B2 |  5/2008 | Cervin et al. |
| 7,659,097 | B2 |  2/2010 | Renninger et al. |
| 7,785,858 | B2 |  8/2010 | Kozlov et al. |
| 7,915,026 | B2 |  3/2011 | Keasling et al. |

(Continued)

FOREIGN PATENT DOCUMENTS

| EP | 2 062 967 A1 | 5/2009 |
| JP | 2008/061506 A | 3/2008 |

(Continued)

OTHER PUBLICATIONS

Schorken et al., "Thiamin-dependent enzymes as catalysts in chemoenzymatic syntheses", Biochimica et Biophysica Acta, vol. 1385, pp. 229-243, 1998.*

(Continued)

*Primary Examiner* — Rebecca Prouty
*Assistant Examiner* — Richard Ekstrom
(74) *Attorney, Agent, or Firm* — Morrison & Foerster LLP

(57) ABSTRACT

The invention provides for methods for the production of mevalonate, isoprene, isoprenoid precursor molecules, and/or isoprenoids in cells via the heterologous expression of phosphoketolase enzymes.

52 Claims, 75 Drawing Sheets

(56) References Cited

U.S. PATENT DOCUMENTS

| | | | |
|---|---|---|---|
| 7,968,321 B1* | 6/2011 | Green et al. | 435/161 |
| 7,981,647 B2* | 7/2011 | Berry et al. | 435/161 |
| 8,173,410 B2 | 5/2012 | Bott et al. | |
| 8,415,136 B1* | 4/2013 | Gardner et al. | 435/254.2 |
| 8,512,988 B2* | 8/2013 | Ajikumar et al. | 435/166 |
| 8,603,800 B2* | 12/2013 | Gardner et al. | 435/254.2 |
| 8,859,261 B2* | 10/2014 | Gardner et al. | 435/254.2 |
| 2005/0287655 A1 | 12/2005 | Tabata et al. | |
| 2006/0040365 A1 | 2/2006 | Kozlov et al. | |
| 2008/0038805 A1 | 2/2008 | Melis | |
| 2008/0261280 A1* | 10/2008 | Hahn et al. | 435/125 |
| 2009/0053797 A1* | 2/2009 | Shiba et al. | 435/254.21 |
| 2009/0137014 A1* | 5/2009 | Tsuruta et al. | 435/157 |
| 2009/0203102 A1 | 8/2009 | Cervin et al. | |
| 2009/0282545 A1 | 11/2009 | Eichelberger et al. | |
| 2010/0003716 A1 | 1/2010 | Cervin et al. | |
| 2010/0048964 A1 | 2/2010 | Calabria et al. | |
| 2010/0086978 A1 | 4/2010 | Beck et al. | |
| 2010/0167370 A1 | 7/2010 | Chotani et al. | |
| 2010/0196977 A1 | 8/2010 | Chotani et al. | |
| 2010/0285549 A1 | 11/2010 | Muramatsu et al. | |
| 2010/0297749 A1 | 11/2010 | Aravanis et al. | |
| 2011/0045563 A1 | 2/2011 | Melis | |
| 2011/0076743 A1 | 3/2011 | Beck et al. | |
| 2011/0159557 A1 | 6/2011 | Beck et al. | |
| 2011/0178261 A1 | 7/2011 | Feher et al. | |
| 2012/0015416 A1* | 1/2012 | Anthony et al. | 435/160 |
| 2012/0156735 A1* | 6/2012 | Dauner et al. | 435/115 |
| 2013/0295616 A1 | 11/2013 | Muramatsu et al. | |
| 2014/0273144 A1* | 9/2014 | Hawkins et al. | 435/167 |

FOREIGN PATENT DOCUMENTS

| | | |
|---|---|---|
| WO | WO 98/02550 A2 | 1/1998 |
| WO | WO 98/02550 A3 | 1/1998 |
| WO | WO 2004/033646 A2 | 4/2004 |
| WO | WO 2004/033646 A3 | 4/2004 |
| WO | WO 2009005704 A1 * | 1/2009 |
| WO | WO 2009/076676 A2 | 6/2009 |
| WO | WO 2009/076676 A3 | 6/2009 |
| WO | WO 2009/132220 A2 | 10/2009 |
| WO | WO 2009/132220 A3 | 10/2009 |
| WO | WO 2009/132220 A9 | 10/2009 |
| WO | WO 2010/003007 A2 | 1/2010 |
| WO | WO 2010/003007 A3 | 1/2010 |
| WO | WO 2010/013077 A1 | 2/2010 |
| WO | WO 2010/031062 A1 | 3/2010 |
| WO | WO 2010/031068 A1 | 3/2010 |
| WO | WO 2010/031076 A2 | 3/2010 |
| WO | WO 2010/031076 A3 | 3/2010 |
| WO | WO 2010/031079 A1 | 3/2010 |
| WO | WO 2010/078457 A2 | 7/2010 |
| WO | WO 2010/078457 A3 | 7/2010 |
| WO | WO 2010/124146 A2 | 10/2010 |
| WO | WO 2010/124146 A3 | 10/2010 |
| WO | WO 2010/148150 A1 | 12/2010 |
| WO | WO 2010/148256 A1 | 12/2010 |
| WO | WO 2011/034863 A1 | 3/2011 |
| WO | WO 2011/159853 A1 | 12/2011 |
| WO | WO 2012/058494 A2 | 5/2012 |
| WO | WO 2012/058494 A3 | 5/2012 |
| WO | WO 2012/149469 A1 | 11/2012 |
| WO | WO 2013/007786 A1 | 1/2013 |

OTHER PUBLICATIONS

Ausubel, F.M. ed. et al. (1987). "Introduction of DNA into Mammalian Cells," Chapter 9 in *Current Protocols in Molecular Biology*.
Baba et al. (2006). "Construction of *Escherichia coli* K-12 In-Frame, Single-Gene Knockout Mutants: the Keio Collection," *Mol. Syst. Biol.*, article No. 2006.0008, pp. 1-11.
Baldwin et. al. (1978). "Novel Kinetic and Structural Properties of the Class-I D-Fructose 1,6-Bisphosphate Aldolase from *Escherichia coli* (Crookes' Strain)," *Biochem. J.* 169(3):643-652.

Berka, R.M. et al. (1989). "The Development of Gene Expression Systems for Filamentous Fungi," *Biotechnology Advances* 7(2):127-154.
Bhayana et al. (1984). "Amino Acid Sequence of *Escherichia coli* Citrate Synthase," *Biochemistry* 23:2900-2905 (Figure 5).
Bologna et al. (Aug. 2007). "*Escherichia coli* Malic Enzymes: Two Isoforms with Substantial Differences in Kinetic Properties, Metabolic Regulation, and Structure," *Journal of Bacteriology* 189(16):5937-5946.
Branlant, G. et al. (1985). "Nucleotide Sequence of the *Escherichia coli* Gap Gene. Different evolutionary behavior of the $NAD^+$-binding domain and of the catalytic domain of D-glyceraldehyde-3-phosphate dehydrogenase," *Eur. J. Biochem.* 150:61-66.
Bunch et al.(1997). "The *ldh*A Gene Encoding the Fermentative Lactate Dehydrogenase of *Escherichia coli*," *Microbiology* 143:187-195.
Campbell et al. (1989). "Improved Transformation Efficiency of *Aspergillus niger* Using the Homologous *nia*D Gene for Nitrate Reductase," *Current Genetics* 16:53-56.
Danner et al. (2011). "Four Terpene Synthases Produce Major Compounds of the Gypsy Moth Feeding-Induced Volatile Bend of *Populus trichocarpa*," *Phytochemistry* 72(9):897-908.
Datsenko, K. et al. (Jun. 6, 2000). "One-step Inactivation of Chromosomal Genes in *Escherichia coli* K-12 using PCR Products," *PNAS* 97(12):6640-6645.
Dawes et al. (1966). "The Route to Ethanol Formation in *Zymomonas mobilis*," *Biochem. J.* 98:795-803.
Duckworth et al. (1987). "Structural Basis for Regulation in Gram-Negative Bacterial Citrate Synthases," *Biochem. Soc. Symp.* 54:83-92.
Egan, S.E. et al. (Jul. 1992). "Molecular Characterization of the Entner-Doudoroff Pathway in *Escherichia coli*: Sequence Analysis and Localization of Promoters for the *edd-eda* Operon," *J. Bact.* 174(14):4638-4646.
Fleige, C. et al. (2011). "Establishment of an Alternative Phosphoketolase-Dependent Pathway for Fructose Catabolism in *Ralstonia eutropha* H16," *Appl. Microbial. Biotechnol.* 91:769-776.
Garms, S. et al. (2010, e-pub. Jul. 20, 2010). "A Multiproduct Terpene Synthase from *Medicago truncatula* Generates Cadalane Sesquiterpenes via Two Different Mechanisms," *J. Org. Chem.* 75(16):5590-5600.
Grill, J-P. et al. (1995). "Characterization of Fructose 6 Phosphate Phosphoketolases Purified from *Bifidobacterium* Species," *Current Microbiology* 31:49-54.
Hedl, M. et al. (Apr. 2002). "*Enterococcus faecalis* Acetoacetyl-Coenzyme a Thiolase/3-Hydroxy-3-Methyglutaryl-Coenzyme A Reductase, a Dual-Function Protein of Isopentenyl Diphosphate Biosynthesis," *Journal of Bacteriology* 184(8):2116-2122.
Hsieh, F-L. et al. (Mar. 2011). "Structure and Mechanism of an Arabidopsis Medium/Long-Chain-Length Prenyl Pyrophosphate Synthase," *Plant Physiology* 155(3):1079-1090.
Jeong, D-W. et al. (2007). "Cloning and Characterization of a Gene Encoding Phosphoketolase in a *Lactobacillus paraplantarum* Isolated from Kimchi," *J. Microbiol. Biotechnol.* 17(5):822-829.
Jones, C.G. et al. (2011, e-pub. Mar. 24, 2011). "Sandalwood Fragrance Biosynthesis Involves Sesquiterpene Synthases of Both the Terpene Synthase (TPA)-a and TPS-b Subfamilies, including Santalene Synthases," *J. Biol. Chem.* 286:17445-17454.
Kakuda, H. et al. (1994). "Identification and Characterization of the *ack*A (Acetate Kinase A)-*pta* (Phosphotransacetylase) Operon and Complementation Analysis of Acetate Utilization by an *ackA-pta* Deletion Mutant of *Escherichia coli*," *J. Biochem.* 116:916-922.
Keeling, C.I. et al. (2011). "Transcriptome Mining, Functional Characterization, and Phylogeny of a Large Terpene Synthase Gene Family in Spruce (*Picea* spp.)," *BMC Plant Biol.* 11:43, 14 pages.
Kotlarz, D. et al. (1975). "Regulation of the Amount and of the Activity of Phosphofructokinases and Pyruvate Kinases in *Escherichia coli*," *Biochima et Biophysica Acta* 381:257-268.
Kumeta, Y. et al. (Dec. 2010). "Characterization of δ-Guaiene Synthases from Cultured Cells of *Aquilaria*, Responsible for the Formation of the Sesquiterpenes in Agarwood," *Plant Physiology* 154(4):1998-2007.

(56) References Cited

OTHER PUBLICATIONS

Lindberg, P. et al. (2010). "Engineering a Platform for Photosynthetic Isoprene Production in Cyanobacteria, Using *Synechocystis* as the Model Organism," *Metabolic Engineering* 12(1):70-79.

Martin, D.M. et al. (2010). "Functional Annotation, Genome Organization and Phylogeny of the Grapevine (*Vitis vinifera*) Terpene Synthase Gene Family Based on Genome Assembly, FLcDNA Cloning, and Enzyme Assays," *BMC Plant Biol.* 10:226, 22 pages.

Martin, V.J. et al. (Jul. 2003). "Engineering a Mevalonate Pathway in *Escherichia coli* for Production of Terpenoids," *Nature Biotechnology* 21(7):796-802.

Maurus, R. et al. (2003). "Insights into the Evolution of Allosteric Properties. The NADH Binding Site of Hexameric Type II Citrate Synthases," *Biochemistry* 42:5555-5565.

Meile, L. et al. (May 2001). "Characterization of the D-Xylulose 5-Phosphate/D-Fructose 6-Phosphate Phosphoketolase Gene (*xfp*) from *Bifidobacterium lactis*," *Journal of Bacteriology* 183(9):2929-2936.

Mergen, G. et al. (2010). "Simultaneous Headspace GC-FID Analysis for Methanol and Ethanol in Blood, Saliva, and Urine: Validation of Method and Comparison of Specimens." *LC GC North America* 28(7):540-543, located at http://www.chromatographyonline.com/lcgc/article/articleDetail.jsp?id=682204, four pages.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Ner, S.S. et al. (Nov. 8, 1983). "Complete Sequence of the *glt* A Gene Encoding Citrate Synthase in *Escherichia coli*," *Biochemistry* 22(23):5243-5249.

Newman, J.D. et. al. (2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95:684-691.

Okamura, E. et al. (Jun. 22, 2010). "Unprecedented Acetoacetyl-coenzyme a Synthesizing Enzyme of the Thiolase Superfamily Involved in the Mevalonate Pathway," *PNAS* 107(25):11265-11270.

Papini, M. et al. (2012, e-pub. Feb. 26, 2012). "Physiological Characterization of Recombinant *Saccharomyces cerevisiae* Expressing the *Aspergillus nidulans* Phosphoketolase Pathway: Validation of Activity Through $^{13}$C-Based Metabolic Flux Analysis," *Applied Microbiol. Biotechnol.* 95(4):1001-1010.

Peekhaus, N. et al. (Jul. 1998). "What's for Dinner?: Entner-Doudoroff Metabolism in *Escherichia coli*," *Journal of Bacteriology* 180(14):3495-3502.

Postma, P.W. et al. (Sep. 1993). "Phosphoenolpyruvate:Carbohydrate Phosphotransferase Systems of Bacteria," *Microbiological Reviews* 57(3):543-594.

Quant, P.A. et al. (1989). "Treatment of Rats With Glucagon or Mannoheptulose Increases Mitochondrial 3-Hydroxy-3-Methylglutaryl-CoA Synthase Activity and Decreases Succinyl-CoA Content in Liver," *Biochem. J.* 262:159-164.

Romanos, M.A. et al. (1992). "Foreign Gene Expression in Yeast: a Review," *Yeast* 8(6):423-488.

Sánchez, A.M. et al. (2005). "Novel Pathway Engineering Design of the Anaerobic Central Metabolic Pathway in *Escherichia coli* to Increase Succinate Yield and Productivity," *Metab. Eng.* 7:229-239.

Sharkey, T.D. et al. (Feb. 2005). "Evolution of the Isoprene Biosynthetic Pathway in Kudzu," *Plant Physiology* 137:700-712.

Shimizu, M. et al. (1969). "Phosphotransacetylase of *Escherichia coli* B, Purification and Properties," *Biochimica et Biophysica Acta* 191:550-558.

Silver, G.M. et al. (Jun. 2, 1995). "Characterization of Aspen Isoprene Synthase, an Enzyme Responsible for Leaf Isoprene Emission to the Atmosphere," *J. Biol. Chem.* 270(22):13010-13016.

Sonderegger, M. et al. (May 2004). "Metabolic Engineering of a Phosphoketolase Pathway for Pentose Catabolism in *Saccharomyces cerevisiae*," *Applied and Environmental Microbiology* 70(5):2892-2897.

Sprenger, G.A. (1995). "Genetics of Pentose-Phosphate Pathway Enzymes of *Escherichia coli* K-12," *Arch. Microbiol.* 164:324-330.

Stokell, D.J. et al. (Sep. 12, 2003). "Probing the Roles of Key Residues in the Unique Regulatory NADH Binding Site of Type II Citrate Synthase of *Escherichia coli*," *The Journal of Biological Chemistry* 278(37):35435-35443.

Stülke, J. et al. (2000). "Regulation of Carbon Catabolism in *Bacillus* Species," *Annu. Rev. Microbiol.* 54:849-880.

Suzuki, R. et al. (2010, e-pub. Jul. 29, 2010) "Overexpression, Crystallization and Preliminary X-Ray Analysis of Xylulose-5-Phosphate/Fructose-6-Phosphate Phosphoketolase from *Bifidobacterium breve*," *Acta Crystallographica* Section F 66(Pt 8):941-943.

Tabata, K. et al. (2004). "Production of Mevalonate by a Metabolically-Engineered *Escherichia coli*," *Biotechnology Letters* 26:1487-1491.

Underwood, S.A. et al. (2002). "Flux through Citrate Synthase Limits the Growth of Ethanologenic *Escherichia coli* KO11 During Xylose Fermentation," *Appl. Environ. Microbiol.* 68(3):1071-1081.

Veiga-da-Cunha, M. et al. (Jul. 1993). "Pathway and Regulation of Erythritol Formation in *Leuconostoc oenos*," *Journal of Bacteriology* 175(13):3941-3948.

Wiegand, G. et al. (1986). "Citrate Synthase: Structure, Control, and Mechanism," *Ann. Rev. Biophys. Biophys. Chem.* 15:97-117.

Wilde, R.J. et al. (1986). "Transcript Analysis of the Citrate Synthase and Succinate Dehydrogenase Genes of *Escherichia coli* K12," *Journal of General Microbiology* 132:3239-3251.

Wolfe, A.J. (2005). "The Acetate Switch," *Microbiol. Mol. Biol. Rev.* 69(1):12-50.

Yevenes, A. et. al. (2008). "Cloning, Expression, Purification, Cofactor Requirements, and Steady State Kinetics of Phosphoketolase-2 from *Lactobacillus plantarum*," *Bioorganic Chemistry* 36:121-127.

International Search Report and the Written Opinion of the International Searching Authority mailed on Feb. 6, 2013, for PCT Application No. PCT/US2012/059136 filed on Oct. 5, 2012, 14 pages.

Stegmann, E. et al. (2008). "Interlocking of Primary and Secondary Metabolism in Antibiotic-Producing Actinomycetes," *Chemical Engineering Transactions* 14:161-167.

\* cited by examiner

FIGURE 4:

| Organsim | Accession | Organsim | Accession |
|---|---|---|---|
| Clostridium carboxidivorans P7 | ZP_05390294.1 | Ferrimonas balearica DSM 9799 | ADN77608.1 |
| Roseburia intestinalis L1-82 | ZP_04743029.2 | Methylobacter tundripaludum SV96 | ZP_08779585.1 |
| Subdoligranulum variabile DSM 15176 | ZP_05979027.2 | Acidithiobacillus ferrivorans SS3 | AEM46566.1 |
| Ruminococcaceae bacterium D16 | ZP_08418749.1 | Anaeromyxobacter dehalogenans 2CP-1 | YP_002493710.1 |
| Bacteroides capillosus ATCC 29799 | ZP_02038271.1 | Stigmatella aurantiaca DW4/3-1 | ZP_01464191.1 |
| Oscillibacter valericigenes Sjm18-20 | BAK98480 | Chlorobaculum parvum NCIB 8327 | ACF12009.1 |
| Listeria grayi DSM 20601 | ZP_07053045.1 | Chlorobium ferrooxidans DSM 13031 | EAT58960.1 |
| Bacillus coagulans 36D1 | AEP00547.1 | Aspergillus fumigatus Af293 | XP_754543.1 |
| Paenibacillus polymyxa E681 | ADM68092.1 | Paracoccidioides brasiliensis Pb18 | EEH44652.1 |
| Mesorhizobium opportunistum WSM2075 | AEH87451.1 | Ajellomyces dermatitidis SLH14081 | EEQ76387.1 |
| Lactobacillus reuteri DSM 20016 | YP_001272262.1 | Phaeodactylum tricornutum CCAP 1055/1 | EEC47950.1 |
| Bifidobacterium longum subsp. Infantis ATCC 15697 | YP_002323176.1 | Acidobacterium sp. MP5ACTX9 | YP_004218333.1 |
| Allochromatium vinosum DSM 180 | ADC61973.1 | Terriglobus saanensis SP1PR4 | YP_004181316.1 | a) SHG0863 CMP1053 (open diamonds) control strain contain empty pTrcHis2B plasmid b) SHG0864 CMP1057 (closed black squares) strain expressing phosphoketolase off of pTrcPhosphoketolase Lreuteri plasmid a) SHG0863 CMP1053 (open diamonds) control strain contain empty pTrcHis2B plasmid b) SHG0864 CMP1057 (closed black squares) strain expressing phophoketolase off of pTrcPhosphoketolase Lreuteri plasmid a) SHG0863 CMP1053 (open diamonds) control strain contain empty pTrcHis2B plasmid b) SHG0864 CMP1057 (closed black squares) strain expressing phophoketolase off of pTrcPhosphoketolase Lreuteri plasmid a) SHG0863 CMP1053 (open diamonds) control strain contain empty pTrcHis2B plasmid b) SHG0864 CMP1057 (closed black squares) strain expressing phophoketolase off of pTrcPhosphoketolase Lreuteri plasmid

FIGURE 15.

atggcagtagattacgattccaagaaatacttggaaagtgttgatgcttactggcgtgcagctaactacctttcagttggtacattgtacttaatgggt
gatccattacttcgccaaccattaaaggcagaagatgttaagcctaagccaattggtcactggggtactattgttcctcaaaacttcatttacgcaca
cttgaaccgtgtaattaagaagtatgaccttgatatgttctacatcgaaggttcaggtcacggtggccaagttatggttaacaactcatacttggatg
gttcatacactgaaatttatcctgaatatactcaagacactaaggaatggctaagttattcaagcacttctcattcccaggcggtactgcatcacac
gctgcacctgaaacaccaggttcaatccacgaaggtggggaacttggttactcactttcacacggtgttggtgctatcttagataacccagaagtta
ttgccgctgttgaaatcggtgatggtgaagctgaaactggtccattaatggcatcatggttctcagacaagttcattaacccaatcaaggatggtgc
ggtattaccaatcatccaagttaacggattcaagatttctaaccctactatcctttcatggatgagcgacgaagaacttactaagtacttcgaaggtat
gggttggaagccatactttgtttcagcttacaagaagctgaccgtgatggtgaattcaagggttacaagcctcacatggaagttcacgaagaaat
ggctaagactttggacaaggttgttgaagaaatcaaggctattcaaaagaacgctcgtgaaaacaatgataactcattaccacaatggccaatgat
tatcttccgtgcacctaagggttggactggtcctaagactgaccttgatggtaacccaattgaaaactcattccgtgcacaccaaattccagttccag
tatcccaagatgacatggaacacaaggacatccttgttgattggttgaagtcatacaagccagaagaattgtttgacgaagatggtcacccagttg
ctcttgttgaagagaacacaccagaaggtaaccgtcgtatggctatgaaccctatcactaatggtggtatcgatcctaagccacttgtattgccaaa
ctaccgtgattttgctattgatgttcaaaatcctggttctgttgtaaagcaagacatgcttgaatggggtaagtacctcaacaagatggctgaattgaa
cccaactaacttccgtggattggtcctgacgaatctaagtcaaaccgtctttacgcattccttgatggtcaaaagcgtcaatggatggaaagtgtcc
acgaaccaaacgacgaagatgtggctccacaaggtcgtatgatcgattcacaactttcagaacaccagctgaaggattccttgaaggttacaca
ttaactggtcgtcacggattcttcgcaacttacgaagcattcggtcgtgttgttgattcaatgcttactcaacacatgaagtggttacgtaaggctaag
gatctttactggcgtcaccaatacccagcattgaactttgttgatacttctactgtattccaacaagatcacaacggttacactcaccaagatccaggt
ctattgactcacttgtttgaaaaggaacgtccagacctcgttaaggaatacttgccagcagatactaactcattaatggctgtatctaacaaggcatt
ccgtaaccaagaatgcatcaacctcttcgtaacttctaagcacccacgtgcacaatggttctctattgatgaagctactcaattggctgacaatggtc
ttggctacattgactgggcatctactgaccaaggtactgaaccagatgttgtatttgcatcttctggtactgaacctactgaagaagctcttgcagcta
ttgacattcttcatgacaacttccctgaattgaagattcgttacatcaacatcatcgaaaattatgcgtttgatgaacactgacaagaaccctgaaggttt
aactgatgctgaattcaatagttacttcactactgacaagccagttatctttgcatggcacggattccgtgacatgatccaagcattgttcttcgatcgt
gctaaccgtaacgttcacattcactcatacgaagaaaatggtgatatcaccactccatcgacatgcgtgtattaaacgaacttgaccggttccactt
agctaaggacgctatccaaagtgttcctggttacgaacaaaagagtgctgcatttgttgccaagatggacaacatgatcaacaagcacaaccact
acatccgttcagaaggtaaggacttaccagaagttactaactggacttggaagggtcttaagtaa (SEQ ID NO:1)

FIGURE 16.

MAVDYDSKKYLESVDAYWRAANYLSVGTLYLMGDPLLRQPLKAEDVKPKPIGHWGTIVP
QNFIYAHLNRVIKKYDLDMFYIEGSGHGGQVMVNNSYLDGSYTEIYPEYTQDTKGMAKLF
KHFSFPGGTASHAAPETPGSIHEGGELGYSLSHGVGAILDNPEVIAAVEIGDGEAETGPLMA
SWFSDKFINPIKDGAVLPIIQVNGFKISNPTILSWMSDEELTKYFEGMGWKPYFVSAYKEAD
RDGEFKGYKPHMEVHEEMAKTLDKVVEEIKAIQKNARENNDNSLPQWPMIIFRAPKGWTG
PKTDLDGNPIENSFRAHQIPVPVSQDDMEHKDILVDWLKSYKPEELFDEDGHPVALVEENT
PEGNRRMAMNPITNGGIDPKPLVLPNYRDFAIDVQNPGSVVKQDMLEWGKYLNKMAELN
PTNFRGFGPDESKSNRLYAFLDGQKRQWMESVHEPNDEDVAPQGRMIDSQLSEHQAEGFL
EGYTLTGRHGFFATYEAFGRVVDSMLTQHMKWLRKAKDLYWRHQYPALNFVDTSTVFQ
QDHNGYTHQDPGLLTHLFEKERPDLVKEYLPADTNSLMAVSNKAFRNQECINLFVTSKHP
RAQWFSIDEATQLADNGLGYIDWASTDQGTEPDVVFASSGTEPTEEALAAIDILHDNFPELK
IRYINIIEIMRLMNTDKNPEGLTDAEFNSYFTTDKPVIFAWHGFRDMIQALFFDRANRNVHIH
SYEENGDITTPFDMRVLNELDRFHLAKDAIQSVPGYEQKSAAFVAKMDNMINKHNHYIRSE
GKDLPEVTNWTWKGLK (SEQ ID NO: 2)

FIGURE 17.

atgacgagtcctgttattggcacccttggaagaagctcagcgctccggtttccgaggaagccctcgaaggcgttgacaagtactggcgcgttg
ccaactacctttccatcggccagatttatctgcgttccaacccgctgatgaaggagcccttcacccgcgaagatgtgaagcatcgtctggtgggcc
actggggcactacccctggcctgaacttcctcatcggccacatcaaccgtttcattgctgaccacggccagaacaccgtgatcatcatgggcccg
ggccacggtggcccggccggtacctcccagtcctacctggacggcacctacaccgagaccttcccgaagatcaccaaggacgaagctggtct
gcagaagttcttccgtcagttctcttacccgggcggtattccgtcccacttcgctccggagaccccgggctccatccacgaggtggtgagctgg
gttacgctcgtcccacgcttacggcgccatcatggacaaacccgagcctgttcgtcccggccatcgtcggcgacggcgaggctgagaccggcc
cgctggctaccggttggcagtccaacaagctcgtgaacccgcgcaccgacggtatcgtgctgccgatcctgcacctcaacggctacaagatcg
ccaacccgaccatcctgtcccgcatctccgacgaagagctccacgagttcttccacggcatgggttacgagcctacgagttcgtcgctggcttc
gatgatgaggaccacatgtccatccaccgccgcttcgccgagctgtgggagaccatctgggacgagatctgcgacatcaaggccaccgctca
gaccgacaacgtgcaccgtccgttctacccgatgctgatcttccgcaccccgaagggctggacctgcccgaagtacatcgacggcaagaaga
ccgaaggctcctggcgttcccaccaggtgccgctggcctccgcccgcgacaccgaggcccacttcgaggtcctcaagaactggctcgagtcct
acaagccggaagagctgttcgacgccaacggcgccgtcaaggacgacgtcctcgccttcatgccgaagggcgagctgcgtatcggtgccaa
cccgaacgccaacggcggtgtgatccgcgacgacctgaagctgccgaacctcgaggactacgaggtcaaggaagtggccgagttcggccac
ggctggggccagctcgaggccacccgctccctggcgcctacacccgcgacatcatcaagaacaaccgcgtgacttccgcatcttcggacc
ggatgagaccgcttccaaccgtctgcaggcttcctacgaagtcaccaacaagcagtgggatgccggctacatctccgacgaggtcgacgagca
catgcgcgtctccggccaggtcgtcgagcagctgtccgagcaccagatgaaggcttcctcgaggcctacctgctgaccggccgtcacggcat
ctggagctcctacgagtccttcgtccacgtgatcgactccatgctgaaccagcacgccaagtggcttgaggctaccgtccgcgagattccgtgg
cgcaagccgatcgcctccatgaacctgctggtctcctccacgtctggcgtcaggaccacaacggcttctcccaccaggatccgggtgtcacct
ccgtcctgctgaacaagtgcttccacaacgaccacgtcatcggcatctacttcgccaccgacgcgaacatgctgctggccatcgccgagaagtg
ctacaagtccaccaacaagatcaacgccatcatcgccggcaagcagcccgccgccacctggctgaccctggacgaggctcgcgccgagctc
gagaagggtgccgccgcttgggactggcctccaccgccaagaccaacgatgaagccgagatcgtgcttgccgccgccggcgacgtcccca
cccaggagatcatggccgcttccgacaagctgaaggaactgggcatcaagttcaaggtcgtgaacgttgtcgacctgctctccctgcagtccgc
caaggagaacgacgaggccctgtccaacgaggagttcgccgacatcttcaccgccgacaagccggtgctgttcgcgtaccactcctacgcc
acgacgtgcgcggtctgatctacgatcgtccgaaccacgacaacttcaacgtccacggctacgaggaggagggctccaccaccacccgtac
gacatggttcgtgtcaaccgcatcgaccgctacgagctgaccgctgaggctctgcgcatgatcgacgccgacaagtacgccgacaagatcgac
gagctcgagaagttccgtgatgaggccttccagttcgccgtcgacaagggctacgaccacccggactacaccgactgggtgtactccggcgtg
aacaccggcaagaagggtgccgtcaccgctaccgccgctaccgctggcgacaacgagtga (SEQ ID NO: 3)

FIGURE 18.

MTSPVIGTPWKKLSAPVSEEALEGVDKYWRVANYLSIGQIYLRSNPLMKEPFTREDVKHRL
VGHWGTTPGLNFLIGHINRFIADHGQNTVIIMGPGHGGPAGTSQSYLDGTYTETFPKITKDE
AGLQKFFRQFSYPGGIPSHFAPETPGSIHEGGELGYALSHAYGAIMDNPSLFVPAIVGDGEA
ETGPLATGWQSNKLVNPRTDGIVLPILHLNGYKIANPTILSRISDEELHEFFHGMGYEPYEFV
AGFDDEDHMSIHRRFAELWETIWDEICDIKATAQTDNVHRPFYPMLIFRTPKGWTCPKYID
GKKTEGSWRSHQVPLASARDTEAHFEVLKNWLESYKPEELFDANGAVKDDVLAFMPKGE
LRIGANPNANGGVIRDDLKLPNLEDYEVKEVAEFGHGWGQLEATRSLGAYTRDIIKNNPRD
FRIFGPDETASNRLQASYEVTNKQWDAGYISDEVDEHMRVSGQVVEQLSEHQMEGFLEAY
LLTGRHGIWSSYESFVHVIDSMLNQHAKWLEATVREIPWRKPIASMNLLVSSHVWRQDHN
GFSHQDPGVTSVLLNKCFHNDHVIGIYFATDANMLLAIAEKCYKSTNKINAIIAGKQPAAT
WLTLDEARAELEKGAAAWDWASTAKTNDEAEIVLAAAGDVPTQEIMAASDKLKELGIKF
KVVNVVDLLSLQSAKENDEALSNEEFADIFTADKPVLFAYHSYAHDVRGLIYDRPNHDNF
NVHGYEEEGSTTTPYDMVRVNRIDRYELTAEALRMIDADKYADKIDELEKFRDEAFQFAV
DKGYDHPDYTDWVYSGVNTGKKGAVTATAATAGDNE (SEQ ID NO: 4)

FIGURE 19.

MTDVRFRHGTGAYVPERIVSNDEVGAPAGVDDDWITRKTGIRQ
RRWAADDQATSDLATAAGRAALKAAGITPEQLTVIAVATSTPDRPQPPTAAYVQHHLG
ATGTAAFDVNAVCSGTVFALSSVAGTLVYRGGYALVIGADLYSRILNPADRKTVVLFG
DGAGAMVLGPTSTGTGPIVRRVALHTFGGLTDLIRVPAGGSRQPLDTDGLDAGLQYFA
MDGREVRRFVTEHLPQLIKGFLHEAGVDAADISHFVPHQANGVMLDEVFGELHLPRAT
MHRTVETYGNTGAASIPITMDAAVRAGSFRPGELVLLAGFGGGMAASFALIEW (SEQ ID
NO: 5)

FIGURE 20:

*L. grayi mvaE:* atggttaaagacattgtaataattgatgccctccgtactccatcggtaagtaccgcggtcagctctcaaagatgacggcggtggaattgggaacc
gcagttacaaaggctctgttcgagaagaacgaccaggtcaaagaccatgtagaacaagtcattttggcaacgttttacaggcagggaacggcc
agaatcccgcccgtcagatcgcccttaattctggcctgtccgcagagataccggcttcgactattaaccaggtgtgtggttctggcctgaaagcaa
taagcatggcgcgccaacagatcctactcggagaagcggaagtaatagtagcaggaggtatcgaatccatgacgaatgcgccgagtattacat
attataataaagaagaagacaccctctcaaagcctgttcctacgatgaccttcgatggtctgaccgacgcgtttagcggaaagattatgggtttaac
agccgaaaatgttgccgaacagtacggcgtatcacgtgaggcccaggacgcctttgcgtatggatcgcagatgaaagcagcaaaggcccaag
aacagggcattttcgcagctgaaatactgcctcttgaaataggggacgaagttattactcaggacgagggggttcgtcaagagaccaccctcga
aaaattaagtctgcttcggaccatttttaaagaagatggtactgttacagcgggcaacgcctcaacgatcaatgatggcgcctcagccgtgatcatt
gcatcaaaggagtttgctgagacaaaccagattccctaccttgcgatcgtacatgatattacagagataggcattgatccatcaataatgggcattg
ctcccgtgagtgcgatcaataaactgatcgatcgtaaccaaattagcatggaagaaatcgatctctttgaaattaatgaggcatttgcagcatcctc
ggtggtagttcaaaaagagttaagcattcccgatgaaaagatcaatattggcggttccggtattgcactaggccatcctcttggcgccacaggagc
gcgcattgtaaccaccctagcgcaccagttgaaacgtacacacggacgctatggtattgcctccctgtgcattggcggtggccttggcctagcaa
tattaatagaagtgcctcaggaagatcagccggttaaaaaattttatcaattggcccgtgaggaccgtctggctagacttcaggagcaagccgtga
tcagcccagctacaaaacatgtactggcagaaatgacacttcctgaagatattgccgacaatctgatcgaaaatcaaatatctgaaatggaaatcc
ctcttggtgtggctttgaatctgagggtcaatgataagagttataccatcccactagcaactgaggaaccgagtgtaatcgctgcctgtaataatggt
gcaaaaatggcaaaccacctgggcggttttcagtcagaattaaaagatggtttcctgcgtgggcaaattgtacttatgaacgtcaaagaacccgca
actatcgagcatacgatcacggcagagaaagcggcaattttcgtgccgcagcgcagtcacatccatcgattgtgaaacgaggtgggggtctaa
aagagatagtagtgcgtacgttcgatgatgatccgacgttcctgtctattgatctgatagttgatactaaagacgcaatgggcgctaacatcattaac
accattctcgagggtgtagccggcttctgagggaaatccttaccgaagaaattctgttctctatttatctaattacgcaaccgaatcaattgtgacc
gccagctgtcgcataccttacgaagcactgagtaaaaaaggtgatggtaaacgaatcgctgaaaaagtggctgctgcatctaaatttgcccagtta
gatccttatcgagctgcaaccccacaacaaaggtattatgaatggtattgaggccgtcgttttggcctcaggaaatgacacacgggcggtcgcggc
agccgcacatgcgtatgcttcacgcgatcagcactatcggggcttaagccagtggcaggttcagaaggcgcgttacacggggagatcagtct
accacttgcactcggcagcgttggcggtgcaattgaggtcttgcctaaagcgaaggcggcattcgaaatcatgggatcacagaggcgaagga
gctggcagaagtcacagctgcggtagggctggcgcaaaacctggcggcgttaagagcgcttgttagtgaaggaatacagcaaggtcacatgtc
gctccaggctcgctctcttgcattatcggtaggtgctacaggcaaggaagttgaaatcctggccgaaaaattacagggctctcgtatgaatcaggc
gaacgctcagaccatactcgcagagatcagatcgcaaaaagttgaattgtga   (SEQ ID NO: 6)

FIGURE 21:

*E. faecium mvaE:* atgaaagaagtggttatgattgatgcggctcgcacacccattgggaaatacagaggtagtcttagtccttttacagcggtggagctggggacact
ggtcacgaaagggctgctggataaaacaaagcttaagaaagacaagatagaccaagtgatattcggcaatgtgcttcaggcaggaaacggaca
aaacgttgcaagacaaatagccctgaacagtggcttaccagttgacgtgccggcgatgactattaacgaagtttgcgggtccggaatgaaagcg
gtgattttagcccgccagttaatacagttaggggaggcagagttggtcattgcaggggggtacggagtcaatgtcacaagcacccatgctgaaac
cttaccagtcagagaccaacgaatacggagagccgatatcatcaatggttaatgacgggctgacggatgcgttttccaatgctcacatgggtctta
ctgccgaaaaggtggcgacccagttttcagtgtcgcgcgaggaacaagaccggtacgcattgtccagccaattgaaagcagcgcacgcggttg
aagccggggtgttctcagaagagattattccggttaagattagcgacgaggatgtcttgagtgaagacgaggcagtaagaggcaacagcacttt
ggaaaaactgggcaccttgcggacggtgttttctgaagagggcacggttaccgctggcaatgcttcaccgctgaatgacggcgctagtgtcgtg
attcttgcatcaaaagaatacgcggaaaacaataatctgccttacctggcgacgataaaggaggttgcggaagttggtatcgatccttctatcatgg
gtattgccccaataaaggccattcaaaagttaacagatcggtcgggcatgaacctgtccacgattgatctgttcgaaattaatgaagcattcgcgg
catctagcattgttgtttctcaagagctgcaattggacgaagaaaaagtgaatatctatggcggggcgatagcttttaggccatccaatcggcgcaa
gcggagcccggatactgacaaccttagcatacggcctcctgcgtgagcaaaagcgttatggtattgcgtcattatgtatcggcggtggtcttggtc
tggccgtgctgttagaagctaatatggagcagacccacaaagacgttcagaagaaaaagtttaccagcttaccccctccgagcggagatcgca
gcttatcgagaagaacgttctgactcaagaaacggcacttattttccaggagcagacgttgtccgaagaactgtccgatcacatgattgagaatca
ggtctccgaagtggaaattccaatgggaattgcacaaaattttcagattaatggcaagaaaaaatggattcctatggcgactgaagaaccttcagt
aatagcggcagcatcgaacggcgccaaaatctgcgggaacatttgcgcggaaacgcctcagcggcttatgcgcgggcagattgtcctgtctgg
caaatcagaatatcaagccgtgataaatgccgtgaatcatcgcaaagaagaactgattctttgcgcaaacgagtcgtacccgagtattgttaaacg
cgggggaggtgttcaggatatttctacgcgggagtttatgggttctttcacgcgtatttatcaatcgacttctggtggacgtcaaggacgcaatgg
gggcaaacatgatcaactctattctcgaaagcgttgcaaatcaactgcgtgaatggttcccggaagaggaaatactgttctccatcctgtcaaactt
cgctacggagtccctggcatctgcatgttgcgagattccttttgaaagacttggtcgtaacaaagaaattggtgaacagatcgccaagaaaattca
acaggcaggggaatatgctaagcttgaccgttaccgcgcggcaacccataacaaggggattatgaacggtatcgaagccgtcgttgccgcaac
gggaaacgacacacgggctgtttccgcttctattcacgcatacgccgcccgtaatggcttgtaccaaggtttaacggattggcagatcaagggcg
ataaactggttggtaaattaacagtcccactggctgtggcgactgtcggtggcgcgtcgaacatattaccaaaagccaaagcttccctcgccatgc
tggatattgattccgcaaaagaactggcccaagtgatcgccgcggtaggtttagcacagaatctggcggccgttacgtgcattagtgacagaagg
cattcagaaaggacacatgggcttgcaagcacgttcttagcgatttcgataggtgccatcggtgaggagatagagcaagtcgcgaaaaaactg
cgtgaagctgaaaaaatgaatcagcaaacggcaatacagattttagaaaaaaattcgcgagaaatga (SEQ ID NO: 7)

FIGURE 22:

*E. gallinarum mvaE:* atggaagaagtggtaattatagatgcacgtcggactccgattggtaaatatcacgggtcgttgaagaagttttcagcggtggcgctggggacggc
cgtggctaaagacatgttcgaacgcaaccagaaaatcaaagaggagatcgcgcaggtcataattggtaatgtcttgcaggcaggaaatggcca
gaaccccgcgcggcaagttgctcttcaatcagggttgtccgttgacattcccgcttctacaattaacgaggtttgtgggtctggtttgaaagctatctt
gatgggcatggaacaaatccaactcggcaaagcgcaagtagtgctggcaggcggcattgaatcaatgacaaatgcgccaagcctgtcccacta
taacaaggcggaggatacgtatagtgtcccagtgtcgagcatgacactggatggtctgacagacgcattttctagtaaacctatgggattaacagc
ggaaaacgtcgcacagcgctacggtatctcccgtgaggcgcaagatcaattcgcatatcaatctcagatgaaagcagcaaaagcgcaggcag
aaaacaaattcgctaaggaaattgtgccactggcgggtgaaactaaaaccatcacagctgacgaagggatcagatcccaaacaacgatggaga
aactggcaagtctcaaacctgttttaaaacctgatggcactgtaaccgcagggaatgctagcaccattaatgacggggccgccctgtgctgcttg
ctagcaaaacttactgcgaaactaatgacataccgtaccttgcgacaatcaaagaaattgttgaagttggaatcgatccggagattatgggcatctc
tccgataaaagcgatacaaacattgttacaaaatcaaaaagttagcctcgaagatattggagttttgaaataaatgaagcctttgccgcaagtagc
atagtggttgaatctgagttgggattagatccggctaaagttaaccgttatgggggtggtatatccttaggtcatgcaattggggcaaccggcgctc
gcctggccacttcactggtgtatcaaatgcaggagatacaagcacgttatggtattgcgagcctgtgcgttggtggtggacttggactggcaatgc
tttagaacgtccaactattgagaaggctaaaccgacagacaaaagttctatgaattgtcaccagctgaacggttgcaagagctggaaaatcaac
agaaaatcagttctgaaactaaacagcagttatctcagatgatgcttgccgaggacactgcaaaccatttgatagaaaatcaaatatcagagattga
actcccaatgggcgtcgggatgaacctgaaggttgatgggaaagcctatgttgtgccaatggcgacggaagagccgtccgtcatcgcggccat
gtctaatggtgccaaaatggccggcgaaattcacactcagtcgaaagaacggctgctcagaggtcagattgttttcagcgcgaagaatccgaat
gaaatcgaacagagaatagctgagaaccaagcttttgattttcgaacgtgccgaacagtcctatcctccattgtgaaaagagagggaggtctccg
ccgcattgcacttcgtcatttcctgccgattctcagcaggagtctgcggaccagtccacattttatcagtggaccttttgtagatgtgaaagacgc
gatggggcaaatatcataaatgcaatacttgagggcgtcgcagccctgttcgcgaatggttccccaatgaggaaattcttttttctattctctcgaa
cttggctacggagagcttagtcacggctgtttgtgaagtcccatttagtgcacttagcaagagaggtggtgcaacggtggcccagaaaattgtgc
aggcgtcgctcttcgcaaagacagacccataccgcgcagtgacccacaacaaagggattatgaacggtgtagaggctgttatgcttgccacag
gcaacgacacgcgcgcagtctcagccgcttgtcatggatacgcagcgcgcaccggtagctatcagggtctgactaactggacgattgagtcgg
atcgcctggtaggcgagataaacactgccgctggccatcgctacagttgaggcgctaccaaagtgttgcccaaagctcaagcggcactggaga
ttagtgatgttcactcttctcaagagcttgcagccttagcggcgtcagtaggtttagtacaaaatctcgcggccctgcgcgcactggtttccgaagg
tatacaaaaagggcacatgtccatgcaagcccggtctctcgcaatcgcggtcggtgctgaaaaagccgagatcgagcaggtcgccgaaaagtt
gcggcagaaccccgccaatgaatcagcagcaggcgctccgttttcttggcgagatccgcgaacaatga (SEQ ID NO: 8)

FIGURE 23:

*E. casseliflavus mvaE:* atggaagaagttgtcatcattgacgcactgcgtactccaataggaaagtaccacggttcgctgaaagattacacagctgttgaactggggacagt
agcagcaaaggcgttgctggcacgaaatcagcaagcaaaagaacacatagcgcaagttattattggcaacgtcctgcaagccggaagtgggc
agaatccaggccgacaagtcagtttacagtcaggattgtcttctgatatccccgctagcacgatcaatgaagtgtgtggctcgggtatgaaagcga
ttctgatgggtatggagcaaattcagctgaacaaagcctctgtggtcttaacaggcggaattgaaagcatgaccaacgcgccgctgtttagttatta
caacaaggctgaggatcaatattcggcgccggttagcacaatgatgcacgatggtctaacagatgctttcagttccaaaccaatgggcttaaccg
cagagaccgtcgctgagagatatggaattacgcgtaaggaacaagatgaatttgcttatcactctcaaatgaaggcggccaaagcccaggcgg
cgaaaaagtttgatcaggaaattgtaccctgacggaaaaatccggaacggttctccaggacgaaggcatcagagccgcgacaacagtcgag
aagctagctgagcttaaaacggtgttcaaaaaagacggaacagttacagcgggtaacgcctctacgataaatgatggcgctgctatggtattaat
agcatcaaaatcttattgcgaagaacaccagattccttatctggccgttataaaggagatcgttgaggtgggtttttgccccccgaaataatgggtattt
cccccattaaggctatagacaccctgctgaaaaatcaagcactgaccatagaggatataggaatatttgagattaatgaagcctttgctgcgagttc
gattgtggtagaacgcgagttgggcctggaccccaaaaaagttaatcgctatggcggtggtatatcactcggccacgcaattgggcgacggg
agctcgcattgcgacgaccgttgcttatcagctgaaagatacccaggagcgctacggtatagcttccttatgcgttggtggggtcttggattggc
gatgcttctggaaaacccatcggccactgcctcacaaactaattttgatgaggaatctgcttccgaaaaaactgagaagaagaagttttatgcgcta
gctcctaacgaacgcttagcgtttttggaagcccaaggcgctattaccgctgctgaaacccctggtcttccaggagatgaccttaaacaaagagac
agccaatcacttaatcgaaaaccaaatcagcgaagttgaaattcctttaggcgtgggcctgaacttacaggtgaatgggaaagcgtataatgttcc
tctggccacggaggaaccgtccgttatcgctgcgatgtcgaatggcgccaaaatggctggtcctattacaacaacaagtcaggagaggctgtta
cggggtcagattgtcttcatggacgtacaggacccagaagcaatattagcgaaagttgaatccgagcaagctaccattttcgcggtggcaaatga
aacataccgtctatcgtgaaaagaggaggaggtctgcgtagagtcattggcaggaatttcagtccggccgaaagtgacttagccacggcgtat
gtatcaattgacctgatggtagatgttaaggatgcaatgggtgctaatatcatcaatagtatcctagaaggtgttgcggaattgtttagaaaatggttc
ccagaagaagaaatcctgttctcaattctctccaatctcgcgacagaaagtctggtaacggcgacgtgctcagttccgtttgataaattgtccaaaa
ctggggaatggtcgacaagtagctggtaaaatagtgcacgcggcggactttgctaagatagatccatacagagctgccacacacaataaaggtatt
atgaatggcgttgaagcgttaatcttagccaccggtaatgacacccgtgcggtgtcggctgcatgccacggttacgcggcacgcaatgggcgaa
tgcaaggggcttacctcttggacgattatcgaagatcggctgataggctctatcacattaccttggctattgcgacagtgggggtgccacaaaaat
cttgccaaaagcacaggccgccctggcgctaactggcgttgagacggcgtcggaactggccagcctggcggcgagtgtgggattagttcaaa
atttggccgcttacgagcactagtgagcgagggcattcagcaagggcacatgagtatgcaagctagatccctggccattagcgtaggtgcgaa
aggtactgaaatagagcaactagctgcgaagctgagggcagcgacgcaaatgaatcaggagcaggctcgtaaatttctgaccgaaataagaaa
ttaa (SEQ ID NO: 9)

FIGURE 24:

*L. grayi mvaS:* atgaccatgaacgttggaatcgataaaatgtcattctttgttccaccttactttgtggacatgactgatctggcagtagcacgggatgtcgatcccaat
aagtttctgattggtattggccaggaccagatggcagttaatccgaaaacgcaggatattgtgacatttgccacaaatgctgccaaaaacatactgt
cagctgaggaccttgataaaattgatatggtcatagtcggcaccgagagtggaatcgatgaatccaaagcgagtgccgtagtgcttcacaggttg
ctcggtatccagaagtttgctcgctcctttgaaatcaaagaagcctgttatgggggtaccgcggcttacagttcgctgtaaaccacattaggaatc
atcctgaatcaaaggttcttgtagttgcatcagatatcgcgaaatacggcctggcttctggaggtgaaccaacgcaaggtgcaggcgctgtggct
atgctcgtctcaactgaccctaagatcattgctttcaacgacgatagcctcgcgcttacacaagatatctatgacttctggcgaccagttggacatga
ctatcctatggtcgacgggcctcttagtacagagacctacatccagtcatttcagaccgtatggcaggaatacacaaaacggtcgcagcatgcac
tggcagactttgctgcccttagctttcatatcccgtatactaaaatgggcaaaaaggcgctgcttgcaatccttgaaggcgaatcagaggaggctc
agaaccgtatactagcaaaatatgaaaagagtatagcctactccagaaaggcgggtaacctgtataccggtagcctgtatctaggacttatttcact
tctggaaaatgcagaagacctaaagctggtgatttaataggcctctttcttacggttccggtgctgttgcggagttttctcaggaaggctggtga
ggactatcaggaacagctacttaaaacaaaacatgccgaacagctggcccatagaaagcaactgacaatcgaggagtacgaaacgatgttctc
cgatcgcttggacgtggacaaagacgccgaatacgaagacacattagcttatagcatttcgtcagtccgaaacaccgtacgtgagtacaggagtt
ga (SEQ ID NO:10)

FIGURE 25:

*E. faecium mvaS:* atgaaaatcggtattgaccgtctgtccttcttcatcccgaatttgtatttggacatgactgagctggcagaatcacgcggggatgatccagctaaata
tcatattggaatcggacaagatcagatggcagtgaatcgcgcaaacgaggacatcataacactgggtgcaaacgctgcgagtaagatcgtgac
agagaaagaccgcgagttgattgatatggtaatcgttggcacggaatcaggaattgaccactccaaagcaagcgccgtgattattcaccatctcct
taaaattcagtcgttcgcccgttctttcgaggtaaaagaagcttgctatggcggaactgctgccctgcacatggcgaaggagtatgtcaaaaatcat
ccggagcgtaaggtcttggtaattgcgtcagacatcgcgcgttatggtttggccagcggaggagaagttactcaaggcgtgggggccgtagcc
atgatgattacacaaaaccccggattctttcgattgaagacgatagtgttttctcacagaggatatctatgattctggcggcctgattactccgagt
tccctgtagtggacgggccccttcaaactcaacgtatatagagagttttcagaaagtttggaaccggcacaaggaattgtccggaagagggctg
gaagattatcaagctattgcttttcacataccctatacgaagatgggtaagaaagcgctccagagtgttttagaccaaaccgatgaagataaccag
gagcgcttaatggctagatatgaggagtctattcgctatagccggagaattggtaacctgtacacaggcagcttgtaccttggtcttacaagcttgtt
ggaaaactctaaaagtttacaaccgggagatcggatcggcctcttttcctatggcagtggtgcggtgtccgagttctttaccgggtatttagaagaa
aattaccaagagtacctgttcgctcaaagccatcaagaaatgctggatagccggactcggattacggtcgatgaatacgagaccatctttcagag
actctgccagaacatggtgaatgcgccgaatatacgagcgacgtcccctttctataaccaagattgagaacgacattcgttattataaaatctga
(SEQ ID NO: 11)

FIGURE 26:

*E. gallinarum mvaS:* atgaacgtcggcattgacaaaattaattttttcgttccaccgtattatctggatatggtcgacctggcccacgcacgcgaagtggaccgaacaaat
tacaattggaattggacaggatcagatggctgtgagcaaaaagacgcacgatatcgtaacattcgcggctagtgccgcgaaggaaattttagaa
cctgaggacttgcaagctatagacatggtatagttggtaccgaatcgggcattgacgagagcaaagcatccgcggtcgttttacatcgtttgttgg
gcgtacaaccttcgctcgcagttttgaaattaaagaagcctgttacggggcaaccgcaggcattcagtttgccaagactcatatacaagcgaacc
cggagagcaaggtcctggtaattgcaagcgatatagctcggtatggtcttcggtcaggtggagagcccacacaaggcgcaggggcagttgcta
tgcttctcacggcaaatcccagaatcctgaccttcgaaaacgacaatctgatgttaacgcaggatatttatgacttctggagaccacttggtcacgct
taccctatggtagatggccacctttccaatcaagtctatattgacagttttaagaaggtctggcaagcacattgcgaacgcaatcaagcttctatatc
cgactatgccgcgattagttttcatattccgtatacaaaaatgggtaagaaagccctgctcgctgttttttgcagatgaagtggaaactgaacaggaa
cgcgttatggcacggtatgaagagtctatcgtatattcacgccggatcggcaacttgtatacgggatcattgtacctggggctgatatccttattgga
aaacagtctcacctgtcggcgggcgaccggataggattgtttagttatgggagtggcgctgtcagcgaattttctccggtcgtttagtggcaggc
tatgaaaatcaattgaacaaagaggcgcatacccagctcctggatcagcgtcagaagctttccatcgaagagtatgaggcgattttttacagattcct
tagaaattgatcaggatgcagcgttctcggatgacctgccatattccatccgcgagataaaaaacacgattcggtactataaggagagctga
(SEQ ID NO:12)

FIGURE 27:

*E. casseliflavus mvaS:* atgaacgttggaattgataaaatcaatttttcgttccgccctatttcattgatatggtggatctcgctcatgcaagagaagttgaccccaacaagttcactataggaa taggccaagatcagatggcagtaaacaagaaaacgcaagatatcgtaacgttcgcgatgcacgccgcgaaggatattctgactaaggaagatttacaggcca tagatatggtaatagtgggggactgagtctgggatcgacgagagcaaggcaagtgctgtcgtattgcatcggcttttaggtattcagccttttgcgcgctcctttga aattaaggaggcatgctatggggccactgccggccttcagtttgcaaaagctcatgtgcaggctaatccccagagcaaggtcctggtggtagcttccgatatag cacgctacggactggcatccggaggagaaccgactcaaggtgtaggtgctgtggcaatgttgattccgctgatccagctatcttgcagttagaaaatgataatc tcatgttgacccaagatatatacgatttttggcgcccggtcgggcatcaatatcctatggtagacggccatctgtctaatgccgtctatatagacagctttaaacaa gtctggcaagcacattgcgagaaaaaccaacggactgctaaagattatgctgcattgtcgttccatattccgtacacgaaaatgggtaagaaagctctgttagcg gtttttgcggaggaagatgagacagaacaaaagcggttaatggcacgttatgaagaatcaattgtatacagtcgtcggactggaaatctgtatactggctcactc tatctgggcctgatttccttactggagaatagtagcagtttacaggcgaacgatcgcataggtctgtttagctatggttcagggggccgttgcggaatttttcagtgg cctcttggtaccgggttacgagaaacaattagcgcaagctgcccatcaagctcttctggacgaccggcaaaaactgactatcgcagagtacgaagccatgttta atgaaaccattgatattgatcaggaccagtcatttgaggatgacttactgtactccatcagagagatcaaaaacactattcgctactataacgaggagaatgaata a (SEQ ID NO:13)

FIGURE 28.

pCMP1090 (PKL from *Bifidobacterium infantis*)

gtttgacagcttatcatcgactgcacggtgcaccaatgcttctggcgtcaggcagccatcggaagctgtggtatggctgtgcaggtcgtaaatcac
tgcataattcgtgtcgctcaaggcgcactcccgttctggataatgttttttgcgccgacatcataacggttctggcaaatattctgaaatgagctgttg
acaattaatcatccggctcgtataatgtgtggaattgtgagcggataacaatttcacacaggaaacagccgcgctgagaaaaagcgaagcggca
ctgctctttaacaatttatcagacaatctgtgtgggcactcgaccggaattatcgattaactttattattaaaaattaaagaggtatatattaatgtatcga
ttaaataaggaggaataaaccatgacgagtcctgttattggcaccccttggaagaagctcagcgctccggtttccgaggaagccctcgaaggcg
ttgacaagtactggcgcgttgccaactacctttccatcggccagatttatctgcgttccaacccgctgatgaaggagcccttcacccgcgaagatg
tgaagcatcgtctggtgggccactggggcactacccctggcctgaacttcctcatcggccacatcaaccgtttcattgctgaccacggccagaac
accgtgatcatcatgggcccgggccacggtggcccggccggtacctcccagtcctacctggacggcacctacaccgagaccttcccgaagat
caccaaggacgaagctggtctgcagaagttcttccgtcagttctcttacccgggcggtattccgtcccacttcgctccggagaccccgggctcca
tccacgagggtggtgagctgggttacgctctgtcccacgcttacggcgccatcatggacaacccgagcctgttcgtcccggccatcgtcggcga
cggcgaggctgagaccggcccgctggctaccggttggcagtccaacaagctcgtgaacccgcgcaccgacggtatcgtgctgccgatcctgc
acctcaacggctacaagatcgccaacccgaccatcctgtcccgcatctccgacgaagagctccacgagttcttccacggcatgggttacgagcc
ctacgagttcgtcgctggcttcgatgatgaggaccacatgtccatccaccgccgcttcgccgagctgtgggagaccatctgggacgagatctgc
gacatcaaggccaccgctcagaccgacaacgtgcaccgtccgttctacccgatgctgatcttccgcaccccgaagggctggacctgcccgaag
tacatcgacggcaagaagaccgaaggctcctggcgttcccaccaggtgccgctggcctccgcccgcgacaccgaggcccacttcgaggtcct
caagaactggctcgagtcctacaagccggaagagctgttcgacgccaacggcgccgtcaaggacgacgtcctcgccttcatgccgaagggcg
agctgcgtatcggtgccaacccgaacgccaacggcggtgtgatccgcgacgacctgaagctgccgaacctcgaggactacgaggtcaagga
agtggccgagttcggccacgagctggggccagctcgaggccacccgctccctgggcgcctacacccgcgacatcatcaagaacaacccgcgt
gacttccgcatcttcggaccggatgagaccgcttccaaccgtctgcaggcttcctacgaagtcaccaacaagcagtgggatgccggctacatct
ccgacgaggtcgacgagcacatgcgcgtctccggccaggtcgtcgagcagctgtccgagcaccagatggaaggcttcctcgaggcctacctg
ctgaccggccgtcacggcatctggagctcctacgagtccttcgtccacgtgatcgactccatgctgaaccagcacgccaagtggcttgaggcta
ccgtccgcgagattccgtggcgcaagccgatcgcctccatgaacctgctggtctcctcccacgtctggcgtcaggaccacaacggcttctccca
ccaggatccgggtgtcacctccgtcctgctgaacaagtgcttccacaacgaccacgtcatcggcatctacttcgccaccgacgcgaacatgctg
ctggccatcgccgagaagtgctacaagtccaccaacaagatcaacgccatcatcgccggcaagcagcccgccgccacctggctgaccctgga
cgaggctcgcgccgagctcgagaaggtgccgccgcttgggactgggcctccaccgccaagaccaacgatgaagccgagatcgtgcttgcc
gccgccggcgacgtccccacccaggagatcatggccgcttccgacaagctgaaggaactgggcatcaagttcaaggtcgtgaacgttgtcga
cctgctctccctgcagtccgccaaggagaacgacgaggccctgtccaacgaggagttcgccgacatcttcaccgccgacaagccggtgctgtt
cgcgtaccactcctacgcccacgacgtgcgcggtctgatctacgatcgtccgaaccacgacaacttcaacgtccacggctacgaggaggagg
gctccaccaccacccgtacgacatggttcgtgtcaaccgcatcgaccgctacgagctgaccgctgaggctctgcgcatgatcgacgccgaca
agtacgccgacaagatcgacgagctcgagaagttccgtgatgaggccttccagttcgccgtcgacaagggctacgaccacccggactacacc
gactgggtgtactccggcgtgaacaccggcaagaagggtgccgtcaccgctaccgccgctaccgctggcgacaacgagtgagaattcgaag
ctttctagaacaaaaactcatctcagaagaggatctgaatagcgccgtcgaccatcatcatcatcattgagtttaaacggtctccagcttgctg
ttttggcggatgagagaagattttcagcctgatacagattaaatcagaacgcagaagcggtctgataaaacagaatttgcctggcggcagtagcg
cggtggtcccacctgacccatgccgaactcagaagtgaaacgccgtagcgccgatggtagtgtggggtctcccatgcgagagtagggaac
tgccaggcatcaaataaaacgaaaggctcagtcgaaagactgggcctttcgttttatctgttgtttgtcggtgaacgctctcctgagtaggacaaat
ccgccgggagcggatttgaacgttgcgaagcaacggcccggagggtggcgggcaggacgcccgccataaactgccaggcatcaaattaag
cagaaggccatcctgacggatggcctttttgcgtttctacaaactctttttgtttattttctaaatacattcaaatatgtatccgctcatgagacaataac
cctgataaatgcttcaataatattgaaaaaggaagagtatgagtattcaacatttccgtgtcgcccttattcccttttttgcggcattttgccttcctgtttt
tgctcacccagaaacgctggtgaaagtaaaagatgctgaagatcagttgggtgcacgagtgggttacatcgaactggatctcaacagcggtaag FIGURE 28. continued atccttgagagttttcgccccgaagaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatcttacggatggcatgacagtaa
gagaattatgcagtgctgccataaccatgagtgataacactgcggccaacttacttctgacaacgatcggaggaccgaaggagctaaccgcttttt
tgcacaacatgggggatcatgtaactcgccttgatcgttgggaaccggagctgaatgaagccataccaaacgacgagcgtgacaccacgatgc
ctgtagcaatggcaacaacgttgcgcaaactattaactggcgaactacttactctagcttcccggcaacaattaatagactggatggaggcggata
aagttgcaggaccacttctgcgctcggcccttccggctggctggtttattgctgataaatctggagccggtgagcgtgggtctcgcggtatcattg
cagcactggggccagatggtaagccctcccgtatcgtagttatctacacgacggggagtcaggcaactatggatgaacgaaatagacagatcg
ctgagataggtgcctcactgattaagcattggtaactgtcagaccaagtttactcatatatactttagattgatttaaaacttcatttttaatttaaaagga
tctaggtgaagatccttttgataatctcatgaccaaaatcccttaacgtgagttttcgttccactgagcgtcagaccccgtagaaaagatcaaagga
tcttcttgagatccttttttctgcgcgtaatctgctgcttgcaaacaaaaaaaccaccgctaccagcggtggtttgtttgccggatcaagagctacca
actcttttccgaaggtaactggcttcagcagagcgcagataccaaatactgtccttctagtgtagccgtagttaggccaccacttcaagaactctgt
agcaccgcctacatacctcgctctgctaatcctgttaccagtggctgctgccagtggcgataagtcgtgtcttaccgggttggactcaagacgata
gttaccggataaggcgcagcggtcgggctgaacggggggttcgtgcacacagcccagcttggagcgaacgacctacaccgaactgagatac
ctacagcgtgagctatgagaaagcgccacgcttcccgaagggagaaaggcggacaggtatccggtaagcggcagggtcggaacaggagag
cgcacgagggagcttccaggggaaacgcctggtatctttatagtcctgtcgggtttcgccacctctgacttgagcgtcgatttttgtgatgctcgt
caggggggcggagcctatggaaaaacgccagcaacgcggccttttacggttcctggccttttgctggccttttgctcacatgttctttcctgcgtta
tcccctgattctgtggataaccgtattaccgcctttgagtgagctgataccgctcgccgcagccgaacgaccgagcgcagcgagtcagtgagcg
aggaagcggaagagcgcctgatgcggtattttctccttacgcatctgtgcggtatttcacaccgcatatggtgcactctcagtacaatctgctctgat
gccgcatagttaagccagtatacactccgctatcgctacgtgactgggtcatggctgcgccccgacacccgccaacacccgctgacgcgccct
gacgggcttgtctgctcccggcatccgcttacagacaagctgtgaccgtctccgggagctgcatgtgtcagaggttttcaccgtcatcaccgaaa
cgcgcgaggcagcagatcaattcgcgcgcgaaggcgaagcggcatgcatttacgttgacaccatcgaatggtgcaaaacctttcgcggtatgg
catgatagcgcccggaagagagtcaattcagggtggtgaatgtgaaaccagtaacgttatacgatgtcgcagagtatgccggtgtctcttatcag
accgtttcccgcgtggtgaaccaggccagccacgtttctgcgaaaacgcgggaaaaagtggaagcggcgatggcggagctgaattacattccc
aaccgcgtggcacaacaactggcgggcaaacagtcgttgctgattggcgttgccacctccagtctggccctgcacgcgccgtcgcaaattgtcg
cggcgattaaatctcgcgccgatcaactgggtgccagcgtggtggtgtcgatggtagaacgaagcggcgtcgaagcctgtaaagcggcggtg
cacaatcttctcgcgcaacgcgtcagtgggctgatcattaactatccgctggatgaccaggatgccattgctgtggaagctgcctgcactaatgttc
cggcgttatttcttgatgtctctgaccagacacccatcaacagtattattttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcgcaat
caaattcagccgatagcggaacgggaaggcgactggagtgccatgtccggttttcaacaaaccatgcaaatgctgaatgagggcatcgttccca
ctgcgatgctggttgccaacgatcagatggcgctggcgcaatgcgcgccattaccgagtccggctgcgcgttggtgcggatatctcggtagt
gggatacgacgataccgaagacagctcatgttatatcccgccgtcaaccaccatcaaacaggattttcgcctgctggggcaaaccagcgtggac
cgcttgctgcaactctctcagggccaggcggtgaagggcaatcagctgttgcccgtctcactggtgaaaagaaaaaccaccctggcgcccaat
acgcaaaccgcctctccccgcgcgttggccgattcattaatgcagctggcacgacaggtttcccgactggaaagcgggcagtgagcgcaacg
caattaatgtgagttagcgcgaattgatctg (SEQ ID NO:15)

FIGURE 29.

pCMP1029 (PKL from *Lactobacillus reuteri*)
gtttgacagcttatcatcgactgcacggtgcaccaatgcttctggcgtcaggcagccatcggaagctgtggtatggctgtgcaggtcgtaaatcac
tgcataattcgtgtcgctcaaggcgcactcccgttctggataatgtttttgcgccgacatcataacggttctggcaaatattctgaaatgagctgttg
acaattaatcatccggctcgtataatgtgtggaattgtgagcggataacaatttcacacaggaaacagccgccgctgagaaaaagcgaagcggca
ctgctctttaacaatttatcagacaatctgtgtgggcactcgaccggaattatcgattaactttattattaaaaattaaagaggtatatattaatgtatcga
ttaaataaggaggaataaacatggcagtagattacgattccaagaaatacttggaaagtgttgatgcttactggcgtgcagctaactacctttcagtt
ggtacattgtacttaatggtgatccattacttcgccaaccattaaaggcagaagatgttaagcctaagccaattggtcactggggtactattgttcct
caaaacttcatttacgcacacttgaaccgtgtaattaagaagtatgaccttgatatgttctacatcgaaggttcaggtcacggtggccaagttatggtt
aacaactcatacttggatggttcatacactgaaatttatcctgaatatactcaagacactaagggaatggctaagttattcaagcacttctcattccca
ggcggtactgcatcacacgctgcacctgaaacaccaggttcaatccacgaaggtggggaacttggttactcactttcacacggtgttggtgctatc
ttagataacccagaagttattgccgctgttgaaatcggtgatggtgaagctgaaactggtccattaatggcatcatggttctcagacaagttcattaa
cccaatcaaggatggtgcggtattaccaatcatccaagttaacggattcaagattctaaccctactatcctttcatggatgagcgacgaagaactta
ctaagtacttcgaaggtatgggttggaagccatactttgtttcagcttacaaagaagctgaccgtgatggtgaattcaagggttacaagcctcacat
ggaagttcacgaagaaatggctaagactttggacaaggttgttgaagaaatcaaggctattcaaaagaacgctcgtgaaaacaatgataactcatt
accacaatggccaatgattatcttccgtgcacctaagggttggactggtcctaagactgaccttgatggtaacccaattgaaaactcattccgtgca
caccaaattccagttccagtatcccaagatgacatggaacacaaggacatccttgttgattggttgaagtcatacaagccagaagaattgtttgacg
aagatggtcacccagttgctcttgttgaagagaacacaccagaaggtaaccgtcgtatggctatgaaccctatcactaatggtggtatcgatccta
agccacttgtattgccaaactaccgtgattttgctattgatgttcaaaatcctggttctgttgtaaagcaagacatgcttgaatggggtaagtacctcaa
caagatggctgaattgaacccaactaacttccgtggatttggtcctgacgaatctaagtcaaaccgtcttacgcattccttgatggtcaaaagcgtc
aatggatggaaagtgtccacgaaccaaacgacgaagatgtggctccacaaggtcgtatgatcgattcacaactttcagaacaccaagctgaagg
attccttgaaggttacacattaactggtcgtcacggattcttcgcaacttacgaagcattcggtcgtgttgttgattcaatgcttactcaacacatgaag
tggttacgtaaggctaaggatctttactggcgtcaccaatacccagcattgaactttgttgatacttctactgtattccaacaagatcacaacggttac
actcaccaagatccaggtctattgactcacttgtttgaaaaggaacgtccagacctcgttaaggaatacttgccagcagatactaactcattaatgg
ctgtatctaacaaggcattccgtaaccaagaatgcatcaacctcttcgtaacttctaagcacccacgtgcacaatggttctctattgatgaagctact
caattggctgacaatggtcttggctacattgactgggcatctactgaccaaggtactgaaccagatgttgtatttgcatcttctggtactgaacctact
gaagaagctcttgcagctattgacattcttcatgacaacttccctgaattgaagattcgttacatcaacatcatcgaaattatgcgtttgatgaacactg
acaagaaccctgaaggtttaactgatgctgaattcaatagttacttcactactgacaagccagttatctttgcatggcacggattccgtgacatgatc
caagcattgttcttcgatcgtgctaaccgtaacgttcacattcactcatacgaagaaaatggtgatatcaccactccattcgacatgcgtgtattaaac
gaacttgaccggttccacttagctaaggacgctatccaaagtgttcctggttacgaacaaaagagtgctgcatttgttgccaagatggacaacatg
atcaacaagcacaaccactacatccgttcagaaggtaaggacttaccagaagttactaactggacttggaagggtcttaagtaagaattcgaagct
ttctagaacaaaaactcatctcagaagaggatctgaatagcgccgtcgaccatcatcatcatcatcattgagtttaaacggtctccagcttggctgtt
ttggcggatgagagaagattttcagcctgatacagattaaatcagaacgcagaagcggtctgataaaacagaatttgcctggcggcagtagcgc
ggtggtcccacctgacccatgccgaactcagaagtgaaacgccgtagcgccgatggtagtgtggggtctcccatgcgagagtagggaact
gccaggcatcaaataaaacgaaaggctcagtcgaaagactgggcctttcgttttatctgttgtttgtcggtgaacgctctcctgagtaggacaaatc
cgccgggagcggatttgaacgttgcgaagcaacggcccggagggtggcgggcaggacgcccgccataaactgccaggcatcaaattaagc
agaaggccatcctgacggatggcctttttgcgtttctacaaactcttttgtttatttttctaaatacattcaaatatgtatccgctcatgagacaataacc
ctgataaatgcttcaataatattgaaaaaggaagagtatgagtattcaacatttccgtgtcgcccttattcccttttttgcggcattttgccttcctgtttt
gctcacccagaaacgctggtgaaagtaaaagatgctgaagatcagttgggtgcacgagtgggttacatcgaactggatctcaacagcggtaag
atccttgagagttttcgccccgaagaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatcttacggatggcatgacagtaa
gagaattatgcagtgctgccataaccatgagtgataacactgcggccaacttacttctgacaacgatcggaggaccgaaggagctaaccgcttttt
tgcacaacatgggggatcatgtaactcgccttgatcgttgggaaccggagctgaatgaagccataccaaacgacgagcgtgacaccacgatgc

FIGURE 29. continued ctgtagcaatggcaacaacgttgcgcaaactattaactggcgaactacttactctagcttcccggcaacaattaatagactggatggaggcggata
aagttgcaggaccacttctgcgctcggcccttccggctggctggtttattgctgataaatctggagccggtgagcgtgggtctcgcggtatcattg
cagcactggggccagatggtaagccctcccgtatcgtagttatctacacgacggggagtcaggcaactatggatgaacgaaatagacagatcg
ctgagataggtgcctcactgattaagcattggtaactgtcagaccaagtttactcatatatactttagattgatttaaaacttcattttaatttaaaagga
tctaggtgaagatccttttgataatctcatgaccaaaatcccttaacgtgagttttcgttccactgagcgtcagaccccgtagaaaagatcaaagga
tcttcttgagatcctttttctgcgcgtaatctgctgcttgcaaacaaaaaaaccaccgctaccagcggtggtttgtttgccggatcaagagctacca
actcttttccgaaggtaactggcttcagcagagcgcagataccaaatactgtccttctagtgtagccgtagttaggccaccacttcaagaactctgt
agcaccgcctacatacctcgctctgctaatcctgttaccagtggctgctgccagtggcgataagtcgtgtcttaccgggttggactcaagacgata
gttaccggataaggcgcagcggtcgggctgaacgggggttcgtgcacacagcccagcttggagcgaacgacctacaccgaactgagatac
ctacagcgtgagctatgagaaagcgccacgcttcccgaagggagaaaggcggacaggtatccggtaagcggcagggtcggaacaggagag
cgcacgagggagcttccaggggaaacgcctggtatctttatagtcctgtcgggtttcgccacctctgacttgagcgtcgatttttgtgatgctcgt
caggggggcggagcctatggaaaaacgccagcaacgcggcctttttacggttcctggccttttgctggccttttgctcacatgttctttcctgcgtta
tcccctgattctgtggataaccgtattaccgcctttgagtgagctgataccgctcgccgcagccgaacgaccgagcgcagcgagtcagtgagcg
aggaagcggaagagcgcctgatgcggtattttctccttacgcatctgtgcggtatttcacaccgcatatggtgcactctcagtacaatctgctctgat
gccgcatagttaagccagtatacactccgctatcgctacgtgactgggtcatggctgcgccccgacacccgccaacacccgctgacgcgccct
gacgggcttgtctgctcccggcatccgcttacagacaagctgtgaccgtctccgggagctgcatgtgtcagaggttttcaccgtcatccgaaa
cgcgcgaggcagcagatcaattcgcgcgcgaaggcgaagcggcatgcatttacgttgacaccatcgaatggtgcaaaacctttcgcggtatgg
catgatagcgcccggaagagagtcaattcagggtggtgaatgtgaaaccagtaacgttatacgatgtcgcagagtatgccggtgtctcttatcag
accgtttcccgcgtggtgaaccaggccagccacgtttctgcgaaaacgcgggaaaaagtggaagcggcgatggcggagctgaattacattccc
aaccgcgtggcacaacaactggcgggcaaacagtcgttgctgattggcgttgccacctccagtctggccctgcacgcgccgtcgcaaattgtcg
cggcgattaaatctcgcgccgatcaactgggtgccagcgtggtggtgtcgatggtagaacgaagcggcgtcgaagcctgtaaagcggcggtg
cacaatcttctcgcgcaacgcgtcagtgggctgatcattaactatccgctggatgaccaggatgccattgctgtggaagctgcctgcactaatgttc
cggcgttatttcttgatgtctctgaccagacacccatcaacagtattattttctcccatgaagacggtacgcgactgggcgtggagcatctggtcgc
attgggtcaccagcaaatcgcgctgttagcgggcccattaagttctgtctcggcgcgtctgcgtctggctggctggcataaatatctcactcgcaat
caaattcagccgatagcggaacgggaaggcgactggagtgccatgtccggttttcaacaaaccatgcaaatgctgaatgagggcatcgttccca
ctgcgatgctggttgccaacgatcagatggcgctggcgcaatgcgcgccattaccgagtccgggctgcgcgttggtgcggatatctcggtagt
gggatacgacgataccgaagacagctcatgttatatcccgccgtcaaccaccatcaaacaggattttcgcctgctggggcaaaccagcgtggac
cgcttgctgcaactctctcagggccaggcggtgaagggcaatcagctgttgcccgtctcactggtgaaaagaaaaaccaccctggcgcccaat
acgcaaaccgcctctccccgcgcgttggccgattcattaatgcagctggcacgacaggtttcccgactggaaagcgggcagtgagcgcaacg
caattaatgtgagttagcgcgaattgatctg (SEQ ID NO:16)

Figure 30 atgagcaccggtgtgcatatgaccagtccggttattgcaccgtgaagaaaactgaatgcaccgttagcgaagcagcaattgaaggtgttgataaatactggcgtgttgc
aaattatctggccattggtcagatttatctgcgtagcaatcgctgcgatcatcagcagaacaccgttgatattatggtccggtcatggtggtccgcaggcaccgagctatctgat
tgaatttctgattggtcatattaatcgctttatcgcgatcatcagcagaacaccgttgatattatggtccggtcatggtggtccgcaggcaccgagctatctgat
ggcacctatacggaatattatccgaaatattcaccaaagatgaagccggtctgcaaaaattcttcgccagtttagctatcccggggtgtattagcgagcctgttgttccggcaattgttggtgatgttgaagcaga
cgggtagcatccatgaaggtggtgaactggtattgaactggttatgcactgagccgtagccgttatgaataatccgagcctgtttgttccggcaattgttggtgatgttgaagcaga
aaccggtccgctggccaccggttgggcagagcaataaaactgttaatccgcgtaccgatggtattgttctgccgattctgcatctgaatggctataaaatcgaaatcgaccatt
ctgagccgcattagtgatgaagaactgcacgaattttttcacggtatggttatgaaccgtatgaattgttgccggtttgatgatgaagatcatatgtcaatcatcgtcgctttgc
cgatatgtttgaaaaccatcttgatgatagatctggatattaaagccgaagcacagacagacaatgatgattaccgtccgtattatccaatgattatcttcgtacccgaaaggttgac
ctgtccgaaatttatcgatggcaaaaaaaccgaaggtagctggcgttgcgttaaagaaaggtgcgttaaagaagatgtgccgaaaggtgaactgcgtattgcttgtgaaaatccgaatgcaaat
tgaaaagctataaaccggaagaactgttcgatgaaactgcgaaactgccgacagcttcgtattttgtccggataaccgcaagcaatcgtcgcaagcagcatatgaagttgccatgtgtggtgtcagctgaaccgcgtgggg
tgtttataccggtgatattcaaaaaccggacagcttcgtattttgtccggataaccgcaagcaatcgtcgcaagcagcatatgaagttgccatgtgtgggtcagctgaaccgcgtcgttgggg
atgcaggttatctgagcgttcggtcggttgatgaacatcacctttgtgatgagcagcagttaccggtcaggtgattgatagcatgctgaacagctgagcgaacatcagatgaaggttctgaaggctatctgtcacc
ggtcgtcatgggtatttggagcagcatgaaagctttgcatgtgaaaagcttggcgtcaggatgcatcagttcaggttgcagttgcagaaaaagcgcagaaaactgaatggccaagcaatggcaagcaatgatctgctgctgaataaacctttaataat
ccgattagcagcgttaatctgctgtttcccggttgatagcagccgttgatagcagccgttagttagcagcatcagttgcaggttgcagaaaaagcgcagaaaactgaatggccaagcaatgatcaatgatcaacaaaaacatgaaaaacatgaaaaacaatgatcaacgccattttcgcaggttaaacagcct
gatcatgatcgacctgatcctgctgaccctggatgaagcacgcgaacactgatggcgagaactgcaaagcaaacctatgaacaaactggtgatttaaattcaaagtggtgaattgttggattgattctgctgaactgcaa
gccgcaacctggctgaccctggatgaagcacgcgagaactgcaaagcaaacctatgaacaaactggtgatttaaattcaaagtggtgaattgttggattgattctgctgaactgcaa
ggcaggcgttggtgatgttccgcaggtgcaagaactgatgtccgcagccagccgcaagaagcagtttaccagcaagagttaccggttacagcgcaagaactgaactggttcactcagtttaccggttgcctctatcatgttatgcacatgatgttcgtggcctgat
ttatgatcgtccgaaccataactttaacgtgcgacgttataaagaaccagacggttagccaccaccccccgtatgataggttcgttaatgataataggtgttaatgatgcgttaatggatgcctatggatctagcgtatgaactgacag
cggaaagcactgcgtatggttgatgtcagcagcaaaaatatgccgatgaaaatcaaagagccccgctatctatcagaggcaagaatgaaaaatcaagcgttcgtgaagcagttcactgcgttgaagcattcagtatgccgttgataaaggtctggatcatccgg
attataccgattggtttgggcctggccttggccttggccttggccttggtgcgtggcgttgcgccggtaacagccaccggtgcgcaaccgcgcagccaccggcaggcgataataa (SEQ ID NO:17)

Figure 31 atgacattagccagtcctctacaaacaaagcctttaacagatgaagaattacgcaagataaacgcttactggcgtgcagctaactatctttcagttggacagatatatctactga
caatccactactgagagaaccgctataagcttgaacacgtcaaaccccaggctcttgggtcactgggaacaacaccagggctgtaactttatctatgctcactgaatcgggtcat
caaaaatatgacctaaaacacgatctatattgctggccctggtcatggtgccctggactagtagcaacacttacctagaaggcactacaccaagtattatcacaacatctcc
caggatgctgaaggaattcagaaactcttcaagcaattttctttcctggtattcccagccacgttgccaccagaaacccctggttcgatccatgaaggcggggaactaggtt
atgcccttgtccacgctttcggtcgcttgataacctgacttgatcgttgctgctgttgtgggtgacggcgaagctgaaacaggtgcttagcaactagctggcattccaac
aagtttcttaaccccgtcatgatgggggttcttgccgatccctgcactgaatggtataaaattgctaatccaacagtactggcacgatcagcgatgaggaattagraagct
tatttgtcggctacggctacaagccctactttgtcgaaggtgacgatccgcagatgtacatccgcagatgccggcgactctagatatagcgatcgccgaaattcaagtatcc
aaagagaagcccgcgctacatgttacactgaacgtcctcagtgccaaagttggacagggccaaaggraagttgatggtaaaaaactg
aaggttcttggcgatcgcaccaagttccctttgggaatatcgccaaacagccagaaactctgaaactctagaagattgaatgaagagttacaaaccagaagaacttctcgac
gctaacggcacactaatcccagaactagcagaattggctccccaaaggccatcgacgcatcgacgatccgcgctaacgggcggtcttttgctgcgacctgaagatg
cccgacttccaaaagtatgctgcgagcggcaagcgatcgctgaagctgcccaagttgcaggaattccctcccggatatatgcaacttaaccaagaaagc
cgcaacttccgcatcgtcgcggtgatcggccccgatgaaacggttcaaatcgcttagggcgtgtgcagaagttacagatcgggatggccagcccagatactcccgaagatgaccacc
tttccccgatgtgctcggggttgatggaaaattctcagcgaacgccaaatggctgaaacggtcttcaaggatggttagaaaggctaacctccctcacaggacgacacgggttctcttgctacgaggcgtttatc
cacatcgtggactcgatgtcaatcagcacgccacccgagacccgttggtttttattgaccatgtagttaataagaaagcagagatcgttcgcgttatttgcccccgatgccaacactctgtatcggt
caagaccataacggttttcccaccaagaccgttgtttattgacaatgtcaactatgtcaacgtcattgccggaaagcaaccagcattgcaatactaaatgatgctgtatcaagcactgcaccaaaggcat
aactgaccattgtttaagaaggcccaactatggccaacgatagaggcgaaccagatgtagtaatggcttgtcgtggggatatcccaccttagaaactttagcggctggggacattctgccgcc
cggtatttgggaatgggcaagcaacgataaagacgcgaaccagatgtagcactacaggccaaaaagtgaacaccccgcacgttgagcgaaaaagacttgacacgatttca
agcacttccctgagttaaaggtgcggtagtgaacgtagtcattgatgacactaccagcttaacctatcgcttaacctagtgatatgtaatcgatcgctcatcgcctattactatgcctattgcctatgcctagcagctgatagcagcagaggcagcagcttatgtcaaaca
ccaccaccacctcccttgatatgtttgtatgttgtgcttaacgagctagatcgctcatcagtgatttgttgtgatggatatatagggcgtaccaagaaggaagga
gcagttgcaagataaactgatcgaacacaaactattacgaacattgagaactcgtgactgaagttcgtggaagtgggacatatgccgacgatatgccgaagtggccctataa (SEQ ID NO:18)

Figure 32 atgtccgacgtgttgtccaacgatctgttgcagaagatggacgcgccattggcgccgcgcgaactacctgtctgtcgacagatctatctcgaggacaatccgctactctgatcag
aagctgcagctcgaccaccatcaagccgcgcttggccactgggtgacgacccccggcctcaatcttctactgtcatccgtggcatcaaccggtgatcaaccggagcatgatctcg
atatgatctacattaccggtcccggccatgccgggcccggcttgttgccaacgcttgttgccaacgagcgctacaccgagcgctatccggcgattgagcgagccgcaacg
gcatgcagcggctgttccgacaattctcctggccgacacgtcgcgagccgcactgctgcgatctcgccgaaacgccgtctcgatcagaggcggcgaactcggctactcgct
ggcgccatgcctatggcgcggcgtcgacaatccgaatctgatcgtccgttcgtgtgcggcgacggcgaggccgaggccggcgctctcgcgacgagttggcactccaaca
agttcctcaatccggcgccgacggcgcggtgctgccgatcctgcatcgaacggcttcaagattgccaacccgaccgtgctgcacggatcacgccgcaggaacctcacc
gacctgatgcgcgctatgagccgcacaggcgacgatccggcgtgtggtgcaccagacgctggtcgacgctggaacgctgctcggcgagatcc
gggccattcaggacaaggctcgcaaccacggcgcgcccatcaggtgccgatcgcgacccggccgatgtcgatcggccgaacacggtcgatgcgcagctatcggccc
cggcaagccgtggagggcacctggcgcgccgatcagcgccgatctgacttcaagaaccccgagcatcgacgtgctgaagactgctgatgcgcagtgctcgatctggccc
gatgagctgttcgacgccaagccaccggactgcgcgacgagctgcagccggcgtgaccgggcccgcgctgaaggccgacgcgggtgctcgaggccgcacttcctgccgac
gctggagccgtgtccggatttccacgactatgccctgcgacggtgaccggcctgttccgacggcgagaccgcatcgaaccggctcgatgcgtgtccagttctgccaaggtctggatgg
gtgatgaagaacagcctcgagagcgaaaacttccgctcagccagatgtgacgtccggtgatgagtgctcagcgagcgatcgagcatcatctgccaaggctatctgctgaccggccg
cggcgatcgaggatgtcgacgtcgatctcgagcgcgtcgtcgctacgaggcgttcatccacatcatcgactcgatgttcaatcagcacgccaaatgctgaaggcgtgcgccacgatccgtggcgaagccgatc
ccacgccttcttcgtgtgctacgagccggatctcgcacgtcggcgcacgacgtttctcgcaccaggatccactgtccaccaccgtcgccaacactgaagaagtcgaacgtg
gcgtcgctgaactatcgtgctgacctcgccgaccggatcacgaggcggccaactgtgtctgctgcttcatcgaccacgctcgccaacactgatcgtccgccagaagcaacgcgctga
gtgcgggatctatctgccgccgatcgacgccaactgtgtctgtctgttgcaccactggcgaccactgctgcgcgtgaccccaactcgtcaactgtcgccgcaagcagccgaatgg
cagtggctgaatatcgacgccgcgttcggcactgcaccgagccggatctgcaccgagccgcacgaggcggcgagccgacgtggtgatgcgcactgcgccggcaagcgcttgatgctgcacggatcgccggc
gacgtgccgacgtcgagacgctgcggcgctgtgcaccgccgccgcttcgacagatccggaacggtggtcaagatgcgtctcaacatcgcagcgatcgcgttcatcggaaccgtggtcgaacgatatgcgccttcgctgcgcaaatggacttgtggaaagtccaagttgcgacctcgtacgcgatcgccgtcgtgaactccggtatcgacgcggcgaagacatgctgctgatccagcggatg
gctccgagcatccgccgacgcgcctgacgacgccgcgttcgacgagcgtgttcaccaccgacaagccggtgatctttcgccttccacgtggatggtggctgatgttctgatcaccggctga
cctatcgccgccaaccacgtcaacatccgcgctcgcccgattccgtcgcgctcgacctcgctgtccacctcgctactggcgcgatcagcgacgatcagcgccgtttgaaggatcgaccgtgactggcctga
ctggcactcgaccgacgatcagcttcgcgagaggttcgcgactggcgctggtcggcctga cggcgacgatctgccagaggttcgcgactggcgctggtcggcctga (SEQ ID NO:19)

Figure 33 atgagctatagtccgcaagtccggaattacccctgctgatcgtattggcgtgcagcaaattatctgagcgttggtgtgcagatttatctgatgataatccgctgctgcgtgaacc
gctgcgtccggaacacattaaaccgcgtctgctgcgtcattggggcaccacaccggtctgaattttatctatgccaatcgtgatccgtatcgctaaacagaaatcggatatg
atttatctgtccgggtcatggcggtcggttgcaaataccggttgggttgcaaatcgaggtacgaatttatccgcatattagccaggatcagcaggtatgcagc
gtctgttcaaacagtttagcttccgggtggtgtattccgagccatgccatgttatttggtgatggtgaactggtgtagccatggcatgcattgaactgggtcatgccttg
gtgcagcatttgataatccggatcgtggttgttccgtgttattggtgatggtgaagcagaaaccggtccgtgagcattagcaggtcgcggtagcagcgcatgtcaaattctgaatccggaacg
tgatggtgcagttctgccgatctgcatctgaatgctataaaatcgaaatgcaagactgctgggacgtagcagtgataagatcgcaccagctgttagcgttatggttatg
aacctctgttgttgtggccatgaaccggataccgcagaaaaccctgatggcgcagaatccgcagaaaccgttgattaaaagtgaaaaatcagcgtagcgtagcgta
atgcaagcaatgatgttccgcgttggccgatgatttatctgcgtagccgataaaaggttggacaggtcggaaaccgttgatgctggtaaaaaagtgaagatttgggtgccatc
aggtgccggttgcagcatgtcgtgaagatgaagctgcaagccgtacaatgtgtcgcctgtcaatgttgcctgctgggatgtgccaatgtcagcagccgatcagattgtgcat
gaactgcaagcccctggtcggggaagtgataaacgtagggtgccaaccgaaccgaacaggcaaacgaaacgttacctcagtcatcgaagatgtggtgctgccatgatattgcatcaggaccg
gtgatattagcgaaccggtacagaaattgcacaggcaaccgaaccatcggggtgcggttcagccgtaatcgttatctgagtgttctgtttcaggtgataatttctgcgtctgttttggtccggatgaaa
ccgcaagcaatcgtcgacaccggtttgatgttaccagccgtacgccgtattgatgaacgtattgatgaacaactggcacgtgatggccgtgttatggaaaattctgag
cgaacatcagtcagggttgcctgaaagcctacgcctgcgcctgtcgacccggttcgcgtcatgatccgtcgtaaccggcatgcatgcctttaatgttatgaagccttaatcatatcgtgatacgatcgttattatcatcaggccaa
atggctgaaagttacccgctaaactgggttggccggttggccgtaaacgttatctgcgtcaagccaggtctgtttgccgtcaggatcatgcggctagtcatcaggatccg
ggttttattgatcatgtgcaaccggtaacaaacaggcaggcggatcgatatcgtgcgtatttatctgcctccggatgcaaatcaacaccgtgtgaagcctgtgtgtggtaggtgtaggtgatgtgcgtacctggatcgtata
atgttattgttgtcaggtaacatgttgtattgcatgttcctgatgcgcgtgaaaccatgtgcagcagttaccccattgtgaagccagttacgcgcagaactgcaacaccagc
ccatgatcagcctgatgtttattgcactgcactgcaacctgacgatcagcatccgcgtgatgtgccaccatgaaaccatgcagcagttgatcgtgccgaaatgctgcgctatcgtattgtt
aatgttgtggatcgctggcacgtctgacctgacctatagccgtaccaatcatcgtaatttcatgtgcgtggctttaatgaagaaggtaccgaccaccccgtttgatatgaccgttctgaac
tatccgacgctgattcaccgtctgacctggcacatcatctggcacaagaagcaatttctgcgcgttccggtctgcagatgtcacatccagaactgcgaagatctgcaacaacgtctgcagaacatcatc
gaactggatcgtctatcatggagatgtgcgaggatctgccgaagttcagaaattggaaatggccgagcgcaaccgcaccggtgcaacaccggtgcccggattaa (SEQ ID NO:20)

Figure 34 atgaaactgagcagcgaagaaaccagcagcaaactgcatggctgcatattggcgtgcagcaaattatctgagcgttggtgtcagtctatctgcgtgctgaaagaaccgct
gaaactggaacatgtgaaaaatatgctgctggtcattggggcaccacaccggttcagaatttatctatcctgaatcgcgtgatcaacaaatgatcgtgatatgattt
atgtgagcggtccgggtcatggtggtccgcagttgttgcaggcacctatctgaagttacatatatccgaatatcaccaggatgaagatggtctgcgtaaac
tgtttaccgagtcagtttagctactccgggtgttattagcagcccagcatccatgcaaggtggtgaactgggttatagcctgagccatagcttggtg
cagttctgataatccgagcctgtttgttgcatgtgtgttgcatgttgaaccgcatgtccgctggcaaccgtcatagcaacctgaatcgctgaccg
atggtgttgtctgccgattctgccatctgaattgctataaaatcagcaatcaggcaatgtgaacactgtttaaaggttatggttggaccc
cgtattttgtggaaggtgaagaaccgtccgcgttggccgtagcccgatgattgttctgcgtagcccgaatgcaggtccgaagaagttgacaggtccgaagaagttgatggctccaaaatgaagtaacttctgcacatcaga
cagatatggaacgtccgcgttggccaagcgcaccgcctgaacatctgcaaatgctgaagattggatgaagaactgtttgatgaaatggtctgaaacg
ttccgctggccgttagcgcaagccaccgcctgaacatctgcaaatgctgaagattggatgaagaactgtttgatgaaatggtctgaaacg
gaactggccgaactggcaccgaaaggtgatcgtcatgtgatgtgcaaatccgcatgcaaatggtggcagctgctgtaatctgctgctgccgattttcgtgattatgcaatt
gccgttaatagtccgggtgttaatgtgaaggtgatacctatgttagccgtcgttctgcgtgatgtgattaagaaaaccagcacgatcgcaacttcgtatttttggtccgat
gaaaccgttagcaatcgtctgaaactggttttgaagcaaccaatcgtcagtgggatgcaatcgtcagtgtcaagcctttgctgacaagtttctgctgataagccaccgttggcgtcagcgtgtatcttaccatcagga
gagcgaacatcagtgtgaaggttggctggaaagttggctggaaagttgaacaaaagccaatatgctgcgtcatgtcgaattgcgtgtttatctgcctccgatgcaaattgtcctgctgagcgtgatgatcattgcctgctagctatcattatg
aaaaatgctgaaaaccaccgtgtgtgcaccctgaacaaatccggacacccggatgtgcagtaaatcaccggcaccggatgcaaatccagttgcaacaggcaaatcattgcctgtattgttggtaattttgccagtaatgatcaggat
tccgggtttctggatcatgttgcaggtaaactcgaccgtcaaatccgggatgttgcaggtaaactcgggttatcgccgagcgtgatgttccggattcgtgctgagcgtgatcattgcctgctgagcgtgatcgatcagga
tgaatgttattggcaggaggtatatggcctgtagcggtgatgttccggatgttccgacggttatgcaaccatgccattgttggaattatgccagtaatgatcaggat
gcagaaccggatgttattatggcctgtagcggtgatgttccggatgttccgacggttatgcaccatgccattgttggaattatgcctgatagctcgatcatgcgaagatgatagctcgatcatgcgaagatgatagctcgatgttattaatgttg
tggacctgtttaaactgcaaaaagcagcgaacatacccatgctctgagcgataaagattatgcccgtttaccgttaataaaccggttgttttgccttcatgttatccgtg
gctggttcatcgtctgacctataatcgtgaactaaatcacaccatgcgtgttgcgtgttataaagaagaaggcaccattaccaccagtttgatatgacagttctgaacgaaatgg
atcgtttcatcgtcaatggcaatgtgatgtgattgatctgcctcagaatccgtgtatctgaaacagctgctgacagataaactgaccgaacacaaacagtatatcaa
agccaatggtaaagacatgccggaaatcctgaattggaaatgaatcagccgaccagtaa (SEQ ID NO:21)

Figure 35 atgacaaagcaccgaaagcgttccgcgtcaggcactgaccgttaccgaactgcaaggaccgcaagaaattgatcgttattggcgtgcagcaaattatcgagcgttggtcagattatctgcaa
gataatccgctgctgcgtgaacgctggtgccggaacacattaaaccgcgtctgctggtctgggtcattgccgttccggttccaccgcatggccgttccaccgatctatccgatgttg
attcgtagccgtgcaccgaaatgatgtgattgttgtccggtcatgttgtccggtccgagtccgttgccaccgcatgcgtggtctggatgtgttatagccagatctatccgatgttg
gtcgtaatgcagaaggtatgcgtcgtctgttcgtcagtttagcttccgggtggtgttccgagccatggcagcagcaccggaaacaccgggtagcatccatgaaggtggtgaactgg
gttatgcactggcacatgcacatggcagttgttggtcagcagttgttggtatggtgaagcagaaaccggtcactgagcgttagcgtagctggcaga
gcattcgtttctgaatccggcacgtgatgtgcagttctgccgattctgccatctgaatgttacaaaattcagttcgaccgttctgcacgttccgaagaagatctgctg
gcacagatgctggtcatggttgaaccgatggttatgaaacgcgtatcggatatccgttgccggtgatgatcatacgttcaccagctgatggcaggcacctgcaagctgtctgaacgtattgatacc
attcgctttcgtcacgtcaagaagatggcgatatgcaaatgttcgttggccgatattgcaaatgtgccgatattccgctgataggctcgtgacagttggacaggtccgcgtcagttgatggtaaaccgg
ttgaagataccggcgtagccatcagttccgctgcagcaacccgttgttccgcctccggattgtcgtattagcagcagccgttgttgaagagttgaaagcgccatgcaaatggtgtcctgctgcgcgaccgtgctgct
gatgaacatggtgcaccgcgctgcacgtcgagttgaactgcagggtgttgaagttgaagttgataggttgaaagcaccgttctcgtgatgttgtggcagcaaatccgcataatttc
gcctgatttcgtgattatgccgggtgaaagttgcactgctggtgcagtttgaaagcaccgacatcgtcgggtgcagatcgtgcagttgccggttgatcagcagctgagtccgga
gcattatggtccggatgaaaccagagcaatcgtctgggtgcagttggcgcaagttggccgagttagccgtgaactgctgacggtattctgctgacggttactgctgtttaatagctatgaagcctttatcatatcgtggat
tggtcgtgttatggaagttcgaatgaacagctgttgatcgtggcctgcaggsgttggcctgcaggsgttggccgtgaactgcgtgaagttaccgctgtcgtccgattagcagcagccgtgcgtcaagccatgttgtcaggatcat
agcatggttaatcagcatgcaaatggctgaaagttagcctgaaagttagcctgaagttggctgttttattgatcacgtggttaacaaaaaaccggtaatcattcgtgtttatctgccaccgagatcgtgttaatacctgctgtgttaccatggatcattg
tctgctagccgcaattcattaatgttattgcaggtaaacacgccagctgataaacagccgcgactatcgtgccgatgaagcagcaatgcacattgtaccgtggtgcaggtatttgggaat
gggcaagcagtgatgaaggtgcagaaccggatgtggttctgcagttgttctgcgggtgatgtgccgacctgagccatgcgcagcgcgatctgcgtcatctgccgg
aactgcgttgttcgttgttaatgtggtatctgatcgtgagcaatgaagttgaacatccgatccgaataatgatacgccatgaccatgatcaaacgcgaataagatctgaataatccg
gtgatttgcattctatgctatccgtgctgatcatcatgatcattatgatgtttattcatcggtgatggttgttatcttgataggttattgatggttgttatcttgtgggtcaggtatataaagaagaaggtacgaccaccccg
ttcgatatggttatgctgaatgatctggatcgtttcatcggtgatgaagatgcaccgtagttgatattcgtaattggggtttgggaaccgtaa (SEQ ID NO:22)

Figure 36 atgacaattgattgggaacgtgaaagcctggcaccgcaggcaccaaagcacgtgatctgaccgaattatcaatcgtaccattacctgtcgtagcaccggttgttcatatgac
cagtccggttattggcaccccgtggaaaaactgaatgcacgttaccgtgaagatctggaaggtgttgataaatactggccgtgttgcaaactatctgagcattgtcagat
ttatctgcgtagcaatccgctgatgatcagtcagaactcgtttaaacatcgtcgttggtcattggcaccacaccggtcatctgatggccactataccgaaacctttccg
cgcttatcgccgatcatgatcaggaacaacaccgtgattattatggtccggtcatgtggtcccgggtcatgtcgccgttctatccggttgattagctatccgggaaaattctttgcgcaaaaattcttttgcaaatattgataactgctcgataaatccgagcctgtttcacccggtgattgcgaccgttctataacaccggtagcatcatgaaggtgt
gaactggttatgcgctgagccatgtcatgatggtgcaattatgataatcgagctgtttgttcttccggtcaattgttggtgatggtgaagcagcagaacgtcgctggccaccgtt
ggcagagccaataaactgttaatccggctaccgatgttattgttctgccgattcgcatcgaatgctataaaatcgaaatccgacccattctgagccgcattagtgatgaaga
actgcacgaattttttcacgttatgggttatgaaccgtataaatttgttgccgttttatgatgaagatcatatgtcaattcatcgtcgttttcagaaactgtggaaaccattgggatgaaatttgcgatattaaagcagcagcacagaccgataagtgcatcgtcgctggcaagcgcacgaagctccttgaaggtctgaaaaattggctgaaagctataaccggaa
gaactgtttgatcgaatgcaaatgcgcgttaaagtgccgttaatggaagaagttgccgaataacgttgccgaataccgttgcgaatatgtctcgctgatactccgtgatatcattcgt
aaactgcgaatctcgcgattttcgtccgatgaaaccgcaagcaatcgtctgcaagcaatgaccaatacagtggaatgcccggtatattcagatgaagt
aattaatcctcgcgattttcgtccgatgaaaccgcaagcaatcgtctgcaagcaatgaccaataaacagtggaatgcccggtatattcagatgaagt
tgatgaacatatgccacgttagcggtcaggttgttgaacagctgagcgaacatcagatgaagttttctggaagcacatatcgtgaccgtcgtcatggtatttggagcagctat
gaaagctttgtgcatgtgattgatagcatgcgaacatgccaaatgctgaaccggtcgtaaaccgattgcaagcatgaatcgctggttagcagctttggcgtcaggatcataatggttttagccatcaggatcggtgttaccagcgttctgctgaataaatgatgattgatcggcatcatttttgcaaccgatgcaaatatgctgctgccattgacaaaatcaacgccatcattgcaggtaaacagcctgccgcaacctgctgaccctggatga
agcacgtgcgaactggcaaaaaggtgcagcagcatgggcaagcgggttgccaagcggtgtgctggcagcggtgattgtccgacc
caagaaattatggcagcaagcgataaactgaaagagctggggcgttaaattcaaagttgttaattgtccgatctgcgagcctgcaaagcgcaaaagaaacgatgaggcac
tgtccgatgaagaattgcagatatctttacagccgataaaaccggttctgtttgcctatcatagttatgcacatgatgttcgtggtctgatttatgatcgtccgaacatgataacttta
acgtgcacggttatgaagaagaaggtagcaccaccaccccgtatgcactcgtgtaactgttcgtgtaatcgtatgatcgctatgaactgacagccgaaacctgcgcatgatgcg
ataaaatgcggataaaaatcgatgaactggaaaaatttcgtgacgaggcattcagtttgccgtgataaaggttatgatcatccggattataccgattgggtgtatagcggttta ataccgataaaagaagagggtgcgttaccgcaaccgcagccgcaaccgcaggcgataatgaataa (SEQ ID NO:23)

Figure 37 atgacactgagcagcagccagcgttgtgcagaagaagaactgcgtcaggttgatcgttattggcgtgcagcgttaatctgagcgttggtcagatttatctgatggataatccg
ctgctgcgtgaactgcgtgaaaccgctgaaaccggaacacattaaaccggacgtctgctgggtcatgcattggggcaccacaccgggtctgaatttatctgaatctgaatctgccattgtcagc
gtgatctgaatatcattatatctgtcggtccggtcatggcggtccggttatggttgcaaatacctgcctgaagttagctatagcgaaatttatccgcagattagcgaagatgca
agccggtattcagaaactgttcgtcagtttagctttccggttggttagcttcggggttggattgcagcatgcgttattggtgtctgattgcagcatgcgttattgtgaactgctggtgaactgcatggtgaactgcctg
agccatgcctttggtgcagttttgataatctggtctgattgcagcatgcgttattggtgatggtgaagcagaaaccggtccgctggcaagcagctggcatggtaacaaattct
gaatccggttcgtgatggtgccgttcgtcggttctgccatcgaatggcatataaaatcgacattctgggtcgtgcatgaatgatgaagatctgcgccagctgtttagc
ggttatggttatgaacctcgtttgttgttagtggccatgaactgagcagcgtcatttcagatggcacgtaccctgaataatttgcactggatatattcaaagatcatcagctgcgtgca
cgtgccgtcgtccgaccaaagttgttcctgccgtgatatccggaataattatctgcgtagccctgaaaggttgacagttgcccccgagagcgttgatggtaaaaagttgaaggttttggg
ctgccccatcaggttccggttagcagcgtctggtgaaatgaacatcgtcagattctggaaatgatgatgaactgaacgtggaaatgatcatcagccgatcactgagaactgctgttctgccagtct
ctgaaacctgaactgcgtgccgtgccctgccgtcaggcaccggtgaaccgcaggttcagagccgtcagcgtgaaatgctggtgtcgtcgttatcctggaatggtggaatggtccggataattttcgtctgttggt
aatttgcagttgaactgaccagccgtggtgaaccgcaagcaatcgctctgagtgatgttttgatgttaccaatcgtacatggctggaagatattgaaccgtatgatgaacaactggcagcagatggtcgtgttaggg
ccggatgaaaccgcaagcaatcgtctgagtgatgttggcctgaaggtctacctgcctgaaggctctatctgctgaccggtctcatgaggcatactgtgttaagccttatcatatcgtggaaagcatgtttaatca
aaatctgagcgaacatcagtgtcaggttgcctcaggttggcctgaaagtaccccgtaaaactgccgtgcatgaactcgtgcatgtcagatatcgtggatacaatatggttatagtcat
caggatcgggttttatggatcatgttgcaggtaaacaaaaagccgatatcgtgcatttctcctccgatgccaataacctgctgtgggttgcagatcattgtctgcaaacctg
ggatcgtattaatgttattgttgcaggtaaacagcctgcagtggctggtgagtgcgaagagcagcagaacatgtgcagcaggttggggccgtgatgcaggttgggctgatctgctgcgcagtatcgtgcgcgagtatcgccggatctga
acgaacaggatggtacagaaccggatgtgttcctgcgtgatgttcctgccgacatggcgaaaccctggcagctgaaaccctggcagctgctgcgcaggcatttgatggtatttttaccagatattaaaccggttgatctt
tgcctttcatgttacgtgttgatatctgcactgcaaaccgtgaacagcatccgcatggcctgcagccgaagcattgatgggtcggttttatggaagaaggtacaaccaccaccccgtttgtatg
acgcttgtaattaaactcgatctgttttcatctggcacaggcgatctcgaggatgttgaggaaccaagctcgagaaactgcaagtaaaagccggatgataagtcgaagatgtaaatatattctggacgatctgcaccgaataa
gccatcactgtattgtgctgaatatgctgaaggatctgcctgaagttcgtaattggaaatggccagcagcagcagcagcaggttcaggtggtgcaccggaataa (SEQ ID NO:24)

Figure 38

Atgacaaatccggttattggcacccgtggcagaaactggatccgtccggttagcgaagaggcaattgaaggtatggataaatactggcgtgtggccaattatatgagcattgg
tcagattatctgcgtagcaatccgctgatgaaagaacgttaccccgttgatgatgttaaacatcgtcggttggttcattgggcaccacacgggtctgaatttctgctgcac
atattaatcgtctgattgcagatcatcagcagcagaacaccgtgttattatggtccggtcatgttggtccggcaggcaccgcacagagctatattgatggcacctataccgaata
ttatccgaacatcaccaaagatgaagccggtctgcaaaaattcttcgcagtttagctatccgggtgtattccgagccgtttgttccgtgcattattggtgatggtgaagcagaaaccggtccgctgcca
ggtgggtgaacctggttatgcactgagccatgcatatggtgcattatggtgatataatccgagcctgttgttccgtgcattattggtgatggtgaagcagaaaccggtccgctgcca
ccggttggcagagcaataaaactggttaatcgcgtaccgatgtgttatttgtctgccgatctgcatcgaatggctataaaatcgcaaatccgaccattctgcacgcattagtgat
gaagaactgcattgattttttcgcgtatggttataccgtataccaccgtatgaatttgttgccgggtttgataatgaagatcatctgagcattcatctgctgtttttgcagaactgttgaaaccatc
tttgatgagatcgcgattataaagcagcagcaagaaccgatgatatgtccgctggcaagtctgacccgtccgtcgttttatccgatgctgattttcgtacccgaaaggttggacctgtccgaattatcgat
ggcaaaaaaccggaaggtgctgcggaactggatcgggctgccgatcatcgcgaagcagcgtatggtgccaatcgcgtatgtgatgcacgcagtctgaaggtctgaaaggctctgaaatgtggtcgtatcgtgaa
gaagaactgttcaatgcagatggcagcattaaagaagatgtaccggcatttatgccgaagcgcacgtatcacgcgatgaagcacagcgtagcctgggtgcatatgtcgtgatatc
gatctgaaactgccggaactgcacagctttcgtgttttggtccggatgaaatcaggtggccaatcgcaagcatcagcctgaatgcaaccatgaagtcaacctatgaaaacacagtgggataatgcgctatcgagc
attaaaaacaaccggacagcttcgtgttttggtccggatgaaatcaggtggccaatcgcaagcaatccgcctgaatgcaaccatgaagtcaacctatgaaaacacagtgggataatgctatcgagc
gcactggttgatgaaaatatggcagtacccggatgatgatgcatgtgatgcatgatcaccaagtgttgcatgtgtgaaagcaaccggttctgcgtaaaccgattagcagcgttaatc
gcagctatgaaagctttgtgcatgttggctcatgcatgtggctcagaatatcataatggtttagccatcagcgtctgctgctgaataaaccttaataatgatcacgtgaccaacactct
tgctggttagcagccatgctgctcaagttgggctcatggcagtcagaatatcataatggtttagccatcagcgtctgctgctgaataaaccttaataatgatcacgtgaccaacactct
attttgccaccgatgcataatgtcagcaagaatatggctcaagtggccaatgcaaaatggaaatgggcaagcaatgtcaaagttgaactgtggtggatctgatcaaactgcaaagcagcaaagaaaacatg
tgatgaagttcgtgccgaactggcagccaagccggtgcagcgaactggttccgcagcgcgtgatgtg
ccgaccaagaaatcatgccaagtgccagcaagtgatgccctgaacaaaatgggcattaaattcaaagttgaactgtggtggatctgatcaaactgcaaagcagcaaagaaaacatg
aagccatgtccgatgaagatttgccgacctgtttacagcacagcagataaaccggttgctgcctatcatagttatgcacagatgcgccgttcgattatcgtccgaaccatg
ataactttaccggttggttggttataaagaacaggttagcaccaccaccccgtttgatgattgttcgtgtgaatgatatggctgttatgcctgcaagcaaaagcactgaactgatt
gatgccgataatgcggacaaaatcaatgaactgaacgagtttcgtaaaaccgcatttcagtttgccgtgataaccgtatgatatcccggaatttaccgattgggtttatcc
ggatgttaaagttaaagttcagcatgcggcgataaacaagcatgctgtcagcaaccgtcagcagccgcagcaccgcagcagccgtcagcagccgcagcaccgcagcagccgataatgaataa (SEQ ID NO:25)

Figure 39 atgagcaccggtgtgcatatgaccagtccggttattggccaccccgtgggaaaaaactgaatgccggttagcgaagcagcaattgaaggtgttgataaatactggcgtgttgc
aaattatctggccattggtcagattatctgcgtagcaatcgctgatgaagaaccgttacccgtgaagatgttaaacatcgtctgttggtcattggtcgttgggccaccacccgggtc
tgaattttctgattggtcatattaatcgctttatcgccgatcatcagcagaaccgtgattattatgggtccggttggtctccgccagcaccgcacagagctatctggat
ggcacctataccgaattattccgaaaatcaccaaagatgaagccggtctgcaaaaattctttcgccagtttagctaccggtggtattccgagccattgttgcaccggaaacac
cgggtagcatccatgaaggtgaactggttgcactgagccatgcatacccgcgtaatcgctacccgatggtcatcgaatgctataatggcaaatccgaccatt
aaccggtccgctggccaccgttgatgaagaactgcacgaattttttcacggttatgaaccgtacagaccaatgattgttgccgtttgatgatgaagatcatatgtaccccgaaaggttggac
ctgagccgcattagtagtcgatatgtgaaaccatcttgatgagatctgcaaaaaaccgaagtagctgccgtgcacatcagttcgcgcaagccaagccatttgaagtctgaaaaactgga
ctgtccgaaatttatcgatgcaaaaaaccggagtagctgccgtgcacatcagttcgcgcaagccaagccatttgaagtctgaaaaactgga
tgaaagctataaccggagagaactgttcgatgaagaagaactgccgttaaagaagatgtgcgagcttatgccgaaggtgaactgaactgcgtatgcgtgttgaaatcgaatgcaaat
ggtggtcgtatcgtgaagatcgaaaactgaaaatccgacatcgatattatcaaaaaccaaccggacagctttcgtgatttttggtccgacaagcaagcaatccccgctatttgtatttttggtccgcaagcagcatatgaagttgggtcagctgggtcaacccgtcgtctggg
tgtttataccccgtgatattatcaaaaaccaaccggacagctttcgtgatttttggtccgcaagcagcaatgaagtttaccaataaacagtggg
atgcaggttatcgagccgtctggttgatgaacacatggcagttaccgatcaggtaacacatcagatgaacatcagatcgaagccaacgccgtcaagctgaccctcgtccgctatctgctgacc
ggtcgtcatgtatttgagcagcagctgctgttgtcatgtgaaagttgtgcatgtgcagcagcatgtgcaacaacgcaacaacaccgtaatcagagcatgtgcaacgccgttccagcgtgctgctgaataaaactttaataat
gatcatgtgaccgtatattcccgttgataagcaacagctgctgttgatgatgcaacctcaggttgcagaaaaggccgcagaatggcaaagccaaaacaatgatgaagttcaggttgtct
gccgcaacctgctgacctgatgtttccgcagccgatgtttccgcaagaactgatggcagcagccgataactgaacaaactggtgttaattcaaagtggtgatctgctgaaactgcaa
agccgcaaagaaaataatgaagcactgaccgatgaagcactgaccgatgaagaagtttacagcagatagtcagtttgccgatgaaactggtgttacggttcatcatagtttatgcagttcgtggcctgat
ttatgatcgtccgaaccatgaacagtaaatgagcactggaaggggtttaaagaacaggagaccgtgcatgtgcacaccacccgtagcaacaacagaaaatcgaaatcaaagagctggaagatttcgtctggaagcatcagtattcgtgttaatgatggatcgctatgaactgacag
cggaagcactgcgtatggttgatgcagcagcaaatatgccgatgaaatcaaagagctggaagatttcgtctggaagcatcagtattcgtgttaatgatggatcgctatgaactgacag
attattaccgattggtttggcctggtctgttaaaaccgataaaaccgtcgcagccaagagccgtttccgttaccgcaaccgtcgccagccaccgcagccgataatgaataa (SEQ ID NO:26)

Figure 40 atgccgcaggttgaacatcagaatagcaccgttctgaccgatgatgaactgcgtgaccctggatgcagcaaattatctgcagcaggtcagatttatctgctg
gcaaatgcactgctgaccgaaccgctgagtccgctgagtccgcacatatcaaaccgctctgtctggggtcattggggcaccagttccggtctgaatcgttcataccatctgaatcgtt
attaaagacgtgatctgatgccctgtgtgttgggtccggtcatggtgttccggcagttctgccggaagttagcggtgtggaagtagctatagcgaaactatctgatata
gccgtgatgcagcaggtatggtgtaaactgtttcgtcagtttagctttcaggggtgtgttccgagccatgttgcaccggaaaacaccgggtactcatgaaggtggaactgg
gttatagcctggcacatgcatatggtcagcatttgataatccggatctgctggttgatgttattggtgatggtgaagcagaaaccggtcgctggcagcaagctggcata
gcaacaaattctggatccggttcatgatggtgcagttctgcatctgcacgttaccgttgatgatcgaatgccatcaggttcatcgtgcactgccgaagccttgatcgtgcctgatcgtgttgcactga
tgagctgctgtgttatgtgcatgaagaaggtgcaaccgaacgtattcgtcatgttccgcgatgattgttgccgatatccggaaagttggacaggtcctgccgagttgatggtcgtcgtcgctt
gaaggcacctggcgtgcgtgccatcagttgccgctcagttgcgtatcgctgataaaccgggtgctgcagtgctgcagtgaatcgctgataaaccgcatgaaatctgcggaacatctgcgtcaacaccgcatgcaacaccgtgtttctgggcgaccctgctgaacaggttatgaacagggttatgaaagataccagcgcac
ttccgcctctggatcgtttgccgttgcctgtccgatcgctgcagttgataaaccgggtgctgcagttgctgcaccctggcatgttctggtgcccgtgttctgggcgaccctgctgaacaggttatgaacagggttatgaaagataccagcgcac
gtcgtgatttcgtcgttggttcgctccggatggaaaatctgagcgacaatacctggtcagggtttggctgcaagcatgtggctatctgcaccgtaaagcggatctgcatgcctgtttagcgttatgaagcattgtg
tggaccgtcatggtcgtgtcgtgtcatggttaatcagcatatcaaatgctgaaaccagcgtaagatccggtttgtgatcatgtgctgcagttgaaaacagccgtgtttgattggctgagcatgaacaggcacgtcacattgtgccgtggtgca
cgtcaggatcataatgttctgcgtagctgtcgtcgtattatgttaatgttgcaggtaaaacagccgtgtttgattggctgagcatgaacaggcacgtcacattgtgccgtggtgca
gttgcagatatcatgttctgcgtagtcgtgattatgttaatgttgcaggtaaaacagccgtgtttgattggctgagcatgaacaggcacgtcacattgtgccgtggtgca
ggtatttgggaatgggcaggcaccaccgaatgatggcgaaccggatgttgttctgccggtgatgtcgccgaccaagaagtactggcagccagcgcactgctgcgt
cgtcatctgcctgcactgcgtgttcgtgttgtgttcatatcatggttaatcatggcatatcatggttaatcatcgcatgcatgaatcgtcatggtaatctgttcatgtaatcgtcatggtaatctgtattccaaacggtcacctggtacgcgtgctcctgaagcacatccgatgcatgaagcacatccgatggtaatcgtcatggtaattgtattccaaacggtcgatggttcatgtcatgttcgtccttacc
accgacaaccggtgattttgcatatcatgttcgtaacgatcgatcgattcatcgtctggtgatggtgttcctgtcgttcatggtttataaagaaatgggtaca
accaccaccccttttgatatgttgttcgtaacgatcgatcgattcatcgtctggtgatggtgttcctgtcgttcatggtttataaagaaatgggtaca
atggcagatgcacgtaccgtcatcatcgtaacatggtgaacatggtgaacatggtgaactgcctgaagttgcaaattgacctgggaagcataa (SEQ ID NO:27)

Figure 41 atgcaagtataataggaagatgaaggaaaaatcacaccggagtatctaaagaaaattgatgcataatgcgtgcagctaatttatatctgtagtcaattgtattg
ctagacaatccattgcttagagaacctttaaaaccagaacatatctaaaaagaaaagttgttggtcactgggtactattcctgtcaaaactttatttatgctcatcttaaccgtgttat
taaaaatatgatttagatatgatttatgtttctggtccagtgtcatggtggacaagtaatggtgtccaatctctttctcagatgaacctatagtgaagtttatccaaatgttagtcgtga
tttgaatggcttaaaaaagctatgtaaacaattctcttttccaggtggaattctagccatatggctcctgaaacaccggttcaataaatgaaggggagaactaggctattcttta
gcacattctttgctgttttgataaccctgtctatttacattaaatggatacaaaattagtaaccctactgtgttgtctcgtattcctaaggatgaacttgcaacatctggcaaatcttgaagaaacg
tccagttactgatgggagcagtgcttcctgttgttgttgttgagacggagaggcagaaacaggaccctcttgcaacatctggcaacatctaaaaattttaaa
gatgaagccttattttgtagaaggtgaagatcctgaaacaatgcataaaattaatggcagaaacattagatatagtaacagaagaaattcttaatattcagaaaaatgctcgtgaa
aataacgattgttcacgaccaagtggccaatgattgttgctacaccaaagggatggacaggtccaaaattgtagatggtgttccaaatgaaggatcttcctgcacacc
aagtaccgcttgcagtagatagatatcacagaaaaactatattagacagaagagagtggcttaagagttataaaaccagaagaattatttgacgaaactaataccgga
actttgaagaattaactccaaagggaaataaagaagaatggcggctaattgtcatgctaatttgcatgctaatggtggttattatacgtacacctgattttcgtgtattatgctgtagatgttc
ctactccagggagcacagttaagcaggattagtgatgattgaactgtgcgtgatgttgtgttaaattaaaacgaagatactcgtaattccgtattttggaccggatgaaacta
tgtctaatagattatgggcagttttgaaggtacgaaacgtcaatgttatcagaaatggttatgaagccttcctcgtattgttgattctatgaatgacgtattgttgattcaatgctaag
cgaacatttatgtgaaggttgaaggttagagggttatcttaacaggacgtcatgttctttaacaggacgtcatgttcattgaagcctttcagttatgaagcttcctcgtattgttgattctatgaatgatgtatactcatcagcagagatcatcaagatccaggttatat
ttaaaggtaacatcacagctaccatggagaacatcagtgaaatgactgcctcatgtgcagcaggatcataatgtagcagcaggatcataatgtatactcatcaagatccaggttatat
taggacatattgtggataaaaaacctgaaatagttagagcatattagagcaaagatgccaataccttattgataaatgcctcatactaaacaagattaattatta
gtaacatcaaaacatccaagacaacagtggttaacaatgatcaagcagttaagcatgttaagcaggaataagacatttggattggcaagtaataagacaagga
cctgatgtagttagctcctgtgagatactccaacattagaggcttggcagctgttacaatccttcatgaacattccagaattaaaagttcgttttgtaaatgtagtggatat
gatgaaattattacctgagaatgagcatcctcatggcttaagcgataaggattataatgcctatttacaacagataagcctgtaatatttgcattccatgaattgcacatttaataa
atcaattaacatatcatcgtgaaaatagagcatatgtaatgatgaagagaggagaactattaacaaccaccatttgatatgcgtgttcaaaataattagatgtttaatcttg
taaaagatgtagtagagaacatttacctcagcttgttcagttaatgataaattagtaacaataaccaataacattcgtgaggttggagaagatt
tgccagaaataactaattggcagtggcatgtataa (SEQ ID NO:28)

Figure 42 atgaccaccgattatagcagtccggcatatctgcaaaaagtggtgatataatactggcgtgcagcaaattatctgagcgttggtcagctgtatctgaaagattatcgctgctgcaac
agccgctgaaagcaagtgatgttaaagttcatccgatttgtcatttgggcaccattgcagatcagattcagaatagcatttatgcacatctgaatcgcgtgatcaacaaatggcctgaa
aatgtttatgtggaagtcgggtcatggtgtcaggttagcaatagctatctgatgcacctatacgaaattatccgaaattaccaccggatgttgaagttatgca
gaaactgttcaaacagttcagcttccgggtgtggttgcaagccatgcagcgggtagccattcatgaaggtgtgaactgtggtatagcattagccatggtgt
tggtgcaattctggatataatccggatgaaatgtcagcagttgttgttgtgataggtgaaagcgaaaccggttccgctggcaaccagctgcagagcacaaattatcaatccgat
taatgatggtgccgttctgccgattctgaatctgaatggctttaaaatcagcaaacccgaccattttggtcgtaccagtgatgcaaaatcaaagaatattcgagagcatgagct
gggaaccgattttgtagaaggtgatgatccggtttggccgtttcgtgccgatgattgttttcgtgcaccgaaagtgcatccggaaaagttggacaggtccgaaaagtcatgatgaagcaatcagcgatccgatggtccgaaagcgtttgagatattgaagatatcagcgaaacatgcatgcaaagtcaaagcgatccgagaacatgccgtga
aaatgatgatgcaacctgccgttggccgatgatatgattattccgtggccgatatgcaaacatgcaacatggaaagatgcaaccgatatcgcagatcagtgcgaaaacccggatatattcgtctgtttggcctgatgaaac
ataccagcaaagaaggtgcaaacgttaaacagcaggatatgcgttggagcgattatctgcgtgatgtgcgatattcaaaaaaaaccggatatattcgtctgtttggcctgatgaaac
catgagcaatcgtctgtatggtgttttgaaacccaatcgtcagtgagcaggaagatatccatccatccggataggcgatcagtgaagcagcagcaggtcgtgttctggatgcaca
gctgagcgaacatcaggcagaaggctgctgaaggctgctgaagtgcaaatgaactgtggcgtaaagacaaatgactgctgtaaaatacccgagcctgaacattattgcagcagcattctgcgtgttgttgatagcatgctgaccag
cactttaaatagctgtgcgtaaaatgactgctggcgcaaaaaatacccgagcctgaacattattgcagcagcattctgcgtgttgttgatagcatgctgaccag
aggatccggtgcactgaccatcgtggtgaccagcaaacatcgcgtcagcaggccgtcagcaggccaccgaaccgcgttagcattgaagaagcaaaacagctggtagataataggcctggttattgattgggccagc
aagaaaaaatcaactacgtggtgaccagcaaacatcgcgtcagcaggccgtcagcaggccaccgaaccgcgttagcattgaagaagcaaaacagctggtagataataggcctggttattgattgggccagc
acgatcaggtaggcgaaccgatatgttttttgcagccgaaactgcgtagccctgaaaaatccggtcgtgagtgatgcagaagtgcagcaattcagctgcgcattaatatgccgaaaatgaaaa
tcgttttgtgaacgtggtggacattctgaaactgcgtagccctgaaaaagatccggtcgtgagtgatgcagaatttgatcactattaccaaagacaaaccggtggtgttg
cctttcatggttatgaagatcgtggtgcgcgatatcttttcgatcgccataacccataatctgtatgtcagttatgcgaaaatggtgatattaccaccccgtttgatgttcgtta
tgaatcagatcgcgttttgacctgcagtacagatctgaattgattggccagccgcaattgcaaatgcgcagcctgccatgaaaaataccggtcagcgaaatattgttcagcagcatgcagataatgctgcaaaacata
acgccctatattcgtgatgcagttgcagtgaaaggttaatgattggccgaagtgcagtggaaaggtctgaaataa (SEQ ID NO:29)

Figure 49
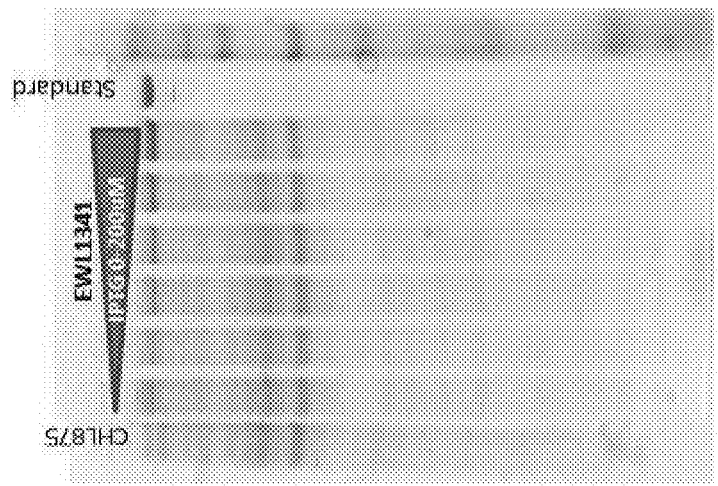
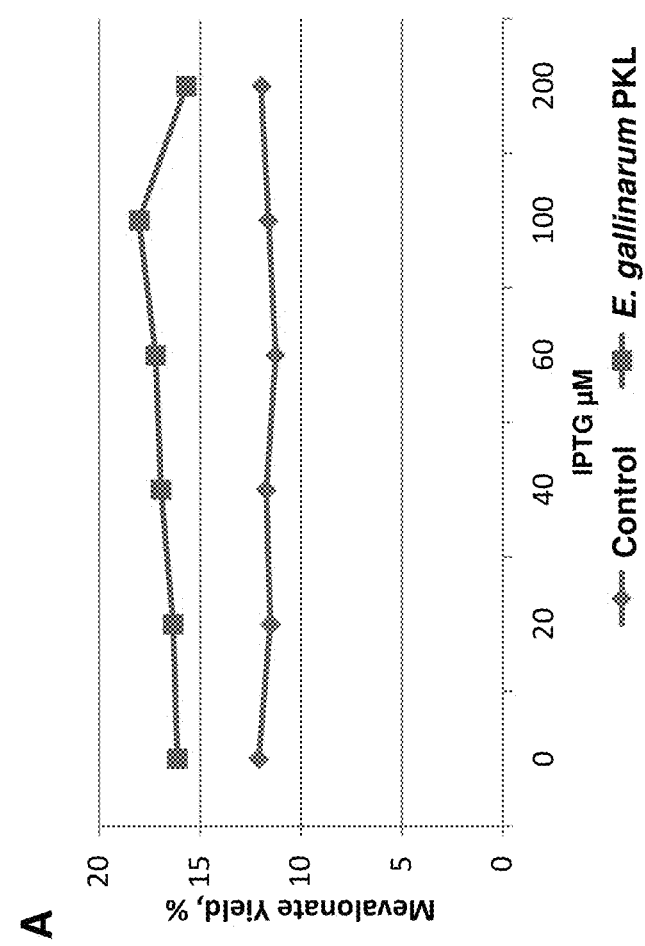

SEQUENCE LISTING

```
<160> NUMBER OF SEQ ID NOS: 51

<210> SEQ ID NO 1
<211> LENGTH: 2412
<212> TYPE: DNA
<213> ORGANISM: Artificial Sequence
<220> FEATURE:
<223> OTHER INFORMATION: Synthetic Construct

<400> SEQUENCE: 1
```

```
atggcagtag attacgattc caagaaatac ttggaaagtg ttgatgctta ctggcgtgca      60
gctaactacc tttcagttgg tacattgtac ttaatgggtg atccattact tcgccaacca     120
ttaaaggcag aagatgttaa gcctaagcca attggtcact ggggtactat tgttcctcaa     180
aacttcattt acgcacactt gaaccgtgta attaagaagt atgaccttga tatgttctac     240
atcgaaggtt caggtcacgg tggccaagtt atggttaaca actcatactt ggatggttca     300
tacactgaaa tttatcctga atatactcaa gacactaagg gaatggctaa gttattcaag     360
cacttctcat tcccaggcgg tactgcatca cacgctgcac ctgaaacacc aggttcaatc     420
cacgaaggtg gggaacttgg ttactcactt tcacacggtg ttggtgctat cttagataac     480
ccagaagtta ttgccgctgt tgaaatcggt gatggtgaag ctgaaactgg tccattaatg     540
gcatcatggt tctcagacaa gttcattaac ccaatcaagg atggtgcggt attaccaatc     600
atccaagtta acggattcaa gatttctaac cctactatcc tttcatggat gagcgacgaa     660
gaacttacta agtacttcga aggtatgggt tggaagccat actttgtttc agcttacaaa     720
gaagctgacc gtgatggtga attcaagggt tacaagcctc acatggaagt tcacgaagaa     780
atggctaaga cttttggacaa ggttgttgaa gaaatcaagg ctattcaaaa gaacgctcgt     840
gaaaacaatg ataactcatt accacaatgg ccaatgatta tcttccgtgc acctaagggt     900
tggactggtc ctaagactga ccttgatggt aacccaattg aaaactcatt ccgtgcacac     960
caaattccag ttccagtatc ccaagatgac atggaacaca aggacatcct tgttgattgg    1020
ttgaagtcat acaagccaga agaattgttt gacgaagatg gtcacccagt tgctcttgtt    1080
gaagagaaca caccgaaagg taaccgtcgt atggctatga ccctatcac taatggtggt    1140
atcgatccta agccacttgt attgccaaac taccgtgatt ttgctattga tgttcaaaat    1200
cctggttctg ttgtaaagca agacatgctt gaatggggta agtacctcaa caagatggct    1260
gaattgaacc caactaactt ccgtggattt ggtcctgacg aatctaagtc aaaccgtctt    1320
tacgcattcc ttgatggtca aaagcgtcaa tggatggaaa gtgtccacga accaaacgac    1380
gaagatgtgg ctccacaagg tcgtatgatc gattcacaac tttcagaaca ccaagctgaa    1440
ggattccttg aaggttacac attaactggt cgtcacggat tcttcgcaac ttacgaagca    1500
ttcggtcgtg ttgttgattc aatgcttact caacacatga agtggttacg taaggctaag    1560
gatctttact ggcgtcacca ataccaagca ttgaactttg ttgatacttc tactgtattc    1620
caacaagatc acaacggtta cactcaccaa gatccaggtc tattgactca cttgtttgaa    1680
aaggaacgtc cagacctcgt taaggaatac ttgccagcag atactaactc attaatggct    1740
gtatctaaca aggcattccg taaccaagaa tgcatcaacc tcttcgtaac ttctaagcac    1800
ccacgtgcac aatggttctc tattgatgaa gctactcaat ggctgacaa tggtcttggc    1860
tacattgact gggcatctac tgaccaaggt actgaaccag atgttgtatt tgcatcttct    1920
ggtactgaac ctactgaaga agctcttgca gctattgaca ttcttcatga aacttccct    1980
gaattgaaga ttcgttacat caacatcatc gaaattatgc gtttgatgaa cactgacaag    2040
aacccctgaag gtttaactga tgctgaattc aatagttact tcactactga caagccagtt    2100
atctttgcat ggcacggatt ccgtgacatg atccaagcat tgttcttcga tcgtgctaac    2160
cgtaacgttc acattcactc atacgaagaa aatggtgata tcaccactcc attcgacatg    2220
cgtgtattaa acgaacttga ccggttccac ttagctaagg acgctatcca aagtgttcct    2280
ggttacgaac aaaagagtgc tgcatttgtt gccaagatgg acaacatgat caacaagcac    2340
aaccactaca tccgttcaga aggtaaggac ttaccagaag ttactaactg gacttggaag    2400
```

```
ggtcttaagt aa                                                    2412
```

<210> SEQ ID NO 2
<211> LENGTH: 803
<212> TYPE: PRT
<213> ORGANISM: Artificial Sequence
<220> FEATURE:
<223> OTHER INFORMATION: Synthetic Construct

<400> SEQUENCE: 2

```
Met Ala Val Asp Tyr Asp Ser Lys Lys Tyr Leu Glu Ser Val Asp Ala
  1               5                  10                  15

Tyr Trp Arg Ala Ala Asn Tyr Leu Ser Val Gly Thr Leu Tyr Leu Met
             20                  25                  30

Gly Asp Pro Leu Leu Arg Gln Pro Leu Lys Ala Glu Asp Val Lys Pro
         35                  40                  45

Lys Pro Ile Gly His Trp Gly Thr Ile Val Pro Gln Asn Phe Ile Tyr
 50                  55                  60

Ala His Leu Asn Arg Val Ile Lys Lys Tyr Asp Leu Asp Met Phe Tyr
 65                  70                  75                  80

Ile Glu Gly Ser Gly His Gly Gly Gln Val Met Val Asn Asn Ser Tyr
                 85                  90                  95

Leu Asp Gly Ser Tyr Thr Glu Ile Tyr Pro Glu Tyr Thr Gln Asp Thr
            100                 105                 110

Lys Gly Met Ala Lys Leu Phe Lys His Phe Ser Phe Pro Gly Gly Thr
        115                 120                 125

Ala Ser His Ala Ala Pro Glu Thr Pro Gly Ser Ile His Glu Gly Gly
    130                 135                 140

Glu Leu Gly Tyr Ser Leu Ser His Gly Val Gly Ala Ile Leu Asp Asn
145                 150                 155                 160

Pro Glu Val Ile Ala Ala Val Glu Ile Gly Asp Gly Glu Ala Glu Thr
                165                 170                 175

Gly Pro Leu Met Ala Ser Trp Phe Ser Asp Lys Phe Ile Asn Pro Ile
            180                 185                 190

Lys Asp Gly Ala Val Leu Pro Ile Ile Gln Val Asn Gly Phe Lys Ile
        195                 200                 205

Ser Asn Pro Thr Ile Leu Ser Trp Met Ser Asp Glu Glu Leu Thr Lys
    210                 215                 220

Tyr Phe Glu Gly Met Gly Trp Lys Pro Tyr Phe Val Ser Ala Tyr Lys
225                 230                 235                 240

Glu Ala Asp Arg Asp Gly Glu Phe Lys Gly Tyr Lys Pro His Met Glu
                245                 250                 255

Val His Glu Glu Met Ala Lys Thr Leu Asp Lys Val Val Glu Glu Ile
            260                 265                 270

Lys Ala Ile Gln Lys Asn Ala Arg Glu Asn Asn Asp Asn Ser Leu Pro
        275                 280                 285

Gln Trp Pro Met Ile Ile Phe Arg Ala Pro Lys Gly Trp Thr Gly Pro
    290                 295                 300

Lys Thr Asp Leu Asp Gly Asn Pro Ile Glu Asn Ser Phe Arg Ala His
305                 310                 315                 320

Gln Ile Pro Val Pro Val Ser Gln Asp Met Glu His Lys Asp Ile
                325                 330                 335

Leu Val Asp Trp Leu Lys Ser Tyr Lys Pro Glu Glu Leu Phe Asp Glu
            340                 345                 350
```

```
Asp Gly His Pro Val Ala Leu Val Glu Glu Asn Thr Pro Glu Gly Asn
            355                 360                 365

Arg Arg Met Ala Met Asn Pro Ile Thr Asn Gly Gly Ile Asp Pro Lys
    370                 375                 380

Pro Leu Val Leu Pro Asn Tyr Arg Asp Phe Ala Ile Asp Val Gln Asn
385                 390                 395                 400

Pro Gly Ser Val Val Lys Gln Asp Met Leu Glu Trp Gly Lys Tyr Leu
                405                 410                 415

Asn Lys Met Ala Glu Leu Asn Pro Thr Asn Phe Arg Gly Phe Gly Pro
            420                 425                 430

Asp Glu Ser Lys Ser Asn Arg Leu Tyr Ala Phe Leu Asp Gly Gln Lys
        435                 440                 445

Arg Gln Trp Met Glu Ser Val His Glu Pro Asn Asp Glu Asp Val Ala
    450                 455                 460

Pro Gln Gly Arg Met Ile Asp Ser Gln Leu Ser Glu His Gln Ala Glu
465                 470                 475                 480

Gly Phe Leu Glu Gly Tyr Thr Leu Thr Gly Arg His Gly Phe Phe Ala
                485                 490                 495

Thr Tyr Glu Ala Phe Gly Arg Val Val Asp Ser Met Leu Thr Gln His
            500                 505                 510

Met Lys Trp Leu Arg Lys Ala Lys Asp Leu Tyr Trp Arg His Gln Tyr
        515                 520                 525

Pro Ala Leu Asn Phe Val Asp Thr Ser Thr Val Phe Gln Gln Asp His
    530                 535                 540

Asn Gly Tyr Thr His Gln Asp Pro Gly Leu Leu Thr His Leu Phe Glu
545                 550                 555                 560

Lys Glu Arg Pro Asp Leu Val Lys Glu Tyr Leu Pro Ala Asp Thr Asn
                565                 570                 575

Ser Leu Met Ala Val Ser Asn Lys Ala Phe Arg Asn Gln Glu Cys Ile
            580                 585                 590

Asn Leu Phe Val Thr Ser Lys His Pro Arg Ala Gln Trp Phe Ser Ile
        595                 600                 605

Asp Glu Ala Thr Gln Leu Ala Asp Asn Gly Leu Gly Tyr Ile Asp Trp
    610                 615                 620

Ala Ser Thr Asp Gln Gly Thr Glu Pro Asp Val Val Phe Ala Ser Ser
625                 630                 635                 640

Gly Thr Glu Pro Thr Glu Glu Ala Leu Ala Ala Ile Asp Ile Leu His
                645                 650                 655

Asp Asn Phe Pro Glu Leu Lys Ile Arg Tyr Ile Asn Ile Ile Glu Ile
            660                 665                 670

Met Arg Leu Met Asn Thr Asp Lys Asn Pro Glu Gly Leu Thr Asp Ala
        675                 680                 685

Glu Phe Asn Ser Tyr Phe Thr Thr Asp Lys Pro Val Ile Phe Ala Trp
    690                 695                 700

His Gly Phe Arg Asp Met Ile Gln Ala Leu Phe Phe Asp Arg Ala Asn
705                 710                 715                 720

Arg Asn Val His Ile His Ser Tyr Glu Glu Asn Gly Asp Ile Thr Thr
                725                 730                 735

Pro Phe Asp Met Arg Val Leu Asn Glu Leu Asp Arg Phe His Leu Ala
            740                 745                 750

Lys Asp Ala Ile Gln Ser Val Pro Gly Tyr Glu Gln Lys Ser Ala Ala
        755                 760                 765

Phe Val Ala Lys Met Asp Asn Met Ile Asn Lys His Asn His Tyr Ile
```

```
              770               775               780
Arg Ser Glu Gly Lys Asp Leu Pro Glu Val Thr Asn Trp Thr Trp Lys
785                 790               795               800

Gly Leu Lys

<210> SEQ ID NO 3
<211> LENGTH: 2478
<212> TYPE: DNA
<213> ORGANISM: Artificial Sequence
<220> FEATURE:
<223> OTHER INFORMATION: Synthetic Construct

<400> SEQUENCE: 3
atgacgagtc ctgttattgg cacccottgg aagaagctca gcgctccggt ttccgaggaa      60
gccctcgaag gcgttgacaa gtactggcgc gttgccaact accttTccat cggccagatt     120
tatctgcgtt ccaacccgct gatgaaggag cccttcaccc gcgaagatgt gaagcatcgt     180
ctggtgggcc actggggcac taccoctggc ctgaacttcc tcatcggcca catcaaccgt     240
ttcattgctg accacggcca gaacaccgtg atcatcatgg gcccgggcca cggtggcccg     300
gccggtacct cccagtccta cctggacggc acctacaccg agaccttccc gaagatcacc     360
aaggacgaag ctggtctgca gaagttcttc cgtcagttct cttacccggg cggtattccg     420
tcccacttcg ctccggagac cccgggctcc atccacgagg tggtgagct gggttacgct     480 ctgtcccacg cttacggcgc catcatggac aacccgagcc tgttcgtccc ggccatcgtc     540
ggcgacggcg aggctgagac cggcccgctg gctaccggtt ggcagtccaa caagctcgtg     600
aacccgcgca ccgacggtat cgtgctgccg atcctgcacc tcaacggcta caagatcgcc     660
aacccgacca tcctgtcccg catctccgac gaagagctcc acgagttctt ccacggcatg     720
ggttacgagc cctacgagtt cgtcgctggc ttcgatgatg aggaccacat gtccatccac     780
cgccgcttcg ccgagctgtg ggagaccatc tgggacgaga tctgcgacat caaggccacc     840
gctcagaccg acaacgtgca ccgtccgttc tacccgatgc tgatcttccg caccccgaag     900
ggctggacct gcccgaagta catcgacggc aagaagaccg aaggctcctg gcgttcccac     960
caggtgccgc tggcctccgc ccgcgacacc gaggcccact cgaggtcct caagaactgg    1020 ctcgagtcct acaagccgga agagctgttc gacgccaacg gcgccgtcaa ggacgacgtc    1080
ctcgccttca tgccgaaggg cgagctgcgt atcggtgcca acccgaacgc caacggcggt    1140
gtgatccgcg acgacctgaa gctgccgaac ctcgaggact acgaggtcaa ggaagtggcc    1200
gagttcggcc acggctgggg ccagctcgag gccacccgct ccctgggcgc ctacacccgc    1260
gacatcatca gaacaaccc gcgtgacttc cgcatcttcg accggatga ccgcttcc        1320 aaccgtctgc aggcttccta cgaagtcacc aacaagcagt gggatgccgg ctacatctcc    1380
gacgaggtcg acgagcacat gcgcgtctcc ggccaggtcg tcgagcagct gtccgagcac    1440
cagatggaag gcttcctcga ggcctacctg ctgaccggcc gtcacggcat ctggagctcc    1500
tacgagtcct tcgtccacgt gatcgactcc atgctgaacc agcacgccaa gtggcttgag    1560
gctaccgtcc gcgagattcc gtggcgcaag ccgatcgcct ccatgaacct gctggtctcc    1620
tcccacgtct ggcgtcagga ccacaacggc ttctcccacc aggatccggg tgtcacctcc    1680
gtcctgctga acaagtgctt ccacaacgac cacgtcatcg gcatctactt cgccaccgac    1740
gcgaacatgc tgctggccat cgccgagaag tgctacaagt ccaccaacaa gatcaacgcc    1800
atcatcgccg gcaagcagcc cgccgccacc tggctgaccc tggacgaggc tcgcgccgag    1860
```

```
ctcgagaagg gtgccgccgc ttgggactgg gcctccaccg ccaagaccaa cgatgaagcc    1920
gagatcgtgc ttgccgccgc cggcgacgtc cccacccagg agatcatggc cgcttccgac    1980
aagctgaagg aactgggcat caagttcaag gtcgtgaacg ttgtcgacct gctctccctg    2040
cagtccgcca aggagaacga cgaggccctg tccaacgagg agttcgccga catcttcacc    2100
gccgacaagc cggtgctgtt cgcgtaccac tcctacgccc acgacgtgcg cggtctgatc    2160
tacgatcgtc cgaaccacga caacttcaac gtccacggct acgaggagga gggctccacc    2220 accacccccgt acgacatggt tcgtgtcaac cgcatcgacc gctacgagct gaccgctgag    2280
gctctgcgca tgatcgacgc cgacaagtac gccgacaaga tcgacgagct cgagaagttc    2340
cgtgatgagg ccttccagtt cgccgtcgac aagggctacg accacccgga ctacaccgac    2400
tgggtgtact ccggcgtgaa caccggcaag aagggtgccg tcaccgctac cgccgctacc    2460
gctggcgaca acgagtga                                                  2478
```

<210> SEQ ID NO 4
<211> LENGTH: 825
<212> TYPE: PRT
<213> ORGANISM: Artificial Sequence
<220> FEATURE:
<223> OTHER INFORMATION: Synthetic Construct

<400> SEQUENCE: 4

```
Met Thr Ser Pro Val Ile Gly Thr Pro Trp Lys Lys Leu Ser Ala Pro
  1               5                  10                  15
Val Ser Glu Glu Ala Leu Glu Gly Val Asp Lys Tyr Trp Arg Val Ala
             20                  25                  30
Asn Tyr Leu Ser Ile Gly Gln Ile Tyr Leu Arg Ser Asn Pro Leu Met
         35                  40                  45
Lys Glu Pro Phe Thr Arg Glu Asp Val Lys His Arg Leu Val Gly His
     50                  55                  60
Trp Gly Thr Thr Pro Gly Leu Asn Phe Leu Ile Gly His Ile Asn Arg
 65                  70                  75                  80
Phe Ile Ala Asp His Gly Gln Asn Thr Val Ile Ile Met Gly Pro Gly
                 85                  90                  95
His Gly Gly Pro Ala Gly Thr Ser Gln Ser Tyr Leu Asp Gly Thr Tyr
            100                 105                 110
Thr Glu Thr Phe Pro Lys Ile Thr Lys Asp Glu Ala Gly Leu Gln Lys
        115                 120                 125
Phe Phe Arg Gln Phe Ser Tyr Pro Gly Gly Ile Pro Ser His Phe Ala
    130                 135                 140
Pro Glu Thr Pro Gly Ser Ile His Glu Gly Gly Glu Leu Gly Tyr Ala
145                 150                 155                 160
Leu Ser His Ala Tyr Gly Ala Ile Met Asp Asn Pro Ser Leu Phe Val
                165                 170                 175
Pro Ala Ile Val Gly Asp Gly Glu Ala Glu Thr Gly Pro Leu Ala Thr
            180                 185                 190
Gly Trp Gln Ser Asn Lys Leu Val Asn Pro Arg Thr Asp Gly Ile Val
        195                 200                 205
Leu Pro Ile Leu His Leu Asn Gly Tyr Lys Ile Ala Asn Pro Thr Ile
    210                 215                 220
Leu Ser Arg Ile Ser Asp Glu Glu Leu His Glu Phe Phe His Gly Met
225                 230                 235                 240
Gly Tyr Glu Pro Tyr Glu Phe Val Ala Gly Phe Asp Asp Glu Asp His
                245                 250                 255
```

```
Met Ser Ile His Arg Arg Phe Ala Glu Leu Trp Glu Thr Ile Trp Asp
            260                 265                 270

Glu Ile Cys Asp Ile Lys Ala Thr Ala Gln Thr Asp Asn Val His Arg
            275                 280                 285

Pro Phe Tyr Pro Met Leu Ile Phe Arg Thr Pro Lys Gly Trp Thr Cys
290                 295                 300

Pro Lys Tyr Ile Asp Gly Lys Lys Thr Glu Gly Ser Trp Arg Ser His
305                 310                 315                 320

Gln Val Pro Leu Ala Ser Ala Arg Asp Thr Glu Ala His Phe Glu Val
                325                 330                 335

Leu Lys Asn Trp Leu Glu Ser Tyr Lys Pro Glu Glu Leu Phe Asp Ala
            340                 345                 350

Asn Gly Ala Val Lys Asp Val Leu Ala Phe Met Pro Lys Gly Glu
            355                 360                 365

Leu Arg Ile Gly Ala Asn Pro Asn Ala Asn Gly Gly Val Ile Arg Asp
            370                 375                 380

Asp Leu Lys Leu Pro Asn Leu Glu Asp Tyr Glu Val Lys Glu Val Ala
385                 390                 395                 400

Glu Phe Gly His Gly Trp Gly Gln Leu Glu Ala Thr Arg Ser Leu Gly
                405                 410                 415

Ala Tyr Thr Arg Asp Ile Ile Lys Asn Asn Pro Arg Asp Phe Arg Ile
            420                 425                 430

Phe Gly Pro Asp Glu Thr Ala Ser Asn Arg Leu Gln Ala Ser Tyr Glu
            435                 440                 445

Val Thr Asn Lys Gln Trp Asp Ala Gly Tyr Ile Ser Asp Glu Val Asp
            450                 455                 460

Glu His Met Arg Val Ser Gly Gln Val Val Glu Gln Leu Ser Glu His
465                 470                 475                 480

Gln Met Glu Gly Phe Leu Glu Ala Tyr Leu Leu Thr Gly Arg His Gly
                485                 490                 495

Ile Trp Ser Ser Tyr Glu Ser Phe Val His Val Ile Asp Ser Met Leu
            500                 505                 510

Asn Gln His Ala Lys Trp Leu Glu Ala Thr Val Arg Glu Ile Pro Trp
            515                 520                 525

Arg Lys Pro Ile Ala Ser Met Asn Leu Leu Val Ser Ser His Val Trp
530                 535                 540

Arg Gln Asp His Asn Gly Phe Ser His Gln Asp Pro Gly Val Thr Ser
545                 550                 555                 560

Val Leu Leu Asn Lys Cys Phe His Asn Asp His Val Ile Gly Ile Tyr
            565                 570                 575

Phe Ala Thr Asp Ala Asn Met Leu Leu Ala Ile Ala Glu Lys Cys Tyr
            580                 585                 590

Lys Ser Thr Asn Lys Ile Asn Ala Ile Ile Ala Gly Lys Gln Pro Ala
            595                 600                 605

Ala Thr Trp Leu Thr Leu Asp Glu Ala Arg Ala Glu Leu Glu Lys Gly
            610                 615                 620

Ala Ala Ala Trp Asp Trp Ala Ser Thr Ala Lys Thr Asn Asp Glu Ala
625                 630                 635                 640

Glu Ile Val Leu Ala Ala Ala Gly Asp Val Pro Thr Gln Glu Ile Met
            645                 650                 655

Ala Ala Ser Asp Lys Leu Lys Glu Leu Gly Ile Lys Phe Lys Val Val
            660                 665                 670
```

```
Asn Val Val Asp Leu Leu Ser Leu Gln Ser Ala Lys Glu Asn Asp Glu
            675                 680                 685

Ala Leu Ser Asn Glu Glu Phe Ala Asp Ile Phe Thr Ala Asp Lys Pro
690                 695                 700

Val Leu Phe Ala Tyr His Ser Tyr Ala His Asp Val Arg Gly Leu Ile
705                 710                 715                 720

Tyr Asp Arg Pro Asn His Asp Asn Phe Asn Val His Gly Tyr Glu Glu
            725                 730                 735

Glu Gly Ser Thr Thr Thr Pro Tyr Asp Met Val Arg Val Asn Arg Ile
                740                 745                 750

Asp Arg Tyr Glu Leu Thr Ala Glu Ala Leu Arg Met Ile Asp Ala Asp
            755                 760                 765

Lys Tyr Ala Asp Lys Ile Asp Glu Leu Glu Lys Phe Arg Asp Glu Ala
770                 775                 780

Phe Gln Phe Ala Val Asp Lys Gly Tyr Asp His Pro Asp Tyr Thr Asp
785                 790                 795                 800

Trp Val Tyr Ser Gly Val Asn Thr Gly Lys Lys Gly Ala Val Thr Ala
                805                 810                 815

Thr Ala Ala Thr Ala Gly Asp Asn Glu
            820                 825

<210> SEQ ID NO 5
<211> LENGTH: 329
<212> TYPE: PRT
<213> ORGANISM: Artificial Sequence
<220> FEATURE:
<223> OTHER INFORMATION: Synthetic Construct

<400> SEQUENCE: 5

Met Thr Asp Val Arg Phe Arg Ile Ile Gly Thr Gly Ala Tyr Val Pro
1               5                   10                  15

Glu Arg Ile Val Ser Asn Asp Glu Val Gly Ala Pro Ala Gly Val Asp
                20                  25                  30

Asp Asp Trp Ile Thr Arg Lys Thr Gly Ile Arg Gln Arg Arg Trp Ala
            35                  40                  45

Ala Asp Asp Gln Ala Thr Ser Asp Leu Ala Thr Ala Ala Gly Arg Ala
    50                  55                  60

Ala Leu Lys Ala Ala Gly Ile Thr Pro Glu Gln Leu Thr Val Ile Ala
65                  70                  75                  80

Val Ala Thr Ser Thr Pro Asp Arg Pro Gln Pro Pro Thr Ala Ala Tyr
                85                  90                  95

Val Gln His His Leu Gly Ala Thr Gly Thr Ala Ala Phe Asp Val Asn
            100                 105                 110

Ala Val Cys Ser Gly Thr Val Phe Ala Leu Ser Ser Val Ala Gly Thr
        115                 120                 125

Leu Val Tyr Arg Gly Gly Tyr Ala Leu Val Ile Gly Ala Asp Leu Tyr
130                 135                 140

Ser Arg Ile Leu Asn Pro Ala Asp Arg Lys Thr Val Val Leu Phe Gly
145                 150                 155                 160

Asp Gly Ala Gly Ala Met Val Leu Gly Pro Thr Ser Thr Gly Thr Gly
                165                 170                 175

Pro Ile Val Arg Arg Val Ala Leu His Thr Phe Gly Gly Leu Thr Asp
            180                 185                 190

Leu Ile Arg Val Pro Ala Gly Gly Ser Arg Gln Pro Leu Asp Thr Asp
        195                 200                 205
```

```
Gly Leu Asp Ala Gly Leu Gln Tyr Phe Ala Met Asp Gly Arg Glu Val
    210                 215                 220
Arg Arg Phe Val Thr Glu His Leu Pro Gln Leu Ile Lys Gly Phe Leu
225                 230                 235                 240
His Glu Ala Gly Val Asp Ala Ala Asp Ile Ser His Phe Val Pro His
                245                 250                 255
Gln Ala Asn Gly Val Met Leu Asp Glu Val Phe Gly Glu Leu His Leu
                260                 265                 270
Pro Arg Ala Thr Met His Arg Thr Val Glu Thr Tyr Gly Asn Thr Gly
            275                 280                 285
Ala Ala Ser Ile Pro Ile Thr Met Asp Ala Ala Val Arg Ala Gly Ser
        290                 295                 300
Phe Arg Pro Gly Glu Leu Val Leu Leu Ala Gly Phe Gly Gly Gly Met
305                 310                 315                 320
Ala Ala Ser Phe Ala Leu Ile Glu Trp
                325
```

```
<210> SEQ ID NO 6
<211> LENGTH: 2439
<212> TYPE: DNA
<213> ORGANISM: Artificial Sequence
<220> FEATURE:
<223> OTHER INFORMATION: L.grayi mvaE

<400> SEQUENCE: 6
atggttaaag acattgtaat aattgatgcc ctccgtactc ccatcggtaa gtaccgcggt      60
cagctctcaa agatgacggc ggtggaattg ggaaccgcag ttacaaaggc tctgttcgag     120
aagaacgacc aggtcaaaga ccatgtagaa caagtcattt ttggcaacgt tttacaggca     180
gggaacggcc agaatcccgc ccgtcagatc gcccttaatt ctggcctgtc cgcagagata     240
ccggcttcga ctattaacca ggtgtgtggt tctggcctga agcaataag catggcgcgc     300
caacagatcc tactcggaga agcggaagta atagtagcag gaggtatcga atccatgacg     360
aatgcgccga gtattacata ttataataaa gaagaagaca ccctctcaaa gcctgttcct     420
acgatgacct tcgatggtct gaccgacgcg tttagcggaa agattatggg tttaacagcc     480
gaaaatgttg ccgaacagta cggcgtatca cgtgaggccc aggacgcctt gcgtatgga     540
tcgcagatga aagcagcaaa ggcccaagaa cagggcattt tcgcagctga atactgcct     600
cttgaaatag ggacgaagt tattactcag gacgaggggg ttcgtcaaga gaccaccctc     660
gaaaaattaa gtctgcttcg gaccattttt aaagaagatg gtactgttac agcgggcaac     720
gcctcaacga tcaatgatgg cgcctcagcc gtgatcattg catcaaagga gtttgctgag     780
acaaaccaga ttccctacct tgcgatcgta catgatatta cagagatagg cattgatcca     840
tcaataatgg gcattgctcc cgtgagtgcg atcaataaac tgatcgatcg taaccaaatt     900
agcatggaag aaatcgatct cttttgaaatt aatgaggcat ttgcagcatc ctcggtggta     960
gttcaaaaag agttaagcat tcccgatgaa aagatcaata ttggcggttc cggtattgca    1020
ctaggccatc ctcttggcgc cacaggagcg cgcattgtaa ccaccctagc gcaccagttg    1080
aaacgtacac acggacgcta tggtattgcc tccctgtgca ttggcggtgg ccttggccta    1140
gcaatattaa tagaagtgcc tcaggaagat cagccggtta aaaattttta tcaattggcc    1200
cgtgaggacc gtctggctag acttcaggag caagccgtga tcagcccagc tacaaaacat    1260
gtactggcag aaatgacact tcctgaagat attgccgaca atctgatcga aaatcaaata    1320
tctgaaatgg aaatccctct tggtgtggct ttgaatctga gggtcaatga taagagttat    1380
```

```
accatcccac tagcaactga ggaaccgagt gtaatcgctg cctgtaataa tggtgcaaaa   1440
atggcaaacc acctgggcgg ttttcagtca gaattaaaag atggtttcct gcgtgggcaa   1500
attgtactta tgaacgtcaa agaacccgca actatcgagc atacgatcac ggcagagaaa   1560
gcggcaattt ttcgtgccgc agcgcagtca catccatcga ttgtgaaacg aggtgggggt   1620
ctaaaagaga tagtagtgcg tacgttcgat gatgatccga cgttcctgtc tattgatctg   1680
atagttgata ctaaagacgc aatgggcgct aacatcatta acaccattct cgagggtgta   1740
gccggctttc tgagggaaat ccttaccgaa gaaattctgt tctctatttt atctaattac   1800
gcaaccgaat caattgtgac cgccagctgt cgcataccct acgaagcact gagtaaaaaa   1860
ggtgatggta aacgaatcgc tgaaaaagtg gctgctgcat ctaaatttgc ccagttagat   1920
ccttatcgag ctgcaaccca caacaaaggt attatgaatg gtattgaggc cgtcgttttg   1980
gcctcaggaa atgacacacg ggcggtcgcg gcagccgcac atgcgtatgc ttcacgcgat   2040
cagcactatc ggggcttaag ccagtggcag gttcagaag gcgcgttaca cggggagatc   2100
agtctaccac ttgcactcgg cagcgttggc ggtgcaattg aggtcttgcc taaagcgaag   2160
gcggcattcg aaatcatggg gatcacagag gcgaaggagc tggcagaagt cacagctgcg   2220
gtagggctgg cgcaaaacct ggcggcgtta agagcgcttg ttagtgaagg aatacagcaa   2280
ggtcacatgt cgctccaggc tcgctctctt gcattatcgg taggtgctac aggcaaggaa   2340
gttgaaatcc tggccgaaaa attacagggc tctcgtatga atcaggcgaa cgctcagacc   2400
atactcgcag agatcagatc gcaaaaagtt gaattgtga                          2439

<210> SEQ ID NO 7
<211> LENGTH: 2442
<212> TYPE: DNA
<213> ORGANISM: Artificial Sequence
<220> FEATURE:
<223> OTHER INFORMATION: E. faecium mvaE

<400> SEQUENCE: 7
atgaaagaag tggttatgat tgatgcggct cgcacaccca ttgggaaata cagaggtagt     60
cttagtcctt ttacagcggt ggagctgggg acactggtca cgaaagggct gctggataaa    120
acaaagctta agaaagacaa gatagaccaa gtgatattcg gcaatgtgct tcaggcagga    180
aacggacaaa acgttgcaag acaaatagcc ctgaacagtg gcttaccagt tgacgtgccg    240
gcgatgacta ttaacgaagt ttgcgggtcc ggaatgaaag cggtgatttt agcccgccag    300
ttaatacagt taggggaggc agagttggtc attgcagggg gtacggagtc aatgtcacaa    360
gcacccatgc tgaaaccta ccagtcagag accaacgaat acggagagcc gatatcatca    420
atggttaatg acgggctgac ggatgcgttt tccaatgctc acatgggtct tactgccgaa    480
aaggtggcga cccagttttc agtgtcgcgc gaggaacaag accggtacgc attgtccagc    540
caattgaaag cagcgcacgc ggttgaagcc ggggtgttct cagaagagat tattccggtt    600
aagattagcg acgaggatgt cttgagtgaa gacgaggcag taagaggcaa cagcactttg    660
gaaaaactgg gcaccttgcg gacggtgttt tctgaagagg gcacggttac cgctggcaat    720
gcttcaccgc tgaatgacgg cgctagtgtc gtgattcttg catcaaaaga atacgcggaa    780
aacaataatc tgcccttacc tggcgacgata aaggaggttg cggaagttgg tatcgatcct    840
tctatcatgg gtattgcccc aataaaggcc attcaaaagt taacgatcg gtcgggcatg    900 aacctgtcca cgattgatct gttcgaaatt aatgaagcat tcgcggcatc tagcattgtt    960
```

| gtttctcaag agctgcaatt ggacgaagaa aaagtgaata tctatggcgg ggcgatagct | 1020 |
| ttaggccatc caatcggcgc aagcggagcc cggatactga caaccttagc atacggcctc | 1080 |
| ctgcgtgagc aaaagcgtta tggtattgcg tcattatgta tcggcggtgg tcttggtctg | 1140 |
| gccgtgctgt tagaagctaa tatggagcag acccacaaag acgttcagaa gaaaaagttt | 1200 |
| taccagctta cccctccga gcggagatcg cagcttatcg agaagaacgt tctgactcaa | 1260 |
| gaaacggcac ttatttttcca ggagcagacg ttgtccgaag aactgtccga tcacatgatt | 1320 |
| gagaatcagg tctccgaagt ggaaattcca atgggaattg cacaaaattt tcagattaat | 1380 |
| ggcaagaaaa aatggattcc tatggcgact gaagaacctt cagtaatagc ggcagcatcg | 1440 |
| aacggcgcca aaatctgcgg gaacatttgc gcggaaacgc ctcagcggct tatgcgcggg | 1500 |
| cagattgtcc tgtctggcaa atcagaatat caagccgtga taaatgccgt gaatcatcgc | 1560 |
| aaagaagaac tgattctttg cgcaaacgag tcgtacccga gtattgttaa acgcggggga | 1620 |
| ggtgttcagg atatttctac gcgggagttt atgggttctt ttcacgcgta tttatcaatc | 1680 |
| gactttctgg tggacgtcaa ggacgcaatg ggggcaaaca tgatcaactc tattctcgaa | 1740 |
| agcgttgcaa ataaactgcg tgaatggttc ccggaagagg aaatactgtt ctccatcctg | 1800 |
| tcaaacttcg ctacggagtc cctggcatct gcatgttgcg agattccttt tgaaagactt | 1860 |
| ggtcgtaaca agaaattgg tgaacagatc gccaagaaaa ttcaacaggc aggggaatat | 1920 |
| gctaagcttg acccttaccg cgcggcaacc cataacaagg ggattatgaa cggtatcgaa | 1980 |
| gccgtcgttg ccgcaacggg aaacgacaca cgggctgttt ccgcttctat tcacgcatac | 2040 |
| gccgcccgta tggcttgta ccaaggttta acggattggc agatcaaggg cgataaactg | 2100 |
| gttggtaaat taacagtccc actggctgtg gcgactgtcg gtggcgcgtc gaacatatta | 2160 |
| ccaaaagcca aagcttccct cgccatgctg gatattgatt ccgcaaaaga actggcccaa | 2220 |
| gtgatcgccg cggtaggttt agcacagaat ctggcggcgt acgtgcatt agtgacagaa | 2280 |
| ggcattcaga aggacacat gggcttgcaa gcacgttctt tagcgatttc gataggtgcc | 2340 |
| atcggtgagg agatagagca agtcgcgaaa aaactgcgtg aagctgaaaa aatgaatcag | 2400 |
| caaacggcaa tacagatttt agaaaaaatt cgcgagaaat ga | 2442 |

<210> SEQ ID NO 8
<211> LENGTH: 2448
<212> TYPE: DNA
<213> ORGANISM: Artificial Sequence
<220> FEATURE:
<223> OTHER INFORMATION: E. gallinarum mvaE

<400> SEQUENCE: 8

| atggaagaag tggtaattat agatgcacgt cggactccga ttggtaaata tcacgggtcg | 60 |
| ttgaagaagt tttcagcggt ggcgctgggg acggccgtgg ctaaagacat gttcgaacgc | 120 |
| aaccagaaaa tcaaagagga gatcgcgcag gtcataattg gtaatgtctt gcaggcagga | 180 |
| aatggccaga accccgcgcg gcaagttgct cttcaatcag ggttgtccgt tgacattccc | 240 |
| gcttctacaa ttaacgaggt ttgtgggtct ggtttgaaag ctatcttgat gggcatggaa | 300 |
| caaatccaac tcgcaaagc gcaagtagtg ctggcaggcg gcattgaatc aatgacaaat | 360 |
| gcgccaagcc tgtcccacta taacaaggcg gaggatacgt atagtgtccc agtgtcgagc | 420 |
| atgacactgg atggtctgac agacgcattt tctagtaaac ctatgggatt aacagcggaa | 480 |
| aacgtcgcac agcgctacgg tatctcccgt gaggcgcaag atcaattcgc atatcaatct | 540 |
| cagatgaaag cagcaaaagc gcaggcagaa aacaaattcg ctaaggaaat tgtgccactg | 600 |

```
gcgggtgaaa ctaaaaccat cacagctgac gaagggatca gatcccaaac aacgatggag      660
aaactggcaa gtctcaaacc tgttttaaa accgatggca ctgtaaccgc agggaatgct      720
agcaccatta atgacggggc cgccttgtg ctgcttgcta gcaaaactta ctgcgaaact      780
aatgacatac cgtaccttgc gacaatcaaa gaaattgttg aagttggaat cgatccggag      840
attatgggca tctctccgat aaaagcgata caaacattgt tacaaaatca aaaagttagc      900
ctcgaagata ttggagtttt tgaaataaat gaagcctttg ccgcaagtag catagtggtt      960
gaatctgagt tgggattaga tccggctaaa gttaaccgtt atggggtgg tatatcctta     1020 ggtcatgcaa ttggggcaac cggcgctcgc ctggccactt cactggtgta tcaaatgcag     1080
gagatacaag cacgttatgg tattgcgagc ctgtgcgttg gtggtggact tggactggca     1140
atgcttttag aacgtccaac tattgagaag gctaaaccga cagacaaaaa gttctatgaa     1200
ttgtcaccag ctgaacggtt gcaagagctg gaaaatcaac agaaaatcag ttctgaaact     1260
aaacagcagt tatctcagat gatgcttgcc gaggacactg caaaccattt gatagaaaat     1320
caaatatcag agattgaact cccaatgggc gtcgggatga acctgaaggt tgatgggaaa     1380
gcctatgttg tgccaatggc gacggaagag ccgtccgtca tcgcggccat gtctaatggt     1440
gccaaaatgg ccggcgaaat tcacactcag tcgaaagaac ggctgctcag aggtcagatt     1500
gttttcagcg cgaagaatcc gaatgaaatc gaacagagaa tagctgagaa ccaagctttg     1560
attttcgaac gtgccgaaca gtcctatcct tccattgtga aaagagaggg aggtctccgc     1620
cgcattgcac ttcgtcattt tcctgccgat tctcagcagg agtctgcgga ccagtccaca     1680 ttttatcag tggacctttt tgtagatgtg aaagacgcga tgggggcaaa tatcataaat     1740
gcaatacttg agggcgtcgc agccctgttt cgcgaatggt tccccaatga ggaaattctt     1800
ttttctattc tctcgaactt ggctacggag agcttagtca cggctgtttg tgaagtccca     1860
tttagtgcac ttagcaagag aggtggtgca acggtggccc agaaaattgt gcaggcgtcg     1920
ctcttcgcaa agacagaccc ataccgcgca gtgacccaca acaaagggat tatgaacggt     1980
gtagaggctg ttatgcttgc cacaggcaac gacacgcgcg cagtctcagc cgcttgtcat     2040
ggatacgcag cgcgcaccgg tagctatcag ggtctgacta actggacgat tgagtcggat     2100
cgcctggtag cgagataac actgccgctg ccatcgcta cagttggagg cgctaccaaa     2160
gtgttgccca agctcaagc ggcactggag attagtgatg ttcactcttc tcaagagctt     2220
gcagccttag cggcgtcagt aggtttagta caaaatctcg cggccctgcg cgcactggtt     2280
tccgaaggta tacaaaaagg gcacatgtcc atgcaagccc ggtctctcgc aatcgcggtc     2340
ggtgctgaaa agccgagat cgagcaggtc gccgaaaagt tgcggcagaa cccgccaatg     2400
aatcagcagc aggcgctccg ttttcttggc gagatccgcg aacaatga                2448
```

<210> SEQ ID NO 9
<211> LENGTH: 2475
<212> TYPE: DNA
<213> ORGANISM: Artificial Sequence
<220> FEATURE:
<223> OTHER INFORMATION: E. casseliflavus mvaE

<400> SEQUENCE: 9

```
atggaagaag ttgtcatcat tgacgcactg cgtactccaa taggaaagta ccacggttcg      60
ctgaaagatt acacagctgt tgaactgggg acagtagcag caaaggcgtt gctggcacga     120
aatcagcaag caaaagaaca catagcgcaa gttattattg gcaacgtcct gcaagccgga     180
```

| | |
|---|---|
| agtgggcaga atccaggccg acaagtcagt ttacagtcag gattgtcttc tgatatcccc | 240 |
| gctagcacga tcaatgaagt gtgtggctcg ggtatgaaag cgattctgat gggtatggag | 300 |
| caaattcagc tgaacaaagc ctctgtggtc ttaacaggcg gaattgaaag catgaccaac | 360 |
| gcgccgctgt ttagttatta caacaaggct gaggatcaat attcggcgcc ggttagcaca | 420 |
| atgatgcacg atggtctaac agatgctttc agttccaaac caatgggctt aaccgcagag | 480 |
| accgtcgctg agagatatgg aattacgcgt aaggaacaag atgaatttgc ttatcactct | 540 |
| caaatgaagg cggccaaagc ccaggcggcg aaaaagtttg atcaggaaat tgtacccctg | 600 |
| acggaaaaat ccggaacggt tctccaggac gaaggcatca gagccgcgac aacagtcgag | 660 |
| aagctagctg agcttaaaac ggtgttcaaa aaagacggaa cagttacagc gggtaacgcc | 720 |
| tctacgataa atgatggcgc tgctatggta ttaatagcat caaaatctta ttgcgaagaa | 780 |
| caccagattc cttatctggc cgttataaag gagatcgttg aggtgggttt tgcccccgaa | 840 |
| ataatgggta tttcccccat taaggctata gacaccctgc tgaaaaatca agcactgacc | 900 |
| atagaggata taggaatatt tgagattaat gaagcctttg ctgcgagttc gattgtggta | 960 |
| gaacgcgagt tgggcctgga ccccaaaaaa gttaatcgct atggcggtgg tatatcactc | 1020 |
| ggccacgcaa ttggggcgac gggagctcgc attgcgacga ccgttgctta tcagctgaaa | 1080 |
| gatacccagg agcgctacgg tatagcttcc ttatgcgttg gtggggtct tggattggcg | 1140 |
| atgcttctgg aaaacccatc ggccactgcc tcacaaacta attttgatga ggaatctgct | 1200 |
| tccgaaaaaa ctgagaagaa gaagttttat gcgctagctc ctaacgaacg cttagcgttt | 1260 |
| ttggaagccc aaggcgctat taccgctgct gaaaccctgg tcttccagga gatgacctta | 1320 |
| aacaaagaga cagccaatca cttaatcgaa aaccaaatca gcgaagttga aattccttta | 1380 |
| ggcgtgggcc tgaacttaca ggtgaatggg aaagcgtata atgttcctct ggccacggag | 1440 |
| gaaccgtccg ttatcgctgc gatgtcgaat ggcgccaaaa tggctggtcc tattacaaca | 1500 |
| acaagtcagg agaggctgtt acggggtcag attgtcttca tggacgtaca ggacccagaa | 1560 |
| gcaatattag cgaaagttga atccgagcaa gctaccatt tcgcggtggc aaatgaaaca | 1620 |
| tacccgtcta tcgtgaaaag aggagggaggt ctgcgtagag tcattggcag gaatttcagt | 1680 |
| ccggccgaaa gtgacttagc cacggcgtat gtatcaattg acctgatggt agatgttaag | 1740 |
| gatgcaatgg gtgctaatat catcaatagt atcctagaag gtgttgcgga attgtttaga | 1800 |
| aaatggttcc cagaagaaga aatcctgttc tcaattctct ccaatctcgc gacagaaagt | 1860 |
| ctggtaacgg cgacgtgctc agttccgttt gataaattgt ccaaaactgg gaatggtcga | 1920 |
| caagtagctg gtaaaatagt gcacgcggcg gactttgcta agatagatcc atacagagct | 1980 |
| gccacacaca ataaaggtat tatgaatggc gttgaagcgt taatcttagc caccggtaat | 2040 |
| gacacccgtg cggtgtcggc tgcatgccac ggttacgcgg cacgcaatgg gcgaatgcaa | 2100 |
| gggcttacct cttggacgat tatcgaagat cggctgatag gctctatcac attacctttg | 2160 |
| gctattgcga cagtgggggg tgccacaaaa atcttgccaa agcacaggc cgccctggcg | 2220 |
| ctaactggcg ttgagacggc gtcggaactg gccagcctgg cggcgagtgt gggattagtt | 2280 |
| caaaatttgg ccgctttacg agcactagtg agcgagggca ttcagcaagg gcacatgagt | 2340 |
| atgcaagcta gatccctggc cattagcgta ggtgcgaaag gtactgaaat agagcaacta | 2400 |
| gctgcgaagc tgagggcagc gacgcaaatg aatcaggagc aggctcgtaa atttctgacc | 2460 |
| gaaataagaa attaa | 2475 |

<210> SEQ ID NO 10
<211> LENGTH: 1158
<212> TYPE: DNA
<213> ORGANISM: Artificial Sequence
<220> FEATURE:
<223> OTHER INFORMATION: L.grayi mvaS

<400> SEQUENCE: 10

| | | | | | |
|---|---|---|---|---|---|
| atgaccatga | acgttggaat | cgataaaatg | tcattctttg | ttccacctta | ctttgtggac | 60 |
| atgactgatc | tggcagtagc | acgggatgtc | gatcccaata | agtttctgat | ggtattggc | 120 |
| caggaccaga | tggcagttaa | tccgaaaacg | caggatattg | tgacatttgc | cacaaatgct | 180 |
| gccaaaaaca | tactgtcagc | tgaggacctt | gataaaattg | atatggtcat | agtcggcacc | 240 |
| gagagtggaa | tcgatgaatc | caaagcgagt | gccgtagtgc | ttcacaggtt | gctcggtatc | 300 |
| cagaagtttg | ctcgctcctt | tgaaatcaaa | gaagcctgtt | atgggggtac | gcggcttta | 360 |
| cagttcgctg | taaaccacat | taggaatcat | cctgaatcaa | aggttcttgt | agttgcatca | 420 |
| gatatcgcga | atacggcct | ggcttctgga | ggtgaaccaa | cgcaaggtgc | aggcgctgtg | 480 |
| gctatgctcg | tctcaactga | ccctaagatc | attgctttca | cgacgatag | cctcgcgctt | 540 |
| acacaagata | tctatgactt | ctggcgacca | gttggacatg | actatcctat | ggtcgacggg | 600 |
| cctcttagta | cagagaccta | catccagtca | tttcagaccg | tatggcagga | atacacaaaa | 660 |
| cggtcgcagc | atgcactggc | agactttgct | gcccttagct | ttcatatccc | gtatactaaa | 720 |
| atgggcaaaa | aggcgctgct | tgcaatcctt | gaaggcgaat | cagaggaggc | tcagaaccgt | 780 |
| atactagcaa | atatgaaaaa | gagtatagcc | tactccagaa | aggcgggtaa | cctgtatacc | 840 |
| ggtagcctgt | atctaggact | tatttcactt | ctggaaaatg | cagaagacct | taaagctggt | 900 |
| gatttaatag | gcctcttttc | ttacggttcc | ggtgctgttg | cggagttttt | ctcaggaagg | 960 |
| ctggttgagg | actatcagga | acagctactt | aaaacaaaac | atgccgaaca | gctggcccat | 1020 |
| agaaagcaac | tgacaatcga | ggagtacgaa | acgatgttct | ccgatcgctt | ggacgtggac | 1080 |
| aaagacgccg | aatacgaaga | cacattagct | tatagcattt | cgtcagtccg | aaacaccgta | 1140 |
| cgtgagtaca | ggagttga | | | | | 1158 |

<210> SEQ ID NO 11
<211> LENGTH: 1155
<212> TYPE: DNA
<213> ORGANISM: Artificial Sequence
<220> FEATURE:
<223> OTHER INFORMATION: E. faecium mvaS

<400> SEQUENCE: 11

| | | | | | |
|---|---|---|---|---|---|
| atgaaaatcg | gtattgaccg | tctgtccttc | ttcatcccga | atttgtattt | ggacatgact | 60 |
| gagctggcag | aatcacgcgg | ggatgatcca | gctaaatatc | atattggaat | cggacaagat | 120 |
| cagatggcag | tgaatcgcgc | aaacgaggac | atcataacac | tgggtgcaaa | cgctgcgagt | 180 |
| aagatcgtga | cagagaaaga | ccgcgagttg | attgatatgg | taatcgttgg | cacggaatca | 240 |
| ggaattgacc | actccaaagc | aagcgccgtg | attattcacc | atctccttaa | aattcagtcg | 300 |
| ttcgcccgtt | ctttcgaggt | aaaagaagct | tgctatggcg | gaactgctgc | cctgcacatg | 360 |
| gcgaaggagt | atgtcaaaaa | tcatccggag | cgtaaggtct | tggtaattgc | gtcagacatc | 420 |
| gcgcgttatg | gtttggccag | cggaggagaa | gttactcaag | gcgtggggc | cgtagccatg | 480 |
| atgattacac | aaaaccccg | gattctttcg | attgaagacg | atagtgtttt | ctctcacaga | 540 |
| gatatctatg | atttctggcg | gcctgattac | tccgagttcc | ctgtagtgga | cgggcccctt | 600 |

```
tcaaactcaa cgtatataga gagttttcag aaagtttgga accggcacaa ggaattgtcc    660
ggaagagggc tggaagatta tcaagctatt gcttttcaca tacccctatac gaagatgggt   720 aagaaagcgc tccagagtgt tttagaccaa accgatgaag ataaccagga gcgcttaatg    780
gctagatatg aggagtctat tcgctatagc cggagaattg gtaacctgta cacaggcagc    840
ttgtaccttg gtcttacaag cttgttggaa aactctaaaa gtttacaacc gggagatcgg    900
atcggcctct tttcctatgg cagtggtgcg gtgtccgagt tctttaccgg gtatttagaa    960
gaaaattacc aagagtacct gttcgctcaa agccatcaag aaatgctgga tagccggact    1020
cggattacgg tcgatgaata cgagaccatc ttttcagaga ctctgccaga acatggtgaa    1080
tgcgccgaat atacgagcga cgtcccctttt tctataacca agattgagaa cgacattcgt   1140
tattataaaa tctga    1155
```

```
<210> SEQ ID NO 12
<211> LENGTH: 1155
<212> TYPE: DNA
<213> ORGANISM: Artificial Sequence
<220> FEATURE:
<223> OTHER INFORMATION: E. gallinarum mvaS

<400> SEQUENCE: 12
atgaacgtcg gcattgacaa aattaatttt tcgttccac cgtattatct ggatatggtc      60
gacctggccc acgcacgcga agtggacccg aacaaattta caattggaat tggacaggat    120
cagatggctg tgagcaaaaa gacgcacgat atcgtaacat tcgcggctag tgccgcgaag    180
gaaattttag aacctgagga cttgcaagct atagacatgg ttatagttgg taccgaatcg    240
ggcattgacg agagcaaagc atccgcggtc gttttacatc gtttgttggg cgtacaacct    300
ttcgctcgca gttttgaaat taagaagcc tgttacgggg caaccgcagg cattcagttt    360
gccaagactc atatacaagc gaacccggag agcaaggtcc tggtaattgc aagcgatata    420
gctcggtatg tcttcggtc aggtggagag cccacacaag gcgcagggc agttgctatg    480 cttctcacgg caaatcccag aatcctgacc ttcgaaaacg acaatctgat gttaacgcag    540
gatatttatg acttctggag accacttggt cacgcttacc ctatggtaga tggccacctt    600
tccaatcaag tctatattga cagttttaag aaggtctggc aagcacattg cgaacgcaat    660
caagcttcta tatccgacta tgccgcgatt agttttcata ttccgtatac aaaaatgggt    720
aagaaagccc tgctcgctgt ttttgcagat gaagtggaaa ctgaacagga acgcgttatg    780
gcacggtatg aagagtctat cgtatattca cgccggatcg gcaacttgta tacgggatca    840
ttgtacctgg ggctgatatc cttattggaa aacagttctc acctgtcggc gggcgaccgg    900
ataggattgt ttagttatgg gagtggcgct gtcagcgaat ttttctccgg tcgtttagtg    960
gcaggctatg aaaatcaatt gaacaaagag gcgcataccc agctcctgga tcagcgtcag    1020
aagctttcca tcgaagagta tgaggcgatt tttacagatt ccttagaaat tgatcaggat    1080
gcagcgttct cggatgacct gccatattcc atccgcgaga taaaaacac gattcggtac    1140 tataaggaga gctga    1155
```

```
<210> SEQ ID NO 13
<211> LENGTH: 1161
<212> TYPE: DNA
<213> ORGANISM: Artificial Sequence
<220> FEATURE:
<223> OTHER INFORMATION: E. casseliflavus mvaS

<400> SEQUENCE: 13
```

```
atgaacgttg gaattgataa aatcaattt  ttcgttccgc cctatttcat tgatatggtg      60
gatctcgctc atgcaagaga agttgacccc aacaagttca ctataggaat aggccaagat     120
cagatggcag taaacaagaa aacgcaagat atcgtaacgt tcgcgatgca cgccgcgaag     180
gatattctga ctaaggaaga tttacaggcc atagatatgg taatagtggg gactgagtct     240
gggatcgacg agagcaaggc aagtgctgtc gtattgcatc ggcttttagg tattcagcct     300
tttgcgcgct cctttgaaat taaggaggca tgctatgggg ccactgccgg ccttcagttt     360
gcaaaagctc atgtgcaggc taatccccag agcaaggtcc tggtggtagc ttccgatata     420
gcacgctacg gactggcatc cggaggagaa ccgactcaag tgtaggtgc tgtggcaatg      480
ttgatttccg ctgatccagc tatcttgcag ttagaaaatg ataatctcat gttgacccaa     540
gatatatacg atttttggcg cccggtcggg catcaatatc ctatggtaga cggccatctg     600
tctaatgccg tctatataga cagctttaaa caagtctggc aagcacattg cgagaaaaac     660
caacggactc taaagattat tgctgcattg tcgttccata ttccgtacac gaaaatgggt     720
aagaaagctc tgttagcggt ttttgcggag gaagatgaga cagaacaaaa gcggttaatg     780
gcacgttatg aagaatcaat tgtatacagt cgtcggactg gaaatctgta tactggctca     840
ctctatctgg gcctgatttc cttactggag aatagtagca gtttacaggc gaacgatcgc     900
ataggtctgt ttagctatgg ttcaggggcc gttgcggaat ttttcagtgg cctcttggta     960
ccgggttacg agaaacaatt agcgcaagct gcccatcaag ctcttctgga cgaccggcaa    1020
aaactgacta tcgcagagta cgaagccatg tttaatgaaa ccattgatat tgatcaggac    1080
cagtcatttg aggatgactt actgtactcc atcagagaga tcaaaaacac tattcgctac    1140
tataacgagg agaatgaata a                                               1161

<210> SEQ ID NO 14
<211> LENGTH: 125
<212> TYPE: DNA
<213> ORGANISM: Artificial Sequence
<220> FEATURE:
<223> OTHER INFORMATION: Synthetic Construct

<400> SEQUENCE: 14
aattcatata aaaacatac  agataaccat ctgcggtgat aaattatctc tggcggtgtt      60
gacataaata ccactggcgg tgatactgag cacatcagca ggacgcactg accaccatga     120
aggtg                                                                 125

<210> SEQ ID NO 15
<211> LENGTH: 6843
<212> TYPE: DNA
<213> ORGANISM: Artificial Sequence
<220> FEATURE:
<223> OTHER INFORMATION: pCMP1090 (PKL from Bifidobacterium infantis)

<400> SEQUENCE: 15
gtttgacagc ttatcatcga ctgcacggtg caccaatgct tctggcgtca ggcagccatc      60
ggaagctgtg gtatggctgt gcaggtcgta aatcactgca taattcgtgt cgctcaaggc     120
gcactcccgt tctggataat gttttttgcg ccgacatcat aacggttctg gcaaatattc     180
tgaaatgagc tgttgacaat taatcatccg gctcgtataa tgtgtggaat tgtgagcgga     240
taacaatttc acacaggaaa cagcgccgct gagaaaaagc gaagcggcac tgctctttaa     300
caatttatca gacaatctgt gtgggcactc gaccggaatt atcgattaac tttattatta     360
```

-continued

| | |
|---|---|
| aaaattaaag aggtatatat taatgtatcg attaaataag gaggaataaa ccatgacgag | 420 |
| tcctgttatt ggcacccctt ggaagaagct cagcgctccg gtttccgagg aagccctcga | 480 |
| aggcgttgac aagtactggc gcgttgccaa ctacctttcc atcggccaga tttatctgcg | 540 |
| ttccaacccg ctgatgaagg agcccttcac ccgcgaagat gtgaagcatc gtctggtggg | 600 |
| ccactggggc actacccctg gcctgaactt cctcatcggc cacatcaacc gtttcattgc | 660 |
| tgaccacggc cagaacaccg tgatcatcat gggcccgggc cacggtggcc ggccggtac | 720 |
| ctcccagtcc tacctggacg gcacctacac cgagaccttc ccgaagatca ccaaggacga | 780 |
| agctggtctg cagaagttct tccgtcagtt ctcttacccg ggcggtattc cgtcccactt | 840 |
| cgctccggag accccgggct ccatccacga gggtggtgag ctgggttacg ctctgtccca | 900 |
| cgcttacggc gccatcatgg acaacccgag cctgttcgtc ccggccatcg tcggcgacgg | 960 |
| cgaggctgag accggcccgc tggctaccgg ttggcagtcc aacaagctcg tgaacccgcg | 1020 |
| caccgacggt atcgtgctgc cgatcctgca cctcaacggc tacaagatcg ccaacccgac | 1080 |
| catcctgtcc cgcatctccg acgaagagct ccacgagttc ttccacggca tgggttacga | 1140 |
| gccctacgag ttcgtcgctg gcttcgatga tgaggaccac atgtccatcc accgccgctt | 1200 |
| cgccgagctg tgggagacca tctgggacga gatctgcgac atcaaggcca ccgctcagac | 1260 |
| cgacaacgtg caccgtccgt tctacccgat gctgatcttc cgcacccga agggctggac | 1320 |
| ctgcccgaag tacatcgacg gcaagaagac cgaaggctcc tggcgttccc accaggtgcc | 1380 |
| gctggcctcc gcccgcgaca ccgaggccca cttcgaggtc ctcaagaact ggctcgagtc | 1440 |
| ctacaagccg gaagagctgt tcgacgccaa cggcgccgtc aaggacgacg tcctcgcctt | 1500 |
| catgccgaag ggcgagctgc gtatcggtgc caacccgaac gccaacggcg gtgtgatccg | 1560 |
| cgacgacctg aagctgccga acctcgagga ctacgaggtc aaggaagtgg ccgagttcgg | 1620 |
| ccacggctgg ggccagctcg aggccacccg ctccctgggc gcctacaccc gcgacatcat | 1680 |
| caagaacaac ccgcgtgact tccgcatctt cggaccggat gagaccgctt ccaaccgtct | 1740 |
| gcaggcttcc tacgaagtca ccaacaagca gtgggatgcc ggctacatct ccgacgaggt | 1800 |
| cgacgagcac atgcgcgtct ccggccaggt cgtcgagcag ctgtccgagc accagatgga | 1860 |
| aggcttcctc gaggcctacc tgctgaccgg ccgtcacggc atctggagct cctacgagtc | 1920 |
| cttcgtccac gtgatcgact ccatgctgaa ccagcacgcc aagtggcttg aggctaccgt | 1980 |
| ccgcgagatt ccgtggcgca agccgatcgc ctccatgaac ctgctggtct cctcccacgt | 2040 |
| ctggcgtcag gaccacaacg gcttctccca ccaggatccg ggtgtcacct ccgtcctgct | 2100 |
| gaacaagtgc ttccacaacg accacgtcat cggcatctac ttcgccaccg acgcgaacat | 2160 |
| gctgctggcc atcgccgaga agtgctacaa gtccaccaac aagatcaacg ccatcatcgc | 2220 |
| cggcaagcag cccgccgcca cctggctgac cctggacgag gctcgcgccg agctcgagaa | 2280 |
| gggtgccgcc gcttgggact gggcctccac cgccaagacc aacgatgaag ccgagatcgt | 2340 |
| gcttgccgcc gccggcgacg tccccaccca ggagatcatg ccgcttccg acaagctgaa | 2400 |
| ggaactgggc atcaagttca aggtcgtgaa cgttgtcgac ctgctctccc tgcagtccgc | 2460 |
| caaggagaac gacgaggccc tgtccaacga ggagttcgcc gacatcttca ccgccgacaa | 2520 |
| gccggtgctg ttcgcgtacc actcctacgc ccacgacgtg cgcggtctga tctacgatcg | 2580 |
| tccgaaccac gacaacttca acgtccacgg ctacgaggag gagggctcca ccaccaccc | 2640 |
| gtacgacatg gttcgtgtca accgcatcga ccgctacgcg ctgaccgctg aggctctgcg | 2700 |
| catgatcgac gccgacaagt acgccgacaa gatcgacgag ctcgagaagt ccgtgatga | 2760 |

```
ggccttccag ttcgccgtcg acaagggcta cgaccacccg gactacaccg actgggtgta    2820
ctccggcgtg aacaccggca agaagggtgc cgtcaccgct accgccgcta ccgctggcga    2880
caacgagtga gaattcgaag cttcctagaa caaaaactca tctcagaaga ggatctgaat    2940
agcgccgtcg accatcatca tcatcatcat tgagtttaaa cggtctccag cttggctgtt    3000
ttggcggatg agagaagatt ttcagcctga tacagattaa atcagaacgc agaagcggtc    3060
tgataaaaca gaatttgcct ggcggcagta gcgcggtggt cccacctgac ccatgccga    3120 actcagaagt gaaacgccgt agcgccgatg gtagtgtggg gtctccccat gcgagagtag    3180
ggaactgcca ggcatcaaat aaaacgaaag gctcagtcga agactgggc ctttcgtttt    3240 atctgttgtt tgtcggtgaa cgctctcctg agtaggacaa atccgccggg agcggatttg    3300
aacgttgcga agcaacggcc cggagggtgg cgggcaggac gcccgccata aactgccagg    3360
catcaaatta agcagaaggc catcctgacg gatggccttt ttgcgtttct acaaactctt    3420
tttgtttatt tttctaaata cattcaaata tgtatccgct catgagacaa taaccctgat    3480
aaatgcttca ataatattga aaaggaaga gtatgagtat tcaacatttc cgtgtcgccc    3540
ttattccctt ttttgcggca ttttgccttc ctgtttttgc tcacccagaa acgctggtga    3600
aagtaaaaga tgctgaagat cagttgggtg cacgagtggg ttacatcgaa ctggatctca    3660
acagcggtaa gatccttgag agttttcgcc ccgaagaacg ttttccaatg atgagcactt    3720
ttaaagttct gctatgtggc gcggtattat cccgtgttga cgccgggcaa gagcaactcg    3780
gtcgccgcat acactattct cagaatgact tggttgagta ctcaccagtc acagaaaagc    3840
atcttacgga tggcatgaca gtaagagaat tatgcagtgc tgccataacc atgagtgata    3900
acactgcggc caacttactt ctgacaacga tcggaggacc gaaggagcta accgcttttt    3960
tgcacaacat gggggatcat gtaactcgcc ttgatcgttg ggaaccggag ctgaatgaag    4020
ccataccaaa cgacgagcgt gacaccacga tgcctgtagc aatggcaaca acgttgcgca    4080
aactattaac tggcgaacta cttactctag cttcccggca acaattaata gactggatgg    4140
aggcggataa agttgcagga ccacttctgc gctcggccct tccggctggc tggtttattg    4200
ctgataaatc tggagccggt gagcgtgggt ctcgcggtat cattgcagca ctggggccag    4260
atggtaagcc ctcccgtatc gtagttatct acacgacggg gagtcaggca actatggatg    4320
aacgaaatag acagatcgct gagataggtg cctcactgat taagcattgg taactgtcag    4380
accaagttta ctcatatata ctttagattg atttaaaact tcatttttaa tttaaaagga    4440
tctaggtgaa gatcctttt gataatctca tgaccaaaat cccttaacgt gagttttcgt    4500
tccactgagc gtcagacccc gtagaaaaga tcaaaggatc ttcttgagat cctttttttc    4560
tgcgcgtaat ctgctgcttg caaacaaaaa aaccaccgct accagcggtg gtttgtttgc    4620
cggatcaaga gctaccaact ctttttccga aggtaactgg cttcagcaga gcgcagatac    4680
caaatactgt ccttctagtg tagccgtagt taggccacca cttcaagaac tctgtagcac    4740
cgcctacata cctcgctctg ctaatcctgt taccagtggc tgctgccagt ggcgataagt    4800
cgtgtcttac cgggttggac tcaagacgat agttaccgga taaggcgcag cggtcgggct    4860 gaacggggg ttcgtgcaca cagcccagct tggagcgaac gacctacacc gaactgagat    4920
acctacagcg tgagctatga gaaagcgcca cgcttcccga agggagaaag gcggacaggt    4980
atccggtaag cggcagggtc ggaacaggag agcgcacgag ggagcttcca gggggaaacg    5040
cctggtatct ttatagtcct gtcgggtttc gccacctctg acttgagcgt cgatttttgt    5100
```

-continued

```
gatgctcgtc aggggggcgg agcctatgga aaaacgccag caacgcggcc ttttttacggt      5160
tcctggcctt ttgctggcct tttgctcaca tgttctttcc tgcgttatcc cctgattctg      5220
tggataaccg tattaccgcc tttgagtgag ctgataccgc tcgccgcagc cgaacgaccg      5280
agcgcagcga gtcagtgagc gaggaagcgg aagagcgcct gatgcggtat tttctcctta      5340
cgcatctgtg cggtatttca caccgcatat ggtgcactct cagtacaatc tgctctgatg      5400
ccgcatagtt aagccagtat acactccgct atcgctacgt gactgggtca tggctgcgcc      5460
ccgacacccg ccaacacccg ctgacgcgcc ctgacgggct tgtctgctcc cggcatccgc      5520
ttacagacaa gctgtgaccg tctccgggag ctgcatgtgt cagaggtttt caccgtcatc      5580
accgaaacgc gcgaggcagc agatcaattc gcgcgcgaag gcgaagcggc atgcatttac      5640
gttgacacca tcgaatggtg caaaacctttt cgcggtatgg catgatagcg cccggaagag      5700
agtcaattca gggtggtgaa tgtgaaacca gtaacgttat acgatgtcgc agagtatgcc      5760
ggtgtctctt atcagaccgt ttcccgcgtg gtgaaccagg ccagccacgt ttctgcgaaa      5820
acgcgggaaa aagtggaagc ggcgatggcg gagctgaatt acattcccaa ccgcgtggca      5880
caacaactgg cgggcaaaca gtcgttgctg attggcgttg ccacctccag tctggccctg      5940
cacgcgccgt cgcaaattgt cgcggcgatt aaatctcgcg ccgatcaact gggtgccagc      6000
gtggtggtgt cgatggtaga cgaagcggc gtcgaagcct gtaaagcggc ggtgcacaat      6060
cttctcgcgc aacgcgtcag tgggctgatc attaactatc cgctggatga ccaggatgcc      6120
attgctgtgg aagctgcctg cactaatgtt ccggcgttat tcttgatgt ctctgaccag      6180
acacccatca acagtattat tttctcccat gaagacggta cgcgactggg cgtggagcat      6240
ctggtcgcat tgggtcacca gcaaatcgcg ctgttagcgg gcccattaag ttctgtctcg      6300
gcgcgtctgc gtctggctgg ctggcataaa tatctcactc gcaatcaaat tcagccgata      6360
gcggaacggg aaggcgactg gagtgccatg tccggttttc aacaaaccat gcaaatgctg      6420
aatgagggca tcgttcccac tgcgatgctg gttgccaacg atcagatggc gctgggcgca      6480
atgcgcgcca ttaccgagtc cgggctgcgc gttggtgcgg atatctcggt agtgggatac      6540
gacgataccg aagacagctc atgttatatc ccgccgtcaa ccaccatcaa acaggatttt      6600
cgcctgctgg ggcaaaccag cgtggaccgc ttgctgcaac tctctcaggg ccaggcggtg      6660
aagggcaatc agctgttgcc cgtctcactg gtgaaaagaa aaaccaccct ggcgcccaat      6720
acgcaaaccg cctctccccg cgcgttggcc gattcattaa tgcagctggc acgacaggtt      6780
tcccgactgg aaagcgggca gtgagcgcaa cgcaattaat gtgagttagc gcgaattgat      6840
ctg                                                                    6843
```

<210> SEQ ID NO 16
<211> LENGTH: 6776
<212> TYPE: DNA
<213> ORGANISM: Artificial Sequence
<220> FEATURE:
<223> OTHER INFORMATION: pCMP1029 (PKL from Lactobacillus reuteri)

<400> SEQUENCE: 16

```
gtttgacagc ttatcatcga ctgcacggtg caccaatgct tctggcgtca ggcagccatc        60
ggaagctgtg gtatggctgt gcaggtcgta atcactgca taattcgtgt cgctcaaggc       120
gcactcccgt tctggataat gttttttgcg ccgacatcat aacggttctg gcaaatattc       180
tgaaatgagc tgttgacaat taatcatccg gctcgtataa tgtgtggaat tgtgagcgga       240
taacaatttc acacaggaaa cagcgccgct gagaaaaagc gaagcggcac tgctctttaa       300
```

| | |
|---|---|
| caatttatca gacaatctgt gtgggcactc gaccggaatt atcgattaac tttattatta | 360 |
| aaaattaaag aggtatatat taatgtatcg attaaataag gaggaataaa catggcagta | 420 |
| gattacgatt ccaagaaata cttggaaagt gttgatgctt actggcgtgc agctaactac | 480 |
| ctttcagttg gtacattgta cttaatgggt gatccattac ttcgccaacc attaaaggca | 540 |
| gaagatgtta agcctaagcc aattggtcac tggggtacta ttgttcctca aaacttcatt | 600 |
| tacgcacact tgaaccgtgt aattaagaag tatgaccttg atatgttcta catcgaaggt | 660 |
| tcaggtcacg gtggccaagt tatggttaac aactcatact tggatggttc atacactgaa | 720 |
| atttatcctg aatatactca agacactaag ggaatggcta agttattcaa gcacttctca | 780 |
| ttcccaggcg gtactgcatc acacgctgca cctgaaacac aggttcaat ccacgaaggt | 840 |
| ggggaacttg gttactcact ttcacacggt gttggtgcta tcttagataa cccagaagtt | 900 |
| attgccgctg ttgaaatcgg tgatggtgaa gctgaaactg gtccattaat ggcatcatgg | 960 |
| ttctcagaca agttcattaa cccaatcaag gatggtgcgg tattaccaat catccaagtt | 1020 |
| aacggattca agatttctaa ccctactatc ctttcatgga tgagcgacga agaacttact | 1080 |
| aagtacttcg aaggtatggg ttggaagcca tactttgttt cagcttacaa agaagctgac | 1140 |
| cgtgatggtg aattcaaggg ttacaagcct cacatggaag ttcacgaaga aatggctaag | 1200 |
| actttggaca aggttgttga agaaatcaag gctattcaaa agaacgctcg tgaaaacaat | 1260 |
| gataactcat taccacaatg gccaatgatt atcttccgtg cacctaaggg ttggactggt | 1320 |
| cctaagactg accttgatgg taacccaatt gaaaactcat tccgtgcaca ccaaattcca | 1380 |
| gttccagtat cccaagatga catggaacac aaggacatcc ttgttgattg gttgaagtca | 1440 |
| tacaagccag aagaattgtt tgacgaagat ggtcacccag ttgctcttgt tgaagagaac | 1500 |
| acaccagaag gtaaccgtcg tatggctatg aaccctatca ctaatggtgg tatcgatcct | 1560 |
| aagccacttg tattgccaaa ctaccgtgat tttgctattg atgttcaaaa tcctggttct | 1620 |
| gttgtaaagc aagacatgct tgaatggggt aagtacctca acaagatggc tgaattgaac | 1680 |
| ccaactaact tccgtggatt tggtcctgac gaatctaagt caaaccgtct ttacgcattc | 1740 |
| cttgatggtc aaaagcgtca atggatggaa agtgtccacg aaccaaacga cgaagatgtg | 1800 |
| gctccacaag gtcgtatgat cgattccaca cttcagaac accaagctga aggattcctt | 1860 |
| gaaggttaca cattaactgg tcgtcacgga ttcttcgcaa cttacgaagc attcggtcgt | 1920 |
| gttgttgatt caatgcttac tcaacacatg aagtggttac gtaaggctaa ggatctttac | 1980 |
| tggcgtcacc aatacccagc attgaacttt gttgatactt ctactgtatt ccaacaagat | 2040 |
| cacaacggtt acactcacca agatccaggt ctattgactc acttgtttga aaaggaacgt | 2100 |
| ccagacctcg ttaaggaata cttgccagca gatactaact cattaatggc tgtatctaac | 2160 |
| aaggcattcc gtaaccaaga atgcatcaac ctcttcgtaa cttctaagca cccacgtgca | 2220 |
| caatggttct ctattgatga agctactcaa ttggctgaca atggtcttgg ctacattgac | 2280 |
| tgggcatcta ctgaccaagg tactgaacca gatgttgtat ttgcatcttc tggtactgaa | 2340 |
| cctactgaag aagctcttgc agctattgac attcttcatg caacttccc tgaattgaag | 2400 |
| attcgttaca tcaacatcat cgaaattatg cgtttgatga acactgacaa gaaccctgaa | 2460 |
| ggtttaactg atgctgaatt caatagttac ttcactactg acaagccagt tatctttgca | 2520 |
| tggcacggat ccgtgacat gatccaagca ttgttcttcg atcgtgctaa ccgtaacgtt | 2580 |
| cacattcact catacgaaga aaatggtgat atcaccactc cattcgacat gcgtgtatta | 2640 |

```
aacgaacttg accggttcca cttagctaag gacgctatcc aaagtgttcc tggttacgaa    2700
caaaagagtg ctgcatttgt tgccaagatg gacaacatga tcaacaagca caaccactac    2760
atccgttcag aaggtaagga cttaccagaa gttactaact ggacttggaa gggtcttaag    2820
taagaattcg aagctttcta gaacaaaaac tcatctcaga gaggatctg aatagcgccg     2880 tcgaccatca tcatcatcat cattgagttt aaacggtctc cagcttggct gttttggcgg    2940
atgagagaag attttcagcc tgatacagat taaatcagaa cgcagaagcg gtctgataaa    3000
acagaatttg cctggcggca gtagcgcggt ggtcccacct gaccccatgc cgaactcaga    3060
agtgaaacgc cgtagcgccg atggtagtgt ggggtctccc catgcgagag tagggaactg    3120
ccaggcatca aataaaacga aaggctcagt cgaaagactg ggcctttcgt tttatctgtt    3180
gtttgtcggt gaacgctctc ctgagtagga caaatccgcc gggagcggat ttgaacgttg    3240
cgaagcaacg gcccggaggg tggcgggcag gacgcccgcc ataaactgcc aggcatcaaa    3300
ttaagcagaa ggccatcctg acggatggcc tttttgcgtt tctacaaact cttttttgttt   3360 attttctaa atacattcaa atatgtatcc gctcatgaga caataaccct gataaatgct     3420
tcaataatat tgaaaaagga agagtatgag tattcaacat ttccgtgtcg cccttattcc    3480
cttttttgcg gcattttgcc ttcctgtttt tgctcaccca gaaacgctgg tgaaagtaaa    3540
agatgctgaa gatcagttgg gtgcacgagt gggttacatc gaactggatc tcaacagcgg    3600
taagatcctt gagagttttc gccccgaaga acgttttcca atgatgagca cttttaaagt    3660
tctgctatgt ggcgcggtat tatcccgtgt tgacgccggg caagagcaac tcggtcgccg    3720
catacactat tctcagaatg acttggttga gtactcacca gtcacagaaa agcatcttac    3780
ggatggcatg acagtaagag aattatgcag tgctgccata accatgagtg ataacactgc    3840
ggccaactta cttctgacaa cgatcggagg accgaaggag ctaaccgctt ttttgcacaa    3900
catgggggat catgtaactc gccttgatcg ttgggaaccg gagctgaatg aagccatacc    3960
aaacgacgag cgtgacacca cgatgcctgt agcaatggca acaacgttgc gcaaactatt    4020
aactggcgaa ctacttactc tagcttcccg gcaacaatta atagactgga tggaggcgga    4080
taaagttgca ggaccacttc tgcgctcggc ccttccggct ggctggttta ttgctgataa    4140
atctggagcc ggtgagcgtg ggtctcgcgg tatcattgca gcactggggc cagatggtaa    4200
gccctcccgt atcgtagtta tctacacgac ggggagtcag gcaactatgg atgaacgaaa    4260
tagacagatc gctgagatag gtgcctcact gattaagcat tggtaactgt cagaccaagt    4320
ttactcatat atactttaga ttgatttaaa acttcatttt taatttaaaa ggatctaggt    4380
gaagatcctt tttgataatc tcatgaccaa aatcccttaa cgtgagtttt cgttccactg    4440
agcgtcagac cccgtagaaa agatcaaagg atcttcttga gatcctttt ttctgcgcgt     4500 aatctgctgc ttgcaaacaa aaaaaccacc gctaccagcg gtggtttgtt tgccggatca    4560
agagctacca actctttttc cgaaggtaac tggcttcagc agagcgcaga taccaaatac    4620
tgtccttcta gtgtagccgt agttaggcca ccacttcaag aactctgtag caccgcctac    4680
atacctcgct ctgctaatcc tgttaccagt ggctgctgcc agtggcgata agtcgtgtct    4740
taccgggttg gactcaagac gatagttacc ggataaggcg cagcggtcgg gctgaacggg    4800
gggttcgtgc acacagccca gcttggagcg aacgacctac accgaactga gatacctaca    4860
gcgtgagcta tgagaaagcg ccacgcttcc cgaagggaga aaggcggaca ggtatccggt    4920
aagcggcagg gtcggaacag gagagcgcac gagggagctt ccagggggaa acgcctggta    4980
tctttatagt cctgtcgggt ttcgccacct ctgacttgag cgtcgatttt tgtgatgctc    5040
```

```
gtcaggggggg cggagcctat ggaaaaacgc cagcaacgcg gccttttttac ggttcctggc    5100 cttttgctgg cctttttgctc acatgttctt tcctgcgtta tccccctgatt ctgtggataa    5160 ccgtattacc gcctttgagt gagctgatac cgctcgccgc agccgaacga ccgagcgcag    5220
cgagtcagtg agcgaggaag cggaagagcg cctgatgcgg tattttctcc ttacgcatct    5280
gtgcggtatt tcacaccgca tatggtgcac tctcagtaca atctgctctg atgccgcata    5340
gttaagccag tatacactcc gctatcgcta cgtgactggg tcatggctgc gccccgacac    5400
ccgccaacac ccgctgacgc gccctgacgg gcttgtctgc tcccggcatc cgcttacaga    5460
caagctgtga ccgtctccgg gagctgcatg tgtcagaggt tttcaccgtc atcaccgaaa    5520
cgcgcgaggc agcagatcaa ttcgcgcgcg aaggcgaagc ggcatgcatt tacgttgaca    5580
ccatcgaatg gtgcaaaacc tttcgcggta tggcatgata cgcccggaa gagagtcaat    5640 tcagggtggt gaatgtgaaa ccagtaacgt tatacgatgt cgcagagtat gccggtgtct    5700
cttatcagac cgtttcccgc gtggtgaacc aggccagcca cgtttctgcg aaaacgcggg    5760
aaaaagtgga agcggcgatg gcggagctga attacattcc caaccgcgtg gcacaacaac    5820
tggcgggcaa acagtcgttg ctgattggcg ttgccacctc cagtctgcc ctgcacgcgc    5880 cgtcgcaaat tgtcgcggcg attaaatctc gcgccgatca actgggtgcc agcgtggtgg    5940
tgtcgatggt agaacgaagc ggcgtcgaag cctgtaaagc ggcggtgcac aatcttctcg    6000
cgcaacgcgt cagtgggctg atcattaact atccgctgga tgaccaggat gccattgctg    6060
tggaagctgc ctgcactaat gttccggcgt tatttcttga tgtctctgac cagacaccca    6120
tcaacagtat tattttctcc catgaagacg gtacgcgact gggcgtggag catctggtcg    6180
cattgggtca ccagcaaatc gcgctgttag cgggcccatt aagttctgtc tcggcgcgtc    6240
tgcgtctggc tggctggcat aaatatctca ctcgcaatca aattcagccg atagcggaac    6300
gggaaggcga ctggagtgcc atgtccggtt ttcaacaaac catgcaaatg ctgaatgagg    6360
gcatcgttcc cactgcgatg ctggttgcca acgatcagat ggcgctgggc gcaatgcgcg    6420
ccattaccga gtccgggctg cgcgttggtg cggatatctc ggtagtggga tacgacgata    6480
ccgaagacag ctcatgttat atcccgccgt caaccaccat caaacaggat tttcgcctgc    6540
tggggcaaac cagcgtggac cgcttgctgc aactctctca gggccaggcg gtgaagggca    6600
atcagctgtt gcccgtctca ctggtgaaaa gaaaaaccac cctggcgccc aatacgcaaa    6660
ccgcctctcc ccgcgcgttg gccgattcat taatgcagct ggcacgacag gtttcccgac    6720
tggaaagcgg gcagtgagcg caacgcaatt aatgtgagtt agcgcgaatt gatctg    6776
```

<210> SEQ ID NO 17
<211> LENGTH: 2496
<212> TYPE: DNA
<213> ORGANISM: Artificial Sequence
<220> FEATURE:
<223> OTHER INFORMATION: Synthetic Construct

<400> SEQUENCE: 17

```
atgagcaccg tgtgcatat gaccagtccg gttattggca ccccgtggaa aaaactgaat      60
gcaccggtta gcgaagcagc aattgaaggt gttgataaat actggcgtgt tgcaaattat    120
ctggccattg gtcagattta tctgcgtagc aatccgctga tgaaagaacc gtttacccgt    180
gaagatgtta acatcgtcct ggttggtcat tggggcacca caccgggtct gaattttctg    240
attggtcata ttaatcgctt tatcgccgat catcagcaga acaccgtgat tattatgggt    300
```

| | |
|---|---|
| ccgggtcatg gtggtccggc aggcaccgca cagagctatc tggatggcac ctataccgaa | 360 |
| tattatccga aaatcaccaa agatgaagcc ggtctgcaaa aattctttcg ccagtttagc | 420 |
| tatccggtg gtattccgag ccatttgca ccggaaacac cgggtagcat ccatgaaggt | 480 |
| ggtgaactgg gttatgcact gagccatgca tatggtgcag ttatgaataa tccgagcctg | 540 |
| tttgttccgg caattgttgg tgatggtgaa gcagaaaccg gtccgctggc caccggttgg | 600 |
| cagagcaata aactggttaa ccgcgtacc gatggtattg ttctgccgat tctgcatctg | 660 |
| aatggctata aaatcgcaaa tccgaccatt ctgagccgca ttagtgatga agaactgcac | 720 |
| gaattttttc acggtatggg ttatgaaccg tatgaatttg ttgccggttt tgatgatgaa | 780 |
| gatcatatgt caattcatcg tcgctttgcc gatatgtttg aaaccatctt tgatgagatc | 840 |
| tgcgatatta agccgaagc acagaccaat gatgttaccc gtccgtatta tccaatgatt | 900 |
| atctttcgta ccccgaaagg ttggacctgt ccgaaattta tcgatggcaa aaaaaccgaa | 960 |
| ggtagctggc gtgcacatca ggttccgctg caagcgcac gtgataccga agcccatttt | 1020 |
| gaagttctga aaaactggat gaaaagctat aaaccggaag aactgttcga tgaaaaggt | 1080 |
| gccgttaaag aagatgtgct gagctttatg ccgaaaggtg aactgcgtat tggtgaaaat | 1140 |
| ccgaatgcaa atggtggtcg tattcgtgaa gatctgaaac tgccgaaact ggacgattat | 1200 |
| gaagtcaaag aagttaaaga atttggccat ggttgggtc agctggaagc aacccgtcgt | 1260 |
| ctgggtgttt atacccgtga tattatcaaa acaacccgg acagctttcg tattttggt | 1320 |
| ccggatgaaa ccgcaagcaa tcgtctgcaa gcagcatatg aagttaccaa taaacagtgg | 1380 |
| gatgcaggtt atctgagcgg tctggttgat gaacacatgg cagttaccgg tcaggttacc | 1440 |
| gaacagctga gcgaacatca gatggaaggt tttctggaag ctatctgct gaccggtcgt | 1500 |
| catggtattt ggagcagcta tgaaagcttt gtgcatgtga ttgatagcat gctgaaccag | 1560 |
| catgccaaat ggctggaagc caccgttcgt gaaattccgt ggcgtaaacc gattagcagc | 1620 |
| gttaatctgc tggttagcag ccatgtttgg cgtcaggatc ataatggttt tagccatcag | 1680 |
| gatccgggtg ttaccagcgt gctgctgaat aaaacctta ataatgatca tgtgatcggc | 1740 |
| atctatttcc cggttgatag caacatgctg ctggcagttg cagaaaaagc atataaaagc | 1800 |
| accaacatga tcaacgccat tttcgcaggt aaacagcctg ccgcaacctg gctgaccctg | 1860 |
| gatgaagcac gcgaagaact ggaaaaaggc gcagcagaat ggaaatgggc aagcaatgca | 1920 |
| aaaaacaatg atgaagttca ggttgttctg gcaggcgtgg gtgatgttcc gcagcaagaa | 1980 |
| ctgatggcag cagccgataa actgaacaaa ctgggtgtta aattcaaagt ggtgaatgtt | 2040 |
| gtggatctgc tgaaactgca aagcgccaaa gaaataatg aagcactgac cgatgaagag | 2100 |
| tttaccgaac tgtttacagc agataaaccg gttctgtttg cctatcatag ttatgcacat | 2160 |
| gatgttcgtg gcctgattta tgatcgtccg aaccatgata actttaacgt gcacggttat | 2220 |
| aaagaacagg gtagcaccac caccccgtat gatatggttc gtgttaatga tatggatcgc | 2280 |
| tatgaactga cagcggaagc actgcgtatg gttgatgcag caaatatgc cgatgaaatc | 2340 |
| aaagagctgg aagattttcg tctggaagca tttcagtatg ccgttgataa aggtctggat | 2400 |
| catccggatt ataccgattg ggtttggcct ggtgttaaaa ccgataaacc tggtgcggtt | 2460 |
| accgcaaccg cagccaccgc aggcgataat gaataa | 2496 |

<210> SEQ ID NO 18
<211> LENGTH: 2382
<212> TYPE: DNA
<213> ORGANISM: Artificial Sequence
<220> FEATURE:
<223> OTHER INFORMATION: Synthetic Construct

<400> SEQUENCE: 18

```
atgacattag ccagtcctct acaaacaaag cctttaacag atgaagaatt acgcaagata    60
aacgcttact ggcgtgcagc taactatctt tcagttggac agatatatct actcgacaat   120
ccactactga gagaaccgct aaagcttgaa cacgtcaaac ccaggctctt gggtcactgg   180
ggaacaacac cagggctgaa ctttatctat gctcacttga atcgggtcat caaaaaatat   240
gacctaaaca cgatctatat tgctggccct ggtcatggtg ccctggact agtagccaac    300
acctacctag aaggcactta caccaagtat tatcacaaca tctcccagga tgctgaagga   360
attcagaaac tcttcaagca attttctttt cctggtggta ttcccagcca cgttgcacca   420
gaaaccctg gttcgatcca tgaaggcggg gaactaggtt atgcccttgt ccacgctttc    480
ggtgctgcct ttgataaccc tgacttgatc gttgctgctg ttgtgggtga cggcgaagct   540
gaaacaggtg ctttagcaac tagctggcat tccaacaagt ttcttaaccc cgtgcatgat   600
ggggctgtac tgccgatcct gcacttgaat gggtataaaa ttgctaatcc aacagtactg   660
gcacggatca gccatgagga attagaaagc ttatttgtcg gctacggcta caagccctac   720
tttgtcgaag gtgacgatcc cgcagatgta catcagcaga tggcggcgac tctagatata   780
gcgatcgccg aaattcaaag tatccaaaga gaagcccgcg tacatggtta cactgaacgt   840
cctcagtggc cgatgattgt catgaaaacc cccaaaggtt ggacagggcc aaaggaagtt   900
gatggtaaaa aaactgaagg ttcttggcga tcgcaccaag ttccctttgg gaatatcgcc   960
aaacagccag aacatctgaa actcctagaa gattggatga gagttacaa accagaagaa  1020
ctcttcgacg ctaacggcac actaatccca gaactagcag aattggctcc caaaggccat  1080
cgacgcatgg gtgacaatcc ccacgctaac ggcggtcttt tgctgcgcga cctgaagatg  1140
cccgacttcc aaaagtatgc tgtagatgtt ctcaaaccag gcaagcgat cgctgaagct   1200
acccaagttg caggaatttt cctccgggat attatgcaac ttaaccaaga aagccgcaac  1260
ttccgcatcg tcggccccga tgaaacggta tcaaatcgct taggcgctgt gctagaagtt  1320
acagatcggg attgggcagc ccagatactc cccgaagatg accaccttc ccccgatggt   1380
cgggtgatgg aaattctcag cgaaactaat tgtcaaggat ggttagaagg ctacctcctc  1440
acaggacgac acgggttttt ctcttgctac gaggcgttta ccacatcgt ggactcgatg   1500
ttcaatcagc acgccaaatg gctgaaaacg actagacata ttccttggcg taaaccaatt  1560
gcttccctta attatctact tacctctcac gtttggcggc aagaccataa cggtttttcc  1620
caccaagacc ctggttttat tgaccatgta gttaataaga agcagagat cgttcgcgtg   1680
tatttgcccc ccgatgccaa cactctgcta tcggtaactg accattgttt aagaagccgc  1740
aactatgtca acgtcatcgt tgccggaaag caaccagcat tgcaataacct aaatatggat  1800
gctgctatca agcactgcac caaaggcatc ggtatttggg aatgggcaag caacgataaa  1860
gacggcgaac cagatgtagt aatggcttgt gctggggata tccccacctt agaaacttta  1920
gcggctgtgg acattctgcg ccagcacttc cctgagttaa aggtgcgggt agtgaacgta  1980
gtcgatttga tgacactaca gccaaaaagt gaacacccgc acggtttgag cgaaaaagac  2040
tttgacacga ttttcaccac cgataaacac attatctttg cctttcatgg ctatccttgg  2100
ctgattcatc gcttaaccta tcgccacacc aatcacgagc agttgcatgt gcgtggctac  2160
aaggaagaag gaaccaccac cactcccttt gatatggttg tgcttaacga gctagatcgc  2220
```

-continued

| | |
|---|---|
| ttccatctag tgatggatgt aatcgatcgc gtaccaaagc taggatatag ggcagcttat | 2280 |
| gtcaaacagc agttgcaaga taaactgatc gaacacaaac attacattga gaagtacggc | 2340 |
| gacgatatgc cggaaattcg tgactggaag tggccctatt aa | 2382 |

<210> SEQ ID NO 19
<211> LENGTH: 2352
<212> TYPE: DNA
<213> ORGANISM: Artifical Sequence
<220> FEATURE:
<223> OTHER INFORMATION: Synthetic Construct

<400> SEQUENCE: 19

| | |
|---|---|
| atgtccgacg tgttgtccaa cgatctgttg cagaagatgg acgcctattg gcgcgccgcg | 60 |
| aactacctgt ctgtcggaca gatctatctg caggacaatc cgctactcga tcagaagctg | 120 |
| cagctcgacc acatcaagcc gcgcctgctt ggccactggg gtacgacccc cggcctcaat | 180 |
| cttctctacg tgcatctcaa ccggctgatc accgagcatg atctcgatat gatctacatt | 240 |
| accggtcccg gccatggcgg gcccggcttg gttgccaacg cgtatctgga aggcacctac | 300 |
| accgagcgct atccggcgat tgagcgcagc cgcaacggca tgcagcggct gttccgacaa | 360 |
| ttctcctggc cgcacggcgt gccgagccac gtctcgccgg aaacgcccgg ctcgatccac | 420 |
| gagggcggcg aactcggcta ctcgctggcg catgcctatg cgcggcgtt cgacaatccg | 480 |
| aatctgatcg tcgcttgcgt ggtcggcgac ggcgaggccg agaccggcgc tctggcgacg | 540 |
| agttggcact ccaacaagtt cctcaatccg gcgcgcgacg gcgcggtgct gccgatcctg | 600 |
| catctgaacg gcttcaagat tgccaacccg accgtgctgg cacggatcac gccgcaggaa | 660 |
| ctcaccgacc tgatgcgcgg ctatggctat gagccgcact tcgtcgaagg cgacgatccg | 720 |
| gcggtggtgc accagacgct ggctgcgacg ctggaacgcg tgctcggcga gatccgggcc | 780 |
| attcaggaca aggctcgcaa ccacggcgac accgagcggc gcgctggcc gatgatcgtg | 840 |
| atgcggaccc cgaaggggtg gaccggcccc aagcaggtcg acggcaagcc ggtggagggc | 900 |
| acctggcgcg cccatcaggt gccgatcgcg gacttcaaga accccgagca tctgacgctg | 960 |
| ctcgaagact ggatgcgcag ctatcggccc gatgagctgt tcgacgccac cggcaagctg | 1020 |
| cgcgacgagc tgcaggcgct ggccgccgac cggccgtcgc cggatgagcgc caatccgcac | 1080 |
| gccaatggcg gcgaattgct ggagccgctg tcgctgcccg atttccacga ctatgcggtg | 1140 |
| acgctgaccg ggcccggcgc gctgaaggcc gaggcgacgc gggtgctcgg caccttcctg | 1200 |
| cgcgacgtga tgaagaacag cctcgagagc gaaaacttcc gcctgttcgg accggacgag | 1260 |
| accgcatcga accggctcga tgcggtgctc caggtctcgc cgaaggagtg gatggcggcg | 1320 |
| atcgaggatg tcgacgtcga tctcagcccg gacggccggg tgatggaggt gctcagcgag | 1380 |
| catctatgcc agggctggct cgaaggctat ctgctgaccg gccgccacgg cttcttctcg | 1440 |
| tgctacgagg cgttcatcca catcatcgac tcgatgttca atcagcacgc caaatggctg | 1500 |
| aaggcgtgcg ccacgatccc gtggcggaag ccgatcgcgt cgctgaacta tctgctgacc | 1560 |
| tcgcacgtct ggcgccagga tcacaacggg ttctcgcacc aggatcccgg cttcatcgac | 1620 |
| cacgtcgcca acaagaagtc gaacgtggtc cggatctatc tgccgccgga tgccaactgt | 1680 |
| ctgctgtcgg tggccgacca ctgcctgcgc agccgcaact acgtcaacct gatcgtcgcc | 1740 |
| ggcaagcagc cggaatggca gtggctggat atcgacgccg ccgttcggca ctgcaccaca | 1800 |
| ggagcccggga tctggcattg gccagcgac gagggcgagc cgacgtggt gatggcctgc | 1860 |
| gccggcgacg tgccgacggt cgagacgctg gcggcggtca agctgctgcg ggagtacgtg | 1920 |

```
ccggacatca agatccgtgt cgtcaacgtg gtcgacctga tggtgctgca gccgagctcc    1980
gagcatccgc acggcctgga cgaccgccgc ttcgacgagc tgttcaccac cgacaagccg    2040
gtgatcttcg ccttccacgg ctatccgtgg ctgatccacc ggctgaccta tcgccgccgc    2100
aaccacgtca acatccacgt ccgcggctac aaggaagagg gcaccaccac cacgccgttc    2160
gacatggtgg tgctgaacga tctcgaccgt atcgcctggc actcgacgc catcctgcgg    2220 attccgcggc tcgccgatca gcgcgatgcc gccacctcgc gctactgggc gacgatgcag    2280
cggcacaagc tgtatatcgg cgaacacggc gacgatctgc cagaggttcg cgactggcgc    2340
tggtcggcct ga                                                        2352

<210> SEQ ID NO 20
<211> LENGTH: 2385
<212> TYPE: DNA
<213> ORGANISM: Artificial Sequence
<220> FEATURE:
<223> OTHER INFORMATION: Synthetic Construct

<400> SEQUENCE: 20
atgagctata gtccggcaag tccggaattt accctgctgg atcgttattg gcgtgcagca      60
aattatctga gcgttggtca gatttatctg atggataatc cgctgctgcg tgaaccgctg     120
cgtccggaac acattaaacc gcgtctgctg ggtcattggg gcaccacacc gggtctgaat     180
tttatctatg cacatctgaa tcgcgtgatc cgtaaacaga atctggatat gatttatatc     240
tgtggtccgg tcatggcgg tcctggtatg gttgcaaata cctggctgga aggtagctat     300
agcgaaattt atccgcatat tagccaggat gcagcaggta tgcagcgtct gttcaaacag     360
tttagctttc cgggtggtat tccgagccat gcagcaccgg aaacaccggg tagcattaat     420
gaaggtggtg aactgggtta tagcctgagc catgcctttg gtgcagcatt tgataatccg     480
gatctggttg ttccgtgtgt tattggtgat ggtgaagcag aaaccggtcc gctggcaagc     540
agctggcatg gtatcaaatt tctgaatccg gaacgtgatg gtgcagttct gccgattctg     600
catctgaatg gctataaaat cgcaaatccg acactgctgg acgtagcag tgatgaagat     660 ctgcaccagc tgtttagcgg ttatggttat gaacctctgt tgtttgtgg ccatgaaccg     720 gaaaaaatgc atccgctgat ggcagaaacc ctggataccg catttagcaa aattgcagca     780
tatcagcgtg aagcacgtag cggtaatgca agcaatgatg ttccgcgttg gccgatgatt     840
attctgcgta gcccgaaagg ttggacaggt ccggaaaccg ttgatggtaa aaaagttgaa     900 gattttggc gtgcccatca ggtgccggtt gcagcatgtc gtgaagatga aggtcatcgt     960
cagattctgg aaacctggat gcgtagctat cagccggatg acctgtttga tgaacagggt    1020
cgtctgaaac tgaactgca agccctggca ccggaaggta taaacgtat gggtgcaagc    1080 ccgtatgcaa atggtggtct gctgcgtcgt gaactggatg caccggatat tgcagaattt    1140
gcatgtgata ttagcgaacc gggtacagaa attgcacagg caaccgaaca tctgggtcgt    1200
tatctgagtg ttctgtttca gcgtaatcgt gataattttc gtctgtttgg tccggatgaa    1260
accgcaagca atcgtctgac accggttttt gatgttacca gccgtacatg gctggaacgt    1320
attgaaccgt atgatgaaca actggcacgt gatggccgtg ttatggaaat tctgagcgaa    1380
catcagtgtc agggttggct ggaaggctat ctgctgaccg tcgtcatgg tctgtttaat    1440 tgttatgaag ccttatcca tatcgtggat agcatgttta atcagcatgc caaatggctg    1500
aaagttaccc gtaaactggg ttggcgtaaa ccgattagca gcctgaatta tctgctgtca    1560
```

```
agccatgttt ggcgtcagga tcataatggt tatagtcatc aggatccggg tttattgat      1620 catgtggcaa acaaaaaagc cgatatcgtg cgtatttatc tgcctccgga tgcaaataca      1680
ctgctgtggg ttggtgatca ttgtctgcgt acctgggatc gtattaatgt tattgttgca      1740
ggtaaacagc ctgcaccgca gtggctggat atggcaagcg cagttaccca ttgtgaagcc      1800
ggtatgggtg aatggcgttg ggcaggtaca acaccagccc atgatcagcc tgatgttgtt      1860
atggcatgtg ccggtgatgt gccgaccatg gaaaccatgg cagcagttga tctgctgcgc      1920
gaaatgctgc cggaactgcg tattcgtgtt gttaatgttg tggatctgct ggcactgcaa      1980
cctgaagatc agcatccgca tggtaaaagt gatgccgaat tgatgcact gtttacccag      2040 gataaaccgg tgattttgc ctttcatggt tatccgacgc tgattcaccg tctgacctat      2100
agccgtacca atcatcgtaa ttttcatgtg cgtggctta tgaagaagg tacgaccacc      2160 accccgtttg atatgaccgt tctgaacgaa ctggatcgct atcatctggc acaagaagca      2220
attctgcgcg ttccgggtct ggcagatgca catccagaac tgctggaaga tctgcaacaa      2280
cgtctggcag aacatcatcg ttatgttcgt gaacatggtg aggatctgcc ggaagttcag      2340
aattggaaat ggccgagcgc aaccgcaccg ggtgtgccgg attaa                     2385

<210> SEQ ID NO 21
<211> LENGTH: 2367
<212> TYPE: DNA
<213> ORGANISM: Artificial Sequence
<220> FEATURE:
<223> OTHER INFORMATION: Synthetic Construct

<400> SEQUENCE: 21
atgaaactga gcagcgaaga aaccagcaaa ctgcatgcat attggcgtgc agcaaattat        60
ctgagcgttg gtcagctgta tctgcgtcat aatccgctgc tgaaagaacc gctgaaactg       120
gaacatgtga aaatatgct gctgggtcat tggggcacca caccgggtca gaattttatc       180
tatacccatc tgaatcgcgt gatcaacaaa tatgatctgg atatgattta tgtgagcggt       240
ccgggtcatg gtggtccggc agttgttgca ggcacctatc tggaaggtac atataccgaa       300
gtttatccga atatcaccca ggatgaagat ggtctgcgta aactgtttac ccagttagc       360 tatccgggtg gtattagcag ccatgcaagc cctccgacac cgggtagcat ccatgaaggt       420
ggtgaactgg gttatagcct gagccatagc ttggtgcag ttctggataa tccgagcctg       480
gttgttgcat gtgttgttgg tgatggtgaa gcagaaaccg gtccgctggc aaccgcatgg       540
catagcaaca aatttctgaa tccgctgacc gatggtgttg ttctgccgat tctgcatctg       600
aatggctata aaatcagcaa tccgaccgtt ctggcacgta ttagccatga agaactggaa       660
caactgttta aaggttatgg ttggaccccg tattttgtgg aaggtgaaga accggaagca       720
atgcatcagg caatggcaac cgtgctggat gaagcaattg agcagattaa agccattaaa       780
ctgaatgcaa ccacccaggc agatatggaa cgtccgcgtt ggccgatgat tgtctgcgt       840 agcccgaaag gttggacagg tccgaaagaa gttgatggct caaaattga aggtaacttt       900 cgtgcacatc agattccgct ggccgttagc gcaagcgcac cgcctgaaca tctgcaaatg       960
ctggaagatt ggatgaaaag ctatcatccg gaagaactgt tgatgaaaa tggtcgtctg      1020 aaaccggaac tggccgaact ggcaccgaaa ggtgatcgtc gtatgggtgc aaatccgcat      1080
gcaaatggtg gccagctgct gcgtaatctg cgtctgccgg attttcgtga ttatgcaatt      1140
gccgttaata gtccgggtgt taatggtgaa ggtgatacct atgttagcgg tcgttttctg      1200
cgtgatgtga ttaaagaaaa ccagcacgat cgcaactttc gtatttttgg tccggatgaa      1260
```

```
accgttagca atcgtctgga actggttttt gaagcaacca atcgtcagtg ggatgcaccg    1320
attattgaac atgatgaatt tctggctcgt gatggtagcg ttatggaaat gctgagcgaa    1380
catcagtgtg aaggttggct ggaaggttat ctgctgaccg tcgtcatgg tctgtttaat     1440 tgttatgaag cctttatcca tatcgtggat agcatgttta atcagcacgc aaaatggctg    1500
aaaaccaccc tggaactgcc gtggcgtcgt aaaattgcaa gcctgaatat tctgctgaca    1560
agcaccgttt ggcgtcagga tcataatggt tttacccatc aggatccggg ttttctggat    1620
catgttgtga acaaaaaagc caatattgtg cgtgtttatc tgcctccgga tgcaaattgt    1680
ctgctgagcg tgatggatca ttgcctgcgt agctatcatt atgtgaatgt tattgtggca    1740
ggtaaacatc cggcaccgca gtggctgaat atggaacagg ccattgcaca ttgtacccgt    1800
ggtattggta tttggaattt tgccagtaat gatcaggatg cagaaccgga tgttattatg    1860
gcctgtagcg gtgatgttcc gaccctggaa attctggcag cagttagcat tattcgtgag    1920
catctgccgc agattcgtat tcgtgttatt aatgttgtgg acctgtttaa actgcaaaaa    1980
agcagcgaac atacccatgg tctgagcgat aaagattatg atgccctgtt taccgttaat    2040
aaaccggttg tttttgcctt tcatggttat ccgtggctgg ttcatcgtct gacctataat    2100
cgtgcaaata acaccaatct gcatgtgcgt ggttataaag aagaaggcac cattaccacc    2160
agttttgata tgacagttct gaacgaaatg gatcgttttc atctggcaat ggatgtgatt    2220
gatcgtctgc ctcagaccgg cacccagggt gtgtatctga acagctgct gacagataaa     2280 ctgaccgaac acaaacagta tatcaaagcc aatggtaaag acatgccgga atcctgaat    2340 tggaaatgga atcagccgac ccagtaa                                        2367

<210> SEQ ID NO 22
<211> LENGTH: 2379
<212> TYPE: DNA
<213> ORGANISM: Artificial Sequence
<220> FEATURE:
<223> OTHER INFORMATION: Synthetic Construct

<400> SEQUENCE: 22
atgacaagca ccgaaagcgt tccgcgtcag gcactgaccg ttaccgaact gcaagaaatt      60
gatcgttatt ggcgtgcagc aaattatctg agcgttggtc agatttatct gcaagataat     120
ccgctgctgc gtgaaccgct ggtgccggaa cacattaaac cgcgtctgct gggtcattgg     180
ggcaccacac cgggtctgaa tttttatctat gcacatctga atcatcagat tcgtagccgt    240
ggcaccgaaa tgatgtggat tgttggtccg ggtcatggtg gtccgagtcc ggttgccacc    300
gcatggctgg atggtgttta tagccagatc tatccggatg ttggtcgtaa tgcagaaggt    360
atgcgtcgtc tgtttcgtca gtttagcttt ccgggtggtg ttccgagcca tgcagcaccg    420
gaaacaccgg gtagcatcca tgaaggtggt gaactgggtt atgcactggc acatgcattt    480
ggtgcagcat ttgataatcc ggatctggtt gttgcagcag ttgttggtga tggtgaagca    540
gaaaccggtg cactgagcgg tagctggcag agcattcgtt ttctgaatcc ggcacgtgat    600
ggtgcagttc tgccgattct gcatctgaat ggttacaaaa ttgcaggtcc gaccgttctg    660
gcacgtattc cggaagaaga tctgctggca cagatgcgtg tcatggttta tgaaccgcat    720
gttgttgccg gtgatgatcc ggataccgtt caccagctga tggcaggcac cctggcaagc    780
tgtctggaac gtattgatac cattcgcttt cgtgcacgtc aagaagatgg cgatattgca    840
aatgttcgtt ggcgtgatga tattctgcgt acccgtgaag gttggacagg tccgcgtgca    900
```

```
gttgatggta aaccggttga agatacctgg cgtagccatc aggttccgct ggcagcaacc      960
cgtgaaaatc cggaacatct gcgcctgctg aagaatggc tgcgtagcta tcgtcctgaa      1020
gaactgtttg atgaacatgg tgcaccgcgt ccggaaacca ccaccgttgt tccgcctccg     1080
gattgtcgta ttagcagcag tccgcatgca aatggtggtc tgctgctgcg cgacctgctg     1140
ctgcctgatt ttcgtgatta tgcagttgaa gttgaacgtc cgggtgttga tatggttgaa     1200 gccaccgtg ttctgggtgg ttttctgcgt gatgttgtgg cagcaaatcc gcataatttt      1260
cgcattatgg gtccggatga aacccagagc aatcgtctgg gtgcagttt tgaaagcacc      1320 gatcgtgcat ggaccaccga acgtctgccg gttgatcagc agctgagtcc ggatggtcgt     1380
gttatggaag ttctgaatga acagctgtgt cagggttggc tggaaggtta tctgctgacc     1440
ggtcgtcatg gtctgtttaa tagctatgaa gcctttatcc atatcgtgga tagcatggtt     1500
aatcagcatg caaaatggct gaaagttagc cgtgaactgc cgtggcgtcg tccgattagc     1560
agcctgaact atctgctgtc aagccatgtt tggcgtcagg atcataatgg ttttagtcat     1620
caggatccgg gttttattga tcacgtggtt aacaaaaaac cggaaatcat tcgtgtttat     1680
ctgccaccgg attgtaatac cctgctgtgt accatggatc attgtctgcg tagccgcaat     1740
ttcattaatg ttgttattgc aggtaaacag ccgcagctga catatctgcc gatggaagca     1800
gcaattgcac attgtacccg tggtgcaggt atttgggaat gggcaagcag tgatgaaggt     1860
gcagaaccga atgtggttct ggcatgtgcg ggtgatgtgc cgaccctgga aaccctggca     1920
gcagccgatc tgctgcgtcg tcatctgccg gaactgcgtg ttcgtgttgt taatgtggtt     1980
gatctgatgc gtctgagcaa tgaaggtgaa catccgcatg ccatgaccga tcgcgaatat     2040 gatacctgt ttacccgtga taaaccggtg attttttgcat ttcatggcta tcgtggctg     2100 attcatcgtc tgacctatcg tcgtgcaggt catccgaatc tgcatgttcg tggttataaa     2160
gaagaaggta cgaccaccac cccgttcgat atggttatgc tgaatgatct ggatcgtttt     2220
catctggtga tggatgttat tgatcgtgtt ccgggtctgg gtgttcgtgc agccggtctg     2280
cgtcagcata tgcaggatga acgcctgcgt tgtcgtgcat atacccgtca gtatggtgaa     2340
gatgcaccgg atattcgtaa ttgggtttgg gaaccgtaa                            2379
```

<210> SEQ ID NO 23
<211> LENGTH: 2586
<212> TYPE: DNA
<213> ORGANISM: Artificial Sequence
<220> FEATURE:
<223> OTHER INFORMATION: Synthetic Construct

<400> SEQUENCE: 23

```
atgacaattg attgggaacg tgaaagcctg gcaccgcagg gcaccaaagc acgtgatctg      60
accgaaatta tcaatcgtac cattacctgt cgtagcaccg tgttcatat gaccagtccg      120 gttattggca ccccgtggaa aaaactgaat gcaccggtta gcgaagaaag tctggaaggt     180
gttgataaat actggcgtgt tgcaaactat ctgagcattg tcagattta tctgcgtagc      240 aatccgctga tgaaagcacc gtttacccgt gaagatgtta acatcgtct ggttggtcat      300 tggggcacca caccgggtct gaattttctg attggtcata ttaatcgctt tatcgccgat     360
catggtcaga acaccgtgat tattatgggt ccgggtcatg gtggtccggc aggcaccagc     420
cagagctatc tggatggcac ctataccgaa accttttccga aaattaccaa agatgaagcc    480
ggtctgcaaa aattctttcg ccagtttagc tatccgggtg gtattccgag ccatttgca     540 ccggaaacac cgggtagcat ccatgaaggt ggtgaactgg gttatgcact gagccatgca   600
```

```
tatggtgcaa ttatggataa tccgagcctg tttgttccgg caattgttgg tgatggtgaa      660
gcagaaaccg gtccgctggc caccggttgg cagagcaata aactggttaa tccgcgtacc      720
gatggtattg ttctgccgat tctgcatctg aatggctata aaatcgcaaa tccgaccatt      780
ctgagccgca ttagtgatga agaactgcac gaattttttc acggtatggg ttatgaaccg      840
tatgaatttg ttgccggttt tgatgatgaa gatcatatgt caattcatcg tcgttttgca      900
gaactgtggg aaaccatttg ggatgaaatt tgcgatatta agcagcagc acagaccgat       960 aatgtgcatc gtccgtttta tccgatgctg attttcgta ccccgaaagg ttggacctgt      1020
ccgaaatata tcgatggcaa aaaaccgaa ggtagctggc gtgcacatca ggttccgctg      1080
gcaagcgcac gtgataccga agcacatttt gaagttctga aaattggct ggaaagctat      1140 aaaccggaag aactgtttga tgcaaatggt gccgttaaag atgatgttct ggcatttatg      1200
ccgaaaggtg aactgcgtat tggtgccaat ccgaatgcca atggtggtgt tattcgtgat      1260
gatctgaaac tgccgaatct ggaagattat gaagttaaag aagttgccga atacggtcat      1320
ggttggggtc agctggaagc aacccgtacc ctgggtgcat ataccgtga tatcattcgt      1380 aataatcctc gcgattttcg cattttggt ccggatgaaa ccgcaagcaa tcgtctgcaa      1440
gcaagctatg aagtgaccaa taaacagtgg gatgccggtt atatttcaga tgaagttgat      1500
gaacatatgc acgttagcgg tcaggttgtt gaacagctga gcaacatca gatggaaggt      1560 tttctggaag catatctgct gaccggtcgt catggtattt ggagcagcta tgaaagcttt      1620
gtgcatgtga ttgatagcat gctgaaccag catgccaaat ggctggaagc caccgttcgt      1680
gaaattccgt ggcgtaaacc gattgcaagc atgaatctgc tggttagcag ccatgtttgg      1740
cgtcaggatc ataatggttt tagccatcag gatccgggtg ttaccagcgt tctgctgaat      1800
aaatgttttc ataatgatca tgtgatcggc atctattttg caaccgatgc aaatatgctg      1860
ctggccattg cagaaaaatg ttacaaaagc accaacaaaa tcaacgccat cattgcaggt      1920
aaacagcctg ccgcaacctg gctgaccctg gatgaagcac gtgccgaact ggcaaaaggt      1980
gcagcagcat gggattgggc aagcaccgca aaaaacaatg atgaagcgga agttgtgctg      2040
gcagcagccg gtgatgttcc gacccaagaa attatggcag caagcgataa actgaaagag      2100
ctgggcgtta aattcaaagt tgttaatgtt gccgatctgc tgagcctgca aagcgcaaaa      2160
gaaaacgatg aggcactgtc cgatgaagaa tttgcagata tctttacagc cgataaaccg      2220
gttctgtttg cctatcatag ttatgcacat gatgttcgtg gtctgattta tgatcgtccg      2280
aaccatgata actttaacgt gcacggttat gaagaagaag gtagcaccac cacccccgtat     2340 gatatggttc gtgttaatcg tattgatcgc tatgaactga cagccgaaac cctgcgcatg      2400
attgatgcca taaatatgc ggataaaatc gatgaactga aaaatttcg tgacgaggca      2460 tttcagtttg ccgtggataa aggttatgat catccggatt ataccgattg ggtgtatagc      2520
ggtgttaata ccgataaaaa aggtgcggtt accgcaaccg cagccaccgc aggcgataat      2580
gaataa                                                               2586
```

<210> SEQ ID NO 24
<211> LENGTH: 2400
<212> TYPE: DNA
<213> ORGANISM: Artificial Sequence
<220> FEATURE:
<223> OTHER INFORMATION: Synthetic Construct

<400> SEQUENCE: 24

```
atgacactga gcagcagcca gcgttgtgca gaagaagaac tgcgtcaggt tgatcgttat      60
tggcgtgcag caaattatct gagcgttggt cagatttatc tgatggataa tccgctgctg     120
cgtgaaccgc tgaaaccgga acacattaaa ccgcgtctgc tgggtcattg gggcaccaca     180
ccgggtctga attttatcta tgcacatctg aatcgtgcca tttgtcagcg tgatctggat     240
atcatttata tctgtggtcc gggtcatggc ggtcctggta tggttgcaaa tacctggctg     300
gaaggtagct atagcgaaat ttatccgcag attagcgaag atgcaagcgg tattcagaaa     360
ctgtttcgtc agtttagctt tccgggtggt attccgagcc atgcagcacc ggaaacaccg     420
ggtagcatta tgaaggtgg tgaactgggt tatagcctga ccatgccttt ggtgcagtt      480
tttgataatc ctggtctgat tgcagcatgc gttattggtg atggtgaagc agaaaccggt     540
ccgctggcaa gcagctggca tggtaacaaa tttctgaatc cggttcgtga tggtgccgtt     600
ctgccggttc tgcatctgaa tggctataaa atcgcaaatc cgaccattct gggtcgcatg     660
aatgatgaag atctgcgcca gctgtttagc ggttatggtt atgaacctct gtttgttagt     720
ggccatgaac ctgagcagat gcatattcag atggcacgta ccctgaatat tgcactggat     780
attatcaaag atcatcagct gcgtgcacgt gccggtcgtc cgaccaaagg tgttccgcgt     840
tggccgatga ttattctgcg tagcccgaaa ggttggacag tccgcagag cgttgatggt      900
aaaaaagttg aaggttttg gcgtgcccat caggttccgg ttagcagctg tcgtgaaaat     960
gatgaacatc gtcagattct ggaaaattgg atgcgtagct atcagccgga tgacctgttt    1020
gatgaacagg gtcgtctgaa acctgaactg cgtgccctgg caccgcaggg tgataaacgt    1080
atgggtgcaa gcccgtttgc aaatggtggt cgtctgcgtc gtgaactggt tcctgccgaa    1140
cgtgcaaaat ttgcagttga actgaccagc cgtggtgaac gcaggttca gagcaccgaa     1200
atgctgggtc gttatctggc agatatttc cccctgaacc cggataattt tcgtctgttt    1260
ggtccggatg aaaccgcaag caatcgtctg agtgatgttt ttgatgttac caatcgtaca    1320
tggctggaag atattgaacc gtatgatgaa caactggcag cagatggtcg tgttatggaa    1380
attctgagcg aacatcagtg tcagggttgg ctggaaggct atctgctgac cggtcgtcat    1440
ggtctgttta ttgttatga agcctttatc catatcgtgg atagcatgtt taatcagcat    1500
gccaaatggc tgaaagttac ccgtaaactg ccgtggcgta accgattag cagcctgaat    1560
tatctgctgt caagccatgt ttggcgtcag gatcataatg ttatagtca tcaggatccg     1620
ggttttatgg atcatgttgc aaacaaaaaa gccgatatcg tgcgtattta tctgcctccg    1680
gatgccaata ccctgctgtg ggttgcagat cattgtctgc aaacctggga tcgtattaat    1740
gttattgttg caggtaaaca gcctgcaccg cagtggctga gtgccgaaga ggcagcagaa    1800
cattgtgcag caggtatggg tatttggccg tgggcaggca ccgaacagga tggtacagaa    1860
ccggatgttg ttctggcatg tgccggtgat gttccgacca tggaaaccct ggcagctgcg    1920
gatctgctgc gcgagtatct gccggatctg agtgttcgtg ttgttaatgt tgttgatatc    1980
atggcactgc aaacccgtga acagcatccg catggcctgt cagccgaagc atttgatggt    2040
attttttaccc agaataaacc ggtgatcttt gcctttcatg ttatccgag cctgattcat    2100
cgtctgacct atcagcgtaa taatcaccgt aattttcatg tgagcggctt tatgaagaa    2160
ggtacaacca ccacccccgtt tgatatgacc gttctgaata aactggatcg tttcatctg    2220
gcacaggcag caattgttca taccgagaaa ctgcaaggta agcggatga tattctggac    2280
gatctgcaag aaaaaattgc agcccatcat cgttatgtgc gtgaatatgg tgaggatctg    2340
cctgaagttc gtaattggaa atggccgagc cagcagggtt caggtggtgc accggaataa    2400
```

<210> SEQ ID NO 25
<211> LENGTH: 2478
<212> TYPE: DNA
<213> ORGANISM: Artificial Sequence
<220> FEATURE:
<223> OTHER INFORMATION: Synthetic Construct

<400> SEQUENCE: 25

| | | | | | |
|---|---|---|---|---|---|
| atgacaaatc | cggttattgg | cacccgtgg | cagaaactgg | atcgtccggt | tagcgaagag | 60 |
| gcaattgaag | gtatggataa | atactggcgt | gtggccaatt | atatgagcat | tggtcagatt | 120 |
| tatctgcgta | gcaatccgct | gatgaaagaa | ccgtttaccc | gtgatgatgt | taaacatcgt | 180 |
| ctggttggtc | attggggcac | cacccgggt | ctgaattttc | tgctggcaca | tattaatcgt | 240 |
| ctgattgcag | atcatcagca | gaacaccgtg | tttattatgg | gtccgggtca | tggtggtccg | 300 |
| gcaggcaccg | cacagagcta | tattgatggc | acctataccg | aatattatcc | gaacatcacc | 360 |
| aaagatgaag | ccggtctgca | aaaattcttt | cgccagttta | gctatccggg | tggtattccg | 420 |
| agccattttg | caccggaaac | accgggtagc | atccatgaag | tggtgaact | gggttatgca | 480 |
| ctgagccatg | catatggtgc | aattatggat | aatccgagcc | tgtttgttcc | gtgcattatt | 540 |
| ggtgatggtg | aagcagaaac | cggtccgctg | gccaccggtt | ggcagagcaa | taaactggtt | 600 |
| aatccgcgta | ccgatggtat | tgttctgccg | attctgcatc | tgaatggcta | taaaatcgca | 660 |
| aatccgacca | ttctggcacg | cattagtgat | gaagaactgc | atgattttt | tcgcggtatg | 720 |
| ggttatcacc | gtatgaatt | tgttgccggt | tttgataatg | aagatcatct | gagcattcat | 780 |
| cgtcgttttg | cagaactgtt | tgaaaccatc | tttgatgaga | tctgcgatat | taaagcagca | 840 |
| gcacagaccg | atgatatgac | ccgtccgttt | tatccgatgc | tgattttcg | tacccgaaa | 900 |
| ggttggacct | gtccgaaatt | tatcgatggc | aaaaaaaccg | aaggtagctg | gcgtgcacat | 960 |
| caggttccgc | tggcaagcgc | acgtgatacc | gaagcacatt | ttgaagttct | gaaaggctgg | 1020 |
| atggaaagct | ataaaccgga | agaactgttc | aatgcagatg | gcagcattaa | agaagatgtt | 1080 |
| accgcatttta | tgccgaaagg | tgaactgcgt | attggtgcca | atccgaatgc | aaatggtggt | 1140 |
| cgtattcgtg | aagatctgaa | actgccggaa | ctggatcagt | atgaaatcac | cggtgttaaa | 1200 |
| gaatatggtc | atggttgggg | tcaggttgaa | gcaccgcgta | gcctgggtgc | atattgtcgt | 1260 |
| gatatcatta | aaacaacccc | ggacagcttt | cgtgttttttg | gtccggatga | aaccgcaagc | 1320 |
| aatcgcctga | tgcaaccta | tgaagttacc | aaaaaacagt | gggataatgg | ctatctgagc | 1380 |
| gcactggtta | tgaaaatat | ggcagttacc | ggtcaggtgg | ttgaacagct | gagcgaacat | 1440 |
| cagtgtgaag | gttttctgga | agcatatctg | ctgaccggtc | gtcatggtat | ttggagcagc | 1500 |
| tatgaaagct | ttgtgcatgt | gattgatagc | atgctgaacc | agcatgccaa | atggctggaa | 1560 |
| gcaaccgttc | gtgaaattcc | gtggcgtaaa | ccgattagca | gcgttaatct | gctggttagc | 1620 |
| agccatgttt | ggcgtcagga | tcataatggt | tttagccatc | aggatccggg | tgttaccagc | 1680 |
| gtgctgctga | ataaaaccct | taataatgat | cacgtgacca | acatctattt | tgccaccgat | 1740 |
| gcaaatatgc | tgctggcaat | tgcagaaaaa | tgcttcaaaa | gcaccaacaa | aatcaacgcc | 1800 |
| attttcgcag | gtaaacagcc | tgccgcaacc | tggattaccc | tggatgaagt | tcgtgccgaa | 1860 |
| ctggaagccg | gtgcagcaga | atggaaatgg | gcaagcaatg | caaaaagcaa | tgatgaagtg | 1920 |
| caggttgttc | tggcagcagc | cggtgatgtg | ccgacccaag | aaattatggc | agcaagtgat | 1980 |
| gccctgaaca | aaatgggcat | taaattcaaa | gttgtgaacg | tggtggatct | gatcaaactg | 2040 |

| | |
|---|---:|
| caaagcagca agaaaacga tgaagccatg tccgatgaag attttgccga cctgtttaca | 2100 |
| gcagataaac cggttctgtt tgcctatcat agttatgcac aggatgttcg cggtctgatt | 2160 |
| tatgatcgtc cgaaccatga taactttacc gtggttggtt ataaagaaca gggtagcacc | 2220 |
| accaccccgt ttgatatggt tcgtgtgaat gatatggatc gttatgccct gcaagcaaaa | 2280 |
| gcactggaac tgattgatgc cgataaatat gcggacaaaa tcaatgaact gaacgagttt | 2340 |
| cgtaaaaccg catttcagtt tgccgtggat aacggttatg atatcccgga atttaccgat | 2400 |
| tgggtttatc cggatgttaa agtggatgaa acaagcatgc tgtcagcaac cgcagccacc | 2460 |
| gcaggcgata atgaataa | 2478 |

```
<210> SEQ ID NO 26
<211> LENGTH: 2496
<212> TYPE: DNA
<213> ORGANISM: Artifical Sequence
<220> FEATURE:
<223> OTHER INFORMATION: Synthetic Construct

<400> SEQUENCE: 26
```

| | |
|---|---:|
| atgagcaccg gtgtgcatat gaccagtccg gttattggca ccccgtggaa aaaactgaat | 60 |
| gcaccggtta gcgaagcagc aattgaaggt gttgataaat actggcgtgt tgcaaattat | 120 |
| ctggccattg gtcagattta tctgcgtagc aatccgctga tgaaagaacc gtttacccgt | 180 |
| gaagatgtta acatcgtct ggttggtcat gggcacca caccgggtct gaattttctg | 240 |
| attggtcata ttaatcgctt tatcgccgat catcagcaga caccgtgat tattatgggt | 300 |
| ccgggtcatg gtggtccggc aggcaccgca cagagctatc tggatggcac ctataccgaa | 360 |
| tattatccga aaatcaccaa agatgaagcc ggtctgcaaa aattctttcg ccagtttagc | 420 |
| tatccgggtg gtattccgag ccattttgca ccggaaacac cgggtagcat ccatgaaggt | 480 |
| ggtgaactgg gttatgcact gagccatgca tatggtgcag ttatgaataa tccgagcctg | 540 |
| tttgttccgg caattgttgg tgatggtgaa gcagaaaccg gtccgctggc caccggttgg | 600 |
| cagagcaata aactggttaa tccgcgtacc gatggtattg ttctgccgat tctgcatctg | 660 |
| aatggctata aaatcgcaaa tccgaccatt ctgagccgca ttagtgatga agaactgcac | 720 |
| gaattttttc acggtatggg ttatgaaccg tatgaatttg ttgccggttt tgatgatgaa | 780 |
| gatcatatgt caattcatcg tcgctttgcc gatatgtttg aaaccatctt tgatgagatc | 840 |
| tgcgatatta agccgaagc acagaccaat gatgttaccc gtccgtatta ccaatgatt | 900 |
| atctttcgta ccccgaaagg ttggacctgt ccgaaattta cgatggcaa aaaaaccgaa | 960 |
| ggtagctggc gtgcacatca ggttccgctg caagcgcac gtgataccga gcccattttt | 1020 |
| gaagttctga aaaactggat gaaaagctat aaaccggaag aactgttcga tgaaaaaggt | 1080 |
| gccgttaaag aagatgtgct gagctttatg ccgaaaggtg aactgcgtat tggtgaaaat | 1140 |
| ccgaatgcaa atggtggtcg tattcgtgaa gatctgaaac tgccgaaact ggacgattat | 1200 |
| gaagtcaaag aagttaaaga atttggccat ggttgggtc agctggaagc aacccgtcgt | 1260 |
| ctgggtgttt ataccccgtga tattatcaaa acaacccgg acagctttcg tattttggt | 1320 |
| ccggatgaaa ccgcaagcaa tcgtctgcaa gcagcatatg aagttaccaa taaacagtgg | 1380 |
| gatgcaggtt atctgagcgg tctggttgat gaacacatgg cagttaccgg tcaggttacc | 1440 |
| gaacagctga gcgaacatca gatggaaggt tttctggaag ctatctgct gaccggtcgt | 1500 |
| catggtatt ggagcagcta tgaaagcttt gtgcatgtga ttgatagcat gctgaaccag | 1560 |
| catgccaaat ggctggaagc caccgttcgt gaaattccgt ggcgtaaacc gattagcagc | 1620 |

-continued

```
gttaatctgc tggttagcag ccatgtttgg cgtcaggatc ataatggttt tagccatcag    1680
gatccgggtg ttaccagcgt gctgctgaat aaaacctta ataatgatca tgtgatcggc     1740
atctatttcc cggttgatag caacatgctg ctggcagttg cagaaaaagc atataaaagc    1800
accaacatga tcaacgccat tttcgcaggt aaacagcctg ccgcaacctg gctgaccctg    1860
gatgaagcac gcgaagaact ggaaaaaggc gcagcagaat ggaaatgggc aagcaatgca    1920
aaaaacaatg atgaagttca ggttgttctg gcaggcgtgg gtgatgttcc gcagcaagaa    1980
ctgatggcag cagccgataa actgaacaaa ctgggtgtta aattcaaagt ggtgaatgtt    2040
gtggatctgc tgaaactgca aagcgccaaa gaaaataatg aagcactgac cgatgaagag    2100
tttaccgaac tgtttacagc agataaaccg ttctgtttg cctatcatag ttatgcacat     2160
gatgttcgtg gcctgattta tgatcgtccg aaccatgata ctttaacgt gcacggttat     2220 aaagaacagg gtagcaccac cacccgtat gatatggttc gtgttaatga tatggatcgc     2280
tatgaactga cagcggaagc actgcgtatg gttgatgcag caaaatatgc cgatgaaatc    2340
aaagagctgg aagattttcg tctggaagca tttcagtatg ccgttgataa aggtctggat    2400
catccggatt ataccgattg ggtttggcct ggtgttaaaa ccgataaacc tggtgcggtt    2460
accgcaaccg cagccaccgc aggcgataat gaataa                              2496
```

<210> SEQ ID NO 27
<211> LENGTH: 2382
<212> TYPE: DNA
<213> ORGANISM: Artifical Sequence
<220> FEATURE:
<223> OTHER INFORMATION: Synthetic Construct

<400> SEQUENCE: 27

```
atgccgcagg ttgaacatca gaatagcacc gttctgaccg atgatgaact gcgtaccctg     60
gatgcacatt ggcgtgcagc aaattatctg gcagcaggtc agatttatct gctggcaaat    120
gcactgctga ccgaaccgct gagtccggca catatcaaac cgcgtctgct gggtcattgg    180
ggcaccagtc cgggtctgaa tctggttcat acccatctga atcgtgttat taaagcacgt    240
gatctggatg ccctgtgtgt ttggggtccg ggtcatggtg gtccggcagt tctggcaaat    300
agctggctgg aagtagcta tagcgaaacc tatcctgata ttagccgtga tgcagcaggt    360
atgggtaaac tgtttcgtca gtttagcttt ccgggtggtg ttccgagcca tgttgcaccg    420
gaaacaccgg gtagcattca tgaaggtggt gaactgggtt atagcctggc acatgcatat    480
ggtgcagcat ttgataatcc ggatctgctg gttgcatgtg ttattggtga tggtgaagca    540
gaaaccggtc cgctggcagc aagctggcat agcaacaaat ttctggatcc ggttcatgat    600
ggtgcagttc tgccgattct gcatctgaat ggctataaaa tcgcaaatcc gaccgtgctg    660
agccgtattc cggaaccgga actggatgag ctgctgcgtg ttatggtca tgaacctctg    720 catgttaccg gtgatgatcc gcatcaggtt catcgtgcac tggccgaagc ctttgatcgt    780
gccctggatc gtgttgcact gatgcagcgt accgcacgtg aagaaggtgc aaccgaacgt    840
attcgttggc cgatgattgt tctgcgcacc ccgaaaggtt ggacaggtcc tgccgaagtt    900
gatggtcgtc cggttgaagg cacctggcgt gcccatcagg tgccgctgcc ggaagttcgt    960
gaaaatccgg aacatctgcg tcagctggaa ggctggctgc gtagctatcg tccggaagaa    1020
ctgtttgatg cagatggccg tccgaccgca gatgtgctgg catgtgttcc gcatggtgca    1080
cgtcgtctgg gtgcaacacc gcatgcaaat ggtggtctgc tgctgcgtcc gctgccgatt    1140
```

```
ccgcctctgg atcgttttgc cgttgcagtt gataaaccgg gtgccaccct gcatgaaccg    1200
acccgtgttc tgggcgacct gctggaacag gttatgaaag ataccagcgc acgtcgtgat    1260
tttcgtctgg ttggtccgga tgaaaccgca agcaatcgtc tggatgcagt ttttgatgca    1320
agcggtaaag catggcaggc acagaccctg ccggttgatg aacatctgga ccgtcatggt    1380
cgtgttatgg aaattctgag cgaacatacc tgtcagggtt ggctggaagg ctatctgctg    1440
accggtcgtc atggcctgtt tagctgttat gaagcatttg tgcatatcgt ggatagcatg    1500
gttaatcagc atatcaaatg gctgaaaacc agccgtgaac tggcatggcg tgcaccgatt    1560
gcaagcctga attacctgct gaccagccat gtttggcgtc aggatcataa tggttttagt    1620
catcaggatc cgggttttgt tgatcatgtg ctgaataaaa gtccggaagc agttcgtgtt    1680
tatctgcctc cggatgcaaa taccctgctg agcgttgcag atcatgttct gcgtagtcgt    1740
gattatgtta atgttgttgt tgcaggtaaa cagccgtgtt ttgattggct gagcatggaa    1800
caggcacgtg cacattgtgc ccgtggtgca ggtatttggg aatgggcagg cacccagaat    1860
gatggcgaac cggatgttgt tctggcctgt gccggtgatg tgccgaccca agaagtactg    1920
gcagccagcg cactgctgcg tcgtcatctg cctgcactgg cggttcgtgt tgttaatgtg    1980
gtggatatga cccgtctgct gcctcgtgaa gcacatccgc atggcatgag cgattttgaa    2040
tatgatggtc tgtttaccac cgacaaaccg gtgattttg catatcatgg ttatccgtgg    2100
ctgattcatc gtctggcata tagccgtacc ggtcatggta tctgcatgt acgtggttat    2160 aaagaaatgg gtacaaccac caccccttt gatatggttg ttcgtaacga tctggatcgc    2220
tatcgtctgg tgatggatgt ggttgatcgt gttcctggtc tgggtgttcg tgcagcagcc    2280
gttcgtcaga caatggcaga tgcacgtacc cgtcatcatg catggattcg tgaacatggc    2340
accgatctgc ctgaagttgc aaaattggac ctgggaagcat aa    2382

<210> SEQ ID NO 28
<211> LENGTH: 2391
<212> TYPE: DNA
<213> ORGANISM: Artifical Sequence
<220> FEATURE:
<223> OTHER INFORMATION: Synthetic Construct

<400> SEQUENCE: 28
atgcaaagta ataggaaaa acataaggat gaaggaaaaa tcacaccgga gtatctaaag      60
aaaattgatg catattggcg tgcagctaat tttatatctg taggtcaatt gtatttgcta    120
gacaatccat tgcttagaga acctttaaaa ccagaacatc taaaaagaaa agttgttggt    180
cactggggta ctattcctgg tcaaaacttt atttatgctc atcttaaccg tgttattaaa    240
aaatatgatt tagatatgat ttatgtttct ggtccaggtc atggtggaca gtaatggtg     300 tccaattctt atctagatgg aacctatagt gaagtttatc caaatgttag tcgtgatttg    360
aatggcttaa aaaagctatg taaacaattc tcttttccag gtggaatttc tagccatatg    420
gctcctgaaa caccgggttc aataaatgaa ggggagaac taggctattc tttagcacat    480
tcttttggtg ctgttttga taaccctgat ttgattactg cttgtgttgt tggagacgga    540
gaggcagaaa caggacctct tgcaacatct tgcaagcaa ataaattttt aaatccagtt    600
actgatggag cagtgcttcc tattttacat ttaaatggat acaaattag taaccctact    660 gtgttgtctc gtattcctaa ggatgaactt gagaaattct ttgaaggaaa cggatggaag    720
ccttattttg tagaaggtga agatcctgaa acaatgcata aattaatggc agaaacatta    780
gatatagtaa cagaagaaat tcttaatatt cagaaaaatg ctcgtgaaaa taacgattgt    840
```

```
tcacgaccaa agtggccaat gattgtattg cgtacaccaa agggatggac aggtccaaaa     900
tttgtagatg gtgttccaaa tgaaggatct ttccgtgcac accaagtacc gcttgcagta     960
gatagatatc atacagaaaa cttagatcaa ttagaagagt ggcttaagag ttataaacca    1020
gaagaattat ttgacgaaaa ctatagacta ataccgaaac ttgaagaatt aactccaaag    1080
ggaaataaga gaatggcggc taatttgcat gctaatggtg gtttattatt acgtgaacta    1140
cgtacacctg attttcgtga ttatgctgta gatgttccta ctccagggag cacagttaag    1200
caggatatga ttgaacttgg aaaatatgtg cgtgatgttg ttaaattaaa cgaagatact    1260
cgtaatttcc gtattttgg accgatgaa actatgtcta atagattatg ggcagttttt       1320
gaaggtacga aacgtcaatg gttatcagaa attaaagagc caaatgatga attcttatcg    1380
aatgatggac gtattgttga ttcaatgcta agcgaacatt tatgtgaagg ttggttagag    1440
ggttatcttt taacaggacg tcatggtttc tttgcaagtt atgaagcctt ccttcgtatt    1500
gttgattcta tgattactca gcatggtaag tggttaaagg taacatcaca gctaccatgg    1560
agaaaagata ttgcttcttt aaatttaata gcaacatcta atgtatggca gcaggatcat    1620
aatggatata ctcatcaaga tccaggttta ttaggacata ttgtggataa aaaacctgaa    1680
atagttagag catatttacc agcagatgcc aataccttat tagccgtatt tgataaatgc    1740
cttcatacta aacacaagat taatttatta gtaacatcaa acatccaag acaacagtgg      1800
ttaacaatgg atcaagcagt taagcatgta gagcaaggaa taagcatttg ggattgggca    1860
agtaatgaca aaggacaaga aacctgatgta gttatagctt cctgtggaga tactccaaca   1920
ttagaggctt tggcagctgt tacaatcctt catgaacatt taccagaatt aaaagttcgt    1980
tttgtaaatg tagtggatat gatgaaatta ttacctgaaa atgagcatcc tcatggctta    2040
agcgataagg attataatgc cttatttaca acagataagc ctgtaatatt tgcattccat    2100
ggatttgcac atttaataaa tcaattaaca tatcatcgtg aaaatagaaa tttcatgta     2160
catggttata tggaagaggg aactattaca acaccatttg atatgcgtgt tcaaaataaa    2220
ttagatcgtt ttaatcttgt aaaagatgta gtagagaatt taccctcagct tggaaatcgt   2280
ggagcacatc ttgttcagtt aatgaatgat aaattagtag aacataacca atacattcgt    2340
gaggttggag aagatttgcc agaaataact aattggcagt ggcatgtata a             2391
```

<210> SEQ ID NO 29
<211> LENGTH: 2367
<212> TYPE: DNA
<213> ORGANISM: Artificial Sequence
<220> FEATURE:
<223> OTHER INFORMATION: Synthetic Construct

<400> SEQUENCE: 29

```
atgaccaccg attatagcag tccggcatat ctgcaaaaag tggataaata ctggcgtgca      60
gcaaattatc tgagcgttgg tcagctgtat ctgaaagatt atccgctgct gcaacagccg     120
ctgaaagcaa gtgatgttaa agttcatccg atttgtcatt ggggcaccat tgcaggtcag    180
aatagcattt atgcacatct gaatcgcgtg atcaacaaat atggcctgaa atgttttat      240
gtggaaggtc cgggtcatgg tggtcaggtt atggttagca atagctatct ggatggcacc    300
tataccgata tttatccgga aattacccag gatgttgaag gtatgcagaa actgttcaaa    360
cagttcagct ttccgggtgg tgttgcaagc catgcagcac cggaaacacc gggtagcatt    420
catgaaggtg gtgaactggg ttatagcatt agccatggtg ttggtgcaat tctggataat    480
```

```
ccggatgaaa ttgcagcagt tgttgttggt gatggtgaaa gcgaaaccgg tccgctggca      540
accagctggc agagcaccaa atttatcaat ccgattaatg atggtgccgt tctgccgatt      600
ctgaatctga atggctttaa aatcagcaac ccgaccattt ttggtcgtac cagtgatgca      660
aaaatcaaag aatatttcga gagcatgagc tgggaaccga ttttgtaga aggtgatgat      720 ccggaaaaag tgcatccggt tctggcaaaa gcaatggatg aagcagttga aaaatcaaa       780 gcgatccaga acatgcccg tgaaaatgat gatgcaaccc tgccggtttg gccgatgatt      840 gttttcgtg caccgaaagg ttggacaggt ccgaaaagct gggatggtga taaaattgaa       900
ggtagctttc gtgcccatca gattccgatt ccggttgatc agaatgatat ggaacatgca      960
gatgcactgg ttgattggct ggaaagctat cagccgaaag aactgtttaa tgaagatggc      1020
agcctgaaag atgacatcaa agaaattatt ccgaccggtg atagccgtat ggcagcaaac      1080
ccgattacca atggtggtgt ggatccgaaa gcactgaatc tgccgaattt tcgtgattat      1140
gcagttgata ccagcaaaga aggtgcaaac gttaaacagg atatgctggt ttggagcgat      1200
tatctgcgtg atgtgatcaa aaaaaacccg ataattttc gtctgtttgg ccctgatgaa       1260
accatgagca atcgtctgta tggtgttttt gaaaccacca atcgtcagtg atggaagat       1320 atccatccgg atagcgatca gtatgaagca gcagcaggtc gtgttctgga tgcacagctg      1380
agcgaacatc aggcagaagg ctggctggaa ggttatgttc tgaccggtcg tcatggtctg      1440
tttgcaagct atgaagcatt tctgcgtgtt gttgatagca tgctgaccca gcactttaaa      1500
tggctgcgta aagcaaatga actggactgg cgcaaaaaat acccgagcct gaacattatt      1560
gcagcaagca ccgttttca gcaggatcat aatggttata cccatcagga tccgggtgca      1620
ctgacccatc tggcagagaa aaaaccggaa tatatccgtg aatatctgcc tgccgatgca      1680 aatacccctgc tggcagtggg tgatgttatt tttcgtagcc aagaaaaaat caactacgtg      1740
gtgaccagca acatccgcg tcagcagtgg tttagcattg aagaagcaaa acagctggta      1800
gataatggcc tgggtattat tgattgggcc agcaccgatc agggtagcga accggatatt      1860
gtttttgcag ccgcaggcac cgaaccgacc ctggaaaccc tggcagcaat tcagctgctg      1920
catgatagct cccggaaat gaaaattcgt tttgtgaacg tggtggacat tctgaaactg      1980
cgtagccctg aaaaagatcc gcgtggtctg agtgatgcag aatttgatca ctatttacc      2040 aaaagacaaac cggtggtgtt tgcctttcat ggttatgaag atctggtgcg cgatatcttt      2100
ttcgatcgcc ataaccataa tctgtatgtg catggttatc gcgaaaatgg tgatattacc      2160
accccgtttg atgttcgtgt tatgaatcag atggatcgtt ttgacctggc aaaaaccgca      2220
attgcagccc agcctgccat ggaaaatacc ggtgcagcat ttgttcagag catggataat      2280
atgctggcaa acataacgc ctatattcgt gatgcaggta cagatctgcc ggaagttaat      2340
gattggcagt ggaaaggtct gaaataa                                          2367
```

<210> SEQ ID NO 30
<211> LENGTH: 32
<212> TYPE: DNA
<213> ORGANISM: Artifical Sequence
<220> FEATURE:
<223> OTHER INFORMATION: Synthetiic Construct (Primer CMP283)

<400> SEQUENCE: 30
ctgtattcat gacgagtcct gttattggca cc                                     32

<210> SEQ ID NO 31
<211> LENGTH: 31

```
<212> TYPE: DNA
<213> ORGANISM: Artificial Sequence
<220> FEATURE:
<223> OTHER INFORMATION: Synthetic Construct (Primer CMP284)

<400> SEQUENCE: 31
ctctatgaat tctcactcgt tgtcgccagc g                                    31

<210> SEQ ID NO 32
<211> LENGTH: 39
<212> TYPE: DNA
<213> ORGANISM: Artificial Sequence
<220> FEATURE:
<223> OTHER INFORMATION: Synthetic Construct (Primer CMP34)

<400> SEQUENCE: 32
taaggaggaa taaacatggc agtagattac gattccaag                            39

<210> SEQ ID NO 33
<211> LENGTH: 40
<212> TYPE: DNA
<213> ORGANISM: Artificial Sequence
<220> FEATURE:
<223> OTHER INFORMATION: Synthetic Construct (Primer CMP 335)

<400> SEQUENCE: 33
ttctagaaag cttcgttact taagacccct ccaagtccag                           40

<210> SEQ ID NO 34
<211> LENGTH: 73
<212> TYPE: DNA
<213> ORGANISM: Artificial Sequence
<220> FEATURE:
<223> OTHER INFORMATION: Synthetic Construct

<400> SEQUENCE: 34
tatttaattt ttaatcatct aatttgacaa tcattcaaca aagttgttac aattaaccct     60
cactaaaggg cgg                                                        73

<210> SEQ ID NO 35
<211> LENGTH: 147
<212> TYPE: DNA
<213> ORGANISM: Artificial Sequence
<220> FEATURE:
<223> OTHER INFORMATION: Synthetic Construct

<400> SEQUENCE: 35
tcaacagctg tatccccgtt gagggtgagt tttgcttttg tatcagccat atattccacc     60
agctatttgt tagtgaataa aagtggttga attatttgct caggatgtgg cathgtcaag   120
ggctaatacg actcactata gggctcg                                       147

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
ggcagtatag gctgttcaca aaatc                                           25

<210> SEQ ID NO 37
<211> LENGTH: 23
<212> TYPE: DNA
```

<213> ORGANISM: Artificial Sequence
<220> FEATURE:
<223> OTHER INFORMATION: Synthetic Construct

<400> SEQUENCE: 37
cttgacccag cgtgcctttc agc                                          23

<210> SEQ ID NO 38
<211> LENGTH: 99
<212> TYPE: DNA
<213> ORGANISM: Artificial Sequence
<220> FEATURE:
<223> OTHER INFORMATION: Synthetic Construct

<400> SEQUENCE: 38
aaaattttca ttctgtgaca gagaaaaagt agccgaagat gacggtttgt cacatggagt    60
tggcaggatg tttgattaca tgggaattag ccatggtcc                          99

<210> SEQ ID NO 39
<211> LENGTH: 100
<212> TYPE: DNA
<213> ORGANISM: Artificial Sequence
<220> FEATURE:
<223> OTHER INFORMATION: Synthetic Construct

<400> SEQUENCE: 39
gaccagccgc gtaacctggc aaaatcggtt acgttgagt aataaatgga tgccctgcgt     60
aagcggggca ttttcttgg tgtaggctgg agctgcttcg                          100

<210> SEQ ID NO 40
<211> LENGTH: 24
<212> TYPE: DNA
<213> ORGANISM: Artificial Sequence
<220> FEATURE:
<223> OTHER INFORMATION: Synthetic Construct

<400> SEQUENCE: 40
ggcttaccgt ttacgctttc cagc                                         24

<210> SEQ ID NO 41
<211> LENGTH: 23
<212> TYPE: DNA
<213> ORGANISM: Artificial Sequence
<220> FEATURE:
<223> OTHER INFORMATION: Synthetic Construct

<400> SEQUENCE: 41
ctaatgcaat acgtgtcccg agc                                          23

<210> SEQ ID NO 42
<211> LENGTH: 32
<212> TYPE: DNA
<213> ORGANISM: Artificial Sequence
<220> FEATURE:
<223> OTHER INFORMATION: Synthetic Construct (Primer CMP283)

<400> SEQUENCE: 42
ctgtattcat gacgagtcct gttattggca cc                                32

<210> SEQ ID NO 43
<211> LENGTH: 31
<212> TYPE: DNA
<213> ORGANISM: Artificial Sequence
<220> FEATURE:
<223> OTHER INFORMATION: Synthetic Construct (Primer CMP284)

```
<400> SEQUENCE: 43
ctctatgaat tctcactcgt tgtcgccagc g                                  31

<210> SEQ ID NO 44
<211> LENGTH: 39
<212> TYPE: DNA
<213> ORGANISM: Artificial Sequence
<220> FEATURE:
<223> OTHER INFORMATION: Synthetic Construct (Primer CMP34)

<400> SEQUENCE: 44
taaggaggaa taaacatggc agtagattac gattccaag                          39

<210> SEQ ID NO 45
<211> LENGTH: 40
<212> TYPE: DNA
<213> ORGANISM: Artificial Sequence
<220> FEATURE:
<223> OTHER INFORMATION: Synthetic Construct (Primer CMP335)

<400> SEQUENCE: 45
ttctagaaag cttcgttact taagacccct ccaagtccag                         40

<210> SEQ ID NO 46
<211> LENGTH: 42
<212> TYPE: DNA
<213> ORGANISM: Artificial Sequence
<220> FEATURE:
<223> OTHER INFORMATION: Synthetic Construct

<400> SEQUENCE: 46
taaggaggaa taaaccatga cattagccag tcctctacaa ac                      42

<210> SEQ ID NO 47
<211> LENGTH: 39
<212> TYPE: DNA
<213> ORGANISM: Artificial Sequence
<220> FEATURE:
<223> OTHER INFORMATION: Synthetic Construct

<400> SEQUENCE: 47
ttctagaaag cttcgttaat agggccactt ccagtcacg                          39

<210> SEQ ID NO 48
<211> LENGTH: 41
<212> TYPE: DNA
<213> ORGANISM: Artificial Sequence
<220> FEATURE:
<223> OTHER INFORMATION: Synthetic Construct

<400> SEQUENCE: 48
taaggaggaa taaaccatgt ccgacgtgtt gtccaacgat c                       41

<210> SEQ ID NO 49
<211> LENGTH: 34
<212> TYPE: DNA
<213> ORGANISM: Artificial Sequence
<220> FEATURE:
<223> OTHER INFORMATION: Synthetic Construct

<400> SEQUENCE: 49
ttctagaaag cttcgtcagg ccgaccagcg ccag                               34

<210> SEQ ID NO 50
```

```
<211> LENGTH: 51
<212> TYPE: DNA
<213> ORGANISM: Artificial Sequence
<220> FEATURE:
<223> OTHER INFORMATION: Synthetic Construct

<400> SEQUENCE: 50
taaggaggaa taaaccatgc aaagtataat aggaaaacat aaggatgaag g            51

<210> SEQ ID NO 51
<211> LENGTH: 45
<212> TYPE: DNA
<213> ORGANISM: Artificial Sequence
<220> FEATURE:
<223> OTHER INFORMATION: Synthetic Construct

<400> SEQUENCE: 51
ttctagaaag cttcgttata catgccactg ccaattagtt atttc                   45
```

UTILIZATION OF PHOSPHOKETOLASE IN THE PRODUCTION OF MEVALONATE, ISOPRENOID PRECURSORS, AND ISOPRENE

CROSS-REFERENCE TO RELATED APPLICATIONS

This application claims priority to U.S. Provisional Patent Application No. 61/545,083, filed Oct. 7, 2011; the disclosure of which is hereby incorporated herein by reference in its entirety.

INCORPORATION BY REFERENCE

The Sequence Listing submitted in an ASCII text file, in accordance with 37 C.F.R. §1.821(c) and (e), is incorporated by herein by reference. The text file name is "643842004000_Sequence_Listing.txt", the date of creation of the text file is Oct. 4, 2012, and the size of the ASCII text file in bytes is 102,077.

FIELD OF THE INVENTION

This present invention relates to cultured recombinant cells comprising a phosphoketolase polypeptide and one or more mevalonate (MVA) pathway polypeptides capable of producing mevalonate, isoprenoid precursors, isoprene and isoprenoids and compositions that include these cultured cells, as well as methods for producing and using the same.

BACKGROUND OF THE INVENTION

R-Mevalonate is an intermediate of the mevalonate-dependent biosynthetic pathway that converts acetyl-CoA to isopentenyl diphosphate and dimethylallyl diphosphate. The conversion of acetyl-CoA to mevalonate can be catalyzed by the thiolase, HMG-CoA synthase and the HMG-CoA reductase activities of the upper mevalonate-dependent biosynthetic pathway (MVA pathway). Commercially, mevalonate has been used as an additive in cosmetics, for the production of biodegradable polymers, and can have value as a chiral building block for the synthesis of other chemicals. The lower mevalonate-dependent biosynthetic pathway utilizes mevalonate as substrate for generating isopentenyl pyrophosphate (IPP) and dimethylallyl diphosphate (DMAPP), which are the terminal products of the mevalonate-dependent pathway. IPP and DMAPP are precursors to isoprene as well as to isoprenoids.

Isoprene (2-methyl-1,3-butadiene) is the critical starting material for a variety of synthetic polymers, most notably synthetic rubbers. Isoprene can be obtained by fractionating petroleum; however, the purification of this material is expensive and time-consuming. Petroleum cracking of the C5 stream of hydrocarbons produces only about 15% isoprene. About 800,000 tons per year of cis-polyisoprene are produced from the polymerization of isoprene; most of this polyisoprene is used in the tire and rubber industry. Isoprene is also copolymerized for use as a synthetic elastomer in other products such as footwear, mechanical products, medical products, sporting goods, and latex. Isoprene can also be naturally produced by a variety of microbial, plant, and animal species. In particular, two pathways have been identified for the natural biosynthesis of isoprene: the mevalonate (MVA) pathway and the non-mevalonate (DXP) pathway. The products of the mevalonate and non-mevalonate pathway are isopentenyl pyrophosphate (IPP) and dimethylallyl diphosphate (DMAPP). DMAPP can be directly converted to isoprene. IPP and DMAPP can be converted to isoprenoids.

Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Conventional means for obtaining mevalonate and isoprenoids include extraction from biological materials (e.g., plants, microbes, and animals) and partial or total organic synthesis in the laboratory. Such means, however, have generally proven to be unsatisfactory. In particular for isoprenoids, given the often times complex nature of their molecular structure, organic synthesis is impractical given that several steps are usually required to obtain the desired product. Additionally, these chemical synthesis steps can involve the use of toxic solvents as can extraction of isoprenoids from biological materials. Moreover, these extraction and purification methods usually result in a relatively low yield of the desired isoprenoid, as biological materials typically contain only minute amounts of these molecules. Unfortunately, the difficulty involved in obtaining relatively large amounts of isoprenoids has limited their practical use.

Recent developments in the production of isoprene, isoprenoid precursor molecules, and isoprenoids disclose methods for the production of isoprene and isoprenoids at rates, titers, and purities that can be sufficient to meet the demands of robust commercial processes (see, for example, International Patent Application Publication No. WO 2009/076676 A2 and U.S. Pat. No. 7,915,026); however, alternate pathways to improve production and yields of the same are still needed.

Provided herein are cultured recombinant cells, compositions of these cells and methods of using these cells to increase production of mevalonate as an intermediate of the mevalonate-dependent biosynthetic pathway as well as to increase production of molecules derived from mevalonate, such as isoprenoid precursors, isoprene and/or isoprenoids.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, compositions of matter comprising recombinant cells, recombinants cells and methods of making and using these recombinant cells for the production of mevalonate, isoprene, isoprenoid precursor molecules, and/or isoprenoids. Recombinant cells that have been engineered can be used to express a phosphoketolase polypeptide. The phosphoketolase enzymes of this invention can use various substrates, as described in greater detail infra. Accordingly, in one aspect, the invention provides for recombinant cells capable of producing of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein culturing of said recombinant cells in a suitable media provides for the production of isoprene. In one embodiment, one or more heterologous nucleic acids encoding a polypeptide having phosphoketolase activity is capable of synthesizing glyceraldehyde 3-phosphate and acetyl phosphate from xylulose 5-phosphate. In another embodiment, one or more heterologous nucleic acids encoding a polypeptide having phosphoketolase activity is capable of synthesizing erythrose 4-phosphate and acetyl phosphate from fructose 6-phosphate. In another embodiment, the heterologous nucleic acid encoding a polypeptide having phosphoketolase activity is selected from the group consisting of: *Bifidobacterium longum, Enterococcus galliniarum, Clostridium acetobutilicum, Nostoc punctiforme, Rhodopseudomonas palustris, Pantoea, Mucilaginibacter paludis, Thermobifida fusca, Bifidobacterium breve, Rahnella aquatili, Bifidobacterium animalis, Gardnerella vaginalis, Streptomyces avermitilis, Lactobacillus plantarum*, and *Lactobacillus reuteri*. In another embodiment, the heterologous nucleic acid encoding a polypeptide having phosphoketolase activity is selected from the group consisting of: *Bifidobacterium longum, Enterococcus galliniarum*, and *Clostridium acetobutilicum*. In another embodiment, the heterologous nucleic acid encoding an isoprene synthase polypeptide is a plant isoprene synthase polypeptide. In another embodiment, the isoprene synthase polypeptide is a polypeptide from *Pueraria* or *Populus* or a hybrid, *Populus alba×Populus tremula*. In another embodiment, the isoprene synthase polypeptide is selected from the group consisting of *Pueraria montana* or *Pueraria lobata, Populus tremuloides, Populus alba, Populus nigra*, and *Populus trichocarpa*. In another embodiment, one or more polypeptides of the complete MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate. In another embodiment, the recombinant cells further comprise one or more nucleic acids encoding one or more 1-deoxy-D-xylulose 5-phosphate (DXP) pathway polypeptides. In another embodiment, the one or more nucleic acids is placed under an inducible promoter or a constitutive promoter. In another embodiment, the one or more nucleic acids is cloned into one or more multicopy plasmids. In another embodiment, the one or more nucleic acids is integrated into a chromosome of the cells. In another embodiment, the recombinant cells are gram-positive bacterial cells, gram-negative bacterial cells, fungal cells, filamentous fungal cells, algal cells or yeast cells. In another embodiment, the recombinant cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae* and *Aspergillus niger, Saccharomyces cerevisieae* and *Yarrowia lipolytica*.

In another aspect, the invention provides for recombinant cells capable of producing isoprenoid precursors, wherein the cells comprise one or more heterologous nucleic acids encoding a polypeptide having phosphoketolase activity and one or more nucleic acids encoding one or more polypeptides of the complete MVA pathway, wherein culturing of said recombinant cells in a suitable media provides for the production of isoprenoid precursors. In one embodiment, the one or more heterologous nucleic acids encoding a polypeptide having phosphoketolase activity is capable of synthesizing glyceraldehyde 3-phosphate and acetyl phosphate from xylulose 5-phosphate. In another embodiment, the one or more heterologous nucleic acids encoding a polypeptide having phosphoketolase activity is capable of synthesizing erythrose 4-phosphate and acetyl phosphate from fructose 6-phosphate. In another embodiment, the heterologous nucleic acid encoding a polypeptide having phosphoketolase activity is selected from the group consisting of: *Bifidobacterium longum, Enterococcus galliniarum, Clostridium acetobutilicum, Nostoc punctiforme, Rhodopseudomonas palustris, Pantoea, Mucilaginibacter paludis, Thermobifida fusca, Bifidobacterium breve, Rahnella aquatili, Bifidobacterium animalis, Gardnerella vaginalis, Streptomyces avermitilis, Lactobacillus plantarum*, and *Lactobacillus reuteri*. In another embodiment, the heterologous nucleic acid encoding a polypeptide having phosphoketolase activity is selected from the group consisting of: *Bifidobacterium longum, Enterococcus galliniarum*, and *Clostridium acetobutilicum*. In another embodiment, one or more polypeptides of the complete MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate. In another embodiment, the one or more nucleic acids is placed under an inducible promoter or a constitutive promoter. In another embodiment, one or more nucleic acids is cloned into one or more multicopy plasmids. In another embodiment, one or more nucleic acids is integrated into a chromosome of the cells. In another embodiment, the recombinant cells are gram-positive bacterial cells, gram-negative bacterial cells, fungal cells, filamentous fungal cells, algal cells or yeast cells. In another embodiment, the recombinant cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae* and *Aspergillus niger, Saccharomyces cerevisieae* and *Yarrowia lipolytica*.

In another aspect, the invention provides for recombinant cells capable of producing of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein culturing of said recombinant cells in a suitable media provides for the production of isoprenoids. In one embodiment, one or more heterologous nucleic acids encoding a polypeptide having phosphoketolase activity is capable of synthesizing glyceraldehyde 3-phosphate and acetyl phosphate from xylulose 5-phosphate. In another embodiment, one or more heterologous nucleic acids encoding a polypeptide having phosphoketolase activity is capable of synthesizing erythrose 4-phosphate and acetyl phosphate from fructose 6-phosphate. In another embodiment, the heterologous nucleic acid encoding a polypeptide having phosphoketolase activity is selected from the group consisting of: *Bifidobacterium longum, Enterococcus galliniarum, Clostridium acetobutilicum, Nostoc punctiforme, Rhodopseudomonas palustris, Pantoea, Mucilaginibacter paludis, Thermobifida fusca, Bifidobacterium breve, Rahnella aquatili, Bifidobacterium animalis, Gardnerella vaginalis, Streptomyces avermitilis, Lactobacillus plantarum,* and *Lactobacillus reuteri.* In another embodiment, the heterologous nucleic acid encoding a polypeptide having phosphoketolase activity is selected from the group consisting of: *Bifidobacterium longum, Enterococcus galliniarum,* and *Clostridium acetobutilicum.* In another embodiment, the isoprenoid is selected from group consisting of monoterpenes, diterpenes, triterpenes, tetraterpenes, sequiterpene, and polyterpene. In another embodiment, the isoprenoid is a sesquiterpene. In another embodiment, the isoprenoid is selected from the group consisting of abietadiene, amorphadiene, carene, α-framesene, β-farnesene, farnesol, geraniol, geranylgeraniol, linalool, limonene, myrcene, nerolidol, ocimene, patchoulol, β-pinene, sabinene, γ-terpinene, terpindene and valencene. In another embodiment, one or more polypeptides of the complete MVA pathway is selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; and (f) an enzyme that converts mevalonate 5-pyrophosphate to isopentenyl pyrophosphate. In another embodiment, one or more nucleic acids is placed under an inducible promoter or a constitutive promoter. In another embodiment, one or more nucleic acids is cloned into one or more multicopy plasmids. In another embodiment, one or more nucleic acids is integrated into a chromosome of the cells. In another embodiment, the recombinant host cells are gram-positive bacterial cells, gram-negative bacterial cells, fungal cells, filamentous fungal cells, algal cells or yeast cells. In another embodiment, the recombinant host cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae* and *Aspergillus niger, Saccharomyces cerevisieae* and *Yarrowia lipolytica.*

In another aspect, the invention provides for methods of producing isoprene comprising: (a) culturing any of recombinant cells listed above and described herein under conditions suitable for producing isoprene and (b) producing isoprene. In another aspect, the invention provides for methods of producing an isoprenoid precursor comprising: (a) culturing any of recombinant cells listed above and described herein under conditions suitable for producing an isoprenoid precursor and (b) producing an isoprenoid precursor. In another aspect, the invention provides for methods of producing an isoprenoid comprising: (a) culturing any of recombinant cells listed above and described herein under conditions suitable for producing an isoprenoid and (b) producing an isoprenoid.

In some aspects, the recombinant cell comprises one or more heterologous nucleic acids encoding a phosphoketolase polypeptide and one or more nucleic acids encoding one or more MVA pathway enzyme(s). In some aspects, the recombinant cells comprise a heterologous nucleic acid encoding polypeptide capable of synthesizing glyceraldehyde 3-phosphate and acetyl phosphate from xylulose 5-phosphate wherein the acetyl phosphate is converted to mevalonate, isoprenoid precursors, isoprene, and/or isoprenoids. In other aspects, the recombinant cells comprise a heterologous nucleic acid encoding polypeptide capable of synthesizing erythrose 4-phosphate and acetyl phosphate from fructose 6-phosphate wherein the acetyl phosphate is converted to mevalonate, isoprenoid precursors, isoprene, and/or isoprenoids.

Accordingly, in certain aspects, the invention provides recombinant cells capable of enhanced production of mevalonate, wherein the cells comprise one or more heterologous nucleic acids encoding a polypeptide having phosphoketolase activity and one or more nucleic acids encoding one or more polypeptides of the upper MVA pathway, wherein culturing of said recombinant cells in a suitable media provides for the production of said polypeptides and mevalonate. In certain embodiments, the cells produce increased amounts of mevalonate compared to mevalonate-producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus,* and/or *Nocardiopsis dassonvillei.* In one embodiment, the recombinant cells comprise one or more copies of a heterologous nucleic acid encoding a phosphoketolase isolated from *Lactobacillus reuteri.* In another embodiment, the recombinant cells comprise one or more copies of a heterologous nucleic acid encoding phosphoketolase isolated from *Bifidobacterium longum.* In still another embodiment, the recombinant cells comprise one or more copies of a heterologous nucleic acid encoding a phosphoketolase isolated from *Ferrimonas balearica.* In yet another embodiment, the recombinant cells comprise one or more copies of a heterologous nucleic acid encoding a phosphoketolase isolated from *Pedobactor saltans.* In another embodiment, the recombinant cells comprise one or more copies of a heterologous nucleic acid encoding a phosphoketolase isolated from *Streptomyces griseus.* In still another embodiment, the recombinant cells comprise one or more copies of a heterologous nucleic acid encoding a phosphoketolase isolated from *Nocardiopsis dassonvillei.*

In other aspects, the present invention provides recombinant cells capable of producing isoprenoid precursors, wherein the cells comprise one or more heterologous nucleic acids encoding a polypeptide having phosphoketolase activity and one or more nucleic acids encoding one or more polypeptides of the complete MVA pathway, wherein culturing of said recombinant cells in a suitable media provides for the production of said polypeptides and isoprenoid precursors. In certain embodiments, the cells produce increased amounts of isoprenoid precursors compared to isoprenoid precursor-producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus,* and/or *Nocardiopsis dassonvillei.* In one embodiment, the recombinant cells comprise one or more copies of a heterologous nucleic acid encoding a phosphoketolase isolated from *Lactobacillus reuteri.* In another embodiment, the recombinant cells comprise one or more copies of a heterologous nucleic acid encoding a phosphoketolase isolated from *Bifidobacterium longum.* In still another embodiment, the recombinant cells comprise one or more copies of a heterologous nucleic acid encoding a phosphoketolase isolated from *Ferrimonas balearica.* In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*.

In still other aspects, the present invention provides recombinant cells capable of producing of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein culturing of said recombinant cells in a suitable media provides for the production of said polypeptides and isoprene. In certain embodiments, the present invention provides recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*.

In yet other aspects, the present invention provides recombinant cells capable of producing of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein culturing of said recombinant cells in a suitable media provides for the production of said polypeptides wherein the cells capable of producing recoverable amounts of isoprenoids. In certain embodiments, the present invention provides recombinant cells capable of enhanced production of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells produce increased amounts of isoprenoids compared to isoprenoid producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In any of the aspects herein, the isoprenoid is selected from group consisting of monoterpenes, diterpenes, triterpenes, tetraterpenes, sequiterpene, and polyterpene. In one aspect, the isoprenoid is a sesquiterpene. In another aspect, the isoprenoid is selected from the group consisting of abietadiene, amorphadiene, carene, α-framesene, β-farnesene, farnesol, geraniol, geranylgeraniol, linalool, limonene, myrcene, nerolidol, ocimene, patchoulol, β-pinene, sabinene, γ-terpinene, terpindene and valencene.

In certain embodiments, the recombinant cells capable of producing mevalonate, isoprene, isoprenoid precursor molecules, and/or isoprenoids comprise one or more nucleic acids encoding a polypeptide capable of synthesizing glyceraldehyde 3-phosphate and acetyl phosphate from xylulose 5-phosphate. In one aspect, the one or more nucleic acids encoding a polypeptide capable of synthesizing glyceraldehyde 3-phosphate and acetyl phosphate from xylulose 5-phosphate is a phosphoketolase gene. In another aspect, the phosphoketolase gene is a gene from *Lactobacillus*. In another aspect, the phosphoketolase gene is from the genus *Lactobacillus reuteri*. In another aspect, the phosphoketolase gene encodes a protein having the amino acid sequence of:

(SEQ ID NO: 2)
MAVDYDSKKYLESVDAYWRAANYLSVGTLYLMGDPLLRQPLKAEDVKP

KPIGHWGTIVPQNFIYAHLNRVIKKYDLDMFYIEGSGHGGQVMVNNSY

LDGSYTEIYPEYTQDTKGMAKLFKHFSFPGGTASHAAPETPGSIHEGG

ELGYSLSHGVGAILDNPEVIAAVEIGDGEAETGPLMASWFSDKFINPI

KDGAVLPIIQVNGFKISNPTILSWMSDEELTKYFEGMGWKPYFVSAYK

EADRDGEFKGYKPHMEVHEEMAKTLDKVVEEIKAIQKNARENNDNSLP

QWPMIIFRAPKGWTGPKTDLDGNPIENSFRAHQIPVPVSQDDMEHKDI

LVDWLKSYKPEELFDEDGHPVALVEENTPEGNRRMAMNPITNGGIDPK

PLVLPNYRDFAIDVQNPGSVVKQDMLEWGKYLNKMAELNPTNFRGFGP

DESKSNRLYAFLDGQKRQWMESVHEPNDEDVAPQGRMIDSQLSEHQAE

-continued

```
GFLEGYTLTGRHGFFATYEAFGRVVDSMLTQHMKWLRKAKDLYWRHQY

PALNFVDTSTVFQQDHNGYTHQDPGLLTHLFEKERPDLVKEYLPADTN

SLMAVSNKAFRNQECINLFVTSKHPRAQWFSIDEATQLADNGLGYIDW

ASTDQGTEPDVVFASSGTEPTEEALAAIDILHDNFPELKIRYINIIEI

MRLMNTDKNPEGLTDAEFNSYFTTDKPVIFAWHGFRDMIQALFFDRAN

RNVHIHSYEENGDITTPFDMRVLNELDRFHLAKDAIQSVPGYEQKSAA

FVAKMDNMINKHNHYIRSEGKDLPEVTNWTWKGLK.
```

In other embodiments, the recombinant cells capable of producing mevalonate, isoprene, isoprenoid precursor molecules, and/or isoprenoids comprise one or more nucleic acids encoding a polypeptide capable of synthesizing erythrose 4-phosphate and acetyl phosphate from fructose-6-phosphate. In one aspect, the one or more nucleic acids encoding a polypeptide capable of synthesizing erythrose 4-phosphate and acetyl phosphate from fructose 6-phosphate is a phosphoketolase gene. In another aspect, the phosphoketolase gene is a gene from *Bifidobacterium*. In another aspect, the phosphoketolase gene is from the genus *Bifidobacterium longum* subspecies *infantis*. In another aspect, the phosphoketolase gene encodes a protein having the amino acid sequence of:

```
                                        (SEQ ID NO: 4)
MTSPVIGTPWKKLSAPVSEEALEGVDKYWRVANYLSIGQIYLRSNPL

MKEPFTREDVKHRLVGHWGTTPGLNFLIGHINRFIADHGQNTVIIMG

PGHGGPAGTSQSYLDGTYTETFPKITKDEAGLQKFFRQFSYPGGIPS

HFAPETPGSIHEGGELGYALSHAYGAIMDNPSLFVPAIVGDGEAETG

PLATGWQSNKLVNPRTDGIVLPILHLNGYKIANPTILSRISDEELHE

FFHGMGYEPYEFVAGFDDEDHMSIHRRFAELWETIVVDEICDIKATA

QTDNVHRPFYPMLIFRTPKGWTCPKYIDGKKTEGSWRSHQVPLASAR

DTEAHFEVLKNWLESYKPEELFDANGAVKDDVLAFMPKGELRIGANP

NANGGVIRDDLKLPNLEDYEVKEVAEFGHGWGQLEATRSLGAYTRDI

IKNNPRDFRIFGPDETASNRLQASYEVTNKQWDAGYISDEVDEHMRV

SGQVVEQLSEHQMEGFLEAYLLTGRHGIVVSSYESFVHVIDSMLNQH

AKWLEATVREIPWRKPIASMNLLVSSHVWRQDHNGFSHQDPGVTSVL

LNKCFHNDHVIGIYFATDANMLLAIAEKCYKSTNKINAIIAGKQPAA

TWLTLDEARAELEKGAAAWDWASTAKTNDEAEIVLAAAGDVPTQEIM

AASDKLKELGIKFKVVNVVDLLSLQSAKENDEALSNEEFADIFTADK

PVLFAYHSYAHDVRGLIYDRPNHDNFNVHGYEEEGSTTTPYDMVRVN

RIDRYELTAEALRMIDADKYADKIDELEKFRDEAFQFAVDKGYDHPD

YTDWVYSGVNTGKKGAVTATAATAGDNE.
```

In one aspect, the invention described herein provides for recombinant cells capable of producing mevalonate, isoprenoids precursor, isoprene and/or isoprenoids comprising one or more heterologous nucleic acids encoding a polypeptide capable of synthesizing glyceraldehyde 3-phosphate and acetyl phosphate from xylulose 5-phosphate and one or more nucleic acids encoding: (a) a peptide that synthesizes acetoacetyl-CoA from malonyl-CoA and acetyl-CoA; (b) one or more mevalonate (MVA) pathway polypeptides; wherein culturing of said recombinant cells in a suitable media provides for the production of said polypeptides and synthesis of mevalonate, isoprenoids precursor, isoprene and/or isoprenoids. In one aspect, the one or more nucleic acids encoding a polypeptide capable of synthesizing glyceraldehyde 3-phosphate and acetyl phosphate from xylulose 5-phosphate is a phosphoketolase gene. In one aspect, the peptide that synthesizes acetoacetyl-CoA from malonyl-CoA and acetyl-CoA is a peptide having derived from *Streptomyces* sp. CL190. In one aspect, the peptide that synthesizes acetoacetyl-CoA from malonyl-CoA and acetyl-CoA is a peptide having the amino acid sequence of SEQ ID NO:5.

In another aspect, the invention provides for recombinant cells capable of producing mevalonate, isoprenoids precursor, isoprene and/or isoprenoids isoprene comprising one or more heterologous nucleic acids encoding a polypeptide capable of synthesizing erythrose 4-phosphate and acetyl phosphate from fructose 6-phosphate and one or more nucleic acids encoding: (a) a peptide that synthesizes acetoacetyl-CoA from malonyl-CoA and acetyl-CoA; (b) one or more mevalonate (MVA) pathway polypeptides; wherein culturing of said recombinant cells in a suitable media provides for the production of said polypeptides and synthesis of mevalonate, isoprenoids precursor, isoprene and/or isoprenoids. In one aspect, the one or more nucleic acids encoding a polypeptide capable of synthesizing erythrose 4-phosphate and acetyl phosphate from fructose 6-phosphate is a phosphoketolase gene. In one aspect, the peptide that synthesizes acetoacetyl-CoA from malonyl-CoA and acetyl-CoA is a peptide having derived from *Streptomyces* sp. CL190. In one aspect, the peptide that synthesizes acetoacetyl-CoA from malonyl-CoA and acetyl-CoA is a peptide having the acid sequence of SEQ ID NO:5.

In another aspect, the one or more heterologous nucleic acids encoding a polypeptide having phosphoketolase activity encodes a polypeptide having an amino acid sequence with 80% or more identity to the amino acid sequence of SEQ ID NO:2 and having a function of synthesizing glyceraldehyde 3-phosphate and acetyl phosphate from xylulose 5-phosphate. In certain embodiments, the one or more heterologous nucleic acids encoding a polypeptide having phosphoketolase activity encodes a polypeptide having 85%, 86%, 87%, 88%, 89%, 90%, 91%, 92%, 93%, 94%, 95%, 96%, 97%, 98%, or 99% sequence identity to the amino acid sequence of SEQ ID NO:2. In another aspect, the one or more heterologous nucleic acids encoding a polypeptide having phosphoketolase activity encodes a polypeptide having an amino acid sequence with 80% or more identity to the amino acid sequence of SEQ ID NO: 4 and having a function of synthesizing erythrose 4-phosphate and acetyl phosphate from fructose 6-phosphate. In certain embodiments, the one or more heterologous nucleic acids encoding a polypeptide having phosphoketolase activity encodes a polypeptide having 85%, 86%, 87%, 88%, 89%, 90%, 91%, 92%, 93%, 94%, 95%, 96%, 97%, 98%, or 99% sequence identity to the amino acid sequence of SEQ ID NO:4.

In any of the aspects herein, the heterologous nucleic acid encoding an isoprene synthase polypeptide is a plant isoprene synthase polypeptide. In any of the aspects herein, the isoprene synthase polypeptide is a polypeptide from *Pueraria* or *Populus* or a hybrid, *Populus alba*×*Populus tremula*. In any of the aspects herein, the isoprene synthase polypeptide is selected from the group consisting of *Pueraria montana* or *Pueraria lobata*, *Populus tremuloides*, *Populus alba*, *Populus nigra*, and *Populus trichocarpa*. In another aspect, the plant isoprene synthase polypeptide is a kudzu isoprene synthase polypeptide. In another aspect, the isoprene synthase is an engineered isoprene synthase, such as those described in U.S. Pat. Publ. No. 2010/0003716 and U.S. Pat. Publ. No. 2011/0076743.

In any of the aspects herein, the invention provides a recombinant host cell, or progeny thereof, comprising cells engineered for increased carbon flux towards mevalonate production wherein the activity of one or more enzymes from the group consisting of: (a) citrate synthase, (b) phosphotransacetylase; (c) acetate kinase; (d) lactate dehydrogenase; (e) glyceraldehyde 3-phosphate dehydrogenase, (f) pyruvate dehydrogenase, (g) Phosphogluconate dehydratase, (h) 2-keto-3-deoxygluconate 6-phosphate aldolase, (i) phsophofructokinase, (j) transketolase, (k) transaldolase, (l) ribulose-5-phosphate-epimerase, and/or (m) ribose-5-phosphate epimerase is modulated.

In any of aspects herein, the cells can further comprise an mvaE gene and an mvaS gene selected from the group consisting of: (a) an mvaE gene and an mvaS gene from *L. grayi*; (b) an mvaE gene and an mvaS gene from *E. faecium*; (c) an mvaE gene and an mvaS gene from *E. gallinarum*; (d) an mvaE gene and an mvaS gene from *E. casseliflavus*; and (e) an mvaE gene and an mvaS gene from *E. faecalis*.

In certain aspects, the one or more nucleic acids encoding one or more MVA pathway polypeptides is a heterologous nucleic acid. In other aspects, the one or more nucleic acids encoding one or more MVA pathway polypeptides is a copy of an endogenous nucleic acid. In any of the aspects herein, one or more MVA pathway polypeptides can be selected from (a) an enzyme that condenses two molecules of acetyl-CoA to form acetoacetyl-CoA; (b) an enzyme that condenses acetoacetyl-CoA with acetyl-CoA to form HMG-CoA (e.g., HMG synthase); (c) an enzyme that converts HMG-CoA to mevalonate; (d) an enzyme that phosphorylates mevalonate to mevalonate 5-phosphate; (e) an enzyme that converts mevalonate 5-phosphate to mevalonate 5-pyrophosphate; (f) an enzyme that converts mevalonate 5-pyrophosphate to isopentenyl pyrophosphate; and (g) an enzyme that converts isopentenyl pyrophosphate to dimethylallyl diphosphate. In any of the aspects herein, one or more MVA pathway polypeptides is selected from (a) an enzyme that condenses acetoacetyl-CoA with acetyl-CoA to form HMG-CoA (e.g., HMG synthase); (b) an enzyme that converts HMG-CoA to mevalonate; (c) an enzyme that phosphorylates mevalonate to mevalonate 5-phosphate; (d) an enzyme that converts mevalonate 5-phosphate to mevalonate 5-pyrophosphate; and (e) an enzyme that converts mevalonate 5-pyrophosphate to isopentenyl pyrophosphate.

In any of the aspects herein, the enzyme that phosphorylates mevalonate to mevalonate 5-phosphate can be selected from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, and *Streptomyces* mevalonate kinase polypeptide, *Streptomyces* CL190 mevalonate kinase polypeptide, or *M. burtonii* mevalonate kinase. In any of the aspects herein, the enzyme that phosphorylates mevalonate to mevalonate 5-phosphate is *M. mazei* mevalonate kinase.

In any of the aspects herein, the recombinant cells can further comprise one or more nucleic acids encoding one or more 1-deoxy-D-xylulose 5-phosphate (DXP) pathway polypeptides. In one aspect, one or more nucleic acids that encode for one or more DXP pathway polypeptides is a heterologous nucleic acid. In another aspect, the one or more nucleic acids encoding one or more DXP pathway polypeptides is a copy of an endogenous nucleic acid. In another aspect, the one or more DXP pathway polypeptides is selected from (a) 1-deoxy-D-xylulose-5-phosphate synthase (DXS), (b) 1-deoxy-D-xylulose-5-phosphate reductoisomerase (DXR), (c) 4-diphosphocytidyl-2C-methyl-D-erythritol synthase (MCT), (d) 4-diphosphocytidyl-2-C-methyl-D-erythritol kinase (CMK), (e) 2C-methyl-D-erythritol 2,4-cyclodiphosphate synthase (MCS), (f) 1-hydroxy-2-methyl-2-(E)-butenyl 4-diphosphate synthase (HDS), and (g) 1-hydroxy-2-methyl-2-(E)-butenyl 4-diphosphate reductase (HDR). In another aspect, the DXP pathway polypeptide is DXS.

In any of the aspects herein, the one or more heterologous nucleic acids is placed under an inducible promoter or a constitutive promoter. In any of the aspects herein, the one or more heterologous nucleic acids is cloned into one or more multicopy plasmids. In any of the aspects herein, the one or more heterologous nucleic acids is integrated into a chromosome of the cells.

In any of the aspects herein, the recombinant host cell is a bacterial, algal, fungal, yeast, or cyanobacterial cell. In one aspect, the host cell is a bacterial cell. In another aspect, the bacterial cell is a gram-positive bacterial cell or gram-negative bacterial cell. In another aspect, the bacterial cell is selected from the group consisting of *E. coli, L. acidophilus, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In another aspect, the bacterial cell is an *E. coli* cell. In another aspect, the bacterial cell is an *L. acidophilus* cell. In another aspect, the is an algal cell. In another aspect, the algal cell is selected from the group consisting of green algae, red algae, glaucophytes, chlorarachniophytes, euglenids, chromista, or dinoflagellates. In another aspect, the host cell is a fungal cell. In another aspect, the fungal cell is a filamentous fungi. In another aspect, the host cell is a yeast cell. In another aspect, the yeast cell is selected from the group consisting of *Saccharomyces* sp., *Schizosaccharomyces* sp., *Pichia* sp., or *Candida* sp. In another aspect, the yeast cell is a *Saccharomyces cerevisiae* cell.

In another aspect, the invention provides for a recombinant host cell capable of producing an isoprenoid comprising one or more nucleic acids encoding a polypeptide capable of synthesizing glyceraldehyde 3-phosphate and acetyl phosphate from xylulose 5-phosphate and one or more nucleic acids encoding: (a) one or more nucleic acids encoding a polyprenyl pyrophosphate synthase; and (b) one or more nucleic acids encoding one or more mevalonate (MVA) pathway polypeptides, wherein culturing of said recombinant host cell in a suitable media provides for production of said polypeptides and synthesis of one or more isoprenoid(s). In one aspect, the one or more nucleic acids encoding one or more MVA pathway polypeptides of (b) is a heterologous nucleic acid. In any of the aspects herein, the one or more MVA pathway polypeptides is selected from the group consisting of (a) an enzyme that converts acetoacetyl-CoA to HMG-Co-A; (b) an enzyme that converts HMG-CoA to mevalonate; (c) an enzyme that phosphorylates mevalonate to mevalonate 5-phosphate; (d) an enzyme that converts mevalonate 5-phosphate to mevalonate 5-pyrophosphate; and (e) an enzyme that converts mevalonate 5-pyrophosphate to isopentenyl pyrophosphate.

In another aspect, the invention provides for a recombinant host cell capable of producing an isoprenoid comprising one or more nucleic acids encoding a polypeptide capable of synthesizing erythrose 4-phosphate and acetyl phosphate from fructose 6-phosphate and one or more nucleic acids encoding: (a) one or more nucleic acids encoding a polyprenyl pyrophosphate synthase; and (b) one or more nucleic acids encoding one or more mevalonate (MVA) pathway polypeptides, wherein culturing of said recombinant host cell in a suitable media provides for production of said polypeptides and synthesis of one or more isoprenoid(s). In one aspect, the one or more nucleic acids encoding one or more MVA pathway polypeptides of (b) is a heterologous nucleic acid. In any of the aspects herein, the one or more MVA pathway polypeptides is selected from the group consisting of (a) an enzyme that converts acetoacetyl-CoA to form HMG-Co-A; (b) an enzyme that converts HMG-CoA to mevalonate; (c) an enzyme that phosphorylates mevalonate to mevalonate 5-phosphate; (d) an enzyme that converts mevalonate 5-phosphate to mevalonate 5-pyrophosphate; and (e) an enzyme that converts mevalonate 5-pyrophosphate to isopentenyl pyrophosphate.

In another aspect, the invention provides for methods of producing mevalonate comprising: (a) culturing a recombinant host cell comprising one or more heterologous nucleic acids encoding (i) a polypeptide having phosphoketolase activity; (ii) and (b) producing mevalonate. In one aspect, the method further comprises recovering the mevalonate produced by the recombinant host cell. In certain embodiments, the methods provide for production of increased amounts of mevalonate compared to mevalonate-producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*.

In other aspects, the invention provides for methods of producing isoprenoid precursors comprising: (a) culturing a recombinant host cell comprising (i) one or more heterologous nucleic acids encoding a polypeptide having phosphoketolase activity; (ii) and one or more nucleic acids encoding one or more polypeptides of the complete MVA pathway, and (b) producing an isoprenoid precursor. In one aspect, the method further comprises recovering the isoprenoid produced by the recombinant host cell. In certain embodiments, the methods comprise recombinant cells that produce increased amounts of isoprenoid precursors compared to isoprenoid precursor-producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*.

In still other aspects, the present invention provides for methods of producing isoprene comprising: (a) culturing a recombinant host cell comprising: (i) one or more heterologous nucleic acids encoding a polypeptide having phosphoketolase activity; (ii) one or more nucleic acids encoding one or more polypeptides of the complete MVA pathway; and (iii) a heterologous nucleic acid encoding an isoprene synthase polypeptide, and (b) producing isoprene. In one aspect, the method further comprises recovering the isoprenoid produced by the recombinant host cell. In certain embodiments, the methods comprise recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*.

In yet other aspects, the present invention provides methods for producing of isoprenoids comprising: (a) culturing a recombinant host cell comprising: (i) one or more heterologous nucleic acids encoding a polypeptide having phosphoketolase activity; (ii) one or more nucleic acids encoding one or more polypeptides of the complete MVA pathway; and (iii) a heterologous nucleic acid encoding an polyprenyl pyrophosphate synthase polypeptide, and (b) producing an isoprenoid. In one aspect, the method further comprises recovering the isoprenoid produced by the recombinant host cell. In certain embodiments, the methods comprise recombinant cells capable of enhanced production of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells produce increased amounts of isoprenoids compared to isoprenoid producing cells that do not comprise the one or more heterologous nucleic acids encoding a polypeptide having phosphoketolase activity. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In any of the aspects herein, the isoprenoid is selected from group consisting of monoterpenes, diterpenes, triterpenes, tetraterpenes, sequiterpene, and polyterpene. In one aspect, the isoprenoid is a sesquiterpene. In another aspect, the isoprenoid is selected from the group consisting of abietadiene, amorphadiene, carene, α-framesene, β-farnesene, farnesol, geraniol, geranylgeraniol, linalool, limonene, myrcene, nerolidol, ocimene, patchoulol, β-pinene, sabinene, γ-terpinene, terpindene and valencene.

In another aspect, the invention provides for methods of producing mevalonate using any of the recombinant cells described herein. In another aspect, the invention provides for methods of producing isoprenoid precursors using any of the recombinant cells described herein. In another aspect, the invention provides for methods of producing isoprene using any of the recombinant cells described herein. In another aspect, the invention provides for methods of producing isoprenoid precursors using any of the recombinant cells described herein. In another aspect, the invention provides for methods of producing isoprenoids using any of the recombinant cells described herein.

BRIEF DESCRIPTION OF THE DRAWINGS

FIG. 4 is a table containing a representative list of phosphoketolase polypeptides. This table is merely representative and not intended to be limiting as any phosphoketolase polypeptide that converts xylulose 5-phosphate to glyceraldehyde 3-phosphate and acetyl phosphate and/or converts fructose 6-phosphate to erythrose 4-phosphate and acetyl phosphate is contemplated for use in the present invention.

Titer=grams Mevalonate/Liter of whole fermentor broth.

Figure 13:
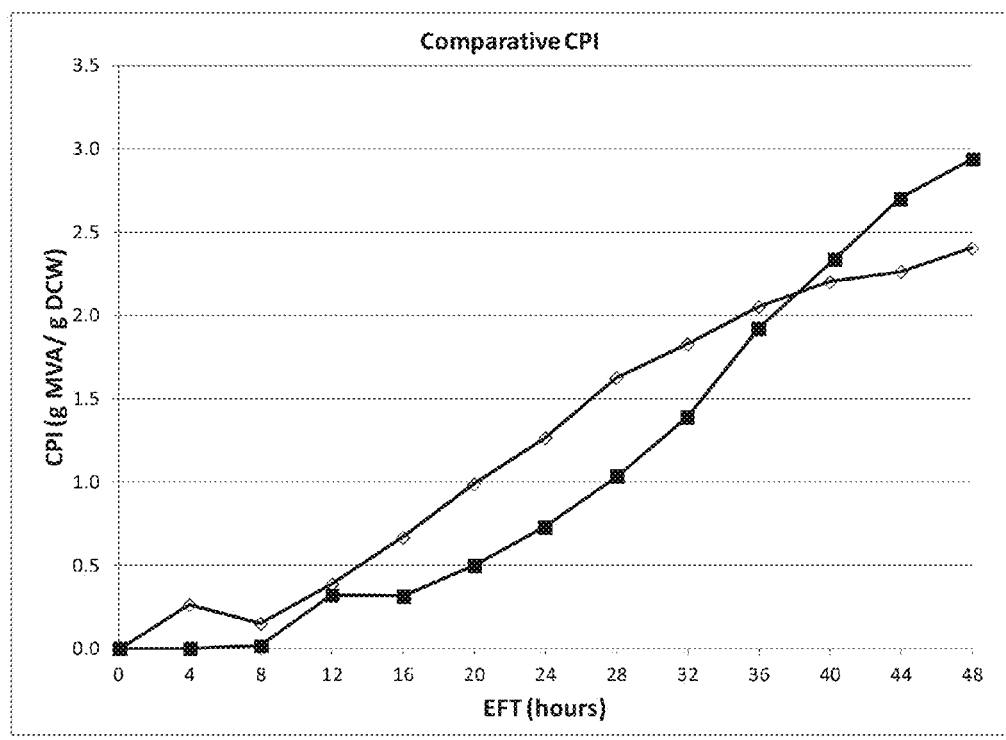

FIG. 13 depicts Cell Productivity Index (CPI) achieved by the phosphoketolase expressing strain (closed black squares) compared the control strain (open diamonds) in the 15-L fermentation over time. Strains were run under the same conditions. Cell Productivity Index (CPI) was calculated using the following formula:

CPI=total grams Mevalonate/total grams dry cell weight.

Figure 14:
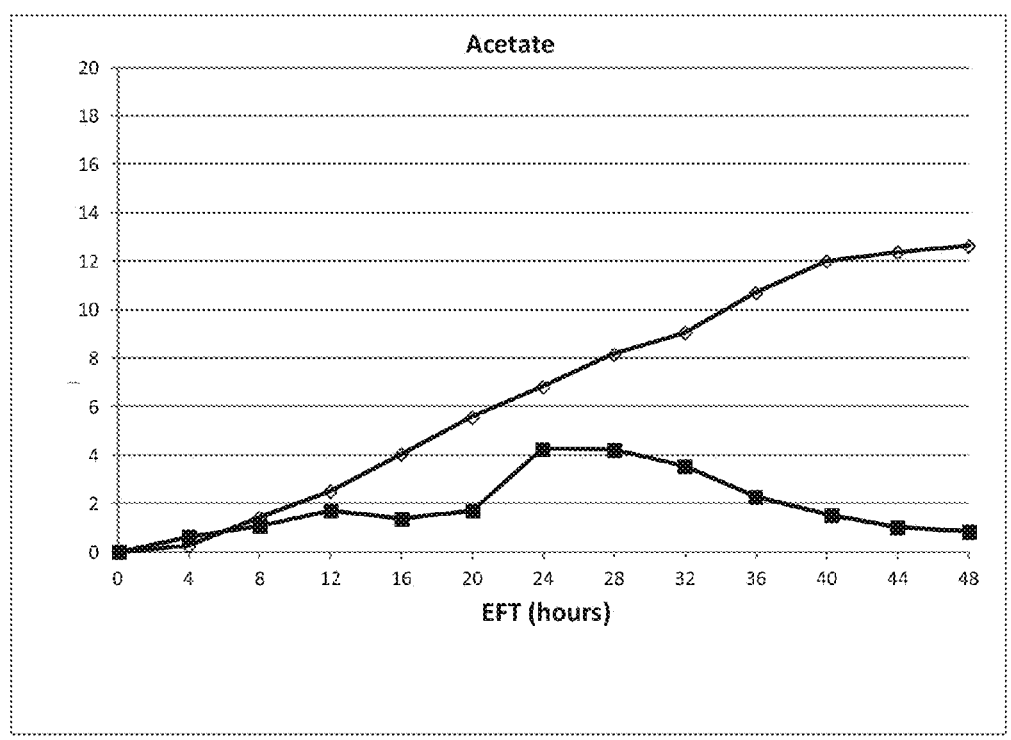

FIG. 14 provides a graph showing that accumulated acetate in the fermentation broth was substantially lower when using the phosphoketolase expressing strain (closed black squares) as compared the control strain (open diamonds) in the 15-L fermentation over time. Strains were run under the same conditions. Acetate was measured by HPLC and the concentration was reported using the following formula:

[Acetate]=grams acetate/Liter of whole fermentor broth.

FIG. 15 provides the nucleotide sequence for the nucleic acid sequence encoding a phosphoketolase from *Lactobacillus reuteri* (SEQ ID NO:1).

FIG. 16 provides the amino acid sequence for a phosphoketoase enzyme from *Lactobacillus reuteri* (SEQ ID NO:2).

FIG. 17 provides the nucleotide sequence for the nucleic acid sequence encoding a phosphoketoase from *Bifidobacterium longum* (SEQ ID NO:3).

FIG. 18 provides the amino acid sequence for a phosphoketoase enzyme from *Bifidobacterium longum* (SEQ ID NO:4).

FIG. 19 provides the amino acid sequence for an acetoacetyl-CoA synthase enzyme from *Streptomyces* sp. CL190 (SEQ ID NO:5).

FIG. 20 provides the nucleotide sequence for the nucleic acid sequence encoding mvaE from *L. grayi* (SEQ ID NO:6).

FIG. 21 provides the nucleotide sequence for the nucleic acid sequence encoding mvaE from *E. faecium* (SEQ ID NO:7).

FIG. 22 provides the nucleotide sequence for the nucleic acid sequence encoding mvaE from *E. gallinarum* (SEQ ID NO:8).

FIG. 23 provides the nucleotide sequence for the nucleic acid sequence encoding mvaE from *E. casseliflavus* (SEQ ID NO:9).

FIG. 24 provides the nucleotide sequence for the nucleic acid sequence encoding mvaS from *L. grayi* (SEQ ID NO:10).

FIG. 25 provides the nucleotide sequence for the nucleic acid sequence encoding mvaS from *E. faecium* (SEQ ID NO:11).

FIG. 26 provides the nucleotide sequence for the nucleic acid sequence encoding mvaS from *E. gallinarum* (SEQ ID NO:12).

FIG. 27 provides the nucleotide sequence for the nucleic acid sequence encoding mvaS from *E. casseliflavus* (SEQ ID NO:13).

FIG. 28 provides the nucleotide sequence for pCMP1090 (SEQ ID NO:15).

FIG. 29 provides the nucleotide sequence for pCMP1029 (SEQ ID NO:16).

FIG. 30 provides the nucleic acid sequence encoding a phosphoketolase from *E. gallinarum* (SEQ ID NO:17).

FIG. 31 provides the nucleic acid sequence encoding a phosphoketolase from *N. punctiforme* (SEQ ID NO:18).

FIG. 32 provides the nucleic acid sequence encoding a phosphoketolase from *R. palustris* (SEQ ID NO:19).

FIG. 33 provides the nucleic acid sequence encoding a phosphoketolase from *Pantoea* (SEQ ID NO:20).

FIG. 34 provides the nucleic acid sequence encoding a phosphoketolase from *M. paludis* (SEQ ID NO:21).

FIG. 35 provides the nucleic acid sequence encoding a phosphoketolase from *T. fusca* (SEQ ID NO:22).

FIG. 36 provides the nucleic acid sequence encoding a phosphoketolase from *B. breve* (SEQ ID NO:23).

FIG. 37 provides the nucleic acid sequence encoding a phosphoketolase from *R. aquatilis* (SEQ ID NO:24).

FIG. 38 provides the nucleic acid sequence encoding a phosphoketolase from *B. animalis* (SEQ ID NO:25).

FIG. 39 provides the nucleic acid sequence encoding a phosphoketolase from *G. vaginalis* (SEQ ID NO:26).

FIG. 40 provides the nucleic acid sequence encoding a phosphoketolase from *S. avermitilis* (SEQ ID NO:27).

FIG. 41 provides the nucleic acid sequence encoding a phosphoketolase from *C. acetobutylicum* (SEQ ID NO:28).

FIG. 42 provides the nucleic acid sequence encoding a phosphoketolase from *L. paraplantarum* (SEQ ID NO:29).

Figure 43:
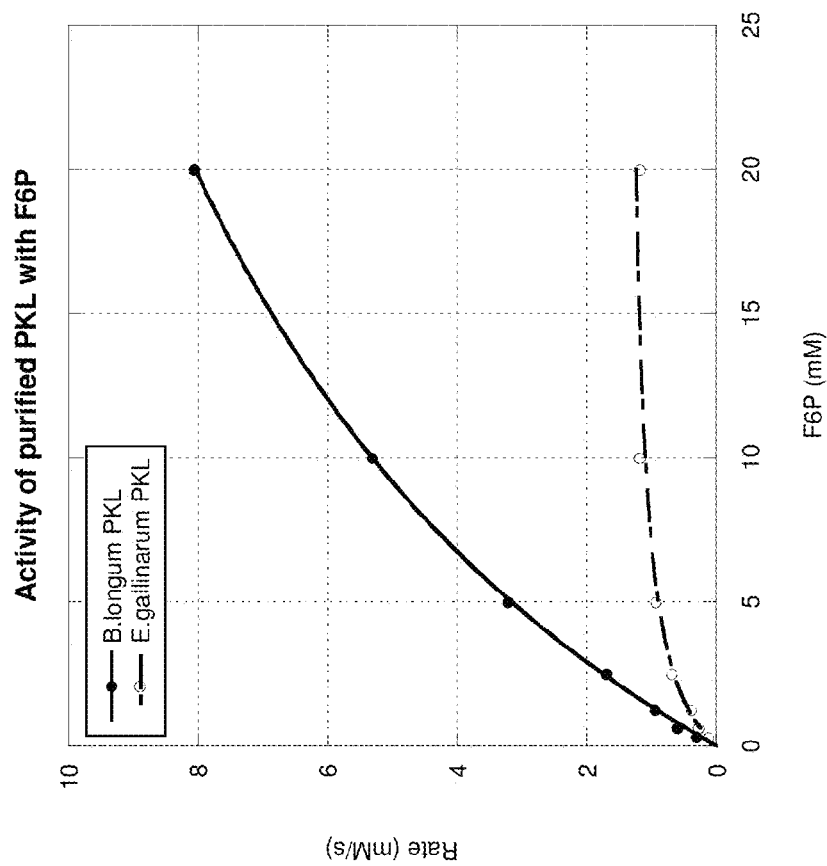

FIG. 43 is a graph showing the activity of PKLs from *B. longum* and *E. gallinarum* in the presence of F6P substrate.

Figure 44:
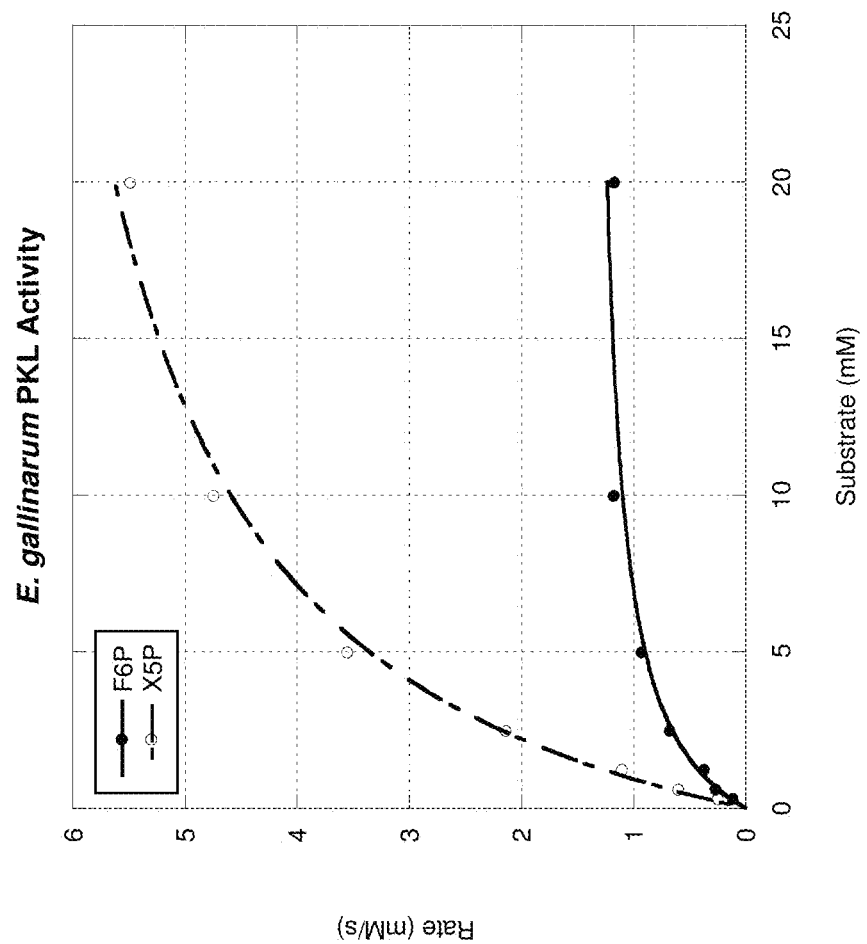

FIG. 44 is a graph showing the activity of PKLs from *E. gallinarum* in the presence of F6P and X5P substrates.

Figure 45:
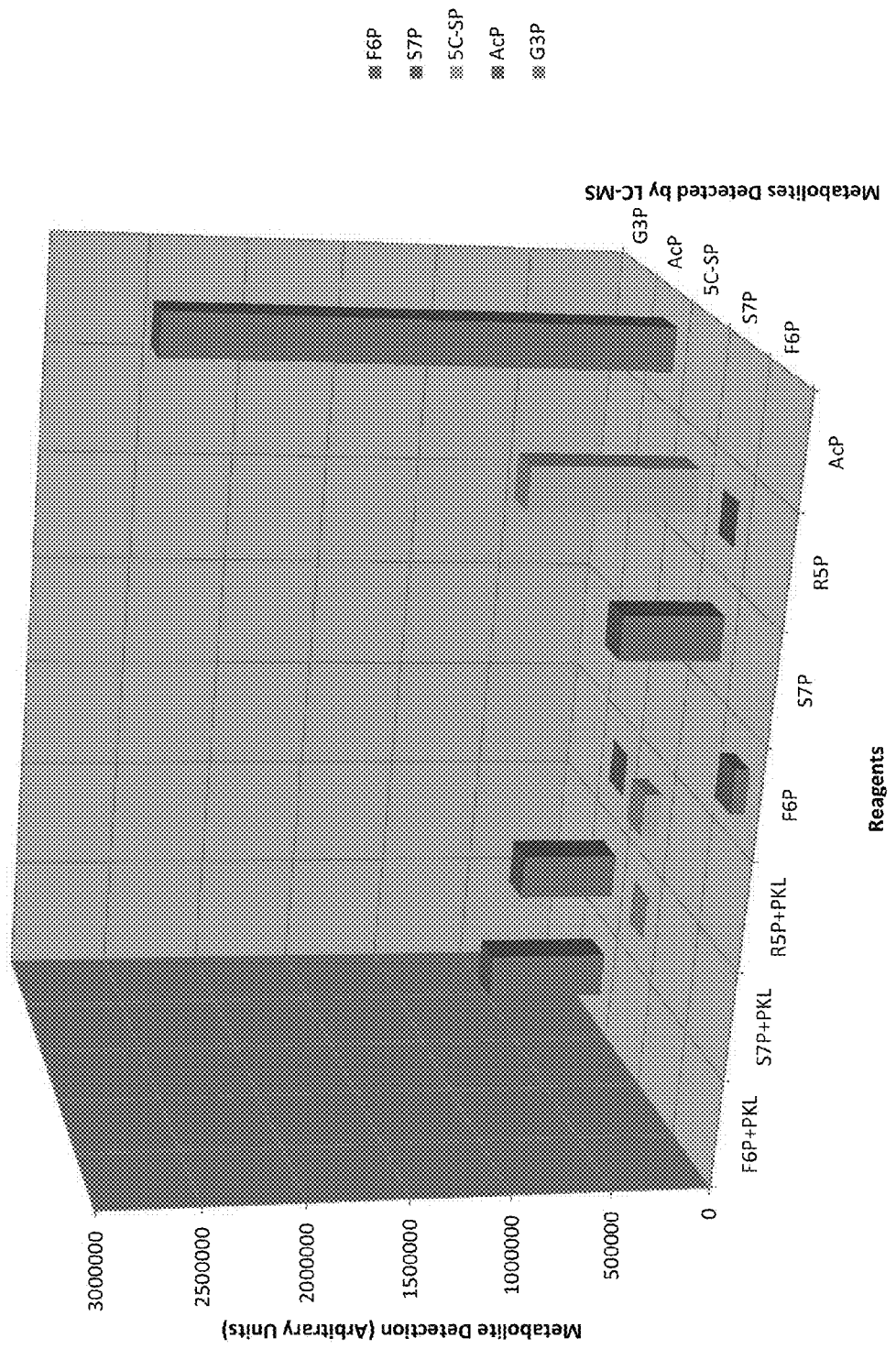

FIG. 45 is a graph showing metabolite formation by a strain expressing *B. longum* PKL in the presence of S7P substrate.

Figure 46:
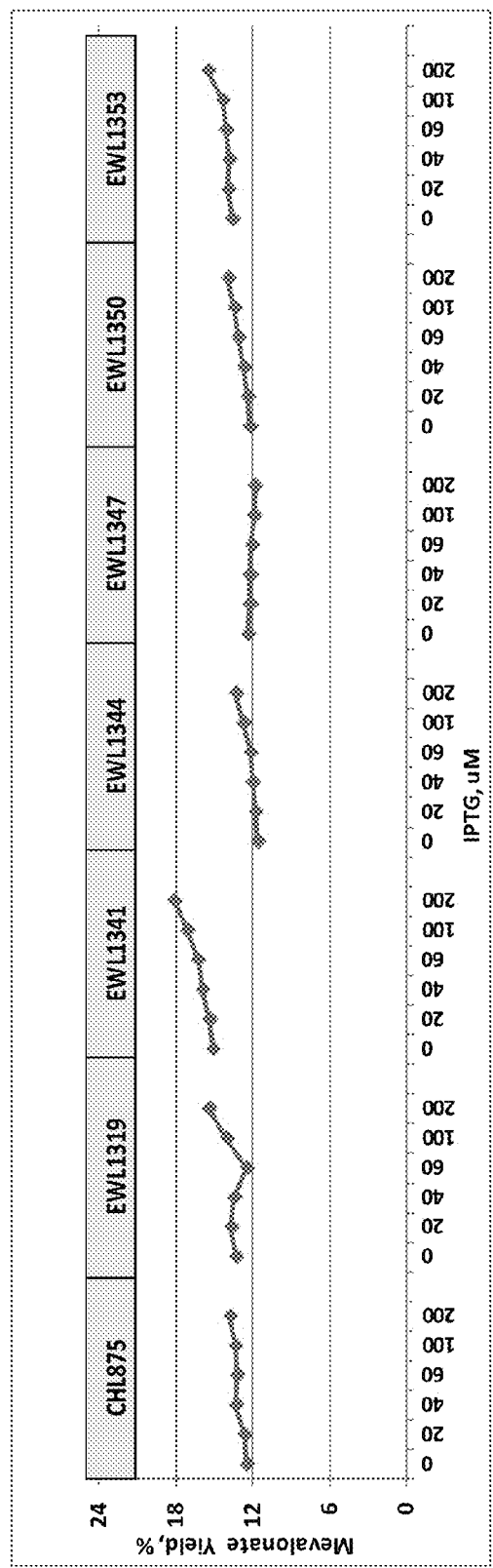

FIG. 46 is a panel of graphs showing MVA yield by strains expressing *B. longum* PKL (EWL1319), *E. gallinarum* PKL (EWL1341), *N. punctiforme* PKL (EWL1344), *R. palustris* PKL (EWL1347), *Pantoea* PKL (EWL1350), or *T. fusca* PKL (EWL1353) as compared to a control strain not expressing PKL (CHL875).

Figure 47:
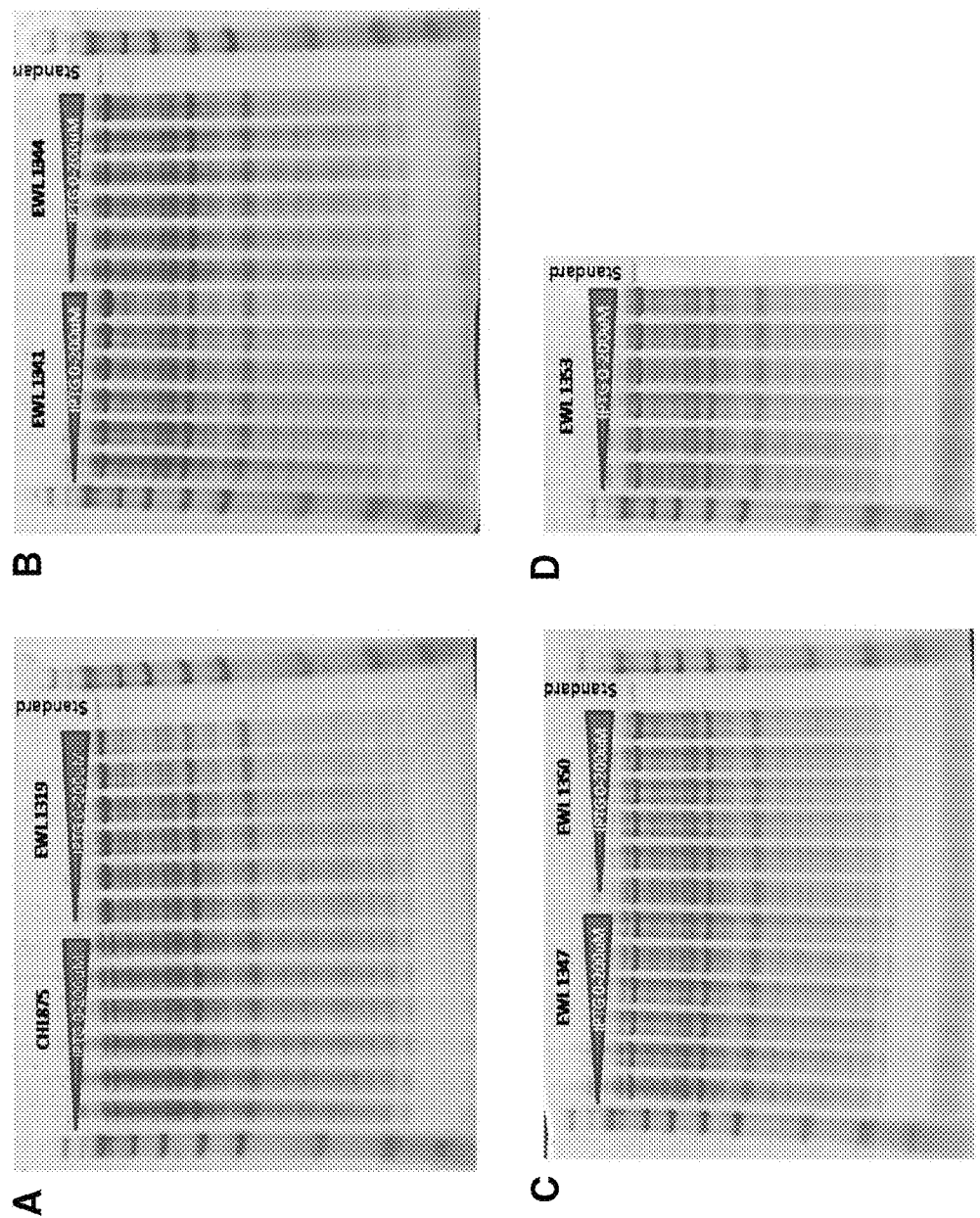

FIG. 47 is a series of SDS-PAGE coomasie stained gels showing protein expression in strains expressing phosphoketolase. A) control strain CHL875 not expressing PKL and strain EWL1319 expressing *B. longum* PKL, B) strain EWL1341 expressing *E. gallinarum* PKL and strain EWL1344 expressing *N. punctiforme* PKL, C) strain EWL1347 expressing *R. palustris* PKL and strain EWL1350 expressing *Pantoea* PKL, and D) strain EWL1353 expressing *T. fusca* PKL with increasing IPTG induction.

Figure 48:
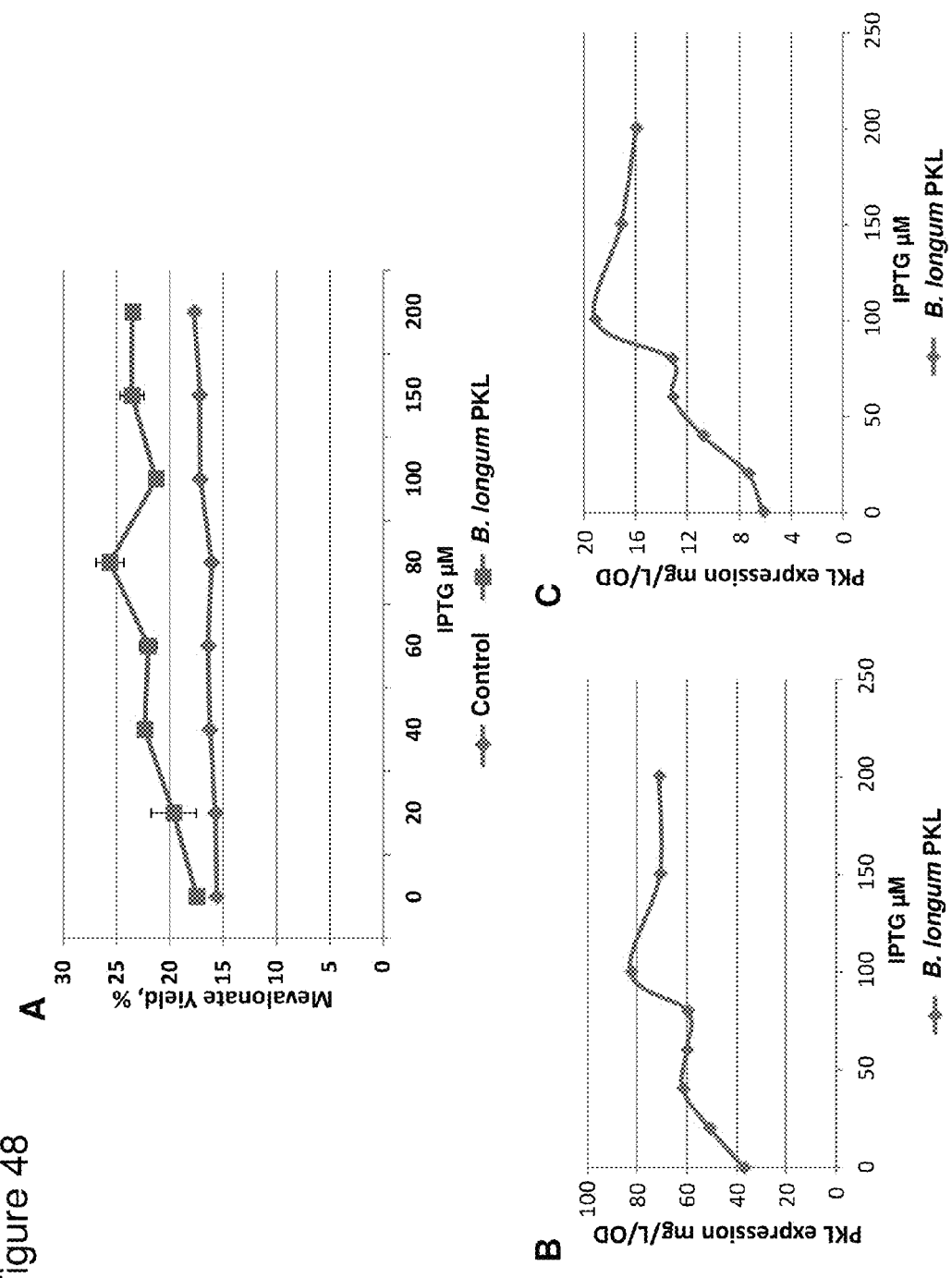

FIG. 48 is a graph showing protein expression and MVA yield by a strain expressing *B. longum* PKL. A) MVA yield by an MVA producing strain expressing *B. longum* PKL (closed square) as compared to an MVA producing control strain not expressing PKL (closed diamonds) with increasing IPTG induction. B) Protein expression of *B. longum* PKL in the soluble fraction of whole cell lysates from strain EWL1319. C) Protein expression of *B. longum* PKL in the insoluble fraction of whole cell lysates from strain EWL1319.

FIG. 49 contains an SDS-PAGE coomasie stained gel and graph showing protein expression and MVA yield by a strain expressing *E. gallinarum* PKL. A) MVA yield by an MVA producing strain expressing *E. gallinarum* PKL (closed square) as compared to an MVA producing control strain not expressing PKL (closed diamonds) with increasing IPTG induction. B) Protein expression in whole cell lysates from strain EWL1341 expressing *E. gallinarum*.

Figure 50:
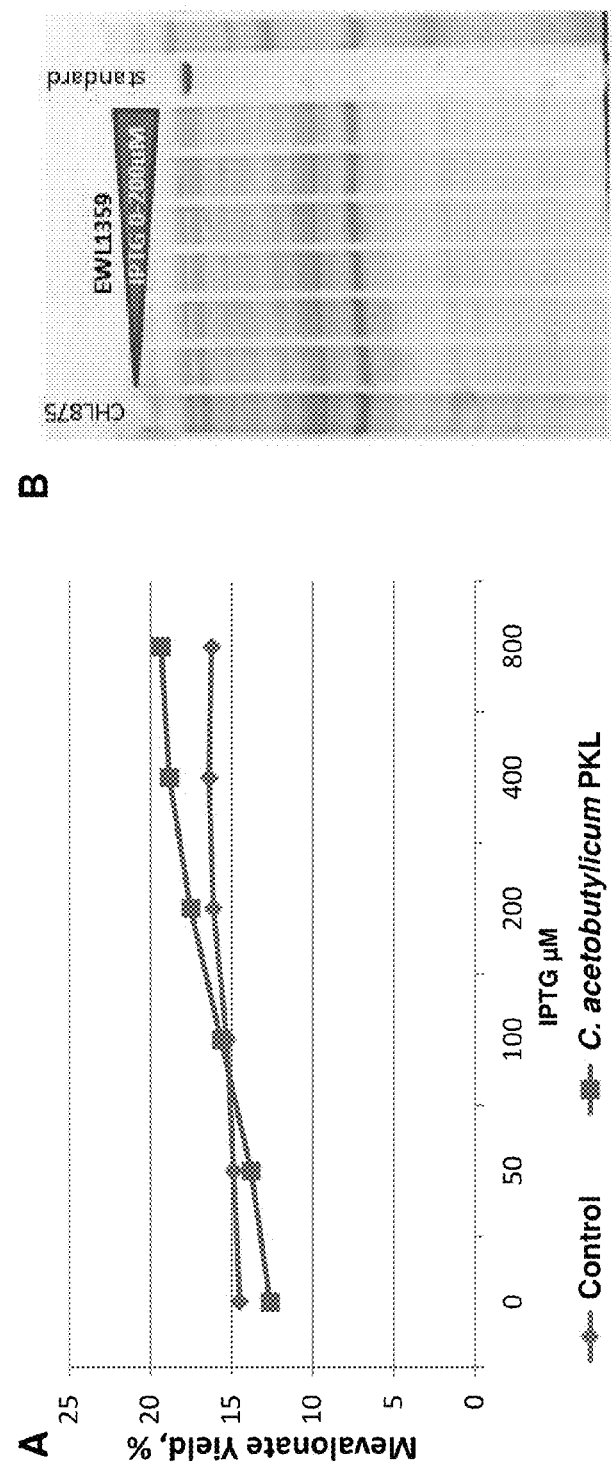

FIG. 50 contains an SDS-PAGE coomasie stained gel and graph showing protein expression and MVA yield by a strain expressing *C. acetobutylicum* PKL. A) MVA yield by an MVA producing strain expressing *C. acetobutylicum* PKL (closed square) as compared to an MVA producing control strain not expressing PKL (closed diamonds) with increasing IPTG induction. B) Protein expression in whole cell lysates from strain EWL1341 expressing *C. acetobutylicum*.

Figure 51:
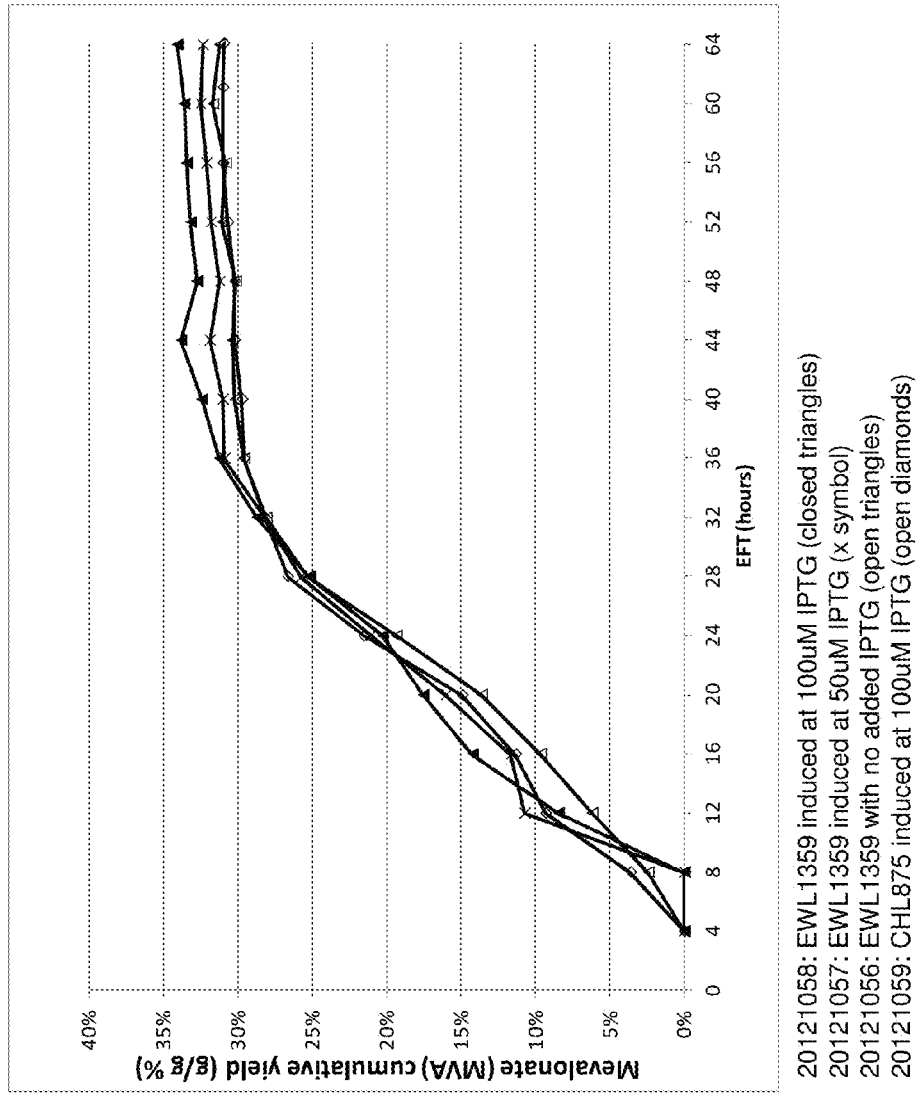

FIG. 51 is a graph showing cumulative yield of MVA on glucose achieved by a strain expressing *C. acetobutylicum* PKL in each 15-L fermentation over time. Closed circle indicates run 20121058: EWL1359 induced at 400 μM IPTG; x symbol indicates run 20121057: EWL1359 induced at 100 μM IPTG; open triangle indicates run 20121056: EWL1359 with no added IPTG; and open diamond indicates run 20121059: CHL875 induced at 100 μM IPTG.

Figure 52:
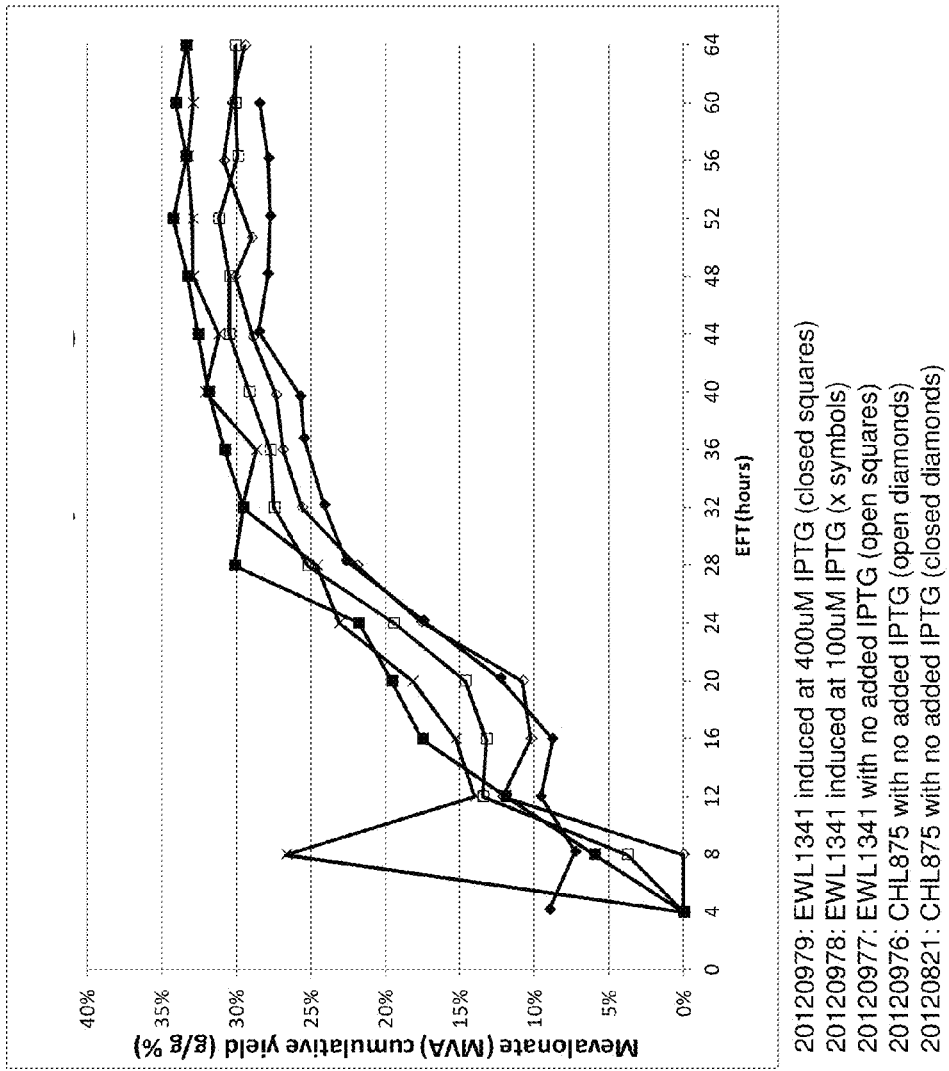

FIG. 52 is a graph showing cumulative yield of MVA on glucose achieved by a strain expressing *E. gallinarum* PKL in each 15-L fermentation over time. Closed square indicates 20120979: EWL1341 induced at 100 μM IPTG; x symbol indicates run 20120978: EWL1341 induced at 50 μM IPTG; open square indicates run 20120977: EWL1341 with no added IPTG; open diamond indicates run 20120976: CHL875 with no added IPTG; and closed diamond indicates run 20120821: CHL875 with no added IPTG.

Figure 53:
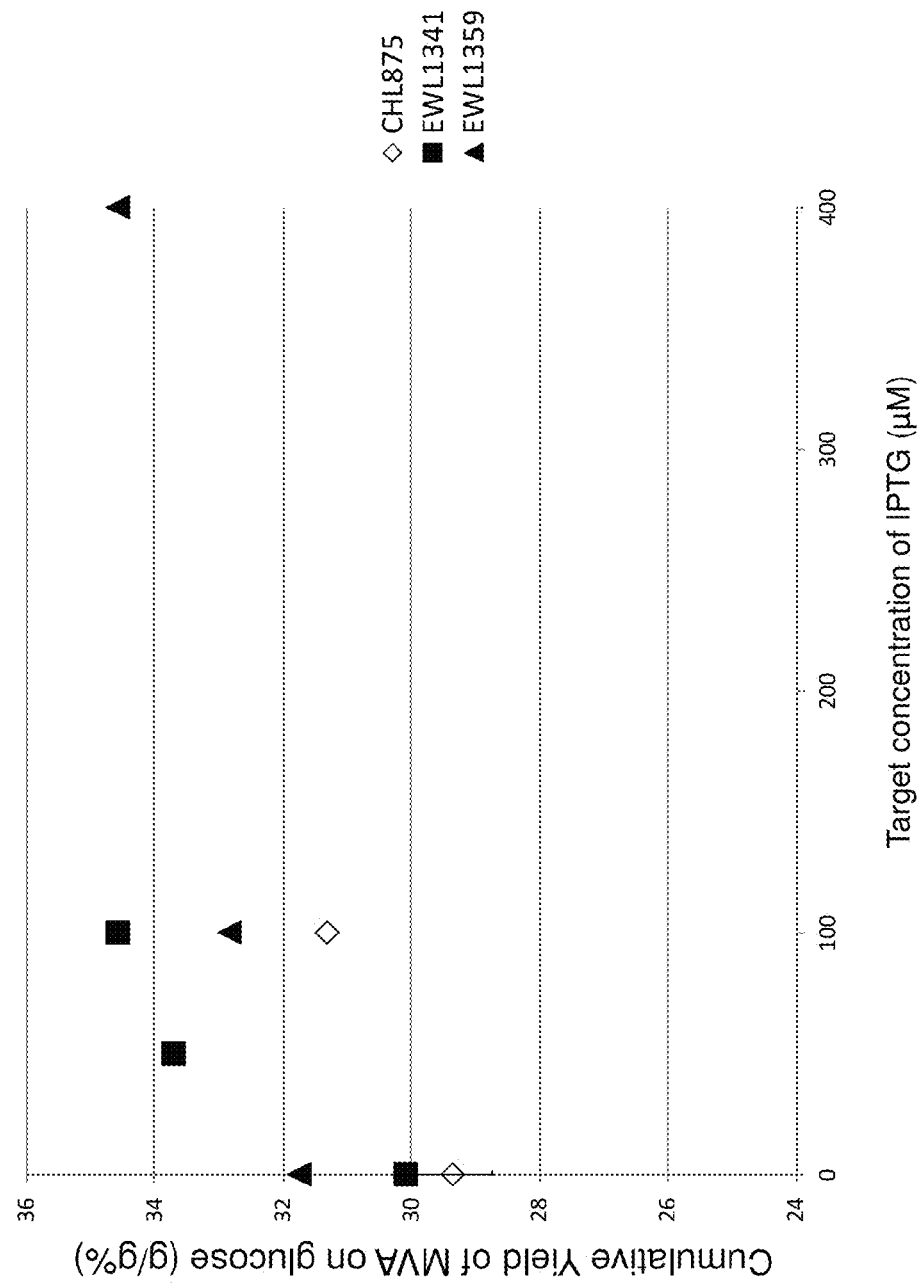

FIG. 53 is a graph showing cumulative yield of MVA on glucose achieved by a strain expressing *E. gallinarum* PKL or *C. acetobutylicum* PKL plotted against the amount of IPTG added. Closed triangles indicate strain EWL1359. Closed squares indicate strain EWL1341. Open diamonds indicate strain CHL875.

Figure 54:
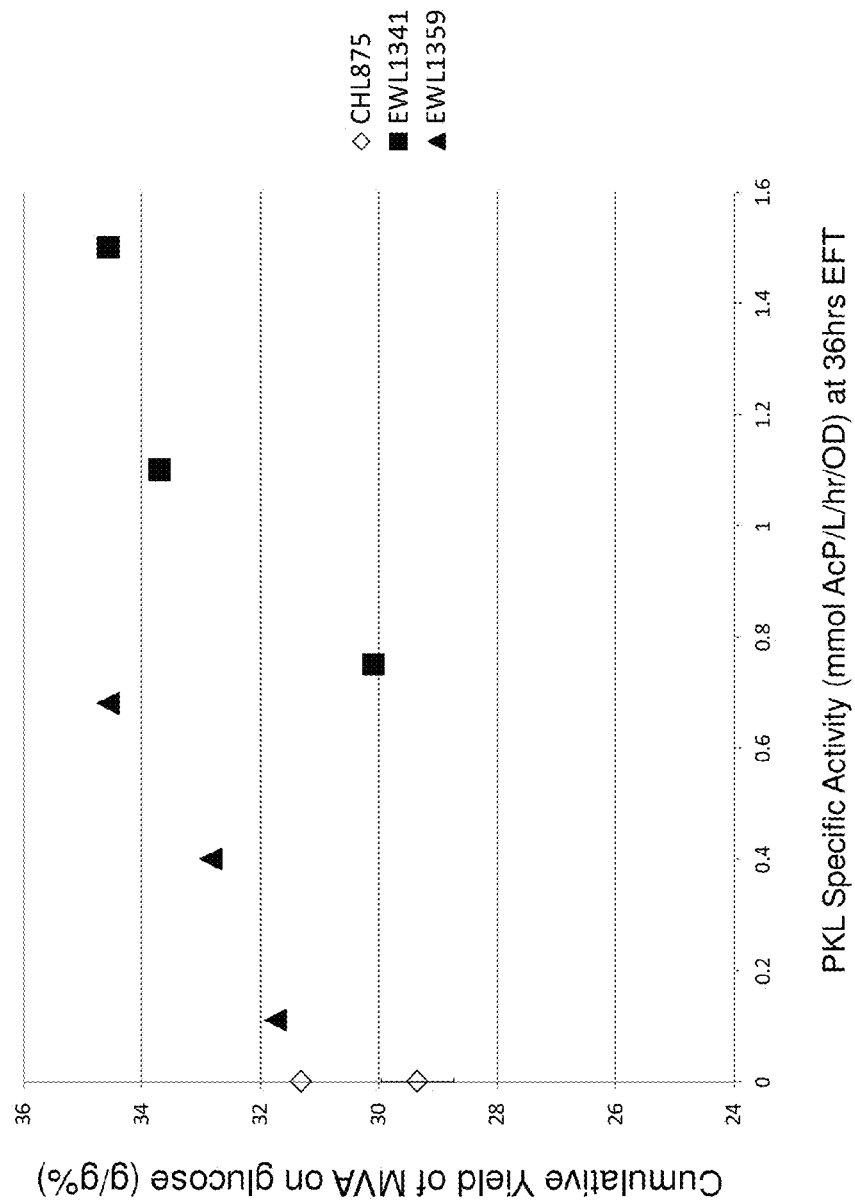

FIG. 54 is a graph showing cumulative yield of MVA on glucose achieved by a strain expressing *E. gallinarum* PKL or *C. acetobutylicum* PKL plotted against the phosphoketolase activity. Closed triangles indicate strain EWL1359. Closed squares indicate strain EWL1341. Open diamonds indicate strain CHL875.

Figure 55:
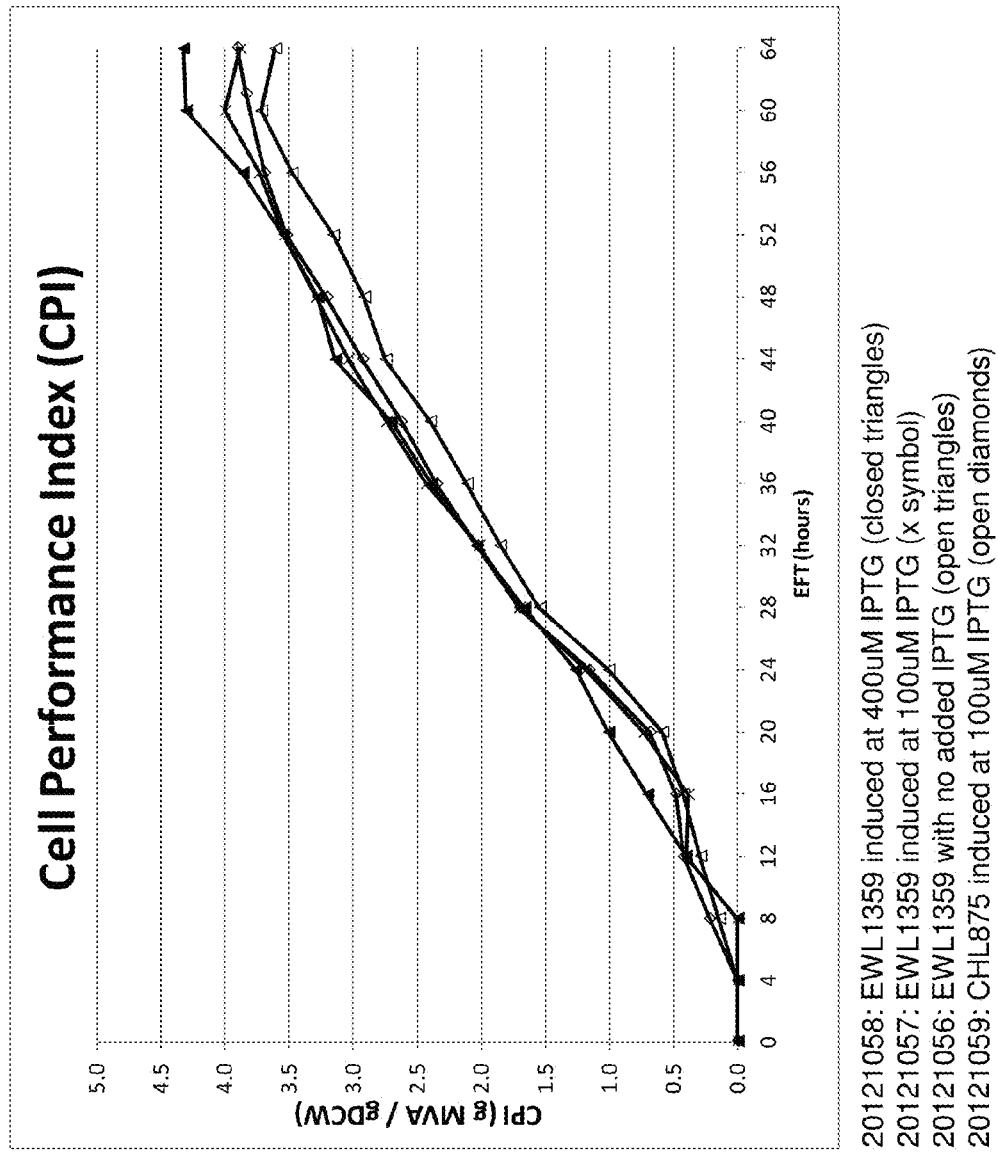

FIG. 55 is a graph showing cell performance index achieved by a strain expressing *C. acetobutylicum* PKL in each 15-L fermentation over time. Closed circle indicates run 20121058: EWL1359 induced at 400 μM IPTG; x symbol indicates run 20121057: EWL1359 induced at 100 μM IPTG; open triangle indicates run 20121056: EWL1359 with no added IPTG; and open diamond indicates run 20121059: CHL875 induced at 100 μM IPTG.

Figure 56:
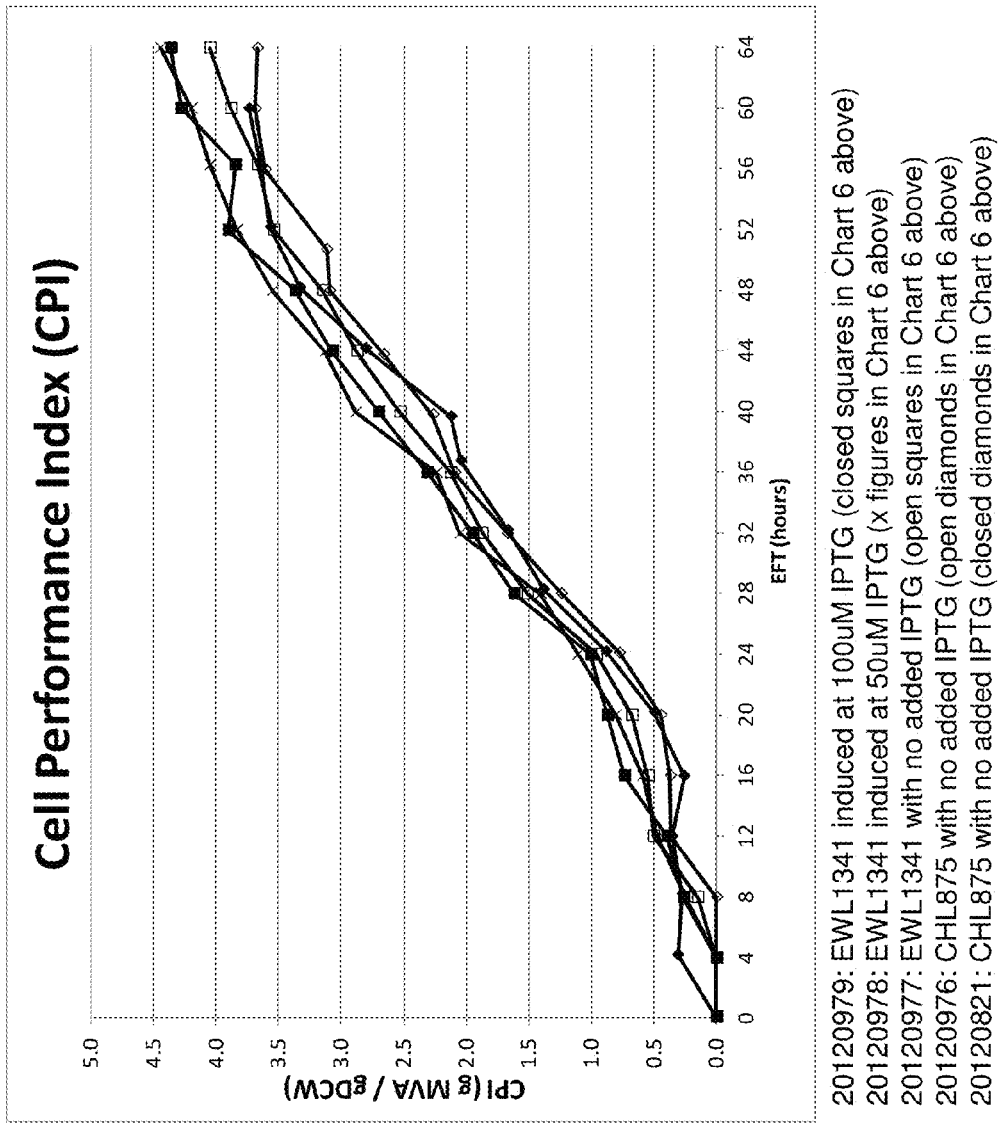

FIG. 56 is a graph showing cell performance index achieved by a strain expressing *E. gallinarum* PKL in each 15-L fermentation over time. Closed square indicates 20120979: EWL1341 induced at 100 μM IPTG; x symbol indicates run 20120978: EWL1341 induced at 50 μM IPTG; open square indicates run 20120977: EWL1341 with no added IPTG; open diamond indicates run 20120976: CHL875 with no added IPTG; and closed diamond indicates run 20120821: CHL875 with no added IPTG.

Figure 57:
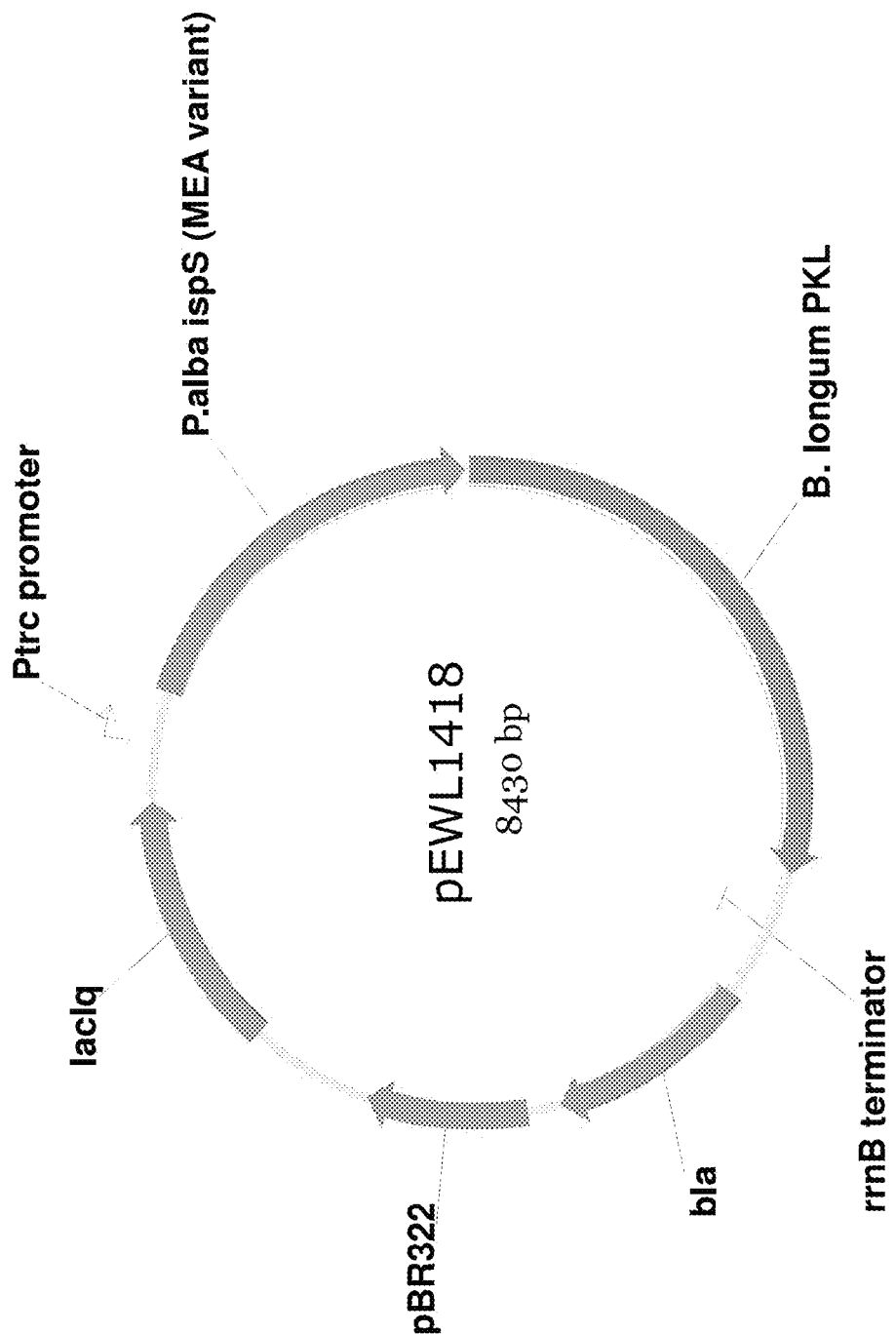

FIG. 57 depicts the plasmid map of pEWL1418, expressing *B. longum* phosphoketolase and *P. alba* isoprene synthase variant.

Figure 58:
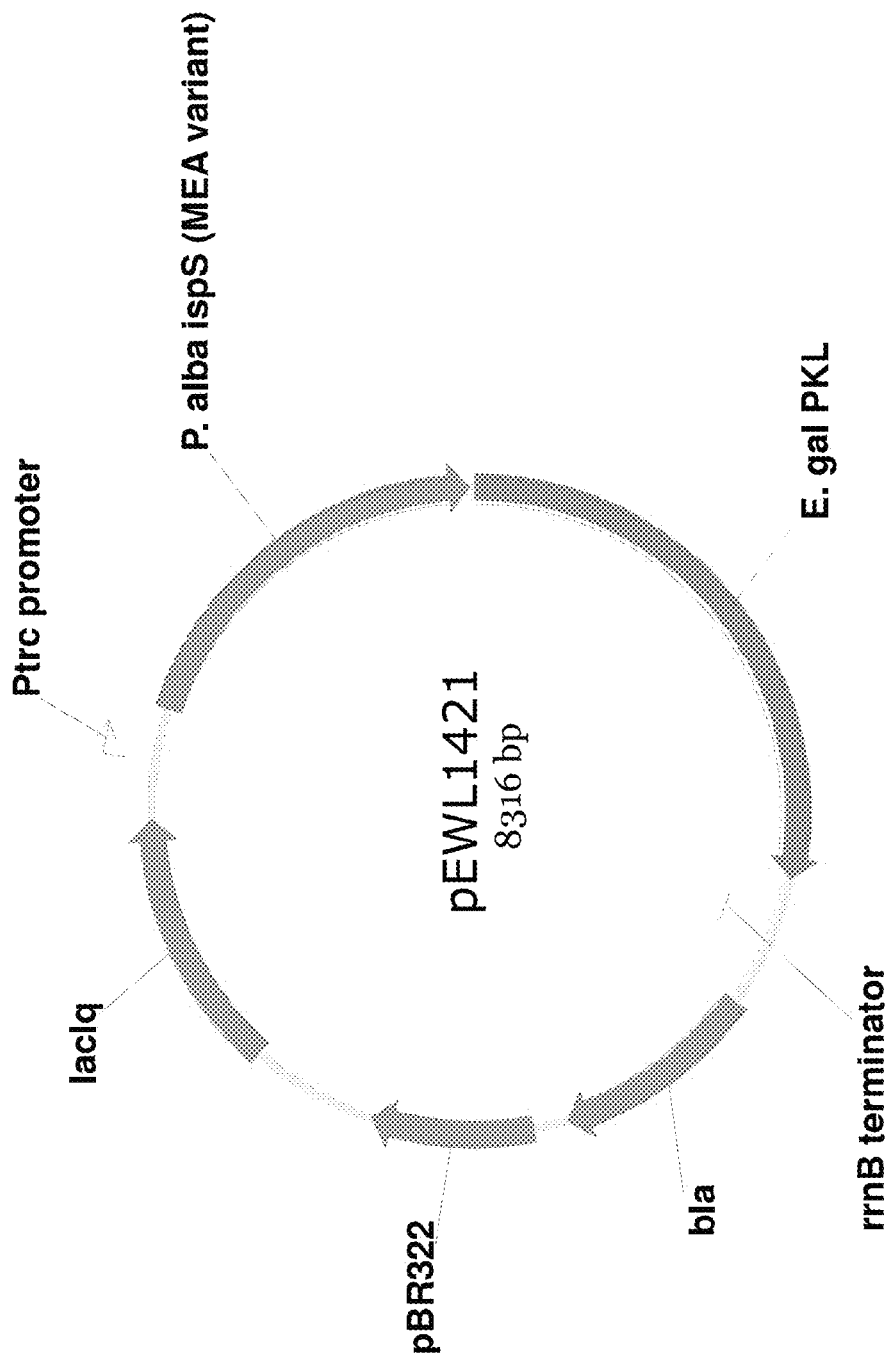

FIG. 58 depicts the plasmid map of pEWL1421, expressing *E. gallinarum* phosphoketolase and *P. alba* isoprene synthase variant.

Figure 59:
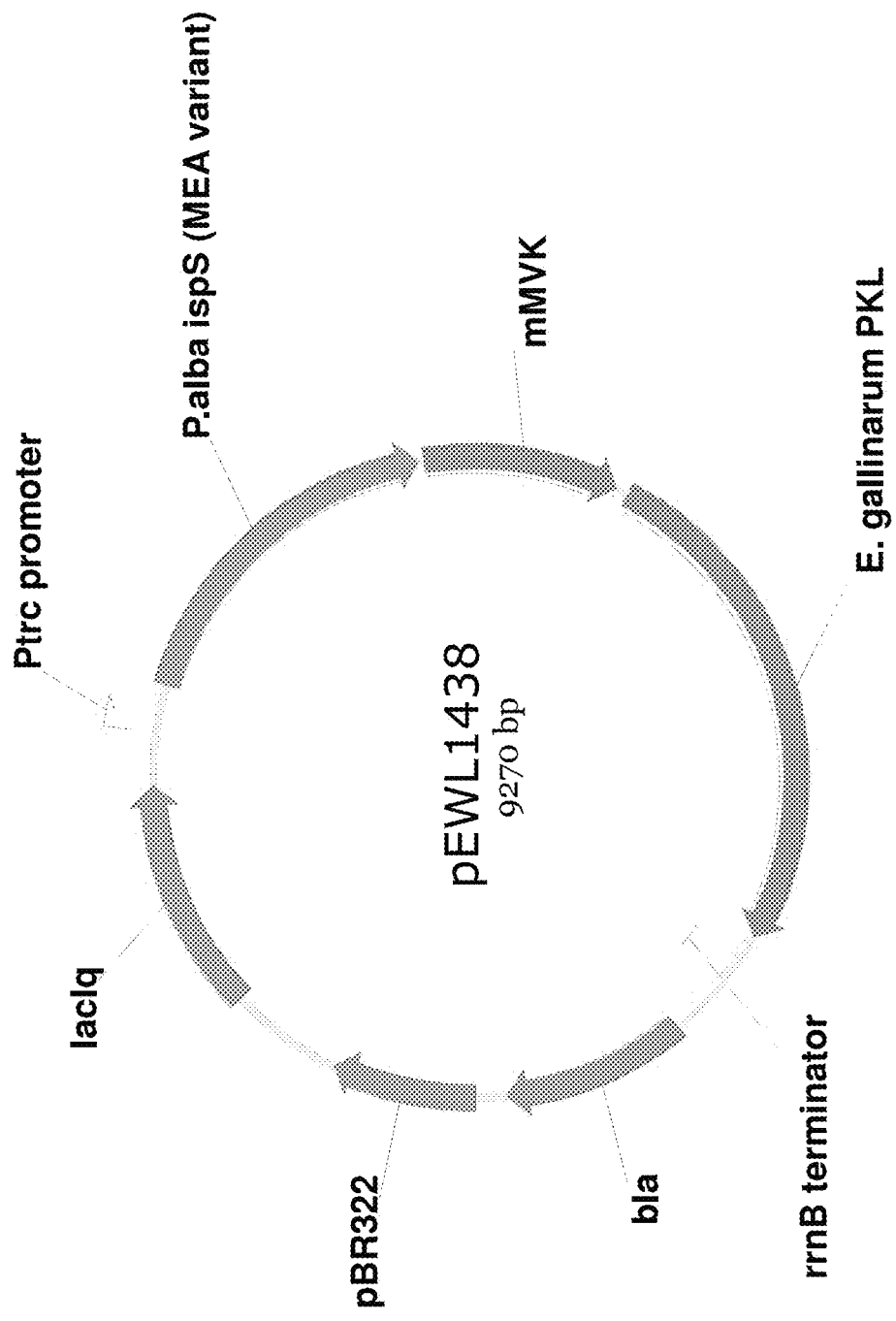

FIG. 59 depicts the plasmid map of pEWL1438, expressing *E. gallinarum* phosphoketolase, *P. alba* isoprene synthase variant, and *M. mazei* mevanolate kinase.

Figure 60:
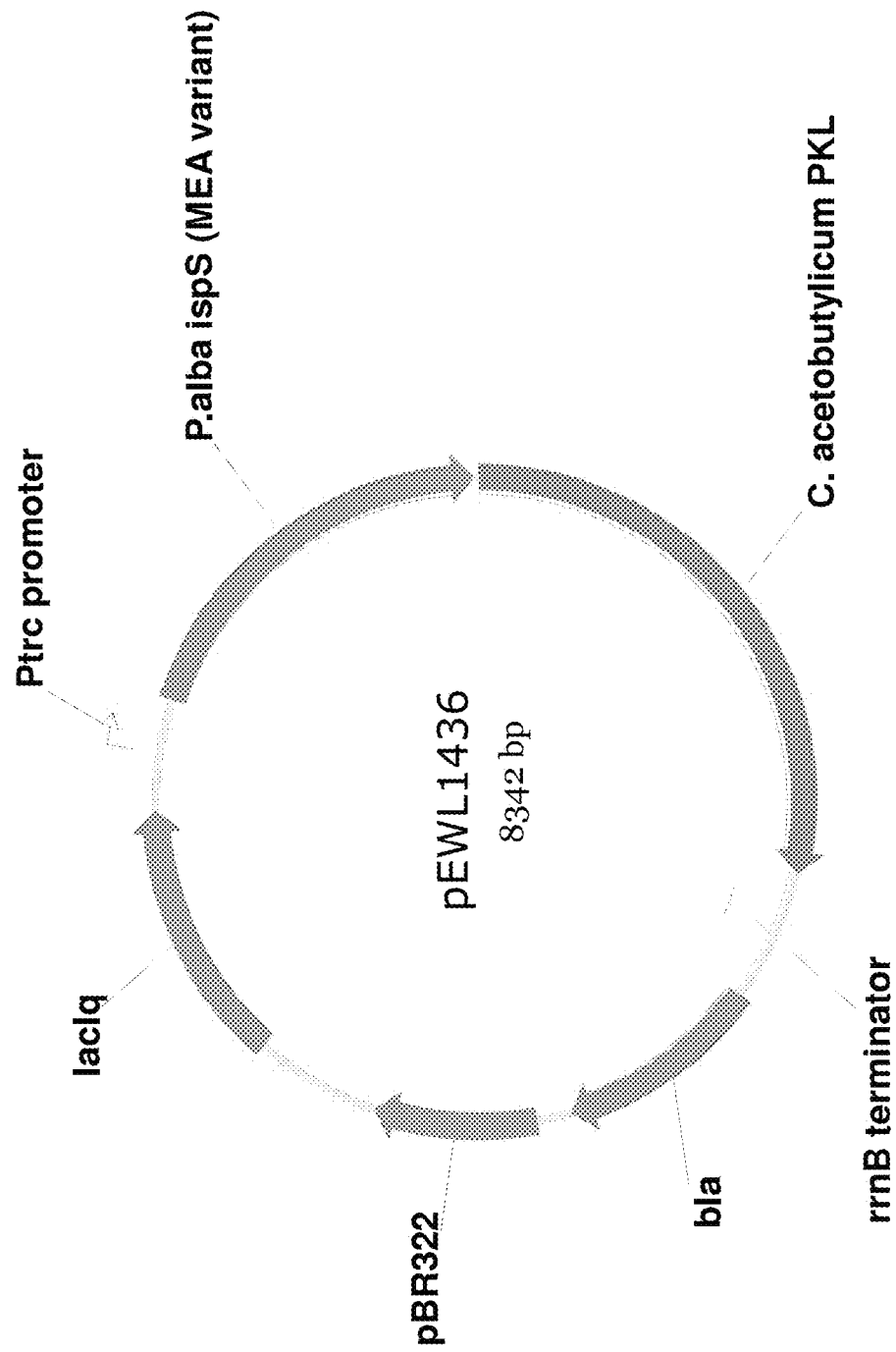

FIG. 60 depicts the plasmid map of pEWL1436, expressing *C. acetobutylicum* phosphoketolase and *P. alba* isoprene synthase variant.

Figure 61:
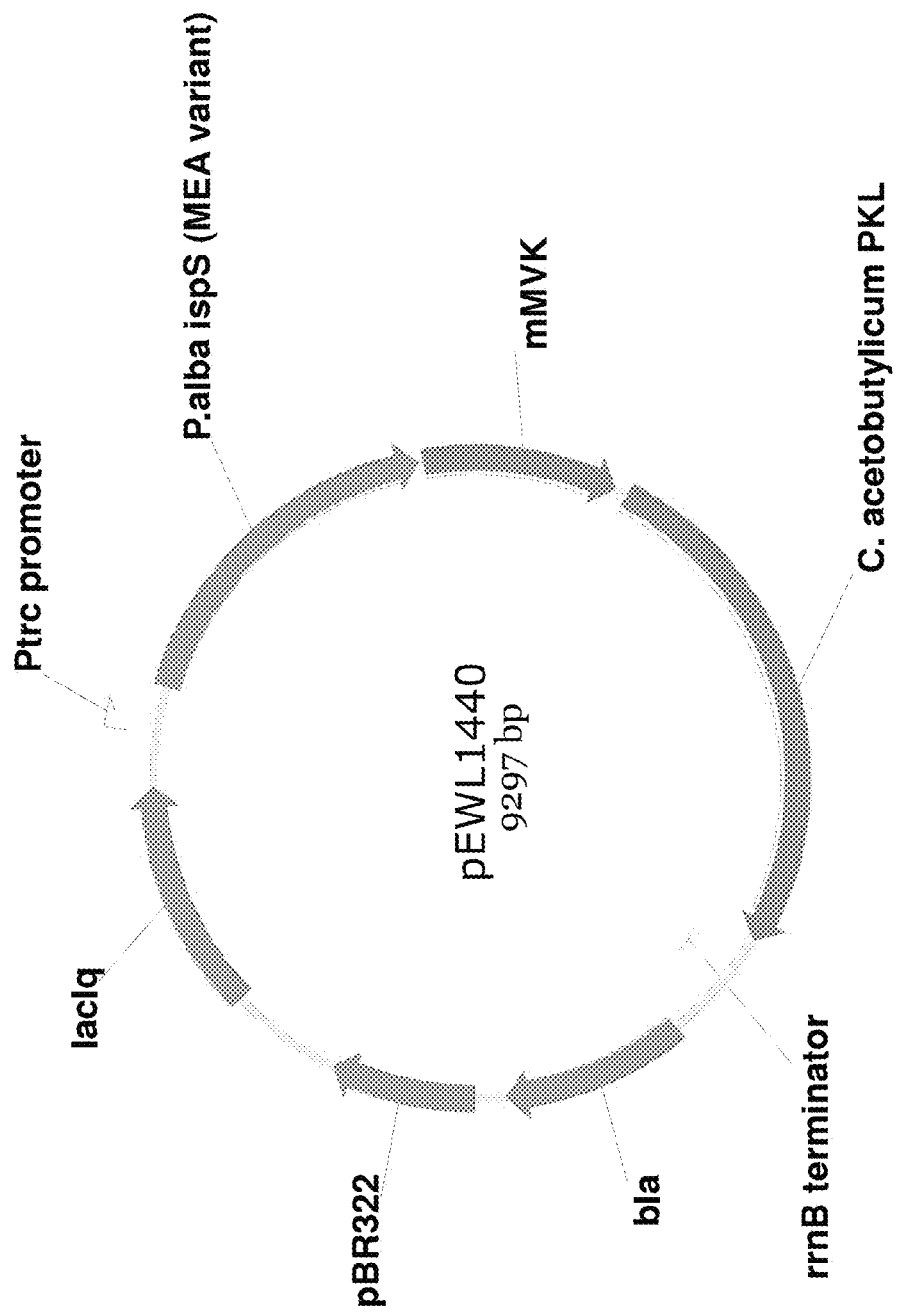

FIG. 61 depicts the plasmid map of pEWL1440, expressing *C. acetobutylicum* phosphoketolase, *P. alba* isoprene synthase variant, and *M. mazei* mevanolate kinase.

Figure 62:
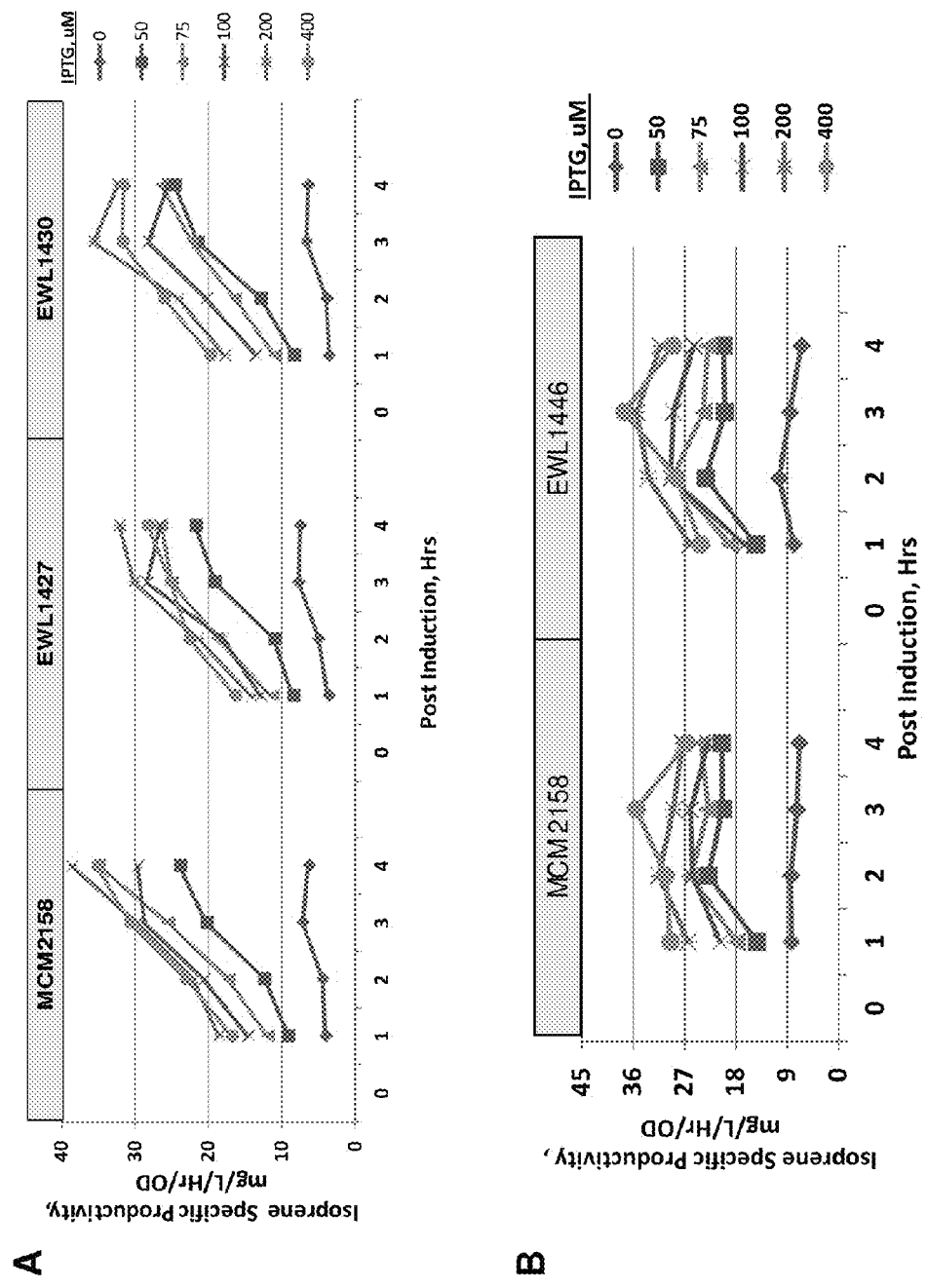

FIG. 62 is a panel of graphs showing isoprene yield by strains expressing phosphoketolase. A) Isoprene yield by strains expressing *B. longum* PKL (strain EWL1427) or *E. gallinarum* PKL (strain EWL1430). B) Isoprene yield by strains expressing *C. acetobutylicum* PKL (EWL1446). Control strain MCM2158 does not express PKL.

Figure 63:
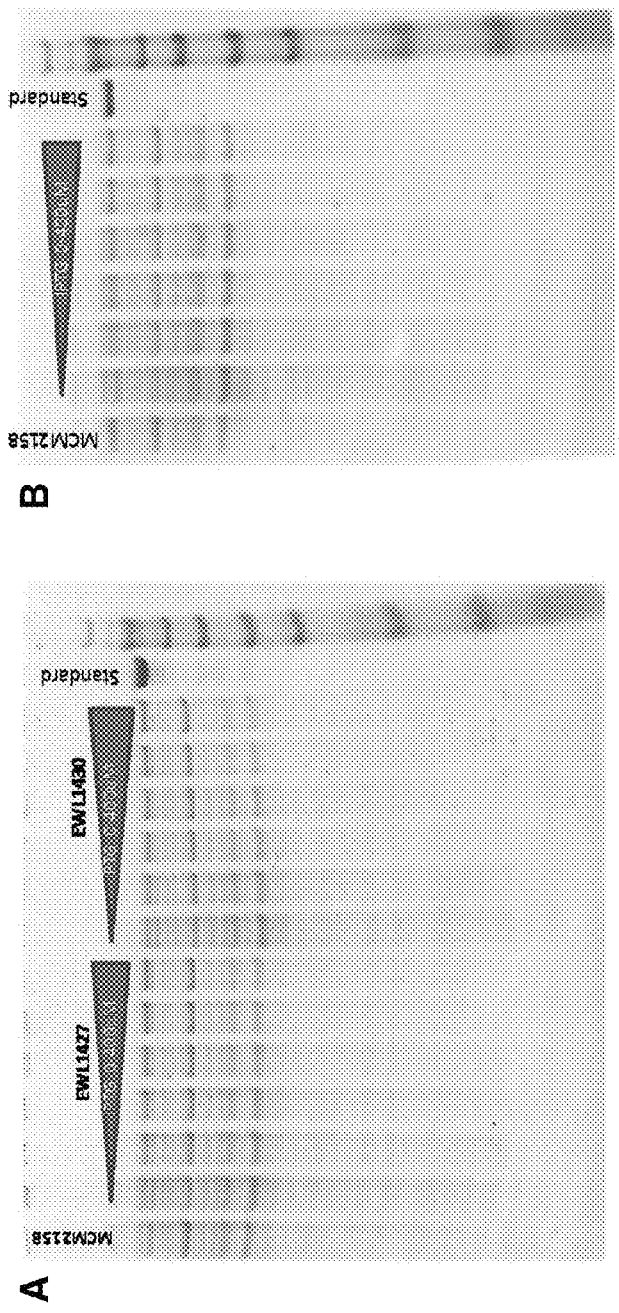

FIG. 63 is a series of SDS-PAGE coomasie stained gels showing protein expression as induced by IPTG. A) strains expressing *B. longum* PKL (EWL1427) or *E. gallinarum* PKL (EWL1430). B) strains expressing *C. acetobutylicum* PKL (EWL1446). Control strain MCM2158 does not express PKL.

Figure 64:
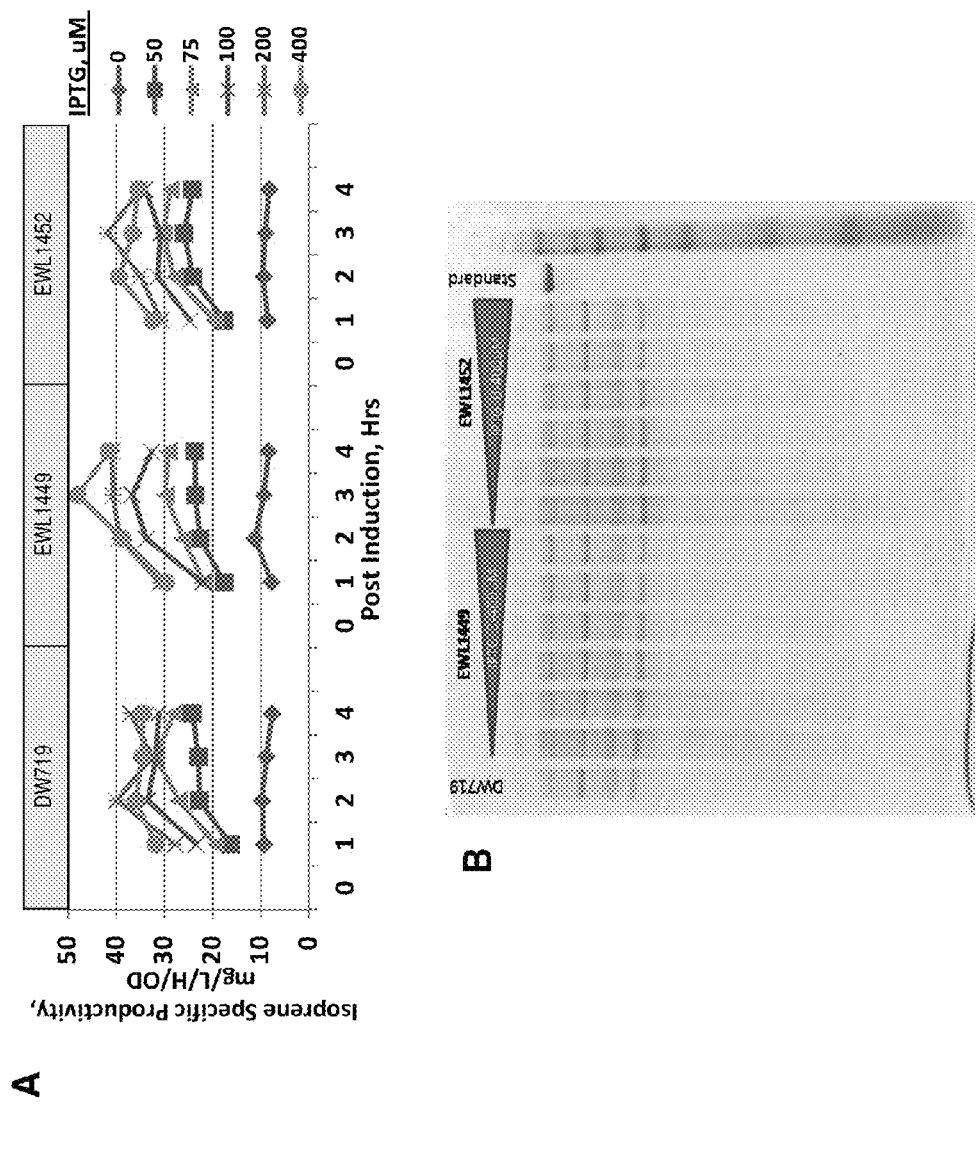

FIG. 64 contains an SDS-PAGE coomasie stained gel and graph showing protein expression and isoprene yield by strains expressing a PKL. A) isoprene yield by an isoprene producing strain expressing *E. gallinarum* PKL (strain EWL1449) or *C. acetobutylicum* PKL (EWL1452) as compared to an MVA producing control strain not expressing PKL (strain DW719) with increasing IPTG induction. B) Protein expression in whole cell lysates from strain EWL1452 and EWL1449.

Figure 65:
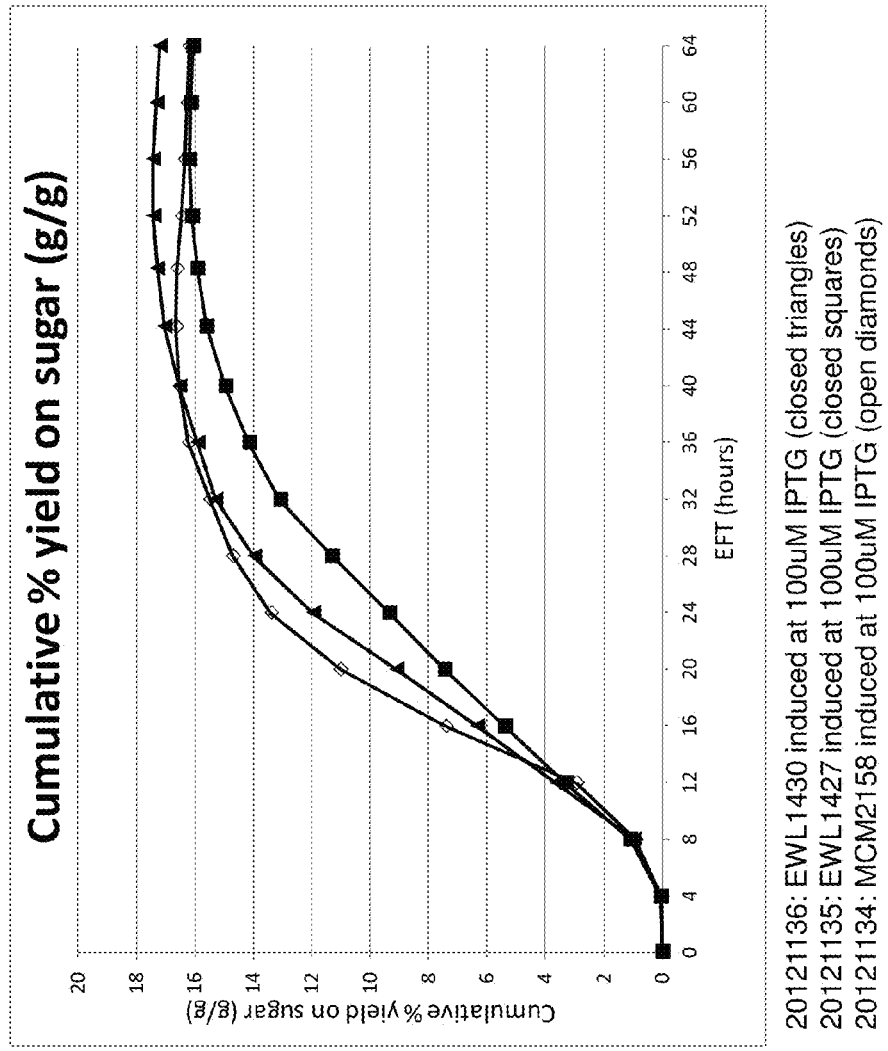

FIG. 65 is a graph showing cumulative yield of isoprene on glucose achieved by strains expressing *B. longum* PKL (strain EWL1427) or *E. gallinarum* PKL (strain EWL1430) in each 15-L fermentation over time. Closed triangle indicates run 20121136: EWL1430 induced at 100 μM IPTG; closed square indicates run 20121135: EWL1427 induced at 100 μM IPTG; and open diamond indicates 20121134: MCM2158 induced at 100 μM IPTG.

Figure 66:
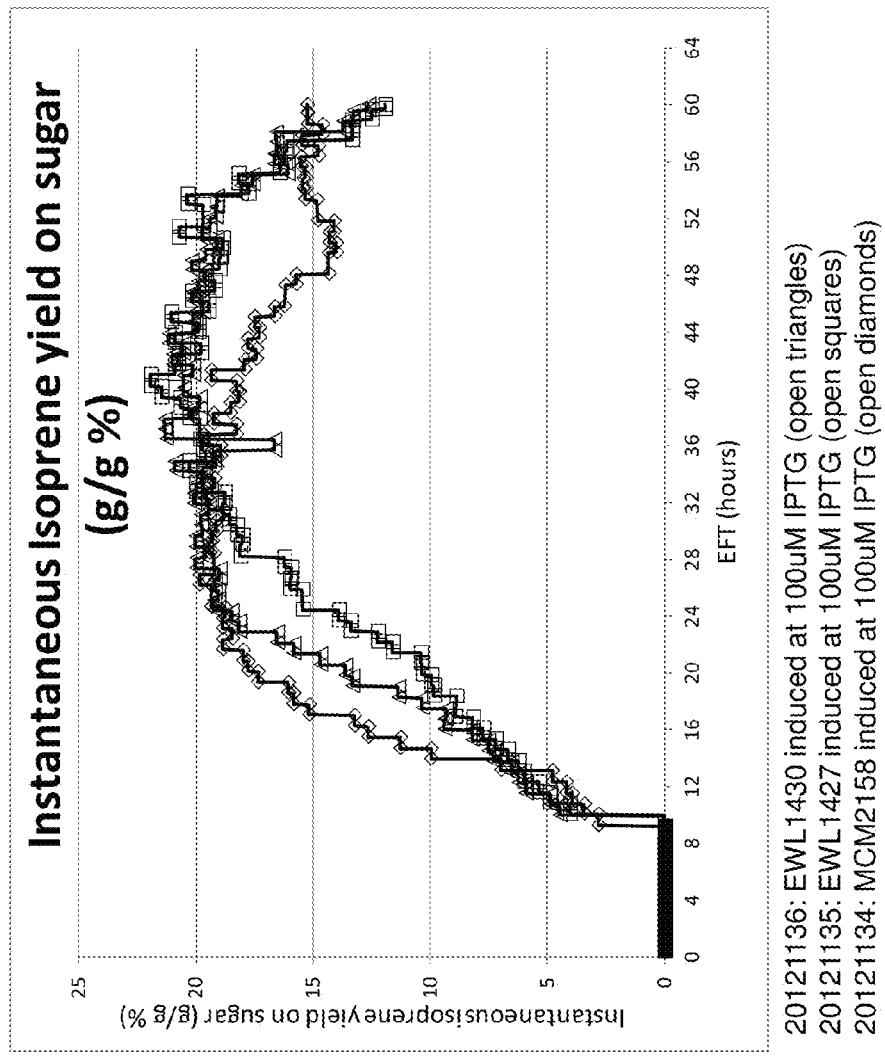

FIG. 66 is a graph showing instantaneous yield of isoprene on glucose achieved by strains expressing *B. longum* PKL (strain EWL1427) or *E. gallinarum* PKL (strain EWL1430) in each 15-L fermentation over time. Open triangle indicates run 20121136: EWL1430 induced at 100 μM IPTG; open square indicates run 20121135: EWL1427 induced at 100 μM IPTG; and open diamond indicates 20121134: MCM2158 induced at 100 μM IPTG.

Figure 67:
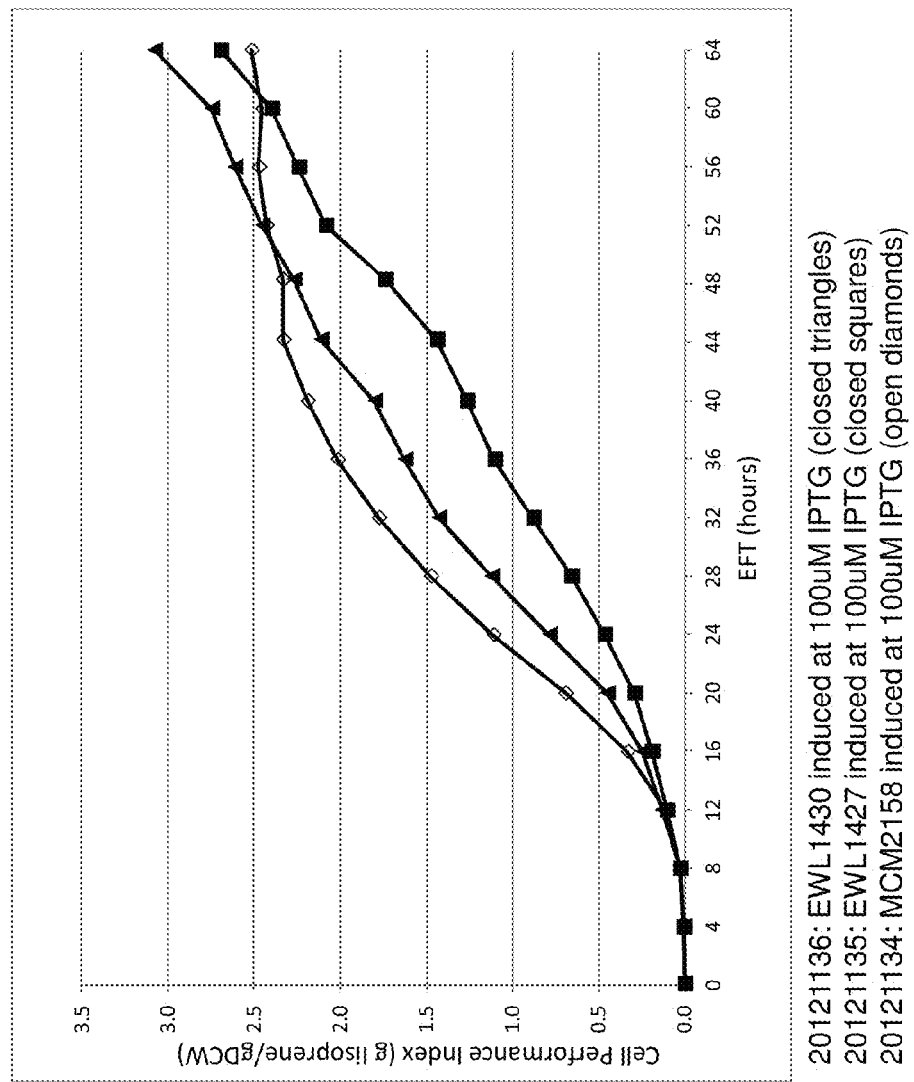

FIG. 67 is a graph showing cell performance index achieved by a strain expressing *B. longum* PKL (strain EWL1427) or *E. gallinarum* PKL (strain EWL1430) in each 15-L fermentation over time. Closed triangle indicates run 20121136: EWL1430 induced at 100 μM IPTG; closed square indicates run 20121135: EWL1427 induced at 100 μM IPTG; and open diamond indicates run 20121134: MCM2158 induced at 100 μM IPTG. gDCW indicates total grams dry cell weight.

Figure 68:
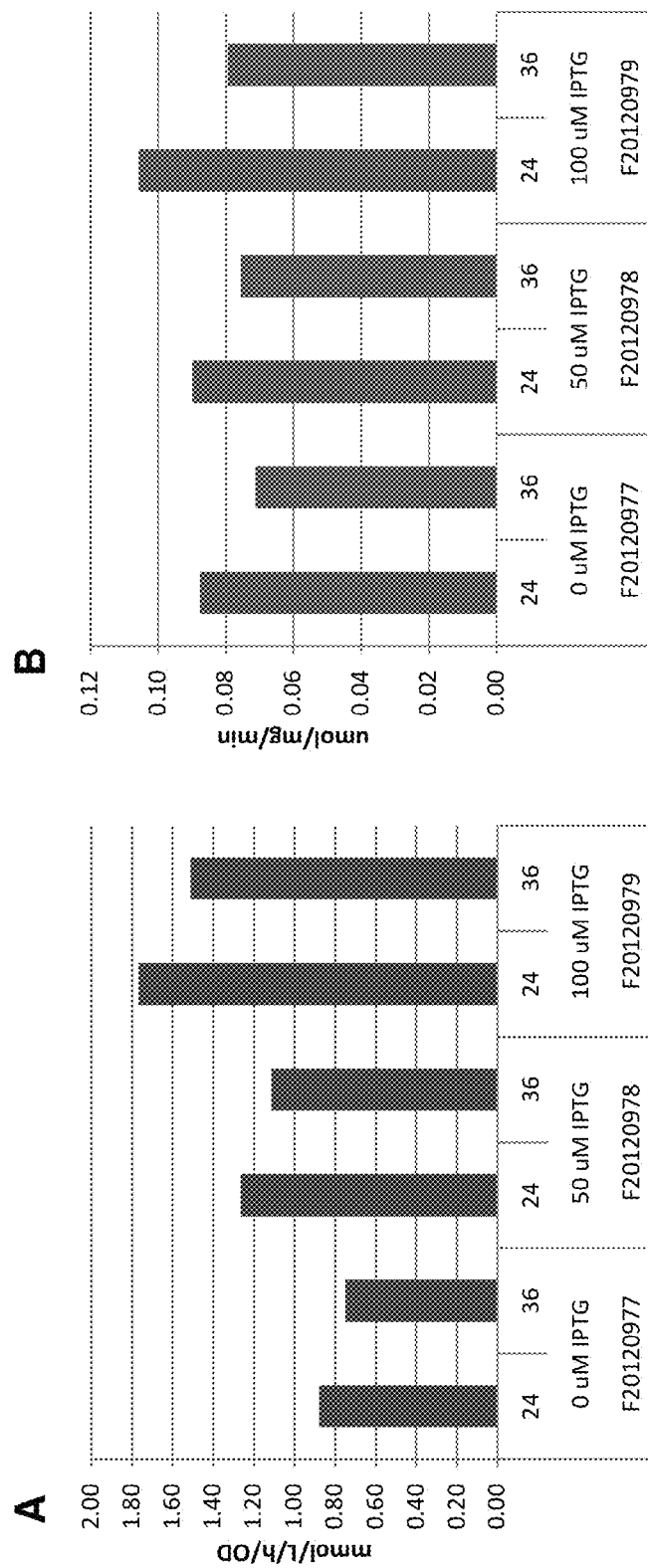

FIG. 68 is a series of graphs showing *E. gallinarum* PKL in vitro activity. A) In vitro AcP specific productivity. B) In vitro PKL specific activity.

Figure 69:
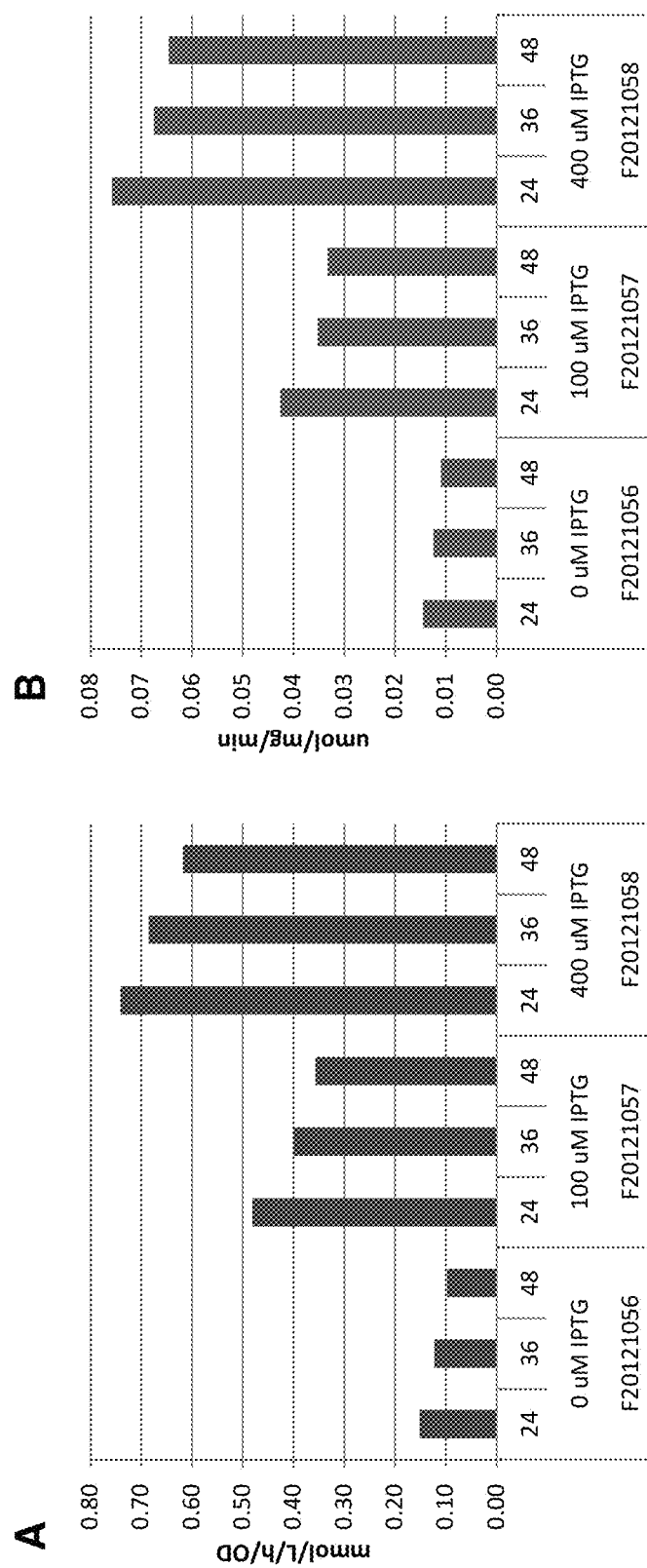

FIG. 69 is a series of graphs showing *C. acetobutylicum* PKL in vitro activity. A) In vitro AcP specific productivity. B) In vitro PKL specific activity.

Figure 70:
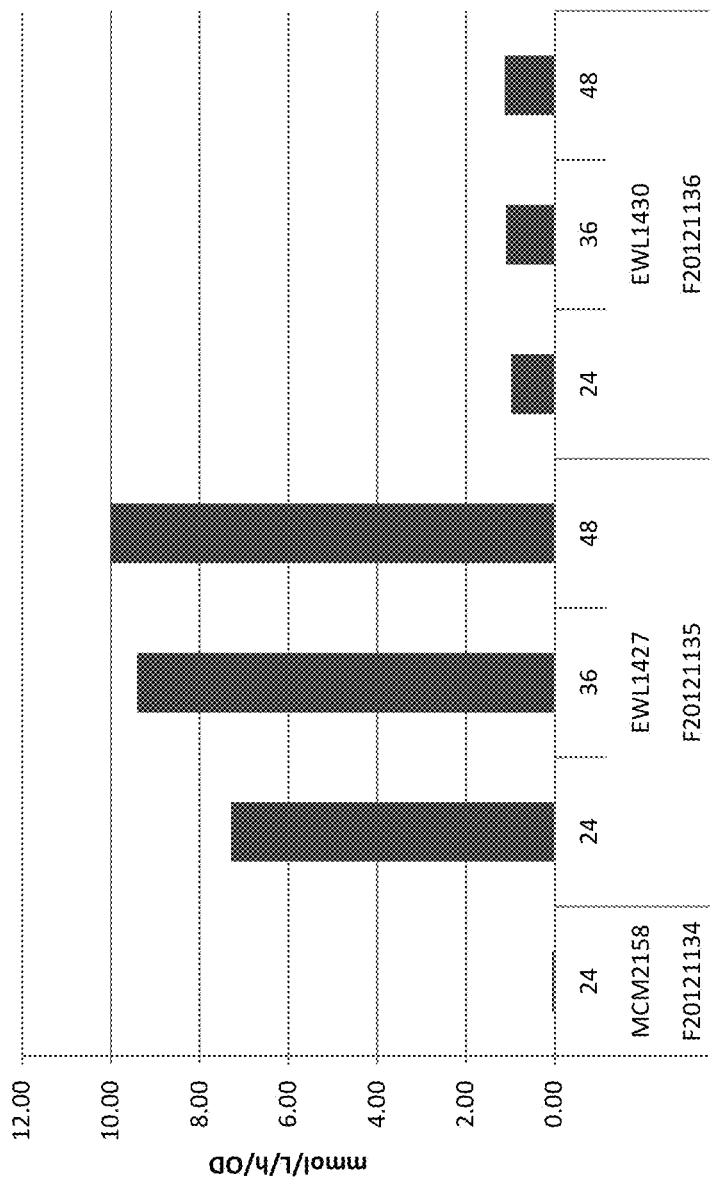

FIG. 70 is a graph showing in vitro AcP specific productivity in isoprene producing strains expressing *B. longum* PKL or *E. gallinarum* PKL.

Figure 71:
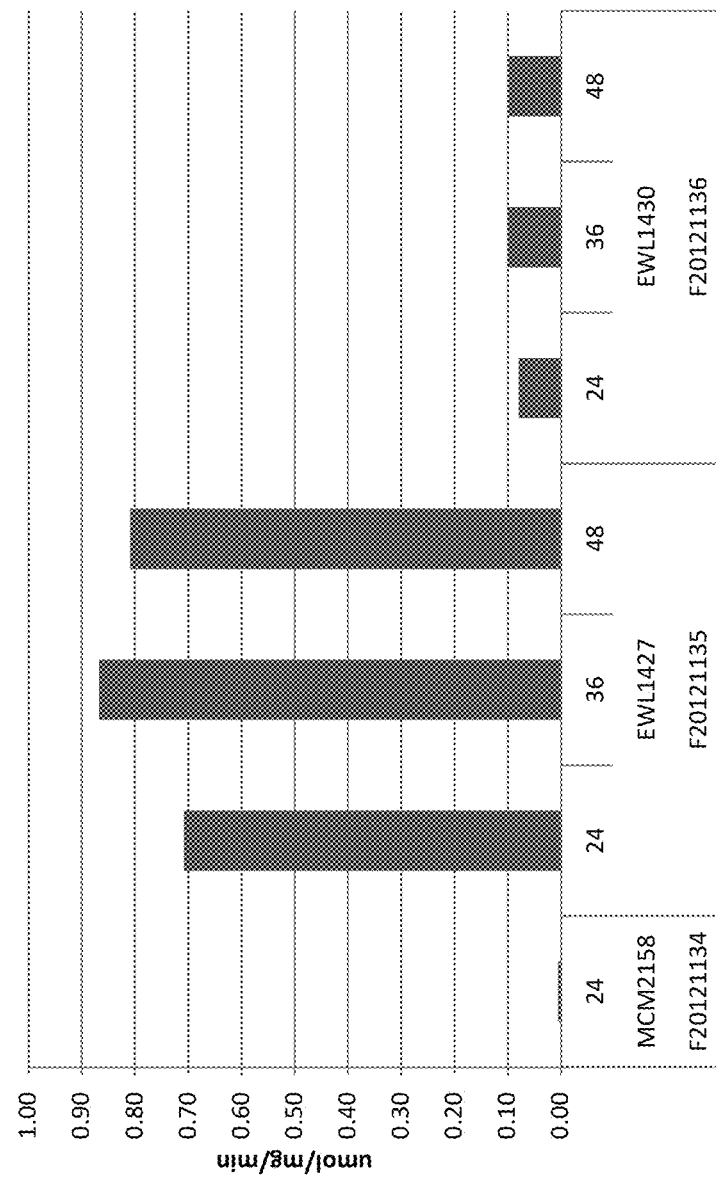

FIG. 71 is a graph showing in vitro PKL activity in isoprene producing strains expressing *B. longum* PKL or *E. gallinarum* PKL.

Figure 72:
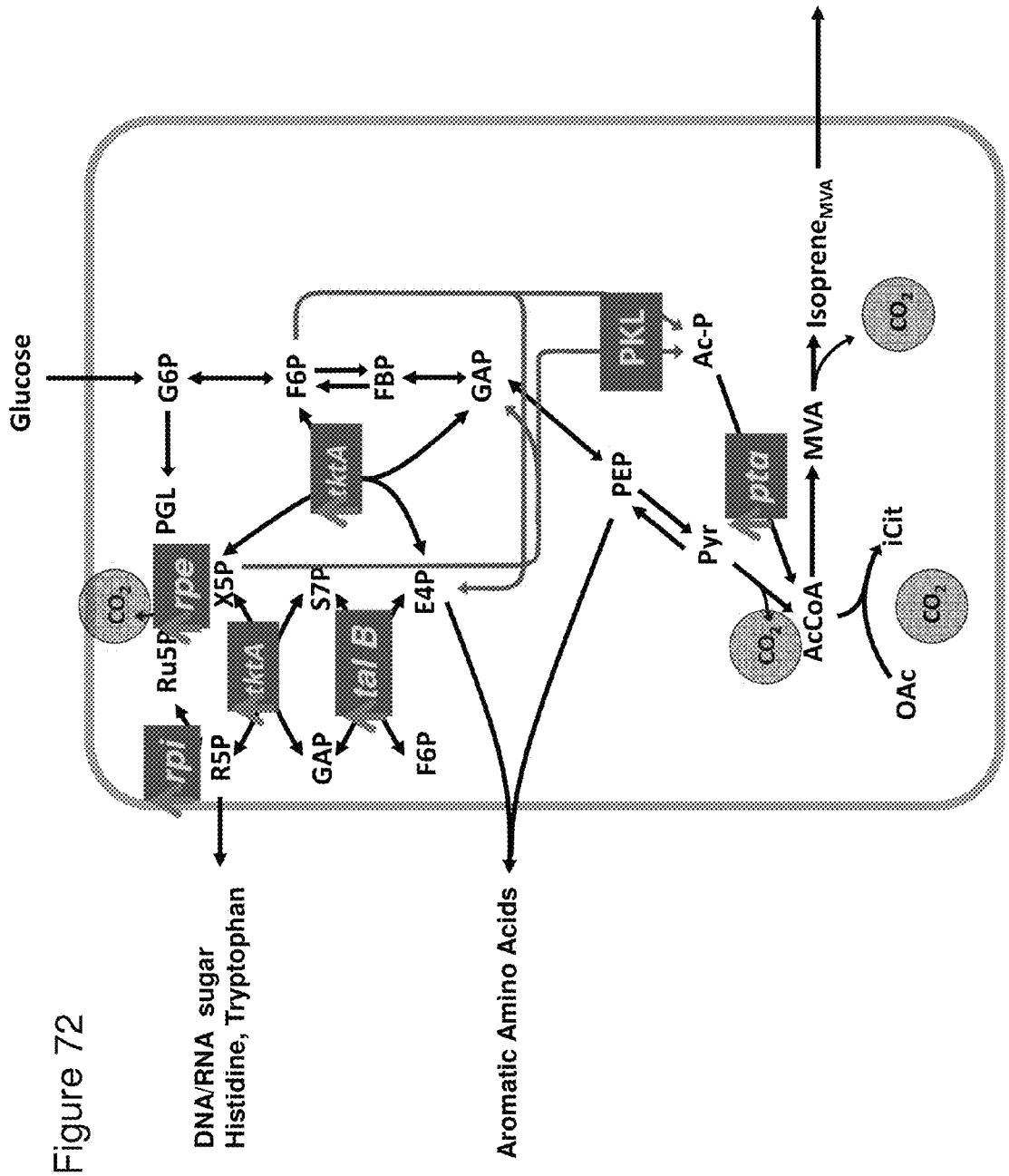

FIG. 72 is a diagram depicting host mutations that are preferably upregulated to increase carbon flux through the phosphoketolase pathway. Genes of interest for modulating carbon flux include moduribose-5-phosphate isomerase A (rpiA), D-ribulose-5-phosphate 3-epimerase (rpe), transketolase A (tktA), transaldolase B (tal B), and/or phosphate acetyltransferase (pta).

Figure 73:
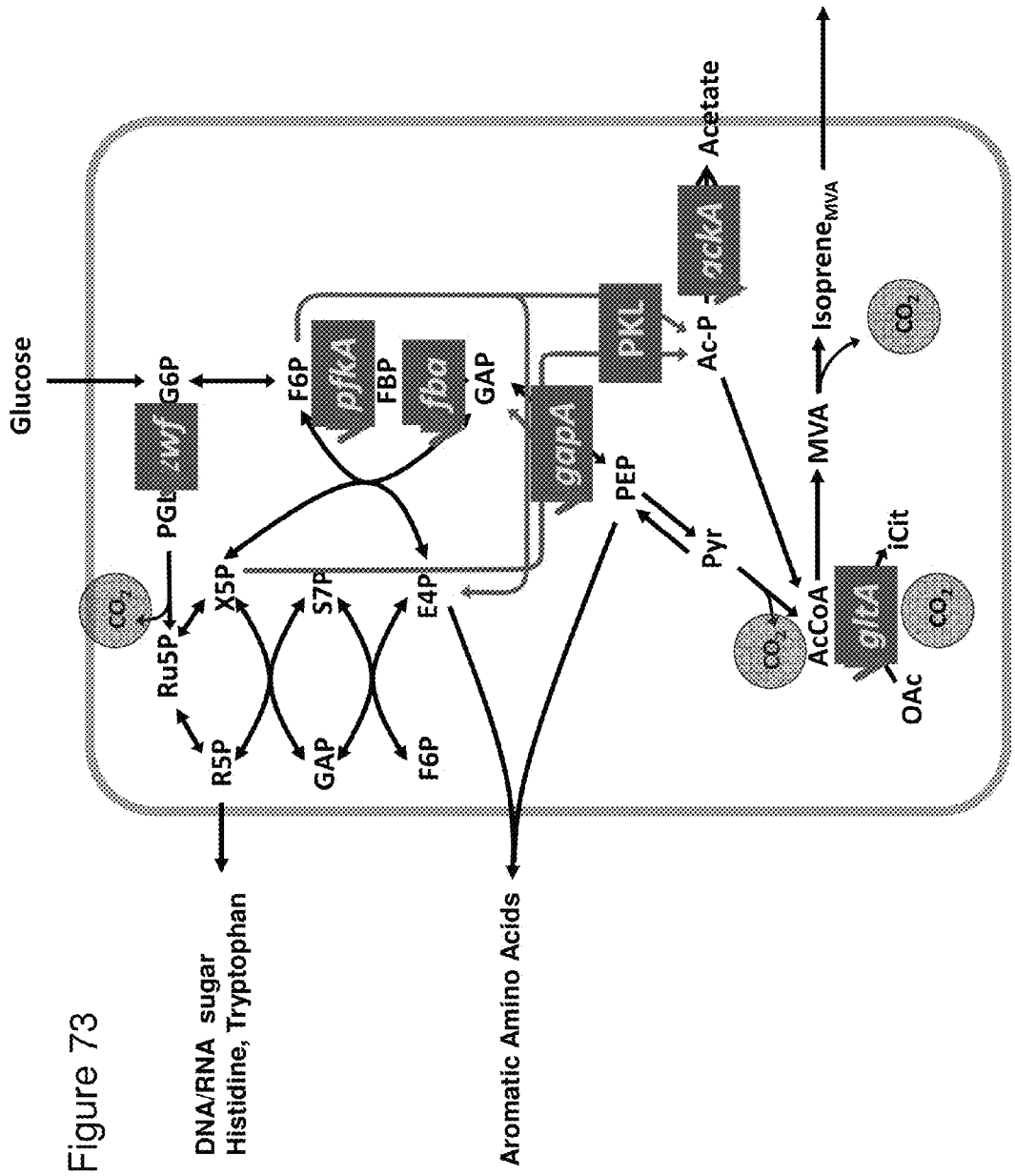

FIG. 73 is a diagram depicting host mutations that are preferably downregulated to increase carbon flux through the phosphoketolase pathway. Genes of interest for modulating carbon flux include glucose-6-phosphate dehydrogenase (zwf), 6-phosphofructokinase-1 (pfkA), fructose bisphosphate aldolase (fba), glyceraldehyde-3-phosphate dehydrogenase A (gapA), Acetate kinase (ackA), citrate synthase (gltA) and/or the pts operon.

DETAILED DESCRIPTION

The invention provided herein discloses, inter alia, compositions and methods for the production of mevalonate, isoprenoid precursor molecules, isoprene and/or isoprenoids in recombinant cells that have been engineered to express a phosphoketolase polypeptide. The phosphoketolase enzymes of this invention can use various substrates, as described in greater detail infra. In certain embodiments, the invention provides for compositions and methods for the production of mevalonate, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate. In other embodiments, the invention provides for compositions and methods for the production of mevalonate, isoprenoid precursor molecules, isoprene and/or isoprenoids in recombinant cells that have been engineered to express a phosphoketolase polypeptide capable of catalyzing the conversion of fructose 6-phosphate to erythrose 4-phosphate and acetyl phosphate. In still other embodiments, the invention provides for compositions and methods for the production of mevalonate, isoprenoid precursor molecules, isoprene and/or isoprenoids in recombinant cells that have been engineered to express a phosphoketolase polypeptide capable of catalyzing the conversion of sedoheptulose-7-phosphate to ribose-5-phosphate and acetyl phosphate. In still other embodiments, the invention provides for compositions and methods for the production of mevalonate, isoprenoid precursor molecules, isoprene and/or isoprenoids in recombinant cells that have been engineered to express a phosphoketolase polypeptide capable of catalyzing the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

Recombinantly expressed phosphoketolase has been used to engineer metabolic pathways in host cells. See U.S. Pat. No. 7,785,858. Sonderegger et al. (Applied and Environmental Microbiology, 2004, 70:5, 2892-97) describe the use of phosphoketolase in *Saccharomyces cerevisiae* for the overproduction of ethanol. Fleige et al. (*Appl Microbial Biotechnol.*, 2011, 91:3, 769-76) describe the expression of a *bifidobacterium* phosphoketolase gene (Meile et al., supra) in a modified *Ralstonia eutropha* strain which restored the capability for the organism to utilize fructose as a sole carbon source for growth. However, utilization of a phosphoketolase to increase carbon flux into the mevalonate pathway has not been described.

The mevalonate-dependent biosynthetic pathway is particularly important for the production of the mevalonate and other isoprenoid precursor molecules, e.g., dimethylallyl diphosphate (DMAPP) and isopentenyl pyrophosphate (IPP). The enzymes of the upper mevalonate pathway convert acetyl CoA, produced from glucose, into mevalonate via three enzymatic reactions. Without being bound to theory, it is believed that increased biosynthesis of acetyl CoA by the use of a phosphoketolase polypeptide can result in increased productivity of the upper mevalonate-dependent biosynthetic pathway which will substantially increase biosynthesis of mevalonate and, consequently, of downstream isoprenoid precursor molecules such as DMAPP and IPP. The increased yield of mevalonate production by this alternate pathway is therefore advantageous for commercial applications.

Theoretically, three molecules of acetyl-CoA can be derived from a single molecule of glucose in a balanced reaction. However, organisms typically produce only up to two molecules of acetyl-CoA, with the remainder mass being lost as $CO_2$. The release of $CO_2$ occurs during the formation of acetyl-CoA from pyruvate, a reaction catalyzed by pyruvate dehydrogenase. The loss of one carbon atom results in decreased production yields of mevalonate, isoprenoid precursors, isoprene, and isoprenoid molecules. An exception to this reaction loss is the Wood-Ljungdahl pathway, which relies on carbon monoxide dehydrogenase and acetyl-CoA synthase enzymes to reduce the carbon dioxide to acetyl-CoA in anaerobic acetogens.

The present invention provides an alternate metabolic process which can potentially produce three molecules of acetyl-CoA from one molecule of glucose using a pathway which does not rely on the Wood-Ljungdahl pathway enzymes. Instead, it makes use of a phosphoketolase enzyme found in certain organisms, particularly among *Bifidobacteria* [see, for example, Biology of the Prokaryotes (ed. Lengeler, Drews and Schlegel); Blackwell Science, New York, 1999, p. 299-301; Meile et al., *J. of Bacteriology*, 2001, 183:9, 2929-36; Jeong et al., *J. Microbiol. Biotechnol.*, 2007, 17:5, 822-829]. Phosphoketolase enzymes allow for formation of acetyl-CoA (via acetyl-phosphate) from xylulose 5-phosphate or fructose 6-phosphate rather than through oxidation of pyruvate as in typical metabolism.

Phosphoketolases have been classified into two types based on their substrate preference: xylulose-5-phosphate (X5P) phosphoketolases, which only act on X5P, and X5P/fructose-6-phosphate (F6P) phosphoketolases, which can act on both X5P and F6P (Suzuki et al., *Acta Cryst.* F66, 2010, 66:8, 941-43). Phosphoketolases catalyze the cleavage of X5P or F6P utilizing inorganic phosphate ($P_i$) to produce acetyl phosphate (acetyl-P), $H_2O$ and glyceraldehyde 3-phosphate or erythrose 4-phosphate. The high-energy metabolite acetyl-P is subsequently converted to acetic acid by acetate kinase to produce ATP from ADP in the pathway. In addition to acetyl-phosphate, the glyceraldehyde 3-phosphate produced from the enzymatic reaction can be recycled through manipulated metabolic pathways so that the maximum yield of 3 acetyl-CoA per glucose can be achieved. Significantly, acetyl-CoA production by phosphoketolase eliminates the loss of carbon (e.g. $CO_2$) as observed from pyruvate dehydrogenase mediated reactions.

As further detailed herein, phosphoketolases can also act upon sedoheptulose-7-phosphate to convert it to ribose-5-phosphate and acetyl phosphate. A non-limiting example of such a phosphoketolase is *Bifidobacterium longum* phosphoketolase, which has catalytic activity with sedoheptulose-7-phosphate.

The present invention is directed to the use of phosphoketolase enzymes in the production of mevalonate, isoprenoid precursors, isoprene and/or isoprenoids to enhance product yield. In particular, the theoretical isoprene product yield is enhanced as represented by the following balanced equations (with the assumption that an organism is capable of producing ATP from the complete oxidation of 1 mol glucose to 6 mol $CO_2$):

MVA Pathway Only $$1.5\text{Glucose} + 2.00 O_2 \rightarrow 1.00 \text{Isoprene} + 4.00 CO_2 + 5.00 H_2O$$

Theoretical yield=0.252 g Isoprene/g Glucose

DXP Pathway 1.25Glucose+0.50$O_2$→1.00Isoprene+2.50$CO_2$+ 3.50$H_2O$

Theoretical yield–0.302 g Isoprene/g Glucose

MVA+Phosphoketolase Pathways 1.22Glucose+0.33$O_2$→1.00Isoprene+2.33$CO_2$+ 3.32$H_2O$ Theoretical yield–0.309 g Isoprene/g Glucose Accordingly, in certain aspects, the invention provides recombinant cells capable of enhanced production of mevalonate, wherein the cells comprise one or more heterologous nucleic acids encoding a polypeptide having phosphoketolase activity and one or more nucleic acids encoding one or more polypeptides of the upper MVA pathway, wherein the cells produce increased amounts of mevalonate compared to cells that do not comprise the one or more heterologous nucleic acids encoding a polypeptide having phosphoketolase activity.

In other aspects, the present invention provides recombinant cells capable of enhanced production of isoprenoid precursors, wherein the cells comprise one or more heterologous nucleic acids encoding a polypeptide having phosphoketolase activity and one or more nucleic acids encoding one or more polypeptides of the complete MVA pathway, wherein the cells produce increased amounts of isoprenoid precursors compared to cells that do not comprise the one or more heterologous nucleic acids encoding a polypeptide having phosphoketolase activity.

In still other aspects, the present invention provides recombinant cells capable of producing of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells are capable of producing recoverable amounts of isoprene. In certain embodiments, the present invention provides recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity.

In yet other aspects, the present invention provides recombinant cells capable of producing of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells are capable of producing recoverable amounts of isoprenoids. In certain embodiments, the present invention provides recombinant cells capable of enhanced production of isoprenoids, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an polyprenyl pyrophosphate synthase polypeptide, wherein the cells produce increased amounts of isoprenoids compared to isoprenoid producing cells that do not comprise the one or more heterologous nucleic acids encoding a polypeptide having phosphoketolase activity.

In any of the aspects herein, the present invention provides recombinant cells, wherein the cells comprise one or more heterologous nucleic acids encoding a polypeptide having phosphoketolase activity and can be further engineered to modulate the activity of one or more of the following genes including ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD), glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH) to improve carbon flux through the phosphoketolase pathway.

In some embodiments, the present invention provides recombinant cells capable of producing of isoprene, wherein the cells comprise one or more heterologous nucleic acids encoding a polypeptide having phosphoketolase activity and (i) one or more nucleic acids encoding one or more polypeptides of the complete MVA pathway, (ii) a heterologous nucleic acid encoding an isoprene synthase polypeptide, and (iii) is further engineered to modulate the activity of one or more genes to increases carbon flux through the phosphoketolase pathway, wherein the cells produce increased amounts of isoprene compared to isoprene-producing cells that do not comprise the one or more heterologous nucleic acids encoding a polypeptide having phosphoketolase activity.

In some embodiments, the present invention provides recombinant cells capable of producing of isopreniods, wherein the cells comprise one or more heterologous nucleic acids encoding a polypeptide having phosphoketolase activity and (i) one or more nucleic acids encoding one or more polypeptides of the complete MVA pathway, (ii) a heterologous nucleic acid encoding an isoprene synthase polypeptide, (iii) is further engineered to modulate the activity of one or more genes to increases carbon flux through the phosphoketolase pathway, and (iv) a heterologous nucleic acid encoding an polyprenyl pyrophosphate synthase polypeptide, wherein the cells produce increased amounts of isoprenoids compared to isoprenoid producing cells that do not comprise the one or more heterologous nucleic acids encoding a polypeptide having phosphoketolase activity.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

DEFINITIONS

The term "isoprene" refers to 2-methyl-1,3-butadiene (CAS#78-79-5). It can be the direct and final volatile C5 hydrocarbon product from the elimination of pyrophosphate from 3,3-dimethylallyl diphosphate (DMAPP). It may not involve the linking or polymerization of IPP molecules to DMAPP molecules. The term "isoprene" is not generally intended to be limited to its method of production unless indicated otherwise herein.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the phosphoketolase gene from *Lactobacillus reuteri, Bifidobacterium longum, Ferrimonas balearica, Pedobacter saltans, Streptomyces griseus,* and/or *Nocardiopsis dassonvillei* and used to transform an *E. coli* is a heterologous nucleic acid.

As used herein, the terms "phosphoketolase", "phosphoketolase enzyme" or "phosphoketolase polypeptide" are used interchangeably and refer to a polypeptide that converts 5-phosphate to glyceraldehyde 3-phosphate and acetyl phosphate and/or converts fructose 6-phosphate to erythrose 4-phosphate and acetyl phosphate. Generally, phosphoketolases act upon ketoses. In certain embodiments, the phosphoketolase polypeptide catalyzes the conversion of xylulose 5-phosphate to glyceraldehyde 3-phosphate and acetyl phosphate. In other embodiments, the phosphoketolase polypeptide catalyzes the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth media containing the minimum nutrients possible for cell growth, generally without the presence of amino acids. Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "isoprenoid" refers to a large and diverse class of naturally-occurring class of organic compounds composed of two or more units of hydrocarbons, with each unit consisting of five carbon atoms arranged in a specific pattern. As used herein, "isoprene" is expressly excluded from the definition of "isoprenoid."

As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

As used herein, "isoprenoid precursor" refers to any molecule that is used by organisms in the biosynthesis of terpenoids or isoprenoids. Non-limiting examples of isoprenoid precursor molecules include, e.g., mevalonate (e.g., mevalonic acid (MVA)), isopentenyl pyrophosphate (IPP) and dimethylallyl diphosphate (DMAPP).

As used herein, the term "mass yield" refers to the mass of the product produced by the recombinant cells divided by the mass of the glucose consumed by the recombinant cells expressed as a percentage.

By "specific productivity," it is meant the mass of the product produced by the recombinant cell divided by the product of the time for production, the cell density, and the volume of the culture.

By "titer," it is meant the mass of the product produced by the recombinant cells divided by the volume of the culture.

As used herein, the term "cell productivity index (CPI)" refers to the mass of the product produced by the recombinant cells divided by the mass of the recombinant cells produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Recombinant Cells Expressing a Phosphoketolase Polypeptide and One or More Polypeptides of the MVA Pathway The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of the isoprenoid precursor molecules DMAPP and IPP, which serve as the basis for the biosynthesis of terpenes, terpenoids, isoprenoids, and isoprene.

The complete MVA pathway can be subdivided into two groups: an upper and lower pathway. In the upper portion of the MVA pathway, acetyl Co-A produced during cellular metabolism is converted to mevalonate via the actions of polypeptides having either: (a) (i) thiolase activity or (ii) acetoacetyl-CoA synthase activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. In the lower MVA pathway, mevalonate is then converted into mevalonate-5-phosphate via the action of mevalonate kinase which is subsequently transformed into 5-diphosphomevalonate by the enzymatic activity of phosphomevalonate kinase. Finally, IPP is formed from 5-diphosphomevalonate by the activity of the enzyme mevalonate-5-pyrophosphate decarboxylase.

Thus, in certain embodiments, the recombinant cells of the present invention are recombinant cells having the ability to produce mevalonate, isoprenoid precursors, isoprene or isoprenoids via the MVA pathway wherein the recombinant cells comprise: (i) a heterologous gene encoding a phosphoketolase capable of synthesizing glyceraldehyde 3-phosphate and acetyl phosphate from xylulose 5-phosphate, (ii) one or more heterologous genes encoding one or more MVA polypeptides, and (iii) one or more heterologous genes involved in mevalonate, isoprenoid precursor, or isoprene or isoprenoid biosynthesis that enables the synthesis of mevalonate, isoprenoid precursors, isoprene or isoprenoids from acetoacetyl-CoA in the host cell. In other embodiments, recombinant cells of the present invention are recombinant cells having the ability to produce mevalonate, isoprenoid precursors, isoprene or isoprenoids wherein the recombinant cells comprise: (i) a heterologous gene encoding a phosphoketolase capable of synthesizing erythrose 4-phosphate and acetyl phosphate from fructose 6-phosphate, (ii) one or more heterologous genes encoding one or more MVA polypeptides, and (iii) one or more heterologous genes involved in mevalonate, isoprenoid precursors, isoprene or isoprenoid biosynthesis that enables the synthesis of produce mevalonate, isoprenoid precursors, isoprene or isoprenoids from acetoacetyl-CoA in the host cell.

Exemplary Phosphoketolase Polypeptides and Nucleic Acids

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. In other embodiments, the phosphoketolase polypeptide catalyzes the conversion of sedoheptulose-7-phosphate to a product (e.g., ribose-5-phosphate) and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produces mevalonate, isoprenoid precursor molecules, isoprene and/or isoprenoids. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein (See for example FIG. 4). Additionally, Table 1 provides a non-limiting list of species and biochemical characteristics of certain exemplary phosphoketolases which may be utilized within embodiments of the invention.

Biochemical characteristics of exemplary phosphoketolases include, but are not limited to, protein expression, protein solubility, and activity. Phosphoketolases can also be selected on the basis of other characteristics, including, but not limited to, diversity amongst different types of organisms (e.g., gram positive bacteria, cyanobacteria, *actinomyces*), facultative low temperature aerobe, close relatives to a desired species (e.g., *E. coli*), and thermotolerance.

As provided herein, phosphoketolase activity can improve production of isoprenoid precursors (e.g., mevalonate), isoprene, and/or isoprenoids. Provided herein is a recombinant host comprising phosphoketolase wherein the cells display at least one property of interest to improve production of isoprenoid precursors (e.g., mevalonate), isoprene, and/or isoprenoids. In some aspects, at least one property of interest is selected from but not limited to the group consisting of specific productivity, yield, titer and cellular performance index.

In certain embodiments, suitable phosphoketolases for use herein include soluble phosphoketolases. Techniques for measuring protein solubility are well known in the art. Techniques for measuring protein solubility include those disclosed herein in the Examples. In some embodiments, a phosphoketolase for use herein includes those with a solubility of at least 20%. In some embodiments, phosphoketolase solubility is between about any of 5% to about 100%, between about 10% to about 100%, between about 15% to about 100%, between about 20% to about 100%, between about 25% to about 100%, between about 30% to about 100%, between about 35% to about 100%, between about 40% to about 100%, between about 45% to about 100%, between about 50% to about 100%, between about 55% to about 100%, between about 60% to about 100%, between about 65% to about 100%, between about 70% to about 100%, between about 75% to about 100%, between about 80% to about 100%, between about 85% to about 100%, or between about 90% to about 100%, In some embodiments, phosphoketolase solubility is between about 5% to about 100%. In some embodiments, solubility is between 5% and 100%. In some embodiments, phosphoketolase solubility is less than about any of 100, 90, 80, 70, 60, 50, 40, 30, 20, or 10 but no less than about 5%. In some embodiments, solubility is greater than about any of 5, 10, 15, 20, 25, 30, 35, 40, 45, 50, 55, 60, 65, 70, 75, 80, 85, 90, or 95%.

Phosphoketolases with a desired kinetic characteristic increases the production of isoprene. Kinetic characteristics include, but are not limited to, specific activity, $K_{cat}$, $K_i$ and $K_m$. In some aspects, the $k_{cat}$ is at least about 0.2, 0.4, 0.6, 0.8, 1.0, 1.2, 1.4, 1.6, 1.8, 2.0, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.1, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, 16.6, 16.8, 17.0, 17.2, 17.4, 17.6, 17.8, 18.0, 18.2, 18.4, 18.6, 18.8, 19.0, 19.2, 19.4, 19.6, 19.8, 20.0, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 200, 300, 400, 500, 600, 700, or 800. In other aspects, the $k_{cat}$ is at least about 0.2, 0.4, 0.6, 0.8, 1.0, 1.1, 1.2, 1.3, 1.4, 1.5, 1.6, 1.7, 1.8, 1.9 2.0, 2.1, 2.2, 2.3, 2.4, 2.5, 2.6, 2.7, 2.8, 2.9, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.1, 8.2, 8.4, 8.6, 8.8, 9.0, 9.2, 9.4, 9.6, 9.8, 10.0, 10.2, 10.4, 10.6, 10.8, 11.0, 11.2, 11.4, 11.6, 11.8, 12.0, 12.2, 12.4, 12.6, 12.8, 13.0, 13.2, 13.4, 13.6, 13.8, 14.0, 14.2, 14.4, 14.6, 14.8, 15.0, 15.2, 15.4, 15.6, 15.8, 16.0, 16.2, 16.4, or 16.6.

In some aspects, the $K_m$ is at least about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 45, 45.5, 46, 46.5, 47, 47.5, 48, 48.5, 49, 49.5, 50, 50.5, 51, 51.5, 52, 52.5, 53, 53.5, 54, 54.5, 55, 55.5, or 56. In other aspects, the $k_m$ is at least about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 17.5, 18, 18.5, 19, 19.5, 20, 20.5, 21, 21.5, or 22.

Properties of interest include, but are not limited to: increased intracellular activity, specific productivity, yield, and cellular performance index as compared to as compared to a recombinant cell that does not comprise the phosphoketolase polypeptide. In some embodiments, specific productivity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6 7, 8, 9, 10 times or more. In one embodiment, specific productivity is about 40 mg/L/OD/hr. In some embodiments, yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, MVA yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, isoprene yield increase of at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, cell performance index increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5 times or more. In other embodiments, intracellular activity increase at least about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10 times or more.

TABLE 1

Kinetic characteristics of phosphoketolases reported in the literature

| Organism | Kinetic constants | Reference |
|---|---|---|
| Bifidobacterium lactis | $k_m$(F6P) = 10 mM<br>$K_m$(X5P) = 55 mM<br>$k_{cat}$(F6P) = 8 s$^{-1}$<br>$k_{cat}$(X5P) = 42 s$^{-1}$ | Meile et al. (2001) J. Bacteriol., v. 183 (9), pp. 2929-2936 |
| Bifidobacterium longum BB536 | $K_m$(F6P) = 26 mM<br>$k_{cat}$ (F6P) = 39 s$^{-1}$ | Grill et al. (1995) Curr. Microbiol., v. 31, pp. 49-54 |
| Bifidobacterium dentium ATCC27534 | $K_m$(F6P) = 23 mM<br>$k_{cat}$ (F6P) = 33 s$^{-1}$ | Grill et al. (1995) Curr. Microbiol., v. 31, pp. 49-54 |
| Bifidobacterium animalis ATCC 25527 | $K_m$(F6P) = 11.5 mM<br>$k_{cat}$ (F6P) = 33 s$^{-1}$ | Grill et al. (1995) Curr. Microbiol., v. 31, pp. 49-54 |
| Bifidobacterium globosum ATCC 25864 | $K_m$(F6P) = 12.5 mM<br>$k_{cat}$ (F6P) = 40 s$^{-1}$ | Grill et al. (1995) Curr. Microbiol., v. 31, pp. 49-54 |
| Lactobacillus plantarum | $K_m$(F6P) = 24 mM<br>$K_m$(X5P) = 3.6 mM<br>$K_m$(Pi) = 2.9 mM (for F6P as a substrate)<br>$K_m$(Pi) = 7.5 mM (for X5P as a substrate) | Yevenes and Frey (2008) Bioorg. Chem., v. 36, pp. 121-127. |

TABLE 1-continued

Kinetic characteristics of phosphoketolases reported in the literature

| Organism | Kinetic constants | Reference |
|---|---|---|
| Bifidobacterium breve | $K_{is}^{E4P}$ = 8 mM$^1$ (for F6P as a substrate)<br>$K_{ii}^{E4P}$ = 4.4 mM$^1$ (for F6P as a substrate)<br>$k_{cat}$(F6P) = 2.7 s$^{-1}$<br>$k_{cat}$(X5P) = 6.1 s$^{-1}$<br>$K_m$(F6P) = 9.7 mM<br>$K_m$Pi = 1.2 mM (for F6P as a substrate)<br>$k_{cat}$ (F6P) = 22.4 s$^{-1}$<br>$k_{cat}$ (X5P) = 44.8 s$^{-1}$ | Suzuki et al. (2010) Acta Cryst., v. F66, pp. 941-943. |
| Lactobacillus paraplantarum C7 | $T_m$ = 45° C., pH$_{opt}$ = 7.0<br>$K_m$(F6P) = 5.1 mM<br>$k_{cat}$(F6P) = 738 s$^{-1}$ | Jeong et al. (2007) J. Microbiol. Biotechnol., v. 17(5), pp. 822-829. |
| Leuconostoc oenos | $K_m$(F6P) = 22 mM<br><br>$K_m$(X5P) = 1.6 mM<br>$k_{cat}$(F6P) = 0.2 s-1<br>$k_{cat}$ (X5P) = 3.5 s$^{-1}$ | Veiga-da-Cunha et al. (1993) J. Bacteriol., v. 175(13), pp. 3941-3948. |

Other phosphoketolases that can be used include, but are not limited to, B. longum, L. plantarum, C. acetobutylicum, L. reuteri, L. paraplantarum, R. palustris, Nostoc punctiforme, B. animalis, B. breve, G. vaginalis, E. gallinarum, M. paludis, Panteoa sp., R. aquatilis, N. punctiforme, S. avermetilis, and T. fusca.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183: 2929-2936, 2001). Any polypeptide identified as having phosphoketolase peptide activity as described herein is suitable for use in the present invention. In some embodiments, the phosphoketolase polypeptide catalyzes the conversion of xylulose 5-phosphate to glyceraldehyde 3-phosphate and acetyl phosphate. In other embodiments, tha phosphoketolase polypeptide catalyzes the conversion of fructose 6-phosphate to erythrose 4-phosphate and acetyl phosphate. In still other embodiments, the phosphoketolase polypeptide capable of catalyzing the conversion of sedoheptulose-7-phosphate to ribose-5-phosphate and acetyl phosphate. In still other embodiments, the phosphoketolase polypeptide catalyzes the conversion of xylulose 5-phosphate to glyceraldehyde 3-phosphate and acetyl phosphate and/or the conversion of fructose 6-phosphate to erythrose 4-phosphate and acetyl phosphate and/or the conversion of sedoheptulose-7-phosphate to ribose-5-phosphate and acetyl phosphate.

Provided herein is a phosphoketolase isolated from a microorganism. In some aspects, a phosphoketolase isolated from the group consisting of a gram positive bacterium, a gram negative bacterium, an aerobic bacterium, an anaerobic bacterium, a thermophilic bacterium, a psychrophilic bacterium, a halophilic bacterium or a cyanobacterium. In some aspects, a phosphoketolase isolated from a fungi. In other aspects, exemplary phosphoketolase nucleic acids include, for example, a phosphoketolase isolated from Lactobacillus reuteri, Bifidobacterium longum, Ferrimonas balearica, Pedobactor saltans, Streptomyces griseus, and/or Nocardiopsis dassonvillei. In other aspects, exemplary phosphoketolase nucleic acids include, for example, a phosphoketolase isolated from Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea sp., Pedobactor saltans, Rahnella aquatilis, Rhodopseudomonas palustris, Streptomyces griseus, Streptomyces avermitilis, Nocardiopsis dassonvillei, and/or Thermobifida fusca. In other aspects, exemplary phosphoketolase nucleic acids include, for example, a phosphoketolase isolated from Clostridium acetobutylicum, Bifidobacterium longum, and/or Enterococcus gallinarum. In any of the aspects described herein, a phosphoketolase nucleic acid can have at least about 99%, 98%, 97%, 96%, 95%, 95%, 93%, 92%, 91%, 90%, 89%, 88%, 87%, 86%, or 85% sequence identity to any of the phosphoketolase nucleic acid sequences described herein. The phosphoketolase nucleic acid encoded by the Lactobacillus reuteri phosphoketolase gene can have at least about 99%, 98%, 97%, 96%, 95%, 95%, 93%, 92%, 91%, 90%, 89%, 88%, 87%, 86%, or 85% sequence identity to SEQ ID NO:1. The phosphoketolase nucleic acid encoded by the Bifidobacterium longum phosphoketolase gene can have at least about 99%, 98%, 97%, 96%, 95%, 95%, 93%, 92%, 91%, 90%, 89%, 88%, 87%, 86%, or 85% sequence identity to SEQ ID NO:3. The phosphoketolase nucleic acid encoded by the Enterococcus gallinarum phosphoketolase gene can have at least about 99%, 98%, 97%, 96%, 95%, 95%, 93%, 92%, 91%, 90%, 89%, 88%, 87%, 86%, or 85% sequence identity to SEQ ID NO:17. The phosphoketolase nucleic acid encoded by the Nostoc punctiforme phosphoketolase gene can have at least about 99%, 98%, 97%, 96%, 95%, 95%, 93%, 92%, 91%, 90%, 89%, 88%, 87%, 86%, or 85% sequence identity to SEQ ID NO:18. The phosphoketolase nucleic acid encoded by the Rhodopseudomonas palustris phosphoketolase gene can have at least about 99%, 98%, 97%, 96%, 95%, 95%, 93%, 92%, 91%, 90%, 89%, 88%, 87%, 86%, or 85% sequence identity to SEQ ID NO:19. The phosphoketolase nucleic acid encoded by the Pantoea sp. phosphoketolase gene can have at least about 99%, 98%, 97%, 96%, 95%, 95%, 93%, 92%, 91%, 90%, 89%, 88%, 87%, 86%, or 85% sequence identity to SEQ ID NO:20. The phosphoketolase nucleic acid encoded by the Mucilaginibacter paludis phosphoketolase gene can have at least about 99%, 98%, 97%, 96%, 95%, 95%, 93%, 92%, 91%, 90%, 89%, 88%, 87%, 86%, or 85% sequence identity to SEQ ID NO:21. The phosphoketolase nucleic acid encoded by the Thermobifida fusca phosphoketolase gene can have at least about 99%, 98%, 97%, 96%, 95%, 95%, 93%, 92%, 91%, 90%, 89%, 88%, 87%, 86%, or 85% sequence identity to SEQ ID NO:22. The phosphoketolase nucleic acid encoded by the *Bifidobacterium breve* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:23. The phosphoketolase nucleic acid encoded by the *Rahnella aquatilis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:24. The phosphoketolase nucleic acid encoded by the *Bifidobacterium animalis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:25. The phosphoketolase nucleic acid encoded by the *Gardnerella vaginalis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:26. The phosphoketolase nucleic acid encoded by the *Streptomyces avermitilis* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:27. The phosphoketolase nucleic acid encoded by the *Clostridium acetobutylicum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:28. The phosphoketolase nucleic acid encoded by the *Lactobacillus paraplantarum* phosphoketolase gene can have at least about 99%, 98%, 97%, 96%, 95%, 95%, 93%, 92%, 91%, 90%, 89%, 88%, 87%, 86%, or 85% sequence identity to SEQ ID NO:29.

In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Lactobacillus reuteri* phosphoketolase nucleic acid sequence SEQ ID NO:1. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Bifidobacterium longum* phosphoketolase nucleic acid sequence SEQ ID NO:3. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Enterococcus gallinarum* phosphoketolase nucleic acid sequence SEQ ID NO:17. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Nostoc punctiforme* phosphoketolase nucleic acid sequence SEQ ID NO:18. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Rhodopseudomonas palustris* phosphoketolase nucleic acid sequence SEQ ID NO:19. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Pantoea* sp. phosphoketolase nucleic acid sequence SEQ ID NO:20. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Mucilaginibacter paludis* phosphoketolase nucleic acid sequence SEQ ID NO:21. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Thermobifida fusca* phosphoketolase nucleic acid sequence SEQ ID NO:22. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Bifidobacterium breve* phosphoketolase nucleic acid sequence SEQ ID NO:23. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Rahnella aquatilis* phosphoketolase nucleic acid sequence SEQ ID NO:24. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Bifidobacterium animalis* phosphoketolase nucleic acid sequence SEQ ID NO:25. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Gardnerella vaginalis* phosphoketolase nucleic acid sequence SEQ ID NO:26. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Streptomyces avermitilis* phosphoketolase nucleic acid sequence SEQ ID NO:27. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Clostridium acetobutylicum* phosphoketolase nucleic acid sequence SEQ ID NO:28. In some embodiments, the phosphoketolase polypeptide can have at least about 99%, 98%, 97%, 96%, 95%, 95%, 93%, 92%, 91%, 90%, 89%, 88%, 87%, 86%, or 85% sequence identity to the phosphoketolase polypeptide encoded by the *Lactobacillus paraplantarum* phosphoketolase polypeptide can have nucleic acid sequence SEQ ID NO:29. In any of the aspects described herein, a phosphoketolase polypeptide can have at least about 99%, 98%, 97%, 96%, 95%, 95%, 93%, 92%, 91%, 90%, 89%, 88%, 87%, 86%, or 85% sequence identity to any of the phosphoketolase polypeptide encoded by any of phosphoketolase nucleic acid sequences described herein.

Additional examples of phosphoketolase enzymes which can be used herein are described in U.S. Pat. No. 7,785,858 and WO 2011/159853, which are incorporated by reference herein, especially with respect to all disclosure about phosphoketolase enzymes.

Upper MVA Pathway Polypeptides

The upper portion of the MVA pathway uses acetyl Co-A produced during cellular metabolism as the initial substrate for conversion to mevalonate via the actions of polypeptides having either: (a) (i) thiolase activity or (ii) acetoacetyl-CoA activity, (b) HMG-CoA reductase, and (c) HMG-CoA synthase enzymatic activity. First, acetyl Co-A is converted to acetoacetyl CoA via the action of a thiolase or an acetoacetyl-CoA synthase (which utilizes acetyl-CoA and malonyl-CoA). Next, acetoacetyl-CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production.

Non-limiting examples of upper MVA pathway polypeptides include acetyl-CoA acetyltransferase (AA-CoA thiolase) polypeptides, acetoacetyl-CoA synthase polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides. Upper MVA pathway polypeptides can include polypeptides, fragments of polypeptides, peptides, and fusions polypeptides that have at least one activity of an upper MVA pathway polypeptide. Exemplary upper MVA pathway nucleic acids include nucleic acids that encode a polypeptide, fragment of a polypeptide, peptide, or fusion polypeptide that has at least one activity of an upper MVA pathway polypeptide. Exemplary MVA pathway polypeptides and nucleic acids include naturally-occurring polypeptides and nucleic acids from any of the source organisms described herein. Thus, it is contemplated herein that any gene encoding an upper MVA pathway polypeptide can be used in the present invention.

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In other embodiments, an acetoacetyl-CoA synthase gene is contemplated within the scope of the present invention in combination with one or more other genes encoding: (i) 3-hydroxy-3-methylglutaryl-CoA synthase (HMG-CoA synthase) polypeptides and 3-hydroxy-3-methylglutaryl-CoA reductase (HMG-CoA reductase) polypeptides. Thus, in certain aspects, any of the combinations of genes contemplated in can be expressed in recombinant cells in any of the ways described herein.

Additional non-limiting examples of upper MVA pathway polypeptides which can be used herein are described in International Patent Application Publication No. WO2009/076676; WO2010/003007 and WO2010/148150.

Genes Encoding mvaE and mvaS Polypeptides

In certain embodiments, various options of mvaE and mvaS genes from *L. grayi, E. faecium, E. gallinarum, E. casseliflavus* and/or *E. faecalis* alone or in combination with one or more other mvaE and mvaS genes encoding proteins from the upper MVA pathway are contemplated within the scope of the invention. In *L. grayi, E. faecium, E. gallinarum, E. casseliflavus,* and *E. faecalis,* the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., *J Bacteriol.* 2002 April; 184(8): 2116-2122). The mvaS gene, on the other hand, encodes a polypeptide having an HMG-CoA synthase activity.

Accordingly, recombinant cells (e.g., *E. coli*) can be engineered to express one or more mvaE and mvaS genes from *L. grayi, E. faecium, E. gallinarum, E. casseliflavus* and/or *E. faecalis,* to produce mevalonate. The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

Exemplary mvaE Polypeptides and Nucleic Acids

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or can not be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of mevalonate, isoprenoid precursors, isoprene, and/or isoprenoids. Examples of gene products of mvaEs that are not degraded or less prone to degradation which can be used include, but are not limited to, those from the organisms *E. faecium, E. gallinarum, E. casseliflavus, E. faecalis,* and *L. grayi.* One of skill in the art can express mvaE protein in *E. coli* BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing *E. coli* BL21 using the methods of detection described herein.

Standard methods, such as those described in Hedl et al., (*J Bacteriol.* 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 200 µl. For the assay, 1 enzyme unit (eu) represents the synthesis or thiolysis in 1 min of 1 µmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)—HMG-CoA, 100 mM KCl, and 100 mM $K_xPO_4$, pH 6.5. Assays employ a final volume of 200 µl. Reactions are initiated by adding the enzyme. For the assay, 1 eu represents the turnover, in 1 min, of 1 µmol of NADP(H). This corresponds to the turnover of 0.5 µmol of HMG-CoA or mevalonate.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium*, *Enterococcus gallinarum* EG2, *Enterococcus faecalis*, and/or *Enterococcus casseliflavus*. The mvaE nucleic acid encoded by the *Listeria grayi*_DSM 20601 mvaE gene can have at least about 99%, 98%, 97%, 96%, 95%, 95%, 93%, 92%, 91%, 90%, 89%, 88%, 87%, 86%, or 85% sequence identity to SEQ ID NO:6. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:7. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:8. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:9. The mvaE nucleic acid encoded by the *Enterococcus faecalis* mvaE gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. *Biotechnology Letters* 26: 1487-1491, 2004).

The mvaE nucleic acid can be expressed in a recombinant cell on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

Exemplary mvaS Polypeptides and Nucleic Acids

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (*Biochem J.*, 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-$MgCl_2$ and 0.2 mM-dithiothreitol at 30° C.; 5 mM-acetyl phosphate, 10 µM-acetoacetyl-CoA and 5 µl samples of extracts can be added, followed by simultaneous addition of acetyl-CoA (100 µM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-MgCl$_2$), is $12.2 \times 10^3$ M$^{-1}$ cm$^{-1}$. By definition, 1 unit of enzyme activity causes 1 µmol of acetoacetyl-CoA to be transformed per minute.

Alternatively, production of mevalonate in recombinant cells can be measured by, without limitation, gas chromatography (see U.S. Patent Application Publication No.: US 2005/0287655 A1) or HPLC (See U.S. Patent Application Publication No.: 2011/0159557 A1). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 µM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevonate containing solutions of known concentration.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria* grayi_DSM 20601, *Enterococcus faecium, Enterococcus gallinarum* EG2, *Enterococcus faecalis*, and/or *Enterococcus casseliflavus*. The mvaS nucleic acid encoded by the *Listeria grayi*_DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:10. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:11. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:12. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:13. The mvaS nucleic acid encoded by the *Enterococcus faecalis* mvaS gene can have at least about 99%, 98%, 97%, 96%, 95%, 95%, 93%, 92%, 91%, 90%, 89%, 88%, 87%, 86%, or 85% sequence identity to the mvaE gene previously disclosed in *E. coli* to produce mevalonate (see US 2005/0287655 A1; Tabata, K. and Hashimoto, S.-I. *Biotechnology Letters* 26: 1487-1491, 2004).

The mvaS nucleic acid can be expressed in a recombinant cell on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Acetoacetyl-CoA Synthase Gene

The acetoacetyl-CoA synthase gene (aka nphT7) is a gene encoding an enzyme having the activity of synthesizing acetoacetyl-CoA from malonyl-CoA and acetyl-CoA and having minimal activity (e.g., no activity) of synthesizing acetoacetyl-CoA from two acetyl-CoA molecules. See, e.g., Okamura et al., *PNAS* Vol 107, No. 25, pp. 11265-11270 (2010), the contents of which are expressly incorporated herein for teaching about nphT7. An acetoacetyl-CoA synthase gene from an actinomycete of the genus *Streptomyces* CL190 strain was described in JP Patent Publication (Kokai) No. 2008-61506 A and US2010/0285549. Acetoacetyl-CoA synthase can also be referred to as acetyl CoA:malonyl CoA acyltransferase. A representative acetoacetyl-CoA synthase (or acetyl CoA:malonyl CoA acyltransferase) that can be used is Genbank AB540131.1.

In any of the aspects or embodiments described herein, an enzyme that has the ability to synthesize acetoacetyl-CoA from malonyl-CoA and acetyl-CoA can be used. Non-limiting examples of such an enzyme are described herein. In certain embodiments described herein, an acetoacetyl-CoA synthase gene derived from an actinomycete of the genus *Streptomyces* having the activity of synthesizing acetoacetyl-CoA from malonyl-CoA and acetyl-CoA can be used. An example of such an acetoacetyl-CoA synthase gene is the gene encoding a protein having the amino. Such a protein having the amino acid sequence of SEQ ID NO:5 corresponds to an acetoacetyl-CoA synthase having activity of synthesizing acetoacetyl-CoA from malonyl-CoA and acetyl-CoA and having no activity of synthesizing acetoacetyl-CoA from two acetyl-CoA molecules.

In one embodiment, the gene encoding a protein having the amino acid sequence of SEQ ID NO:5 can be obtained by a nucleic acid amplification method (e.g., PCR) with the use of genomic DNA obtained from an actinomycete of the *Streptomyces* sp. CL190 strain as a template and a pair of primers that can be designed with reference to JP Patent Publication (Kokai) No. 2008-61506 A.

As described herein, an acetoacetyl-CoA synthase gene for use in the present invention is not limited to a gene encoding a protein having the amino acid sequence of SEQ ID NO:5 from an actinomycete of the *Streptomyces* sp. CL190 strain. Any gene encoding a protein having the ability to synthesize acetoacetyl-CoA from malonyl-CoA and acetyl-CoA and which does not synthesize acetoacetyl-CoA from two acetyl-CoA molecules can be used in the presently described methods. In certain embodiments, the acetoacetyl-CoA synthase gene can be a gene encoding a protein having an amino acid sequence with high similarity or substantially identical to the amino acid sequence of SEQ ID NO:5 and having the function of synthesizing acetoacetyl-CoA from malonyl-CoA and acetyl-CoA. The expression "highly similar" or "substantially identical" refers to, for example, at least about 80% identity, at least about 85%, at least about 90%, at least about 91%, at least about 92%, at least about 93%, at least about 94%, at least about 95%, at least about 96%, at least about 97%, at least about 98%, and at least about 99% identity. As used above, the identity value corresponds to the percentage of identity between amino acid residues in a different amino acid sequence and the amino acid sequence of SEQ ID NO:5, which is calculated by performing alignment of the amino acid sequence of SEQ ID NO:5 and the different amino acid sequence with the use of a program for searching for a sequence similarity.

In other embodiments, the acetoacetyl-CoA synthase gene may be a gene encoding a protein having an amino acid sequence derived from the amino acid sequence of SEQ ID NO:5 by substitution, deletion, addition, or insertion of 1 or more amino acid(s) and having the function of synthesizing acetoacetyl-CoA from malonyl-CoA and acetyl-CoA. Herein, the expression "more amino acids" refers to, for example, 2 to 30 amino acids, preferably 2 to 20 amino acids, more preferably 2 to 10 amino acids, and most preferably 2 to 5 amino acids.

In still other embodiments, the acetoacetyl-CoA synthase gene may consist of a polynucleotide capable of hybridizing to a portion or the entirety of a polynucleotide having a nucleotide sequence complementary to the nucleotide sequence encoding the amino acid sequence of SEQ ID NO:5 under stringent conditions and capable of encoding a protein having the function of synthesizing acetoacetyl-CoA from malonyl-CoA and acetyl-CoA. Herein, hybridization under stringent conditions corresponds to maintenance of binding under conditions of washing at 60° C. two times SSC. Hybridization can be carried out by conventionally known methods such as the method described in J. Sambrook et al. Molecular Cloning, A Laboratory Manual, 3rd Ed., Cold Spring Harbor Laboratory (2001).

As described herein, a gene encoding an acetoacetyl-CoA synthase having an amino acid sequence that differs from the amino acid sequence of SEQ ID NO:5 can be isolated from potentially any organism, for example, an actinomycete that is not obtained from the *Streptomyces* sp. CL190 strain. In addition, acetoacetyl-CoA synthase genes for use herein can be obtained by modifying a polynucleotide encoding the amino acid sequence of SEQ ID NO:5 by a method known in the art. Mutagenesis of a nucleotide sequence can be carried out by a known method such as the Kunkel method or the gapped duplex method or by a method similar to either thereof. For instance, mutagenesis may be carried out with the use of a mutagenesis kit (e.g., product names; Mutant-K and Mutant-G (TAKARA Bio)) for site-specific mutagenesis, product name; an LA PCR in vitro Mutagenesis series kit (TAKARA Bio), and the like.

The activity of an acetoacetyl-CoA synthase having an amino acid sequence that differs from the amino acid sequence of SEQ ID NO:5 can be evaluated as described below. Specifically, a gene encoding a protein to be evaluated is first introduced into a host cell such that the gene can be expressed therein, followed by purification of the protein by a technique such as chromatography. Malonyl-CoA and acetyl-CoA are added as substrates to a buffer containing the obtained protein to be evaluated, followed by, for example, incubation at a desired temperature (e.g., 10° C. to 60° C.). After the completion of reaction, the amount of substrate lost and/or the amount of product (acetoacetyl-CoA) produced are determined. Thus, it is possible to evaluate whether or not the protein being tested has the function of synthesizing acetoacetyl-CoA from malonyl-CoA and acetyl-CoA and to evaluate the degree of synthesis. In such case, it is possible to examine whether or not the protein has the activity of synthesizing acetoacetyl-CoA from two acetyl-CoA molecules by adding acetyl-CoA alone as a substrate to a buffer containing the obtained protein to be evaluated and determining the amount of substrate lost and/or the amount of product produced in a similar manner.

Recombinant Cells Capable of Increased Production of Mevalonate

The recombinant cells (e.g., recombinant bacterial cells) described herein can produce mevalonate at an amount and/or concentration greater than that of the same cells without any manipulation to the various enzymatic pathways described herein. Thus, the recombinant cells (e.g., bacterial cells) that have been engineered for modulation in the various pathways described herein are useful in the enhance production of mevalonate.

Accordingly, in certain aspects, the invention provides recombinant cells capable of enhanced production of mevalonate, wherein the cells comprise one or more heterologous nucleic acids encoding a polypeptide having phosphoketolase activity and one or more nucleic acids encoding one or more polypeptides of the upper MVA pathway, wherein the cells produce increased amounts of mevalonate compared to cells that do not comprise the one or more heterologous nucleic acids encoding a polypeptide having phosphoketolase activity.

In certain aspects, the recombinant cells described herein comprise one or more copies of a heterologous nucleic acid encoding a phosphoketolase isolated from *Lactobacillus reuteri*, *Bifidobacterium longum*, *Ferrimonas balearica*, *Pedobactor saltans*, *Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other aspects, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei*, and/or *Thermobifida furca*. In yet other aspects, the recombinant cells described herein comprise one or more copies of a heterologous nucleic acid encoding a phosphoketolase isolated from *Clostridium acetobutylicum, Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*.

In one embodiment, the recombinant cells further comprise one or more copies of a heterologous nucleic acid encoding mvaE and mvaS polypeptides from *L. grayi, E. faecium, E. gallinarum, E. casseliflavus*, and/or *E. faecalis*. In another embodiment, the recombinant cells further comprise an acetoacetyl-CoA synthase and one or more nucleic acids encoding one or more polypeptides of the upper MVA pathway.

In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

In one aspect, the recombinant cells described herein can produce mevalonate at a higher volumetric productivity than that of the same cells lacking one or more copies of a heterologous nucleic acid encoding a polypeptide having phosphoketolase activity. In certain embodiments, the recombinant cell can produce greater than 2.00 g/L/hr of mevalonate. Alternatively, the recombinant cells can produce greater than about 1.0 g/L/hr, 1.2 g/L/hr, 1.4 g/L/hr, 1.6 g/L/hr, 1.8 g/L/hr, 2.0 g/L/hr, 2.2 g/L/hr, 2.4 g/L/hr, 2.6 g/L/hr, 2.8 g/L/hr, 3.0 g/L/hr, 3.2 g/L/hr, 3.4 g/L/hr, 3.6 g/L/hr, 3.8 g/L/hr, 4.0 g/L/hr, 4.2 g/L/hr, 4.4 g/L/hr, 4.6 g/L/hr, 4.8 g/L/hr, 5.0 g/L/hr, 5.2 g/L/hr, 5.4 g/L/hr, 5.6 g/L/hr, 5.8 g/L/hr, 6.0 g/L/hr of mevalonate, inclusive, as well as any numerical value in between these numbers.

In one aspect, the recombinant cells described herein can produce mevalonate at a higher titer than that of the same cells lacking one or more copies of a heterologous nucleic acid encoding a polypeptide having phosphoketolase activity. These recombinant cells can produce greater than about 100 g/L peak titer of mevalonate after 48 hours of fermentation. Alternatively, the recombinant cells can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers.

In other embodiments, the recombinant cells described herein further comprise one or more mutations which increase carbon flux towards the MVA pathway and can thus produce higher titers of mevalonate in comparison to cells which have not been similarly engineered. In such embodiments, the recombinant cells described herein produce mevalonate at a higher peak titer than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, the recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

In one aspect, the recombinant cells described herein can produce mevalonate at a higher cell productivity index (CPI) for mevalonate than that of the same cells lacking one or more copies of a heterologous nucleic acid encoding a polypeptide having phosphoketolase activity. The recombinant cells can have a CPI for mevalonate of at least about 3.0 (g/g). Alternatively, the recombinant cells can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers.

In certain embodiments, the recombinant cells described herein further comprise one or more mutations which increase carbon flux towards the MVA pathway which results in a higher cell productivity index (CPI) for mevalonate in comparison to cells which have not been similarly engineered. Additionally, the recombinant cells described herein have a higher CPI than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

Additionally, the cells described herein have a higher mass yield of mevalonate from glucose than that of the same cells lacking one or more copies of a heterologous nucleic acid encoding phosphoketolase polypeptide having phosphoketolase activity. The recombinant cells can produce a mass yield of mevalonate from glucose of at least about 28%. Alternatively, the recombinant cells can produce a mass yield of mevalonate from glucose of at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or 55%, inclusive, as well as any numerical value in between these numbers.

In certain embodiments, the recombinant cells described herein further comprise one or more mutations which increase carbon flux towards the MVA pathway which results in a higher mass yield of mevalonate in comparison to cells which have not been similarly engineered. Additionally, the recombinant cells described herein have a higher mass yield of mevalonate than that of the same cells lacking one or more copies of a heterologous nucleic acid encoding phosphoketolase polypeptide having phosphoketolase activity. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

In one aspect, the recombinant cells described herein produce mevalonate while accumulating less acetate in the fermentation broth as compared to the same cells lacking one or more copies of a heterologous nucleic acid encoding a polypeptide having phosphoketolase activity. The recombinant cells can produce increased levels of mevalonate while accumulating less than 4.5 g/L of acetate in the fermentation broth over a 48 hr fermentation. Alternatively, the recombinant cells can produce increased levels of mevalonate while accumulating less than about 8.0 g/L, 7.5 g/L, 7.0 g/L, 6.5 g/L, 6.0 g/L, 5.5 g/L, 5.0 g/L, 4.5 g/L, 4.0 g/L, 3.5 g/L, 3.0 g/L, 2.5 g/L, 2.0 g/L, or 1.5 g/L, of acetate in the fermentation broth over a 48 hr fermentation inclusive, as well as any numerical value in between these numbers. In certain embodiments, the decreased accumulation of acetate in the fermentation broth can improve cell viability during the fermentation run.

In certain embodiments, the recombinant cells described herein further comprise one or more mutations which increase carbon flux towards the MVA pathway which results increased levels of mevalonate while accumulating less acetate in the fermentation broth in comparison to cells which have not been similarly engineered. In certain embodiments, the decreased accumulation of acetate in the fermentation broth can improve cell viability during the fermentation run.

Methods of Using Recombinant Recombinant Cells to Produce Increased Amounts of Mevalonate Also provided herein are methods for the production of mevalonate. In some aspects, the method for producing mevalonate comprises: (a) culturing a composition comprising recombinant cells which have been engineered to increase carbon flux as described herein (including any of the recombinant cells described above), or progeny thereof, capable of producing mevalonate; and (b) producing mevalonate. In some aspects, the method of producing mevalonate comprises the steps of culturing any of the recombinant cells described herein under conditions suitable for the production of mevalonate and allowing the recombinant cells to produce mevalonate. In some aspects, the method of producing mevalonate further comprises a step of recovering the mevalonate.

As described herein, the methods of producing mevalonate comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate. In certain embodiment, the phosphoketolase polypeptide is from *Lactobacillus reuteri*, *Bifidobacterium longum*, *Ferrimonas balearica*, *Pedobactor saltans*, *Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. Additionally, the recombinant cells can produce mevalonate in concentrations greater than that of the same cells lacking one or more heterologous copies of a gene encoding an phosphoketolase polypeptide from *Lactobacillus reuteri*, *Bifidobacterium longum*, *Ferrimonas balearica*, *Pedobactor saltans*, *Streptomyces griseus*, and/or *Nocardiopsis dassonvillei* along with one or more heterologous nucleic acids expressing one or more MVA pathway peptides, when the cells are cultured in minimal medium. In certain embodiments, the one or more copies of a heterologous nucleic acid encoding an phosphoketolase polypeptide from *Lactobacillus reuteri*, *Bifidobacterium longum*, *Ferrimonas balearica*, *Pedobactor saltans*, *Streptomyces griseus*, and/or *Nocardiopsis dassonvillei* is a heterologous nucleic acid that is integrated into the host cell's chromosome.

In certain embodiments, the phosphoketolase polypeptide is from *Clostridium acetobutylicum*, *Lactobacillus reuteri*, *Lactobacillus plantarum*, *Lactobacillus paraplantarum*, *Bifidobacterium longum*, *Bifidobacterium animalis*, *Bifidobacterium breve*, *Enterococcus gallinarum*, *Gardnerella vaginalis*, *Ferrimonas balearica*, *Mucilaginibacter paludis*, *Nostoc punctiforme*, *Nostoc punctiforme* PCC 73102, *Pantoea*, *Pedobactor saltans*, *Rahnella aquatilis*, *Rhodopseudomonas palustris*, *Streptomyces griseus*, *Streptomyces avermitilis*, *Nocardiopsis dassonvillei*, and/or *Thermobifida fusca*. In other embodiments, the phosphoketolase polypeptide is from *Clostridium acetobutylicum*, *Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. Additionally, the recombinant cells can produce mevalonate in concentrations greater than that of the same cells lacking one or more heterologous copies of a gene encoding an phosphoketolase polypeptide from *Clostridium acetobutylicum*, *Lactobacillus reuteri*, *Lactobacillus plantarum*, *Lactobacillus paraplantarum*, *Bifidobacterium longum*, *Bifidobacterium animalis*, *Bifidobacterium breve*, *Enterococcus gallinarum*, *Gardnerella vaginalis*, *Ferrimonas balearica*, *Mucilaginibacter paludis*, *Nostoc punctiforme*, *Nostoc punctiforme* PCC 73102, *Pantoea*, *Pedobactor saltans*, *Rahnella aquatilis*, *Rhodopseudomonas palustris*, *Streptomyces griseus*, *Streptomyces avermitilis*, *Nocardiopsis dassonvillei*, and/or *Thermobifida fusca* along with one or more heterologous nucleic acids expressing one or more MVA pathway peptides, when the cells are cultured in minimal medium. In certain embodiments, the one or more copies of a heterologous nucleic acid encoding an phosphoketolase polypeptide from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca* is a heterologous nucleic acid that is integrated into the host cell's chromosome.

The instant methods for the production of mevalonate produce can produce mevalonate using cells having a volumetric productivity of greater than 2.00 g/L/hr of mevalonate. Alternatively, the recombinant cells can produce greater than about 1.0 g/L/hr, 1.2 g/L/hr, 1.4 g/L/hr, 1.6 g/L/hr, 1.8 g/L/hr, 2.0 g/L/hr, 2.2 g/L/hr, 2.4 g/L/hr, 2.6 g/L/hr, 2.8 g/L/hr, 3.0 g/L/hr, 3.2 g/L/hr, 3.4 g/L/hr, 3.6 g/L/hr, 3.8 g/L/hr, 4.0 g/L/hr. 4.2 g/L/hr, 4.4 g/L/hr, 4.6 g/L/hr, 4.8 g/L/hr, 5.0 g/L/hr, 5.2 g/L/hr, 5.4 g/L/hr, 5.6 g/L/hr, 5.8 g/L/hr, 6.0 g/L/hr of mevalonate, inclusive, as well as any numerical value in between these numbers. In some aspects, the method of producing mevalonate further comprises a step of recovering the mevalonate.

In other embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells produce mevalonate with a higher peak titer after 48 hours of fermentation than that of the same cells lacking one or more heterologous copies of a gene encoding an phosphoketolase polypeptide. In certain embodiments, the phosphoketolase polypeptide is from *Lactobacillus reuteri, Bifidobacterium longum, Ferrimonas balearica, Pedobactor saltans, Streptomyces griseus,* and/or *Nocardiopsis dassonvillei.* In one embodiment, the recombinant cells comprise one or more copies of a heterologous nucleic acid encoding a phosphoketolase isolated from *Lactobacillus reuteri.* In another embodiment, the recombinant cells comprise one or more copies of a heterologous nucleic acid encoding a phosphoketolase isolated from *Bifidobacterium longum.* In still another embodiment, the recombinant cells comprise one or more copies of a heterologous nucleic acid encoding a phosphoketolase isolated from *Ferrimonas balearica.* In yet another embodiment, the recombinant cells comprise one or more copies of a heterologous nucleic acid encoding a phosphoketolase isolated from *Pedobactor saltans.* In another embodiment, the recombinant cells comprise one or more copies of a heterologous nucleic acid encoding a phosphoketolase isolated from *Streptomyces griseus.* In another embodiment, the recombinant cells comprise one or more copies of a heterologous nucleic acid encoding a phosphoketolase isolated from *Nocardiopsis dassonvillei.* In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca.* In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum.* In one embodiment, the recombinant cells comprise one or more copies of a heterologous nucleic acid encoding a phosphoketolase isolated from *Clostridium acetobutylicum.* In another embodiment, the recombinant cells comprise one or more copies of a heterologous nucleic acid encoding a phosphoketolase isolated from *Bifidobacterium longum.* In still another embodiment, the recombinant cells comprise one or more copies of a heterologous nucleic acid encoding a phosphoketolase isolated from *Enterococcus gallinarum.*

The instant methods for the production of mevalonate can produce mevalonate using cells that can produce a peak titer of greater than about 100 g/L peak titer of mevalonate after 48 hours of fermentation. Alternatively, the recombinant cells can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate after 48 hours of fermentation, inclusive, as well as any numerical value in between these numbers. In some aspects, the method of producing mevalonate further comprises a step of recovering the mevalonate.

In other embodiments, the methods of producing mevalonate can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells have a CPI for mevalonate higher than that of the same cells lacking one or more heterologous copies of a gene encoding an phosphoketolase polypeptide. In certain embodiments, the phosphoketolase polypeptide is from *Lactobacillus reuteri, Bifidobacterium longum, Ferrimonas balearica, Pedobactor saltans, Streptomyces griseus,* and/or *Nocardiopsis dassonvillei.* In one embodiment, the recombinant cells comprise one or more copies of a heterologous nucleic acid encoding a phosphoketolase isolated from *Lactobacillus reuteri.* In another embodiment, the recombinant cells comprise one or more copies of a heterologous nucleic acid encoding a phosphoketolase isolated from *Bifidobacterium longum.* In still another embodiment, the recombinant cells comprise one or more copies of a heterologous nucleic acid encoding a phosphoketolase isolated from *Ferrimonas balearica.* In yet another embodiment, the recombinant cells comprise one or more copies of a heterologous nucleic acid encoding a phosphoketolase isolated from *Pedobactor saltans.* In another embodiment, the recombinant cells comprise one or more copies of a heterologous nucleic acid encoding a phosphoketolase isolated from *Streptomyces griseus.* In still another embodiment, the recombinant cells comprise one or more copies of a heterologous nucleic acid encoding a phosphoketolase isolated from *Nocardiopsis dassonvillei.* In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifido-* bacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei, and/or Thermobifida fusca. In yet other embodiments, the recombinant cells described herein comprise one or more copies of a heterologous nucleic acid encoding a phosphoketolase isolated from Clostridium acetobutylicum, Bifidobacterium longum, and/or Enterococcus gallinarum. In one embodiment, the recombinant cells comprise one or more copies of a heterologous nucleic acid encoding a phosphoketolase isolated from Clostridium acetobutylicum. In another embodiment, the recombinant cells comprise one or more copies of a heterologous nucleic acid encoding a phosphoketolase isolated from Bifidobacterium longum. In still another embodiment, the recombinant cells comprise one or more copies of a heterologous nucleic acid encoding a phosphoketolase isolated from Enterococcus gallinarum.

The instant methods for the production of mevalonate can produce mevalonate using cells with a CPI for mevalonate of at least about 3.0 (g/g). Alternatively, the recombinant cells can have a CPI for mevalonate of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In some aspects, the method of producing mevalonate further comprises a step of recovering the mevalonate.

In certain embodiments, the methods of producing mevalonate can comprise the steps of: (a) culturing recombinant cells (including, but not limited to, E. coli cells) that do not endogenously express a phosphoketolase polypeptide, wherein the cells heterologously express one or more copies of a gene encoding a phosphoketolase polypeptide along with one or more heterologous nucleic acids expressing one or more MVA pathway peptides; and (b) producing mevalonate, wherein the recombinant cells display decreased oxygen uptake rate (OUR) as compared to that of the same cells lacking one or more heterologous copies of a gene encoding an phosphoketolase polypeptide. In certain embodiments, the recombinant cells expressing one or more heterologous copies of a gene encoding an phosphoketolase polypeptide display up to 1-fold, 2-fold, 3-fold, 4-fold, 5-fold, 6-fold or 7-fold decrease in OUR as compared to recombinant cells that do not express a phosphoketolase.

Provided herein are methods of using any of the cells described above for enhanced mevalonate production. The production of mevalonate by the cells can be enhanced by the expression of one or more heterologous nucleic acids encoding a phosphoketolase polypeptide. In certain embodiments, the phosphoketolase polypeptide is from Lactobacillus reuteri, Bifidobacterium longum, Ferrimonas balearica, Pedobactor saltans, Streptomyces griseus, and/or Nocardiopsis dassonvillei. In one embodiment, the recombinant cells comprise one or more copies of a heterologous nucleic acid encoding a phosphoketolase isolated from Lactobacillus reuteri. In another embodiment, the recombinant cells comprise one or more copies of a heterologous nucleic acid encoding a phosphoketolase isolated from Bifidobacterium longum. In still another embodiment, the recombinant cells comprise one or more copies of a heterologous nucleic acid encoding a phosphoketolase isolated from Ferrimonas balearica. In yet another embodiment, the recombinant cells comprise one or more copies of a heterologous nucleic acid encoding a phosphoketolase isolated from Pedobactor saltans. In another embodiment, the recombinant cells comprise one or more copies of a heterologous nucleic acid encoding a phosphoketolase isolated from Streptomyces griseus. In still another embodiment, the recombinant cells comprise one or more copies of a heterologous nucleic acid encoding a phosphoketolase isolated from Nocardiopsis dassonvillei. In other embodiments, the recombinant cells described herein comprise one or more copies of a heterologous nucleic acid encoding a phosphoketolase isolated from Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei, and/or Thermobifida fusca. In yet other embodiments, the recombinant cells described herein comprise one or more copies of a heterologous nucleic acid encoding a phosphoketolase isolated from Clostridium acetobutylicum, Bifidobacterium longum, and/or Enterococcus gallinarum. In one embodiment, the recombinant cells comprise one or more copies of a heterologous nucleic acid encoding a phosphoketolase isolated from Clostridium acetobutylicum. In another embodiment, the recombinant cells comprise one or more copies of a heterologous nucleic acid encoding a phosphoketolase isolated from Bifidobacterium longum. In still another embodiment, the recombinant cells comprise one or more copies of a heterologous nucleic acid encoding a phosphoketolase isolated from Enterococcus gallinarum.

The production of mevalonate can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate by mevalonate-producing cells without the expression of one or more heterologous nucleic acids encoding a phosphoketolase polypeptide. In certain embodiments described herein, the host cells have been further engineered increased carbon flux to MVA production. In other embodiments, the recombinant cells described herein comprise one or more copies of a heterologous nucleic acid encoding a phosphoketolase isolated from Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei, and/or Thermobifida fusca. In yet other embodiments, the recombinant cells described herein comprise one or more copies of a heterologous nucleic acid encoding a phosphoketolase isolated from Clostridium acetobutylicum, Bifidobacterium longum, and/or Enterococcus gallinarum. In one embodiment, the recombinant cells comprise one or more copies of a heterologous nucleic acid encoding a phosphoketolase isolated from Clostridium acetobutylicum. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*.

In other aspects, the methods described herein can provide for the enhanced production of mevalonate can by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of mevalonate by mevalonate-producing cells without the expression of one or more heterologous nucleic acids encoding a phosphoketolase polypeptide. In certain embodiments described herein, the host cells have been further engineered increased carbon flux to MVA production.

In addition, more specific cell culture conditions can be used to culture the cells in the methods described herein. For example, in some aspects, the method for the production of mevalonate comprises the steps of (a) culturing recombinant cells (including, but not limited to, *E. coli* cells) that do not endogenously have a phosphoketolase gene in minimal medium at 34° C., wherein the recombinant cells heterologously express one or more copies of a heterologous gene encoding a phosphoketolase polypeptide on a low to medium copy plasmid and under the control of a strong promoter; and (b) producing mevalonate. In certain embodiments, the phosphoketolase polypeptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei*, and/or *Thermobifida fusca*. In yet other embodiments, the recombinant cells described herein comprise one or more copies of a heterologous nucleic acid encoding a phosphoketolase isolated from *Clostridium acetobutylicum, Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. In some aspects, the method of producing mevalonate further comprises a step of recovering the mevalonate.

Recombinant Cells Capable of Producing Isoprene

Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

Isoprene is produced from DMAPP by the enzymatic action of isoprene synthase. Therefore, without being bound to theory, it is thought that increasing the cellular production of mevalonate in recombinant cells by any of the compositions and methods described above will likewise result in the production of higher amounts of isoprene. Increasing the molar yield of mevalonate production from glucose translates into higher molar yields of isoprenoid precursors, isoprene and/or isoprenoids produced from glucose when combined with appropriate enzymatic activity levels of mevalonate kinase, phosphomevalonate kinase, diphosphomevalonate decarboxylase, isopentenyl diphosphate isomerase (e.g., the lower MVA pathway) and other appropriate enzymes for isoprene and isoprenoid production.

As described herein, the present invention provides recombinant cells capable of producing of isoprene, wherein the cells comprise one or more heterologous nucleic acids encoding a polypeptide having phosphoketolase activity and (i) one or more nucleic acids encoding one or more polypeptides of the complete MVA pathway (i.e., the upper MVA pathway and the lower MVA pathway) and (ii) a heterologous nucleic acid encoding an isoprene synthase polypeptide, wherein the cells are capable of producing recoverable amounts of isoprene. In certain embodiments, the present invention provides recombinant cells capable of enhanced production of isoprene, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding an isoprene synthase polypeptide, wherein the cells produce increased amounts of isoprene compared to isoprene-producing cells that do not comprise the one or more heterologous nucleic acids encoding a polypeptide having phosphoketolase activity.

Production of isoprene can also be made by using any of the recombinant host cells described herein further comprising one or more of the enzymatic pathways manipulations wherein enzyme activity is modulated to increase carbon flow towards mevalonate production. The recombinant cells described herein that have various enzymatic pathways manipulated for increased carbon flow to mevalonate production can be used to produce isoprene. In one embodiment, the recombinant cells can be further engineered to increase the activity of one or more of the following genes selected from the group consisting of ribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of M. mazei mevalonate kinase, Lactobacillus mevalonate kinase polypeptide, Lactobacillus sakei mevalonate kinase polypeptide, yeast mevalonate kinase polypeptide, Saccharomyces cerevisiae mevalonate kinase polypeptide, Streptococcus mevalonate kinase polypeptide, Streptococcus pneumoniae mevalonate kinase polypeptide, Streptomyces mevalonate kinase polypeptide, Streptomyces CL190 mevalonate kinase polypeptide, and M. Burtonii mevalonate kinase polypeptide. In another aspect, the enzyme that phosphorylates mevalonate to mevalonate 5-phosphate is M. mazei mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from Saccharomyces cerevisiae, Enterococcus faecalis, or Methanosarcina mazei.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus Methanosarcina and, more specifically, the lower MVK polypeptide can be from Methanosarcina mazei. In some embodiments, the lower MVK polypeptide can be from M. burtonii. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variant.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from Saccharomyces cerevisiae, Enterococcus faecalis, or Methanosarcina mazei. In some aspects, the MVK polypeptide is selected from the group consisting of Lactobacillus mevalonate kinase polypeptide, Lactobacillus sakei mevalonate kinase polypeptide, yeast mevalonate kinase polypeptide, Saccharomyces cerevisiae mevalonate kinase polypeptide, Streptococcus mevalonate kinase polypeptide, Streptococcus pneumoniae mevalonate kinase polypeptide, Streptomyces mevalonate kinase polypeptide, Streptomyces CL190 mevalonate kinase polypeptide, Methanosarcina mazei mevalonate kinase polypeptide, and M. Burtonii mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Nucleic Acids Encoding Isoprene Synthase Polypeptides

In some aspects of the invention, the cells described in any of the compositions or methods described herein (including host cells that have been engineered for increased carbon flux toward the MVA pathway as described herein) further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In a particular aspect, the cells are engineered to over-express the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba*× *Populus tremula*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., *J. Biol. Chem.* 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 μL of 1M $MgCl_2$, 1 mM (250 μg/ml) DMAPP, 65 μL of Plant Extract Buffer (PEB) (50 mM Tris-HCl, pH 8.0, 20 mM $MgCl_2$, 5% glycerol, and 2 mM DTT) can be added to 25 μL of cell extract in a 20 ml Headspace vial with a metal screw cap and teflon coated silicon septum (Agilent Technologies) and cultured at 37° C. for 15 minutes with shaking. The reaction can be quenched by adding 200 μL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba*×*Populus tremula*, or a variant thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., *Plant Physiology* 137: 700-712, 2005), *Pueraria lobata*, poplar (such as *Populus alba, Populus nigra, Populus trichocarpa*, or *Populus alba*×*tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making cells encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, WO2010/148256, WO 2012/058494, and U.S. Pat. No. 8,173,410.

Nucleic Acids Encoding DXP Pathway Polypeptides

In some aspects of the invention, the cells described in any of the compositions or methods described herein (including host cells that have been engineered for increased carbon flux toward the MVA pathway as described herein) further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde 3-phosphate into 1-deoxy-D-xylulose-5-phosphate in vitro, in a cell extract, or in vivo. Exemplary DXS polypeptides and nucleic acids and methods of measuring DXS activity are described in more detail in International Publication Nos. WO 2009/076676, WO 2010/003007, WO 2009/132220, and U.S. Patent Publ. Nos. US 2009/0203102, 2010/0003716 and 2010/0048964.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No. WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde 3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, WO 2010/003007, WO 2009/132220, and U.S. Patent Publ. Nos. US 2009/0203102, 2010/0003716, and 2010/0048964.

In particular, DXS polypeptides convert pyruvate and D-glyceraldehyde 3-phosphate into 1-deoxy-D-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-D-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2,4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2,4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

Source Organisms for Lower MVA Pathway, Isoprene Synthase, IDI, and DXP Pathway Polypeptides Isoprene synthase, IDI, DXP pathway, and/or lower MVA pathway nucleic acids (and their encoded polypeptides) can be obtained from any organism that naturally contains isoprene synthase, IDI, DXP pathway, and/or lower MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of Archaea such as *Methanosarcina mazei*.

As used herein, "the genus *Bacillus*" includes all species within the genus "*Bacillus*," as known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

In some aspects, the source organism is a gram-positive bacterium. Non-limiting examples include strains of *Streptomyces* (e.g., *S. lividans*, *S. coelicolor*, or *S. griseus*) and *Bacillus*. In some aspects, the source organism is a gram-negative bacterium, such as *E. coli* or *Pseudomonas* Sp.

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: *Chroococcales, Pleurocapsales, Oscillatoriales, Nostocales,* or *Stigonematales.*

Recombinant Cells Capable of Increased Production of Isoprene

The recombinant cells described herein (including host cells that have been engineered for increased carbon flux as described herein) have the ability to produce isoprene concentration greater than that of the same cells lacking one or more copies of a heterologous nucleic acid phosphoketolase polypeptides, one or more copies of a heterologous nucleic acid encoding a MVA pathway polypeptide, and one or more heterologous nucleic acids encoding an isoprene synthase polypeptide when cultured under the same conditions. The cells can further comprise one or more heterologous nucleic acids encoding an IDI polypeptide. In certain embodiments, the phosphoketolase polypeptide is from *Lactobacillus reuteri, Bifidobacterium longum, Ferrimonas balearica, Pedobactor saltans, Streptomyces griseus,* and/or *Nocardiopsis dassonvillei.* In one embodiment, the recombinant cells comprise one or more copies of a heterologous nucleic acid encoding a phosphoketolase isolated from *Lactobacillus reuteri.* In another embodiment, the recombinant cells comprise one or more copies of a heterologous nucleic acid encoding a phosphoketolase isolated from *Bifidobacterium longum.* In still another embodiment, the recombinant cells comprise one or more copies of a heterologous nucleic acid encoding a phosphoketolase isolated from *Ferrimonas balearica.* In yet another embodiment, the recombinant cells comprise one or more copies of a heterologous nucleic acid encoding a phosphoketolase isolated from *Pedobactor saltans.* In another embodiment, the recombinant cells comprise one or more copies of a heterologous nucleic acid encoding a phosphoketolase isolated from *Streptomyces griseus.* In still another embodiment, the recombinant cells comprise one or more copies of a heterologous nucleic acid encoding a phosphoketolase isolated from *Nocardiopsis dassonvillei.* In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca.* In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum.* In one embodiment, the recombinant cells comprise one or more copies of a heterologous nucleic acid encoding a phosphoketolase isolated from *Clostridium acetobutylicum.* In another embodiment, the recombinant cells comprise one or more copies of a heterologous nucleic acid encoding a phosphoketolase isolated from *Bifidobacterium longum.* In still another embodiment, the recombinant cells comprise one or more copies of a heterologous nucleic acid encoding a phosphoketolase isolated from *Enterococcus gallinarum.*

In some aspects, the one or more copies of a heterologous nucleic acid encoding phosphoketolase, one or more copies of a heterologous nucleic acid encoding a MVA pathway polypeptide, and one or more heterologous nucleic acids encoding an isoprene synthase polypeptide are heterologous nucleic acids that are integrated into the host cell's chromosomal nucleotide sequence. In other aspects, the one or more heterologous nucleic acids are integrated into plasmid. In still other aspects, at least one of the one or more heterologous nucleic acids is integrated into the cell's chromosomal nucleotide sequence while at least one of the one or more heterologous nucleic acid sequences is integrated into a plasmid. The recombinant cells can produce at least 5% greater amounts of isoprene compared to isoprene-producing cells that do not comprise the phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprene, inclusive, as well as any numerical value in between these numbers.

In one aspect of the invention, provided herein are recombinant cells comprising one or more heterologous nucleic acids encoding a phosphoketolase polypeptide, one or more heterologous nucleic acids encoding a mevalonate (MVA) pathway polypeptide(s), one or more heterologous nucleic acids encoding a DXP pathway polypeptide(s), and one or more heterologous nucleic acids encoding an isoprene synthase polypeptide. The cells can further comprise one or more heterologous nucleic acids encoding an IDI polypeptide. In certain embodiments, the phosphoketolase polypeptide is from *Lactobacillus reuteri, Bifidobacterium longum, Ferrimonas balearica, Pedobactor saltans, Streptomyces griseus,* and/or *Nocardiopsis dassonvillei.* In one embodiment, the recombinant cells comprise one or more copies of a heterologous nucleic acid encoding a phosphoketolase isolated from *Lactobacillus reuteri.* In another embodiment, the recombinant cells comprise one or more copies of a heterologous nucleic acid encoding a phosphoketolase isolated from *Bifidobacterium longum.* In still another embodiment, the recombinant cells comprise one or more copies of a heterologous nucleic acid encoding a phosphoketolase isolated from *Ferrimonas balearica.* In yet another embodiment, the recombinant cells comprise one or more copies of a heterologous nucleic acid encoding a phosphoketolase isolated from *Pedobactor saltans.* In another embodiment, the recombinant cells comprise one or more copies of a heterologous nucleic acid encoding a phosphoketolase isolated from *Streptomyces griseus.* In still another embodiment, the recombinant cells comprise one or more copies of a heterologous nucleic acid encoding a phosphoketolase isolated from *Nocardiopsis dassonvillei.* In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca.* In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum.* In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. Any of the one or more heterologous nucleic acids can be operably linked to constitutive promoters, can be operably linked to inducible promoters, or can be operably linked to a combination of inducible and constitutive promoters. The one or more heterologous nucleic acids can additionally be operably linked to strong promoters, weak promoters, and/or medium promoters. One or more of the heterologous nucleic acids encoding phosphoketolase, a mevalonate (MVA) pathway polypeptide(s), a DXP pathway polypeptide(s), and an isoprene synthase polypeptide can be integrated into a genome of the host cells or can be stably expressed in the cells. The one or more heterologous nucleic acids can additionally be on a vector.

The production of isoprene by the cells according to any of the compositions or methods described herein can be enhanced (e.g., enhanced by the expression of one or more heterologous nucleic acids encoding a phosphoketolase polypeptide, an isoprene synthase polypeptide, MVA pathway polypeptide(s), and/or a DXP pathway polypeptide(s)). As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding a phosphoketolase peptide. In certain embodiments described herein, the host cells have been further engineered increased carbon flux to MVA production.

The production of isoprene by the recombinant cells described herein can be enhanced by about 5% to about 1,000,000 folds. In certain aspects, the production of isoprene can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by cells that do not express one or more heterologous nucleic acids encoding phosphoketolase peptide. In certain embodiments described herein, the host cells have been further engineered to increased carbon flux to MVA production thereby providing enhanced production of isoprene as compared to the production of isoprene by cells that do not express one or more heterologous nucleic acids encoding phosphoketolase peptide and which have not been engineered for increased carbon flux to mevalonate production.

In other aspects, the production of isoprene by the recombinant cells described herein can also be enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds as compared to the production of isoprene by cells that do not express one or more heterologous nucleic acids encoding phosphoketolase peptide. In certain embodiments described herein, the host cells have been further engineered increased carbon flux to MVA production thereby providing enhanced production of isoprene as compared to the production of isoprene by cells that do not express one or more heterologous nucleic acids encoding phosphoketolase peptide and which have not been engineered for increased carbon flux to mevalonate production.

Methods of Using the Recombinant Cells to Produce Isoprene

Also provided herein are methods for producing isoprene comprising culturing any of the recombinant cells described herein. In one aspect, isoprene can be produced by culturing recombinant cells comprising one or more heterologous nucleic acids encoding an phosphoketolase polypeptide, one or more MVA pathway polypeptides, and an isoprene synthase polypeptide. In certain embodiments, the phosphoketolase polypeptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei*, and/or *Thermobifida fusca*. In yet other embodiments, the recombinant cells described herein comprise one or more copies of a heterologous nucleic acid encoding a phosphoketolase isolated from *Clostridium acetobutylicum, Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*.

In another aspect, isoprene can be produced by culturing recombinant cells comprising modulation in any of the enzymatic pathways described herein and one or more heterologous nucleic acids encoding a phosphoketolase peptide, a MVA pathway polypeptide, and an isoprene synthase polypeptide. In certain embodiments, the phosphoketolase polypeptide is from *Lactobacillus reuteri*, *Bifidobacterium longum*, *Ferrimonas balearica*, *Pedobactor saltans*, *Streptomyces griseus*, and/or *Nocardiopsis dassonvillei*. In other embodiments, the recombinant cells described herein comprise one or more copies of a heterologous nucleic acid encoding a phosphoketolase isolated from *Clostridium acetobutylicum*, *Lactobacillus reuteri*, *Lactobacillus plantarum*, *Lactobacillus paraplantarum*, *Bifidobacterium longum*, *Bifidobacterium animalis*, *Bifidobacterium breve*, *Enterococcus gallinarum*, *Gardnerella vaginalis*, *Ferrimonas balearica*, *Mucilaginibacter paludis*, *Nostoc punctiforme*, *Nostoc punctiforme* PCC 73102, *Pantoea*, *Pedobactor saltans*, *Rahnella aquatilis*, *Rhodopseudomonas palustris*, *Streptomyces griseus*, *Streptomyces avermitilis*, *Nocardiopsis dassonvillei*, and/or *Thermobifida fusca*. In yet other embodiments, the recombinant cells described herein comprise one or more copies of a heterologous nucleic acid encoding a phosphoketolase isolated from *Clostridium acetobutylicum*, *Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. The isoprene can be produced from any of the cells described herein and according to any of the methods described herein. Any of the cells can be used for the purpose of producing isoprene from carbohydrates, including, but not limited to, six carbon sugars such as glucose. In other embodiments, the phosphoketolase polypeptide is from *Clostridium acetobutylicum*, *Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*.

Thus, provided herein are methods of producing isoprene comprising culturing cells comprising one or more heterologous nucleic acids encoding a phosphoketolase polypeptide and an isoprene synthase in a suitable condition for producing isoprene and (b) producing isoprene. In certain embodiments, the phosphoketolase polypeptide is from *Lactobacillus reuteri*, *Bifidobacterium longum*, *Ferrimonas balearica*, *Pedobactor saltans*, *Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum*, *Lactobacillus reuteri*, *Lactobacillus plantarum*, *Lactobacillus paraplantarum*, *Bifidobacterium longum*, *Bifidobacterium animalis*, *Bifidobacterium breve*, *Enterococcus gallinarum*, *Gardnerella vaginalis*, *Ferrimonas balearica*, *Mucilaginibacter paludis*, *Nostoc punctiforme*, *Nostoc punctiforme* PCC 73102, *Pantoea*, *Pedobactor saltans*, *Rahnella aquatilis*, *Rhodopseudomonas palustris*, *Streptomyces griseus*, *Streptomyces avermitilis*, *Nocardiopsis dassonvillei*, and/or *Thermobifida fusca*. In yet other embodiments, the recombinant cells described herein comprise one or more copies of a heterologous nucleic acid encoding a phosphoketolase isolated from *Clostridium acetobutylicum*, *Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*.

The cells can further comprise one or more nucleic acid molecules encoding the MVA pathway polypeptide(s) described above (e.g., the complete MVA pathway) and any of the isoprene synthase polypeptide(s) described above (e.g. *Pueraria* isoprene synthase). In some aspects, the recombinant cells can be one of any of the cells described herein. Any of the isoprene synthases or variants thereof described herein, any of the host cell strains described herein, any of the promoters described herein, and/or any of the vectors described herein can also be used to produce isoprene using any of the energy sources (e.g. glucose or any other six carbon sugar) described herein can be used in the methods described herein. In some aspects, the method of producing isoprene further comprises a step of recovering the isoprene. In other embodiments, the phosphoketolase polypeptide is from *Clostridium acetobutylicum*, *Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*.

In certain aspects, provided herein are methods of making isoprene comprising culturing recombinant cells comprising one or more heterologous nucleic acids encoding a phosphoketolase polypeptide from *Clostridium acetobutylicum*, *Lactobacillus reuteri*, *Lactobacillus plantarum*, *Lactobacillus paraplantarum*, *Bifidobacterium longum*, *Bifidobacterium animalis*, *Bifidobacterium breve*, *Enterococcus gallinarum*, *Gardnerella vaginalis*, *Ferrimonas balearica*, *Mucilaginibacter paludis*, *Nostoc punctiforme*, *Nostoc punctiforme* PCC 73102, *Pantoea*, *Pedobactor saltans*, *Rahnella aquatilis*,

*Rhodopseudomonas palustris, Streptomyces griseus, Streptomyces avermitilis, Nocardiopsis dassonvillei,* and/or *Thermobifida fusca*, an mvaE and an mvaS polypeptide from *L. grayi, E. faecium, E. gallinarum, E. casseliflavus,* and/or *E. faecalis*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above. In some aspects, the recombinant cells can be any of the cells described herein.

In certain aspects, provided herein are methods of making isoprene comprising culturing recombinant cells comprising one or more heterologous nucleic acids encoding a phosphoketolase polypeptide from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above. In some aspects, the recombinant cells can be any of the cells described herein. The recombinant cells described herein that have various enzymatic pathways manipulated for increased carbon flow to mevalonate production can be used to produce isoprene. In some aspects, the recombinant cells can be further engineered to increase the activity of one or more of the following genes selected from the group consisting of rribose-5-phosphate isomerase (rpiA and/or rpiB), D-ribulose-5-phosphate 3-epimerase (rpe), transketolase (tktA and/or tktB), transaldolase B (tal B), phosphate acetyltransferase (pta and/or eutD). In another embodiment, these recombinant cells can be further engineered to decrease the activity of one or more genes of the following genes including glucose-6-phosphate dehydrogenase (zwf), 6-phosphofructokinase-1 (pfkA and/or pfkB), fructose bisphosphate aldolase (fba, fbaA, fbaB, and/or fbaC), glyceraldehyde-3-phosphate dehydrogenase (gapA and/or gapB), acetate kinase (ackA), citrate synthase (gltA), EI (ptsI), EIICB$^{Glc}$ (ptsG), EIIA$^{Glc}$ (crr), and/or HPr (ptsH).

In certain aspects, provided herein are methods of making isoprene comprising culturing recombinant cells comprising one or more heterologous nucleic acids encoding a phosphoketolase polypeptide from *Clostridium acetobutylicum, Bifidobacterium longum,* and/or *Enterococcus gallinarum*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above. In some aspects, the recombinant cells can be any of the cells described herein. The recombinant cells described herein that have various enzymatic pathways manipulated for increased carbon flow to mevalonate production can be used to produce isoprene. In some aspects, the recombinant cells can be further engineered to increase the activity of one or more of the following genes selected from the group consisting of rpiA, rpe, tktA, tal B, pta and/or eutD. In another aspect, these strains can be further engineered to decrease the activity of one or more genes of the following genes including zwf, pfkA, fba, gapA, ackA, gltA and/or pts.

In some aspects, the amount of isoprene produced is measured at the peak absolute productivity time point. In some aspects, the peak absolute productivity for the cells is about any of the amounts of isoprene disclosed herein. In some aspects, the amount of isoprene produced is measured at the peak specific productivity time point. In some aspects, the peak specific productivity for the cells is about any of the amounts of isoprene per cell disclosed herein. In some aspects, the cumulative, total amount of isoprene produced is measured. In some aspects, the cumulative total productivity for the cells is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

In certain embodiments, the methods of producing isoprene can comprise the steps of: (a) culturing recombinant cells (including, but not limited to, *E. coli* cells) that do not endogenously express a phosphoketolase polypeptide, wherein the cells heterologously express one or more copies of a gene encoding a phosphoketolase polypeptide along with (i) one or more nucleic acids expressing one or more MVA pathway peptides and (ii) an isoprene synthase and (b) producing isoprene, wherein the recombinant cells display decreased oxygen uptake rate (OUR) as compared to that of the same cells lacking one or more heterologous copies of a gene encoding an phosphoketolase polypeptide. In certain embodiments, the recombinant cells expressing one or more heterologous copies of a gene encoding an phosphoketolase polypeptide display up to 1-fold, 2-fold, 3-fold, 4-fold, 5-fold, 6-fold or 7-fold decrease in OUR as compared to recombinant cells that do not express a phosphoketolase.

Also provided herein are methods the production of isoprene comprising cells having enhanced isoprene production capabilities. The production of isoprene by the cells described herein can be enhanced by the expression of one or more heterologous nucleic acids encoding a phosphoketolase polypeptide, one or more copies of a heterologous nucleic acid encoding one or more polypeptides of the complete MVA pathway polypeptide, and one or more heterologous nucleic acids encoding an isoprene synthase polypeptide. In certain embodiments, the phosphoketolase polypeptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei*, and/or *Thermobifida fusca*. In yet other embodiments, the recombinant cells described herein comprise one or more copies of a heterologous nucleic acid encoding a phosphoketolase isolated from *Clostridium acetobutylicum, Bifidobacterium longum*, and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding a phosphoketolase polypeptide, a MVA pathway polypeptide(s) and an isoprene synthase polypeptide. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the isoprene-producing cells that do not endogenously express phosphoketolase enzyme. In certain embodiments described herein, the methods described herein comprise host cells have been further engineered to increased carbon flux to MVA production thereby providing enhanced production of isoprene as compared to the production of isoprene by isoprene-producing cells that do not express one or more heterologous nucleic acids encoding phosphoketolase peptide and which have not been engineered for increased carbon flux to mevalonate production. In certain embodiments, the phosphoketolase polypeptide is from *Clostridium acetobutylicum, Bifidobacterium longum*, and/or *Enterococcus gallinarum*.

In other aspects, the methods described herein are directed to the enhanced production of isoprene by the cells described herein (e.g., enhanced by the expression of one or more heterologous nucleic acids encoding a phosphoketolase polypeptide). In certain embodiments, the phosphoketolase polypeptide is from *Lactobacillus reuteri, Bifidobacterium longum, Ferrimonas balearica, Pedobactor saltans, Streptomyces griseus*, and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from

*Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca*. In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by an isoprene-producing cells without the expression of one or more heterologous nucleic acids encoding a phosphoketolase polypeptide. The production of isoprene can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprene by isoprene-producing cells without the expression of one or more heterologous nucleic acids encoding phosphoketolase. In certain embodiments described herein, the methods described herein comprise host cells have been further engineered to increased carbon flux to MVA production thereby providing enhanced production of isoprene as compared to the production of isoprene by cells that do not express one or more heterologous nucleic acids encoding phosphoketolase peptide and which have not been engineered for increased carbon flux to mevalonate production. In certain embodiments, the phosphoketolase polypeptide is from *Clostridium acetobutylicum, Bifidobacterium longum,* and/or *Enterococcus gallinarum*.

In addition, more specific cell culture conditions can be used to culture the cells in the methods described herein. For example, in some aspects, the method for the production of isoprene comprises the steps of (a) culturing recombinant cells (including, but not limited to, *E. coli* cells) that do not endogenously have a phosphoketolase gene in minimal medium at 34° C., wherein the recombinant cells heterologously express (i) one or more copies of a heterologous gene encoding a phosphoketolase polypeptide on a low to medium copy plasmid and under the control of a strong promoter, (ii) one or more copies of a heterologous nucleic acid encoding one or more polypeptides of the MVA pathway polypeptide (upper MVA pathway and lower MVA pathway), and (iii) one or more heterologous nucleic acids encoding an isoprene synthase polypeptide; and (b) producing isoprene. In certain embodiments, the phosphoketolase polypeptide is from *Lactobacillus reuteri, Bifidobacterium longum, Ferrimonas balearica, Pedobactor saltans, Streptomyces griseus,* and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida furca*. In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. In some aspects, the method of producing isoprene further comprises a step of recovering the isoprene.

Recombinant Cells Capable of Increased Production of Isoprenoid Precursors and/or Isoprenoids Isoprenoids can be produced in many organisms from the synthesis of the isoprenoid precursor molecules which are the end products of the MVA pathway. As stated above, isoprenoids represent an important class of compounds and include, for example, food and feed supplements, flavor and odor compounds, and anticancer, antimalarial, antifungal, and antibacterial compounds.

As a class of molecules, isoprenoids are classified based on the number of isoprene units comprised in the compound.

Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged isoprenoids.

Isoprenoids can be produced from the isoprenoid precursor molecules IPP and DMAPP. These diverse compounds are derived from these rather simple universal precursors and are synthesized by groups of conserved polyprenyl pyrophosphate synthases (Hsieh et al., *Plant Physiol.* 2011 March; 155(3):1079-90). The various chain lengths of these linear prenyl pyrophosphates, reflecting their distinctive physiological functions, in general are determined by the highly developed active sites of polyprenyl pyrophosphate synthases via condensation reactions of allylic substrates (dimethylallyl diphosphate ($C_5$-DMAPP), geranyl pyrophosphate ($C_{10}$-GPP), farnesyl pyrophosphate ($C_{15}$-FPP), geranylgeranyl pyrophosphate ($C_{20}$-GGPP)) with corresponding number of isopentenyl pyrophosphates ($C_5$-IPP) (Hsieh et al., *Plant Physiol.* 2011 March; 155(3):1079-90).

Production of isoprenoid precursors and/or isoprenoids can be made by using any of the recombinant host cells that comprise one or more copies of a heterologous nucleic acid encoding a phosphoketolase for increased production of isoprenoid precursors and/or isoprenoids. In some aspects, these cells further comprise one or more heterologous nucleic acids encoding polypeptides of the MVA pathway, IDI, and/or the DXP pathway, as described above, and a heterologous nucleic acid encoding a polyprenyl pyrophosphate synthase polypeptide. Without being bound to theory, it is thought that increasing the cellular production of mevalonate in recombinant cells by any of the compositions and methods described above will similarly result in the production of higher amounts of isoprenoid precursor molecules and/or isoprenoids. Increasing the molar yield of mevalonate production from glucose translates into higher molar yields of isoprenoid precursor molecules and/or isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production. The recombinant cells described herein that have various enzymatic pathways manipulated for increased carbon flow to mevalonate production can be used to produce isoprenoid precursors and/or isoprenoids. In some aspects, the recombinant cells can be further engineered to increase the activity of one or more of the following genes selected from the group consisting of rpiA, rpe, tktA, talB, pta and/or eutD. In another aspect, these strains can be further engineered to decrease the activity of one or more genes of the following genes including zwf, pfkA, fba, gapA, ackA, gltA and/or pts.

Types of Isoprenoids

The recombinant cells of the present invention are capable of increased production of isoprenoids and the isoprenoid precursor molecules DMAPP and IPP. Examples of isoprenoids include, without limitation, hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid can be, without limitation, geranyl pyrophosphate, eucalyptol, limonene, or pinene. In some aspects, the sesquiterpenoid is farnesyl pyrophosphate, artemisinin, or bisabolol. In some aspects, the diterpenoid can be, without limitation, geranylgeranyl pyrophosphate, retinol, retinal, phytol, taxol, forskolin, or aphidicolin. In some aspects, the triterpenoid can be, without limitation, squalene or lanosterol. The isoprenoid can also be selected from the group consisting of abietadiene, amorphadiene, carene, α-framesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some aspects, the tetraterpenoid is lycopene or carotene (a carotenoid). As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes. In some aspects, the carotenoids are selected from the group consisting of xanthophylls and carotenes. In some aspects, the xanthophyll is lutein or zeaxanthin. In some aspects, the carotenoid is α-carotene, β-carotene, γ-carotene, β-cryptoxanthin or lycopene.

Heterologous Nucleic Acids Encoding Polyprenyl Pyrophosphate Synthases Polypeptides In some aspects of the invention, the cells described in any of the compositions or methods herein further comprise one or more nucleic acids encoding a mevalonate (MVA) pathway polypeptide(s), as described above, as well as one or more nucleic acids encoding a polyprenyl pyrophosphate synthase polypeptides(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to overexpress the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of an isoprene synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in *E. coli*. The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells.

In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., Plant Physiol. 2011 March; 155(3):1079-90; Danner et al., *Phytochemistry.* 2011 Apr. 12 [Epub ahead of print]; Jones et al., *J Biol. Chem.* 2011 Mar. 24 [Epub ahead of print]; Keeling et al., BMC Plant Biol. 2011 Mar. 7; 11:43; Martin et al., BMC Plant Biol. 2010 Oct. 21; 10:226; Kumeta & Ito, *Plant Physiol.* 2010 December; 154(4):1998-2007; and Köllner & Boland, *J Org. Chem.* 2010 Aug. 20; 75(16):5590-600.

Recombinant Cells Capable of Increased Production of Isoprenoid Precursors and/or Isoprenoids The recombinant cells (e.g., recombinant bacterial cells) described herein have the ability to produce isoprenoid precursors and/or isoprenoids at a amount and/or concentration greater than that of the same cells lacking one or more copies of a heterologous nucleic acid encoding phosphoketolase, one or more copies of a heterologous nucleic acid encoding a MVA pathway polypeptide, and one or more heterologous nucleic acids encoding a polyprenyl pyrophosphate synthase polypeptide when cultured under the same conditions. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus,* and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme PCC 73102, Pantoea, Pedobactor saltans, Rahnella aquatilis, Rhodopseudomonas palustris, Streptomyces griseus, Streptomyces avermitilis, Nocardiopsis dassonvillei,* and/or *Thermobifida furca*. In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. In some aspects, the one or more copies of a heterologous nucleic acid encoding phosphoketolase, one or more copies of a heterologous nucleic acid encoding a MVA pathway polypeptide, and one or more heterologous nucleic acid encoding a polyprenyl pyrophosphate synthase polypeptide are heterologous nucleic acids that are integrated into the host cell's chromosome. The recombinant cells can produce at least 5% greater amounts of isoprenoid precursors and/or isoprenoids when compared to isoprenoids and/or isoprenoid precursor-producing recombinant cells that do not comprise phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive, as well as any numerical value in between these numbers compared to the production of isoprenoids and/or isoprenoid-precursors by isoprenoids and/or isoprenoid-precursors-producing cells which do not express of one or more heterologous nucleic acids encoding a phosphoketolase. In certain embodiments described herein, the methods herein comprise host cells have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase peptide and which have not been engineered for increased carbon flux to mevalonate production.

In one aspect of the invention, there are provided recombinant cells comprising one or more heterologous nucleic acids encoding a phosphoketolase polypeptide, one or more heterologous nucleic acids encoding one or more complete MVA pathway polypeptide(s) (i.e., the upper MVA pathway and the lower MVA pathway), one or more heterologous nucleic acids encoding polyprenyl pyrophosphate synthase and/or one or more heterologous nucleic acids encoding a DXP pathway polypeptide(s). The cells can further comprise one or more heterologous nucleic acids encoding an IDI polypeptide. Additionally, the polyprenyl pyrophosphate synthase polypeptide can be an FPP synthase polypeptide. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus,* and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca*. In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. The one or more heterologous nucleic acids can be operably linked to constitutive promoters, can be operably linked to inducible promoters, or can be operably linked to a combination of inducible and constitutive promoters. The one or more heterologous nucleic acids can additionally be operably linked strong promoters, weak promoters, and/or medium promoters. One or more of the heterologous nucleic acids encoding a phosphoketolase polypeptide, one or more complete MVA pathway polypeptide(s) (i.e., the upper MVA pathway and the lower MVA pathway), a polyprenyl pyrophosphate synthase polypeptide and/or one or more heterologous nucleic acids encoding a DXP pathway polypeptide(s) can be integrated into a genome of the host cells or can be stably expressed in the cells. In certain embodiments, the one or more copies of a heterologous nucleic acid encoding phosphoketolase peptide is from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida furca*. In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. The one or more heterologous nucleic acids can additionally be on one or more vectors.

Provided herein are recombinant cells which can provide enhanced isoprenoid precursor and/or isoprenoid production. The production of isoprenoid precursors and/or isoprenoids by the cells can be enhanced by the expression of one or more heterologous nucleic acids encoding a phosphoketolase polypeptide, one or more heterologous nucleic acids encoding one or more polypeptide(s) of the complete MVA pathway (i.e., the upper MVA pathway and lower MVA pathway), and one or more heterologous nucleic acids encoding a polyprenyl pyrophosphate synthase polypeptide. In certain embodiments, the one or more copies of a heterologous nucleic acid encoding phosphoketolase peptide is from *Lactobacillus reuteri, Bifidobacterium longum, Ferrimonas balearica, Pedobactor saltans, Streptomyces griseus,* and/or *Nocardiopsis dassonvillei*. In one embodiment, the recombinant cells comprise one or more copies of a heterologous nucleic acid encoding a phosphoketolase isolated from *Lactobacillus reuteri*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Ferrimonas balearica*. In yet another embodiment, the recombinant cells comprise one or more copies of a heterologous nucleic acid encoding a phosphoketolase isolated from *Pedobactor saltans*. In another embodiment, the recombinant cells comprise one or more copies of a heterologous nucleic acid encoding a phosphoketolase isolated from *Streptomyces griseus*. In still another embodiment, the recombinant cells comprise one or more copies of a heterologous nucleic acid encoding a phosphoketolase isolated from *Nocardiopsis dassonvillei*. In other embodiments, the recombinant cells described herein comprise one or more copies of a heterologous nucleic acid encoding a phosphoketolase isolated from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca*. In yet other embodiments, the recombinant cells described herein comprise one or more copies of a heterologous nucleic acid encoding a phosphoketolase isolated from *Clostridium acetobutylicum, Bifidobacterium longum,* and/or *Enterococcus gallinarum*. In one embodiment, the recombinant cells comprise one or more copies of a heterologous nucleic acid encoding a phosphoketolase isolated from *Clostridium acetobutylicum*. In another embodiment, the recombinant cells comprise one or more copies of a heterologous nucleic acid encoding a phosphoketolase isolated from *Bifidobacterium longum*. In still another embodiment, the recombinant cells comprise one or more copies of a heterologous nucleic acid encoding a phosphoketolase isolated from *Enterococcus gallinarum*. As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase, one or more polypeptide(s) of the complete MVA pathway, and a polyprenyl pyrophosphate synthase polypeptide. The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid and/or isoprenoid precursors by cells without the expression of one or more heterologous nucleic acids encoding a phosphoketolase. In certain embodiments described herein, the recombinant host cells have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase polypeptide and which have not been engineered for increased carbon flux to mevalonate production.

The production of isoprenoid precursors and/or isoprenoids by the cells described herein can be enhanced (e.g., enhanced by the expression of one or more heterologous nucleic acids encoding the phosphoketolase polypeptides from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca*, one or more heterologous nucleic acids encoding a lower MVA pathway polypeptide, and one or more heterologous nucleic acids encoding a polyprenyl pyrophosphate synthase polypeptide). The production of isoprenoid precursors and/or isoprenoids can be enhanced by about 5% to about 1,000,000 folds. The production of isoprenoid precursors and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursors and/or isoprenoids by naturally-occurring cells (e.g., cells without the expression of one or more heterologous nucleic acids encoding phosphoketolase polypeptide from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca* along with one or more heterologous nucleic acids expressing one or more MVA pathway peptides and which have not been engineered for increased carbon flux to mevalonate production.

In other embodiments, the recombinant cells described herein can provide for the production of isoprenoid precursors and/or isoprenoids can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursors and/or isoprenoids by isoprenoid precursors and/or isoprenoids producing recombinant cells which do not express of one or more heterologous nucleic acids encoding a phosphoketolase polypeptide Methods of Using the Recombinant Cells to Produce Isoprenoids and/or Isoprenoid Precursor Molecules Also provided herein are methods of producing isoprenoid precursor molecules and/or isoprenoids comprising culturing recombinant cells (e.g., recombinant bacterial cells) that comprise one or more heterologous nucleic acids encoding a phosphoketolase and an polyprenyl pyrophosphate synthase polypeptide. In certain embodiments, the recombinant cells further comprise one or more one or more heterologous nucleic acids encoding an upper MVA pathway polypeptide and a lower MVA pathway polypeptide. The isoprenoid precursor molecules and/or isoprenoids can be produced from any of the cells described herein and according to any of the methods described herein. Any of the cells can be used for the purpose of producing isoprenoid precursor molecules and/or isoprenoids from carbohydrates, including six carbon sugars such as glucose.

In certain aspects, provided herein are methods of making isoprenoid precursor molecules and/or isoprenoids comprising culturing recombinant cells comprising one or more heterologous nucleic acids encoding a phosphoketolase polypeptide from *Lactobacillus reuteri, Bifidobacterium longum, Ferrimonas balearica, Pedobactor saltans, Streptomyces griseus*, and/or *Nocardiopsis dassonvillei*, an mvaE and an mvaS polypeptide from *L. grayi, E. faecium, E. gallinarum, E. casseliflavus*, and/or *E. faecalis*, in a suitable condition for producing isoprenoid precursor molecules and/or isoprenoids, and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the recombinant cells can be any of the cells described herein. Any of the polyprenyl pyrophosphate synthase or variants thereof described herein, any of the host cell strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

In certain aspects, provided herein are methods of making isoprenoid precursor molecules and/or isoprenoids comprising culturing recombinant cells comprising one or more heterologous nucleic acids encoding a phosphoketolase polypeptide from *Clostridium acetobutylicum, Bifidobacterium longum*, and/or *Enterococcus gallinarum*, an mvaE and an mvaS polypeptide from *L. grayi, E. faecium, E. gallinarum, E. casseliflavus*, and/or *E. faecalis*, in a suitable condition for producing isoprenoid precursor molecules and/or isoprenoids, and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the recombinant cells can be any of the cells described herein. Any of the polyprenyl pyrophosphate synthase or variants thereof described herein, any of the host cell strains described herein, any of the promoters described herein, and/or any of the vectors described herein can also be used to produce isoprenoid precursor molecules and/or isoprenoids using any of the energy sources (e.g. glucose or any other six carbon sugar) described herein. In some aspects, the method of producing isoprenoid precursor molecules and/or isoprenoids further comprises a step of recovering the isoprenoid precursor molecules and/or isoprenoids.

The method of producing isoprenoid precursor molecules and/or isoprenoids can similarly comprise the steps of: (a) culturing recombinant cells (including, but not limited to, *E. coli* cells) that do not endogenously have a phosphoketolase, wherein the recombinant cells heterologously express one or more copies of a gene encoding a phosphoketolase polypeptide; and (b) producing isoprenoid precursor molecules and/or isoprenoids, wherein the recombinant cells produce greater amounts of isoprenoid precursors and/or isoprenoids when compared to isoprenoids and/or isoprenoid precursor-producing cells that do not comprise the phosphoketolase polypeptide.

The instant methods for the production of isoprenoid precursor molecules and/or isoprenoids can produce at least 5% greater amounts of isoprenoid precursors and/or isoprenoids when compared to isoprenoids and/or isoprenoid precursor-producing recombinant cells that do not comprise a phosphoketolase polypeptide. Alternatively, the recombinant cells can produce greater than about 1%, 2%, 3%, 4%, 5%, 6%, 7%, 8%, 9%, 10%, 11%, 12%, 13%, 14%, or 15% of isoprenoid precursors and/or isoprenoids, inclusive. In some aspects, the method of producing isoprenoid precursor molecules and/or isoprenoids further comprises a step of recovering the isoprenoid precursor molecules and/or isoprenoids.

Provided herein are methods of using any of the cells described above for enhanced isoprenoid and/or isoprenoid precursor molecule production. The production of isoprenoid precursor molecules and/or isoprenoids by the cells can be enhanced by the expression of one or more heterologous nucleic acids encoding phosphoketolase, and/or the mvaE and mvaS polypeptides from *L. grayi, E. faecium, E. gallinarum, E. casseliflavus*, and/or *E. faecalis*, one or more heterologous nucleic acids encoding a lower MVA pathway polypeptide, and one or more heterologous nucleic acids encoding a polyprenyl pyrophosphate synthase polypeptide. As used herein, "enhanced" isoprenoid precursor and/or isoprenoid production refers to an increased cell productivity index (CPI) for isoprenoid precursor and/or isoprenoid production, an increased titer of isoprenoid precursors and/or isoprenoids, an increased mass yield of isoprenoid precursors and/or isoprenoids, and/or an increased specific productivity of isoprenoid precursors and/or isoprenoids by the cells described by any of the compositions and methods described herein compared to cells which do not have one or more heterologous nucleic acids encoding a phosphoketolase, a polyprenyl pyrophosphate synthase polypeptide, a lower MVA pathway polypeptide(s), the mvaE and mvaS polypeptides from *L. grayi, E. faecium, E. gallinarum, E. casseliflavus*. The production of isoprenoid precursor molecules and/or isoprenoids can be enhanced by about 5% to about 1,000,000 folds. The production of isoprenoid precursor molecules and/or isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid precursor molecules and/or isoprenoids by cells without the expression of one or more heterologous nucleic acids encoding a phosphoketolase polypeptide. In certain embodiments described herein, the methods comprise recombinant host cells that have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase peptide and which have not been engineered for increased carbon flux to mevalonate production.

The production of isoprenoid precursor molecules and/or isoprenoids can also enhanced by the methods described herein by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoid precursor molecules and/or isoprenoids by isoprenoid precursors and/or isoprenoid-producing cells without the expression of one or more heterologous nucleic acids encoding a phosphoketolase polypeptide. In certain embodiments described herein, the methods comprise recombinant host cells that have been further engineered to increased carbon flux to MVA production thereby providing enhanced production of isoprenoids and/or isoprenoid-precursors as compared to the production of isoprenoids and/or isoprenoid-precursors by isoprenoids and/or isoprenoid-precursors-producing cells that do not express one or more heterologous nucleic acids encoding phosphoketolase peptide and which have not been engineered for increased carbon flux to mevalonate production.

In addition, more specific cell culture conditions can be used to culture the cells in the methods described herein. For example, in some aspects, the method for the production of isoprenoid precursor molecules and/or isoprenoids comprises the steps of (a) culturing recombinant cells (including, but not limited to, *E. coli* cells) which comprise a heterologous nucleic acid which encodes a phosphoketolase polypeptide and that do not endogenously have an mvaE gene and an mvaS gene from *L. grayi, E. faecium, E. gallinarum, E. casseliflavus*, and/or *E. faecalis* in minimal medium at 34° C., wherein the recombinant cells heterologously express one or more copies of a gene encoding a phosphoketolase polypeptide from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobacter saltans, Rahnella aquatilis, Rhodopseudomonas palustris, Streptomyces griseus, Streptomyces avermitilis, Nocardiopsis dassonvillei*, and/or *Thermobifida fusca* on a low to medium copy plasmid and under the control of a strong promoter; and (b) producing isoprenoid precursor molecules and/or isoprenoids. In some aspects, the methods further comprise a step of recovering the isoprenoid precursor molecules and/or isoprenoids. In some aspects, wherein the recombinant cells heterologously express one or more copies of a gene encoding a phosphoketolase polypeptide from *Clostridium acetobutylicum, Bifidobacterium longum*, and/or *Enterococcus gallinarum*.

Vectors

Suitable vectors can be used for any of the compositions and methods described herein. For example, suitable vectors can be used to optimize the expression of one or more copies of a gene encoding a phosphoketolase, an upper MVA pathway polypeptide including, but not limited to, mvaE and an mvaS polypeptide, a lower MVA pathway polypeptide, an isoprene synthase, or a polyprenyl pyrophosphate synthase in a particular host cell (e.g., *E. coli*). In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of a phosphoketolase, an upper MVA pathway polypeptide including, but not limited to, mvaE and an mvaS polypeptide, a lower MVA pathway polypeptide, an mvaE and an mvaS nucleic acid from *L. grayi, E. faecium, E. gallinarum, E. casseliflavus*, and/or *E. faecalis*, an isoprene synthase, or a polyprenyl pyrophosphate synthase nucleic acid(s) integrate into the genome of host cells without a selective marker.

Any one of the vectors characterized herein or used in the Examples of the present disclosure can be used in the present invention.

Transformation Methods

Nucleic acids encoding one or more copies of a phosphoketolase, an upper MVA pathway polypeptide including, but not limited to, mvaE and an mvaS polypeptide, a lower MVA pathway polypeptide, and/or lower MVA pathway polypeptides can be inserted into a cell using suitable techniques. Additionally, isoprene synthase, IDI, DXP pathway, and/or polyprenyl pyrophosphate synthase nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, $2^{nd}$ ed., Cold Spring Harbor, 1989; and Campbell et al., *Curr. Genet.* 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. Patent Publ. No. 2009/0203102, WO 2010/003007, US Publ. No. 2010/0048964, WO 2009/132220, and US Publ. No. 2010/0003716.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any cell or progeny thereof that can be used to heterologously express genes can be used to express one or more a phosphoketolase isolated from *Lactobacillus reuteri, Bifidobacterium longum, Ferrimonas balearica, Pedobacter saltans, Streptomyces griseus*, and/or *Nocardiopsis dassonvillei* along with one or more heterologous nucleic acids expressing one or more MVA pathway peptides, isoprene synthase, IDI, DXP pathway polypeptide(e), and/or polyprenyl pyrophosphate synthase polypeptides. In some embodiments, the host cell is a gram-positive bacterium. Non-limiting examples include strains of *Streptomyces* (e.g., *S. lividans, S. coelicolor,* or *S. griseus*), *Bacillus, Listeria* (e.g., *L. monocytoge-* nes) or *Lactobacillus* (e.g., L. spp). In some embodiments, the source organism is a gram-negative bacterium, such as *E. coli, Pseudomonas* sp, or *H. pylori*.

Bacteria cells, including gram positive or gram negative bacteria can be used to express any of the heterologous genes described above. In particular, the mvaE and mvaS genes can be expressed in any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprenoid precursors, isoprene, and isoprenoids can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprenoid precursors, isoprene, and isoprenoids. Facutative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A. sojae, A. japonicus, A. nidulans,* or *A. awamori, Fusarium* sp., such as *F. roseum, F. graminum F. cerealis, F. oxysporuim,* or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum,* or *F. solani*. In certain embodiments, plasmids or plasmid components for use herein include those described in U.S. patent pub. No. US 2011/0045563.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6):423-488). In certain embodiments, plasmids or plasmid components for use herein include those described in U.S. Pat. No. 7,659,097 and U.S. patent pub. No. US 2011/0045563.

The host cell can additionally be a species of algae, such as a green algae, red algae, glaucophytes, chlorarachniophytes, euglenids, chromista, or dinoflagellates. (See, e.g., Saunders & Warmbrodt, *"Gene Expression in Algae and Fungi, Including Yeast,"* (1993), National Agricultural Library, Beltsville, Md.). In certain embodiments, plasmids or plasmid components for use herein include those described in U.S. Patent Pub. No. US 2011/0045563. In some aspects, the host cell is a cyanobacterium, such as cyanobacterium classified into any of the following groups based on morphology: *Chlorococcales, Pleurocapsales, Oscillatoriales, Nostocales,* or *Stigonematales* (See, e.g., Lindberg et al., Metab. Eng., (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863.

*E. coli* host cells can be used to express one or more phosphoketolase enzymes from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida furca* along with one or more heterologous nucleic acids encoding one or more MVA pathway polypeptides, isoprene synthase, IDI, DXP pathway polypeptide(e), and/or polyprenyl pyrophosphate synthase polypeptides. In one aspect, the host cell is a recombinant cell of an *Escherichia coli (E. coli)* strain, or progeny thereof, capable of producing mevalonate that expresses one or more nucleic acids encoding phosphoketolase from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida furca* along with one or more heterologous nucleic acids expressing one or more MVA pathway peptides. The *E. coli* host cells can produce mevalonate in amounts, peak titers, and cell productivities greater than that of the same cells lacking one or more heterologously expressed nucleic acids encoding phosphoketolase polypeptides from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Ferrimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca* along with one or more heterologous nucleic acids expressing one or more MVA pathway peptides. In addition, the one or more heterologously expressed nucleic acids encoding phosphoketolase polypeptide from *Clostridium acetobutylicum, Lactobacillus reuteri, Lactobacillus plantarum, Lactobacillus paraplantarum, Bifidobacterium longum, Bifidobacterium animalis, Bifidobacterium breve, Enterococcus gallinarum, Gardnerella vaginalis, Fer-*

*rimonas balearica, Mucilaginibacter paludis, Nostoc punctiforme, Nostoc punctiforme* PCC 73102, *Pantoea, Pedobactor saltans, Rahnella aquatilis, Rhodopseudomonas palustris, Streptomyces griseus, Streptomyces avermitilis, Nocardiopsis dassonvillei,* and/or *Thermobifida fusca* along with one or more heterologous nucleic acids expressing one or more MVA pathway peptides in *E. coli* can be chromosomal copies (e.g., integrated into the *E. coli* chromosome). In other aspects, the *E. coli* cells are in culture. In some aspects the one or more phosphoketolase enzymes is from *Clostridium acetobutylicum, Bifidobacterium longum,* and/or *Enterococcus gallinarum.* In any aspects, the one or more phosphoketolase enzymes are any phosphoketlase enzymes as disclosed herein.

Exemplary Host Cell Modifications

Citrate Synthase Pathway

Citrate synthase catalyzes the condensation of oxaloacetate and acetyl-CoA to form citrate, a metabolite of the tricarboxylic acid (TCA) cycle (Ner, S. et al. 1983. *Biochemistry,* 22: 5243-5249; Bhayana, V. and Duckworth, H. 1984. Biochemistry 23: 2900-2905). In *E. coli,* this enzyme, encoded by gltA, behaves like a trimer of dimeric subunits. The hexameric form allows the enzyme to be allosterically regulated by NADH. This enzyme has been widely studied (Wiegand, G., and Remington, S. 1986. Annual Rev. Biophysics Biophys. Chem. 15: 97-117; Duckworth et al. 1987. Biochem Soc Symp. 54:83-92; Stockell, D. et al. 2003. J. Biol. Chem. 278: 35435-43; Maurus, R. et al. 2003. Biochemistry. 42:5555-5565). To avoid allosteric inhibition by NADH, replacement by or supplementation with the *Bacillus subtilis* NADH-insensitive citrate synthase has been considered (Underwood et al. 2002. Appl. Environ. Microbiol. 68:1071-1081; Sanchez et al. 2005. Met. Eng. 7:229-239).

The reaction catalyzed by citrate synthase is directly competing with the thiolase catalyzing the first step of the mevalonate pathway, as they both have acetyl-CoA as a substrate (Hedl et al. 2002. J. Bact. 184:2116-2122). Therefore, one of skill in the art can modulate citrate synthase expression (e.g., decrease enzyme activity) to allow more carbon to flux into the mevalonate pathway, thereby increasing the eventual production of mevalonate, isoprene and isoprenoids. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis.* The activity of citrate synthase can also be modulated (e.g., decreased) by replacing the endogenous citrate synthase gene promoter with a synthetic constitutively low expressing promoter. The gene encoding citrate synthase can also be deleted. The decrease of the activity of citrate synthase can result in more carbon flux into the mevalonate dependent biosynthetic pathway in comparison to cells that do not have decreased expression of citrate synthase. In any aspects of the invention, provided herein are recombinant cells comprising one or more heterologously expressed nucleic acids encoding phosphoketolase polypeptides as disclosed herein and further engineered to decrease the activity of citrate synthase (gltA). Activity modulation (e.g., decreased) of citrate synthase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a citrate synthase isozyme.

Pathways involving Phosphotransacetylase and/or Acetate Kinase

Phosphotransacetylase ((encoded in *E. coli* by (i) pta (Shimizu et al. 1969. Biochim. Biophys. Acta 191: 550-558 or (ii) eutD (Bologna et al. 2010. J of Microbiology. 48:629-636) catalyzes the reversible conversion between acetyl-CoA and acetyl phosphate (acetyl-P), while acetate kinase (encoded in *E. coli* by ackA) (Kakuda, H. et al. 1994. J. Biochem. 11:916-922) uses acetyl-P to form acetate. These genes can be transcribed as an operon in *E. coli.* Together, they catalyze the dissimilation of acetate, with the release of ATP. Thus, it is possible to increase the amount of acetyl-P going towards acetyl-CoA by enhancing the activity of phosphotransacetylase. In certain embodiments, enhancement is achieved by placing an upregulated promoter upstream of the gene in the chromosome, or to place a copy of the gene behind an adequate promoter on a plasmid. In order to decrease the amount of acetyl-coA going towards acetate, the activity of acetate kinase gene (e.g., the endogenous acetate kinase gene) can be decreased or attenuated. In certain embodiments, attenuation is achieved by deleting acetate kinase (ackA). This is done by replacing the gene with a chloramphenicol cassette followed by looping out of the cassette. In some aspects, the activity of acetate kinase is modulated by decreasing the activity of an endogenous acetate kinase. This can be accomplished by replacing the endogenous acetate kinase gene promoter with a synthetic constitutively low expressing promoter. In certain embodiments, it the attenuation of the acetated kinase gene should be done disrupting the expression of the phosphotransacetylase (pta) gene. Acetate is produced by *E. coli* for a variety of reasons (Wolfe, A. 2005. Microb. Mol. Biol. Rev. 69:12-50). Without being bound by theory, deletion of ackA could result in decreased carbon being diverted into acetate production (since ackA use acetyl-CoA) and thereby increase the yield of mevalonate, isoprenoid precursors, isoprene and/or isoprenoids.

In some aspects, the recombinant cells described herein produce decreased amounts of acetate in comparison to cells that do not have attenuated endogenous acetate kinase gene expression or enhanced phosphotransacetylase. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done to the endogenous acetate kinase gene expression or phosphotransacetylase gene expression.

The activity of phosphotransacetylase (pta and/or eutD) can be increased by other molecular manipulations of the enzymes. The increase of enzyme activity can be and increase in any amount of specific activity or total activity as compared to when no manipulation has been effectuated. In some instances, the increase of enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In one embodiment the activity of pta is increased by altering the promoter and/or rbs on the chromosome, or by expressing it from a plasmid. In any aspects of the invention, provided herein are recombinant cells comprising one or more heterologously expressed nucleic acids encoding phosphoketolase polypeptides as disclosed herein and further engineered to increase the activity of phosphotransacetylase (pta and/or eutD). Activity modulation (e.g., increased) of phosphotransacetylase isozymes is also contemplated herein. In any aspects of the invention, provided herein are recombinant cells comprising one or more heterologously expressed nucleic acids encoding phosphoketolase polypeptides as disclosed herein and further engineered to increase the activity of a phosphotransacetylase (pta and/or eutD) isozyme.

The activity of acetate kinase (ackA) can also be decreased by other molecular manipulations of the enzymes. The decrease of enzyme activity can be any amount of reduction of specific activity or total activity as compared to when no manipulation has been effectuated. In some instances, the enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of acetate kinase (ackA). Activity modulation (e.g., decreased) of acetate kinase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a acetate kinase isozyme.

In some cases, attenuating the activity of the endogenous acetate kinase gene results in more carbon flux into the mevalonate dependent biosynthetic pathway in comparison to cells that do not have attenuated endogenous acetate gene expression.

Pathways Involving Lactate Dehydrogenase

Figure 1:
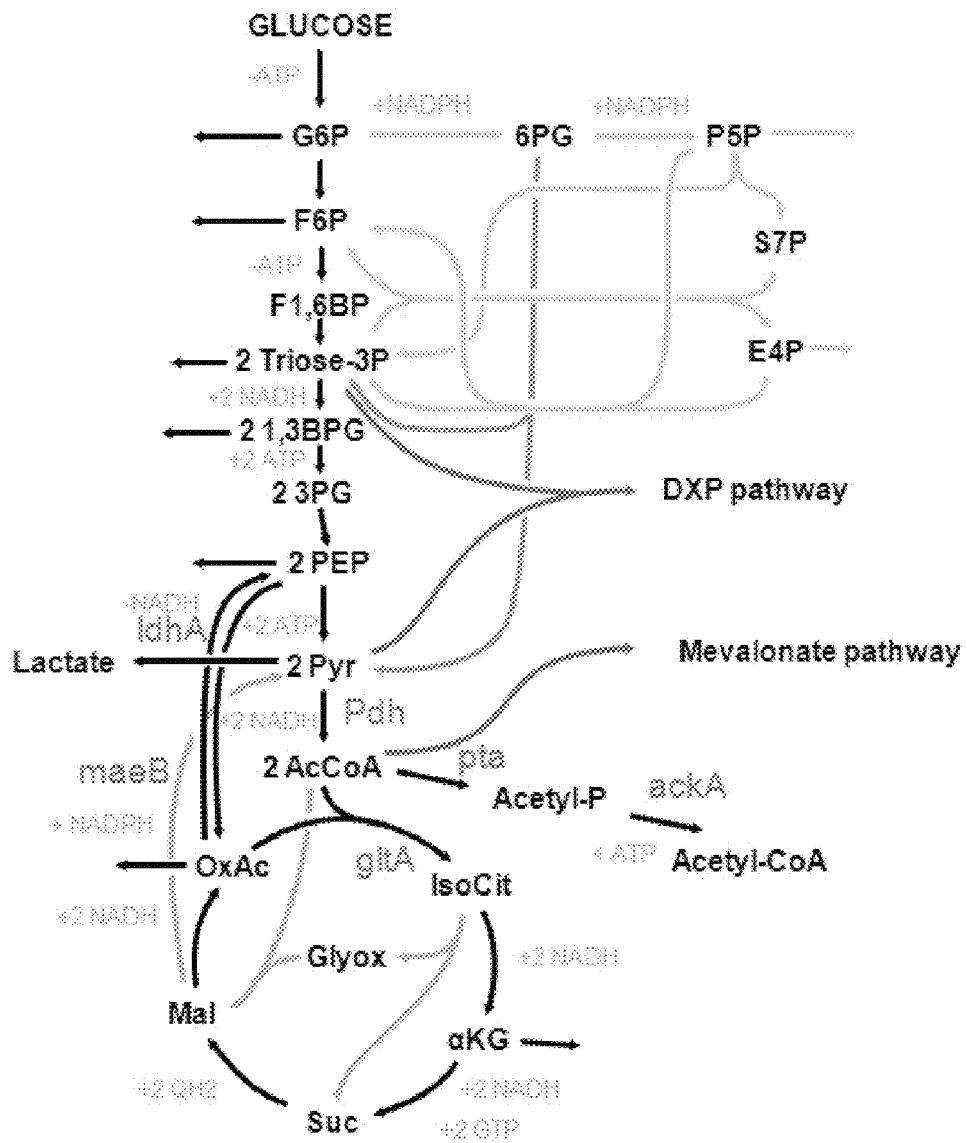
FIG. 1 depicts the metabolic pathway for glucose metabolism in *E. coli*. Reactions associated with ATP or NADH production or use as well as key enzymes involved in carbon flux are represented. Abbreviation 'P5P' indicate the pool of metabolites consisting of xylulose 5 phosphate, ribulose-5 phosphate, and ribose-5 phosphate. Abbreviation 'Triose-3P' indicates the pool of metabolites consisting of glyceraldehyde 3 phosphate and dihydroxyacetone phosphate.
Figure 2:
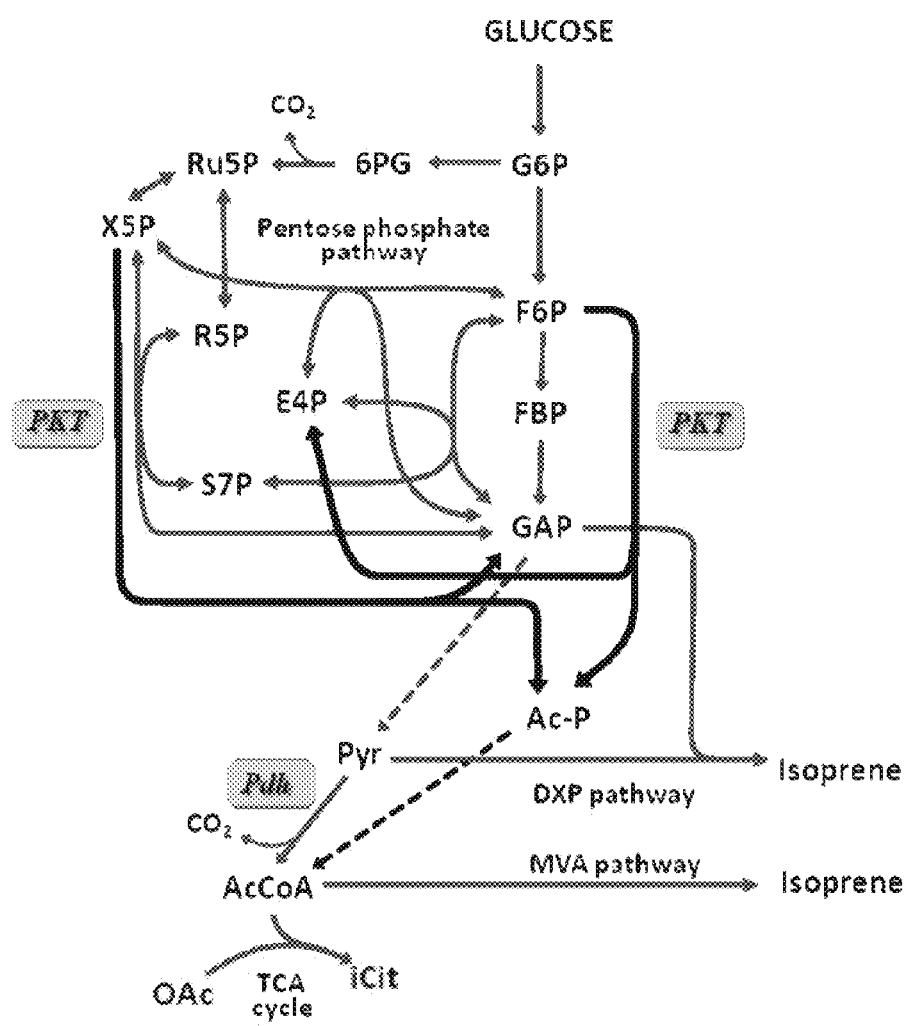
FIG. 2 depicts an engineered metabolic pathway with phosphoketolase (PKT) present. PKTs have been classified into two types based on substrate preference: xylulose-5-phosphate (X5P) phosphoketolases (EC 4.1.2.9), which only act on X5P, and xylulose-5-phosphate/fructose-6-phosphate (F6P) phosphoketolases (EC 4.1.2.22), which act on both X5P and F6P with comparable activities. Acetyl phosphate (Ac-P) formed from F6P and/or X5P in PKT-catalyzed reaction(s) is subsequently converted to acetyl-CoA for use in the MVA pathway. Other products of PKT-catalyzed reaction, namely glyceraldehyde 3-phosphate (GAP) and erythrose 4-phosphate (E4P) produced from X5P and F6P, respectively, can be recycled through manipulated metabolic pathways to maximize yield.
Figure 3:
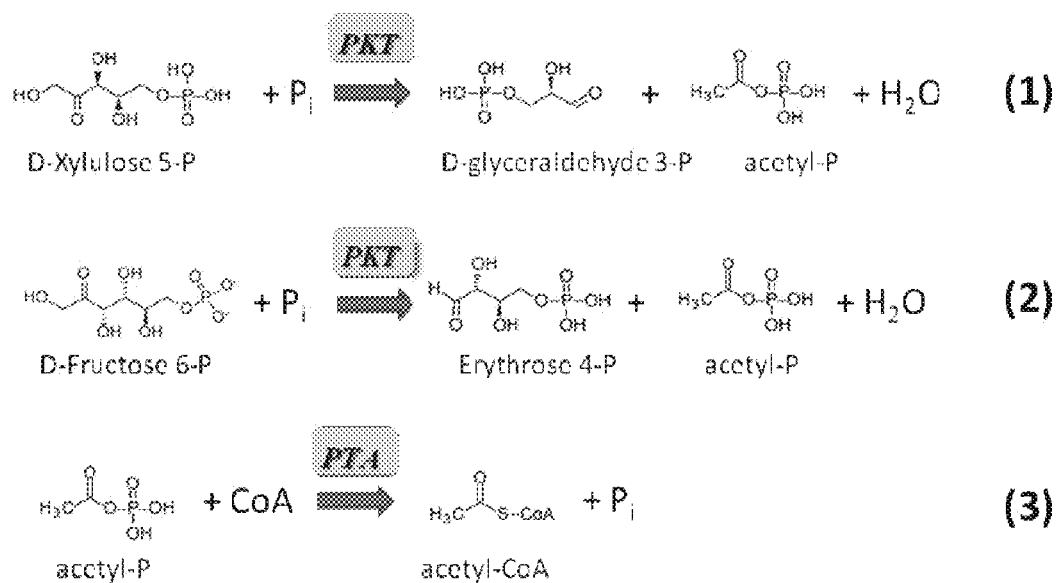
FIG. 3 depicts the reactions involving phosphoketolase reactants and products. Reactions (1) and (2) depict reactions catalyzed by phosphoketolase enzymes. Reaction (3) depicts the conversion of acetyl-P to acetyl-Coa, which is catalyzed by the Phosphotransacetylase (pta) enzyme.

In *E. coli*, D-Lactate is produced from pyruvate through the enzyme lactate dehydrogenase (encoded by ldhA—FIG. 1) (Bunch, P. et al. 1997. Microbiol. 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene, isoprenoid precursor and isoprenoids production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant cell produces decreased amounts of lactate in comparison to cells that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Accordingly, in some cases, attenuation of the activity of the endogenous lactate dehydrogenase gene results in more carbon flux into the mevalonate dependent biosynthetic pathway in comparison to cells that do not have attenuated endogenous lactate dehydrogenase gene expression.

Pathways Involving Glyceraldehyde 3-phosphate

Glyceraldehyde 3-phosphate dehydrogenase (gapA and/or gapB) is a crucial enzyme of glycolysis catalyzes the conversion of glyceraldehyde 3-phosphate into 1,3-biphospho-D-glycerate (Branlant G. and Branlant C. 1985. Eur. J. Biochem. 150:61-66).

In order to direct carbon towards the phosphoketolase enzyme, glyceraldehyde 3-phosphate dehydrogenase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of glyceraldehyde 3-phosphate dehydrogenase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of glyceraldehyde 3-phosphate dehydrogenase is modulated by decreasing the activity of an endogenous glyceraldehyde 3-phosphate dehydrogenase. This can be accomplished by replacing the endogenous glyceraldehyde 3-phosphate dehydrogenase gene promoter with a synthetic constitutively low expressing promoter. The gene encoding glyceraldehyde 3-phosphate dehydrogenase can also be deleted. The gene encoding glyceraldehyde 3-phosphate dehydrogenase can also be replaced by a *Bacillus* enzyme catalyzing the same reaction but producing NADPH rather than NADH. The decrease of the activity of glyceraldehyde 3-phosphate dehydrogenase can result in more carbon flux into the mevalonate-dependent biosynthetic pathway in comparison to cells that do not have decreased expression of glyceraldehyde 3-phosphate dehydrogenase. In any aspects of the invention, provided herein are recombinant cells comprising one or more heterologously expressed nucleic acids encoding phosphoketolase polypeptides as disclosed herein and further engineered to decrease the activity of glyceraldehyde 3-phosphate dehydrogenase (gapA and/or gapB). Activity modulation (e.g., decreased) of glyceraldehyde 3-phosphate dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glyceraldehyde 3-phosphate dehydrogenase (gapA and/or gapB) isozyme.

Pathways Involving the Entner-Doudoroff Pathway

The Entner-Doudoroff (ED) pathway is an alternative to the Emden-Meyerhoff-Parnass (EMP-glycolysis) pathway.

Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803). Fructose bisphophate aldolase (fba, fbaA, fbaB, and/or fbaC) interacts with the Entner-Doudoroff pathway and reversibly catalyzes the conversion of fructose 1,6-bisphosphate into dihydroxyacetone phosphate (DHAP) and glyceraldehyde 3-phosphate (GAP) (Baldwin S. A., et. al., Biochem J. (1978) 169(3):633-41).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. J. Bact. 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or an 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Metabolites that can be directed into the phosphoketolase pathway can also be diverted into the ED pathway or EMP pathway. To avoid metabolite loss and to increase fructose-6-phosphate (F6P) concentration, fructose bisphophate aldolase (e.g., the endogenous fructose bisphophate aldolase) activity is attenuated. In some cases, attenuating the activity of the endogenous fructose bisphophate aldolase (fba, fbaA, fbaB, and/or fbaC) gene results in more carbon flux into the mevalonate dependent biosynthetic pathway in comparison to cells that do not have attenuated endogenous fructose bisphophate aldolase (fba, fbaA, fbaB, and/or fbaC) gene expression. In some aspects, attenuation is achieved by deleting fructose bisphophate aldolase (fba, fbaA, fbaB, and/or fbaC). Deletion can be accomplished by replacing the gene with a chloramphenicol or kanamycin cassette followed by looping out of the cassette. In some aspects, the activity of fructose bisphophate aldolase is modulated by decreasing the activity of an endogenous fructose bisphophate aldolase. This can be accomplished by replacing the endogenous fructose bisphophate aldolase gene promoter with a synthetic constitutively low expressing promoter. Without these enzymatic activities, more carbon can flux through the phosphoketolase enzyme, thus increasing the yield of mevalonate, isoprene or isoprenoids. The activity of fructose bisphophate aldolase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In any aspects of the invention, provided herein are recombinant cells comprising one or more heterologously expressed nucleic acids encoding phosphoketolase polypeptides as disclosed herein and further engineered to decrease the activity of fructose bisphophate aldolase (fba, fbaA, fbaB, and/or fbaC). Activity modulation (e.g., decreased) of fructose bisphophate aldolase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a fructose bisphophate aldolase isozyme.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA and/or tktB), transaldolase (talA or talB), ribulose-5-phosphate-epimerase and (or) ribose-5-phosphate epimerase, ribose-5-phosphate isomerase (rpiA and/or rpiB) and/or ribulose-5-phosphate 3-epimerase (rpe)) (Sprenger. 1995. Arch. Microbiol. 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase, ribose-5-phosphate isomerase A, ribose-5-phosphate isomerase B, and/or ribulose-5-phosphate 3-epimerase) expression can be modulated (e.g., increase enzyme activity) to allow more carbon to flux towards fructose 6-phosphate and xylulose 5-phosphate, thereby increasing the eventual production of mevalonate, isoprene and isoprenoids. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase.

This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

In any aspects of the invention, provided herein are recombinant cells comprising one or more heterologously expressed nucleic acids encoding phosphoketolase polypeptides as disclosed herein and further engineered to increase the activity of transketolase (tktA and/or tktB). In any aspects of the invention, provided herein are recombinant cells comprising one or more heterologously expressed nucleic acids encoding phosphoketolase polypeptides as disclosed herein and further engineered to decrease the activity of transketolase (tktA and/or tktB). In any aspects of the invention, provided herein are recombinant cells comprising one or more heterologously expressed nucleic acids encoding phosphoketolase polypeptides as disclosed herein and further engineered to increase the activity of transaldolase (talA or talB). In any aspects of the invention, provided herein are recombinant cells comprising one or more heterologously expressed nucleic acids encoding phosphoketolase polypeptides as disclosed herein and further engineered to increase the activity of ribose-5-phosphate isomerase (rpiA and/or rpiB). In any aspects of the invention, provided herein are recombinant cells comprising one or more heterologously expressed nucleic acids encoding phosphoketolase polypeptides as disclosed herein and further engineered to increase the activity of ribulose-5-phosphate 3-epimerase (rpe). Activity modulation (e.g., decreased or increased) of glucose 6-phosphate 1-dehydrogenase (zwf), 6-phosphogluconolactonase (pgl), 6-phosphogluconate dehydrogenase (gnd), transketolase (tktA and/or tktB), transaldolase (talA or talB), ribulose-5-phosphate-epimerase, ribose-5-phosphate epimerase, ribose-5-phosphate isomerase (rpiA and/or rpiB) and/or ribulose-5-phosphate 3-epimerase (rpe) isozymes is also contemplated herein. In any aspects of the invention, provided herein are recombinant cells comprising one or more heterologously expressed nucleic acids encoding phosphoketolase polypeptides as disclosed herein and further engineered to increase the activity of a glucose 6-phosphate 1-dehydrogenase (zwf) isozyme. In any aspects of the invention, provided herein are recombinant cells comprising one or more heterologously expressed nucleic acids encoding phosphoketolase polypeptides as disclosed herein and further engineered to increase the activity of a transketolase (tktA and/or tktB) isozyme. In any aspects of the invention, provided herein are recombinant cells comprising one or more heterologously expressed nucleic acids encoding phosphoketolase polypeptides as disclosed herein and further engineered to decrease the activity of a transketolase (tktA and/or tktB) isozyme. In any aspects of the invention, provided herein are recombinant cells comprising one or more heterologously expressed nucleic acids encoding phosphoketolase polypeptides as disclosed herein and further engineered to increase the activity of a transaldolase (talA or talB) isozyme. In any aspects of the invention, provided herein are recombinant cells comprising one or more heterologously expressed nucleic acids encoding phosphoketolase polypeptides as disclosed herein and further engineered to increase the activity of a ribose-5-phosphate isomerase (rpiA and/or rpiB) isozyme. In any aspects of the invention, provided herein are recombinant cells comprising one or more heterologously expressed nucleic acids encoding phosphoketolase polypeptides as disclosed herein and further engineered to increase the activity of a ribulose-5-phosphate 3-epimerase (rpe) isozyme.

In order to direct carbon towards the phosphoketolase enzyme, glucose 6-phosphate 1-dehydrogenase can be modulated (e.g., decrease enzyme activity). In some aspects, the activity of glucose 6-phosphate 1-dehydrogenase (zwf) (e.g., the endogenous glucose 6-phosphate 1-dehydrogenase gene) can be decreased or attenuated. In certain embodiments, attenuation is achieved by deleting glucose 6-phosphate 1-dehydrogenase. In some aspects, the activity of glucose 6-phosphate 1-dehydrogenase is modulated by decreasing the activity of an endogenous glucose 6-phosphate 1-dehydrogenase. This can be accomplished by replacing the endogenous glucose 6-phosphate 1-dehydrogenase gene promoter with a synthetic constitutively low expressing promoter. In any aspects of the invention, provided herein are recombinant cells comprising one or more heterologously expressed nucleic acids encoding phosphoketolase polypeptides as disclosed herein and further engineered to decrease the activity of glucose 6-phosphate 1-dehydrogenase (zwf). Activity modulation (e.g., decreased) of glucose 6-phosphate 1-dehydrogenase isozymes is also contemplated herein. In any aspects of the invention, provided herein are recombinant cells comprising one or more heterologously expressed nucleic acids encoding phosphoketolase polypeptides as disclosed herein and further engineered to decrease the activity of a glucose 6-phosphate 1-dehydrogenase isozyme.

Pathways Involving Phosphofructokinase

Phosphofructokinase is a crucial enzyme of glycolysis which catalyzes the phosphorylation of fructose 6-phosphate. E. coli has two isozymes encoded by pfkA and pfkB. Most of the phosphofructokinase activity in the cell is due to pfkA (Kotlarz et al. 1975 Biochim. Biophys. Acta 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene and isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

In any aspects of the invention, provided herein are recombinant cells comprising one or more heterologously expressed nucleic acids encoding phosphoketolase polypeptides as disclosed herein and further engineered to decrease the activity of fructose 6-phosphate (pfkA and/or pfkB).

Activity modulation (e.g., decreased) of fructose 6-phosphate isozymes is also contemplated herein. In any aspects of the invention, provided herein are recombinant cells comprising one or more heterologously expressed nucleic acids encoding phosphoketolase polypeptides as disclosed herein and further engineered to decrease the activity of a fructose 6-phosphate isozyme.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataac-catctgcggtgataaattatctctggcg-gtgttgacataaataccactggcggtgatactgagcacatca gcaggacgcact-gaccaccatgaaggtg—lambda promoter, GenBank NC_001416, SEQ ID NO:14), in front of the operon or using one or more synthetic constitutively expressing promoters.

Accordingly, in one aspect, the activity of pyruvate dehydrogenase is modulated by increasing the activity of one or more enzymes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of the genes encoding these enzymes can be manipulated for increasing activity of pyruvate dehydrogenase. In another aspect, the activity of the pyruvate dehydrogenase complex can be modulated by attenuating the activity of an endogenous pyruvate dehydrogenase complex repressor, further detailed below. The activity of an endogenous pyruvate dehydrogenase complex repressor can be attenuated by deletion of the endogenous pyruvate dehydrogenase complex repressor gene.

In some cases, one or more genes encoding the pyruvate dehydrogenase complex are endogenous genes. Another way to increase the activity of the pyruvate dehydrogenase complex is by introducing into the cell one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant cells can produce increased amounts of acetyl Co-A in comparison to cells wherein the activity of pyruvate dehydrogenase is not modulated. Modulating the activity of pyruvate dehydrogenase can result in more carbon flux into the mevalonate dependent biosynthetic pathway in comparison to cells that do not have modulated pyruvate dehydrogenase expression.

Pathways Involving the Phosphotransferase System

The phosphoenolpyruvate dependent phosphotransferase system (PTS) is a multicomponent system that simultaneously transports and phosphorylates its carbohydrate substrates across a membrane in a process that is dependent on energy provided by the glycolytic intermediate phosphoenolpyruvate (PEP). The genes that regulate the PTS are mostly clustered in operons. For example, the pts operon (ptsHIcrr) of *Escherichia coli* is composed of the ptsH, ptsI and crr genes coding for three proteins central to the phosphoenolpyruvate dependent phosphotransferase system (PTS), the HPr (ptsH), enzyme I (ptsI) and EIIIGlc (crr) proteins. These three genes are organized in a complex operon in which the major part of expression of the distal gene, crr, is initiated from a promoter region within ptsI. In addition to the genes of the pts operon, ptsG encodes the glucose-specific transporter of the phosphotransferase system, ptsG Transcription from this promoter region is under the positive control of catabolite activator protein (CAP)-cyclic AMP (cAMP) and is enhanced during growth in the presence of glucose (a PTS substrate). Furthermore, the ppsA gene encodes for phosphoenolpyruvate synthetase for the production of phosphoenolpyruvate (PEP) which is required for activity of the phosphotransferase system (PTS). Carbon flux is directed by the phosphoenolpyruvate synthetase through the pyruvate dehydrogenase pathway or the PTS pathway. See Postma, P. W., et al., Microbiol Rev. (1993), 57(3):543-94) which is incorporated herein by reference in its entirety.

In certain embodiments described herein, the down regulation (e.g. attenuation) of the pts operon can enhance acetate utilization by the host cells. The down regulation of PTS operon activity can be any amount of reduction of specific activity or total activity as compared to when no manipulation has been effectuated. In some instances, the decrease of activity of the complex is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In certain embodiments, attenuation is achieved by deleting the pts operon. In some aspects, the activity of the PTS system is modulated by decreasing the activity of an endogenous pts operon. This can be accomplished by replacing the endogenous promoter(s) within the pts operon with synthetic constitutively low expressing promoter(s). In any aspects of the invention, provided herein are recombinant cells comprising one or more heterologously expressed nucleic acids encoding phosphoketolase polypeptides as disclosed herein and further engineered to decrease the activity of the pts operon. In any aspects of the invention, provided herein are recombinant cells comprising one or more heterologously expressed nucleic acids encoding phosphoketolase polypeptides as disclosed herein and further engineered to decrease the activity of EI (ptsI). In any aspects of the invention, provided herein are recombinant cells comprising one or more heterologously expressed nucleic acids encoding phosphoketolase polypeptides as disclosed herein and further engineered to decrease the activity of EIICB$^{Glc}$ (ptsG). In any aspects of the invention, provided herein are recombinant cells comprising one or more heterologously expressed nucleic acids encoding phosphoketolase polypeptides as disclosed herein and further engineered to decrease the activity of EIIA$^{Glc}$ (crr). In any aspects of the invention, provided herein are recombinant cells comprising one or more heterologously expressed nucleic acids encoding phosphoketolase polypeptides as disclosed herein and further engineered to decrease the activity of HPr (ptsH). To decrease carbon loss through pyruvate dehydrogenase while increasing the PEP pool for glucose uptake, the activity of phosphoenolpyruvate synthetase (ppsA) can be increased. In any aspects of the invention, provided herein are recombinant cells comprising one or more heterologously expressed nucleic acids encoding phosphoketolase polypeptides as disclosed herein and further engineered to increase the activity of phosphoenolpyruvate synthetase (ppsA). In any further aspect of the invention, the PTS is downregulated and a glucose transport pathway is upregulated. A glucose transport pathway includes, but is not limited to, galactose (galP) and glucokinase (glk). In some embodiments, the pts operon is downregulated, the galactose (galP) gene is upregulated, and the glucokinase (glk) gene is upregulated. Activity modulation (e.g., decreased) of isozymes of the PTS is also contemplated herein. In any aspects of the invention, provided herein are recombinant cells comprising one or more heterologously expressed nucleic acids encoding phosphoketolase polypeptides as disclosed herein and further engineered to decrease the activity of PTS isozymes.

Pathways Involving Xylose Utilization

In certain embodiments described herein, the utilization of xylose is desirable to convert suger derived from plant biomass into desired products, such as mevalonate, such as isoprenoid precursors, isoprene and/or isoprenoids. In some organisms, xylose utilization requires use of the pentose phosphate pathway for conversion to fructose-6-phosphate for metabolism. Organisms can be engineered for enhanced xylose utilization, either by deactivating the catabolite repression by glucose, or by heterologous expression of genes from the xylose operon found in other organisms. The xylulose pathway can be engineered as described below to enhance production of mevalonate, isoprenoid precursors, isoprene and/or isoprenoids via the phosphoketolase pathway.

Enhancement of xylose uptake and conversion to xylulose-5-phosphate followed by direct entry into the phosphoketolase pathway would be a benefit. Without being bound by theory, this allows the carbon flux to bypass the pentose phosphate pathway (although some glyceraldehyde-3-phosphate may be cycled into PPP as needed). Enhanced expression of xyulokinase can be used to increase the overall production of xylulose-5-phosphate. Optimization of xyluokinase expression and activity can be used to enhance xylose utilization in a strain with a phosphoketolase pathway. The desired xyulokinase may be either the endogeneous host's enzyme, or any heterologous xyulokinase compatible with the host. In one embodiment, other components of the xylose operon can be overexpressed for increased benefit (e.g., xylose isomerase). In another embodiment, other xylose pathway enzymes (e.g. xylose reductase) may need to be attenuated (e.g., reduced or deleted activity).

Accordingly, the host cells engineered to have phosphoketolase enzymes as described herein can be further engineered to overexpress xylulose isomerase and/or xyulokinase, either the endocgenous forms or heterologous forms, to improve overall yield and productivity of mevalonate, isoprenoid precursors, isoprene and/or isoprenoids.

Pathways Involving Transaldolase and Transketolase Enzymes of Pentose Phosphate Pathway Some microorganisms capable of anaerobic or heterofermentative growth incorporate a phosphoketolase pathway instead of or in addition to a glycolytic pathway. This pathway depends on the activity of the pentose phosphate pathway enzymes transaldolase and transketolase. Accordingly, the host cells engineered to have phosphoketolase enzymes as described herein can be further engineered to overexpress a transketolase and transaldolase, either the endogeneous forms or heterologous forms, to improve pathway flux, decrease the levels of potentially toxic intermediates, reduce the diversion of intermediates to non-productive pathways, and improve the overall yield and productivity of mevalonate, isoprenoid precursors, isoprene and/or isoprenoids.

Combinations of Mutations

It is understood that for any of the enzymes and/or enzyme pathways described herein, molecular manipulations that modulate any combination (two, three, four, five, six, seven, eight, nine, ten, eleven, twelve, thirteen, or fourteen) of the enzymes and/or enzyme pathways described herein is expressly contemplated. For ease of the recitation of the combinations, citrate synthase (gltA) is designated as A, phosphotransacetylase (pta) is designated as B, acetate kinase (ackA) is designated as C, lactate dehydrogenase (ldhA) is designated as D, glyceraldehyde 3-phosphate dehydrogenase (gap) is designated as E, and pyruvate decarboxylase (aceE, aceF, and/or lpdA) is designated as F, phosphogluconate dehydratase (edd) is designated as G, 2-keto-4-deoxygluconate 6-phosphate aldolase (eda) is designated as H phosphofructokinase is designated as I, transaldolase is designated as J, transketolase is designated as K, ribulose-5-phosphate-epimerase is designated as L, ribose-5-phosphate epimerase is designated as M, xylukinase is designated as N, xylose isomerase is designated as O, and xylitol reductase is designated as P, ribose-5-phosphate isomerase (rpi) is designated as Q, D-ribulose-5-phosphate 3-epimerase (rpe) is designated as R, phosphoenolpyruvate synthetase (pps) is designated as S, fructose bisphosphate aldolase (fba) is designated as T, EI (ptsI) is designated as U, EIICB$^{Glc}$ (ptsG) is designated as V, EIIA$^{Glc}$ (crr) is designated as W, HPr (ptsH) is designated as X, galactose (galP) is designated as Y, glucokinase (glk) is designated as Z, glucose-6-phosphate dehydrogenase (zwf) is designated as AA. As discussed above, aceE, aceF, and/or lpdA enzymes of the pyruvate decarboxylase complex can be used singly, or two of three enzymes, or three of three enzymes for increasing pyruvate decarboxylase activity. Thus, any and all combination of enzymes designated as A-M herein is expressly contemplated as well as any and all combination of enzymes designated as A-AA. Furthermore, any combination described above can be used in combination with any of the enzymes and/or enzyme pathways described herein (e.g., phosphoketolase, MVA pathway polypeptides, isoprene synthase, DXP pathway polypeptides).

Other Regulators and Factors for Increased Production

Other molecular manipulations can be used to increase the flow of carbon towards mevalonate production. One method is to reduce, decrease or eliminate the effects of negative regulators for pathways that feed into the mevalonate pathway. For example, in some cases, the genes aceEF-lpdA are in an operon, with a fourth gene upstream pdhR. The gene pdhR is a negative regulator of the transcription of its operon. In the absence of pyruvate, it binds its target promoter and represses transcription. It also regulates ndh and cyoABCD in the same way (Ogasawara, H. et al. 2007. J. Bact. 189:5534-5541). In one aspect, deletion of pdhR regulator can improve the supply of pyruvate, and hence the production of mevalonate, isoprenoid precursors, isoprene, and isoprenoids.

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehyde-3-phosphate dehydrogenase. The activity of glyceraldehyde-3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

Figure 5:
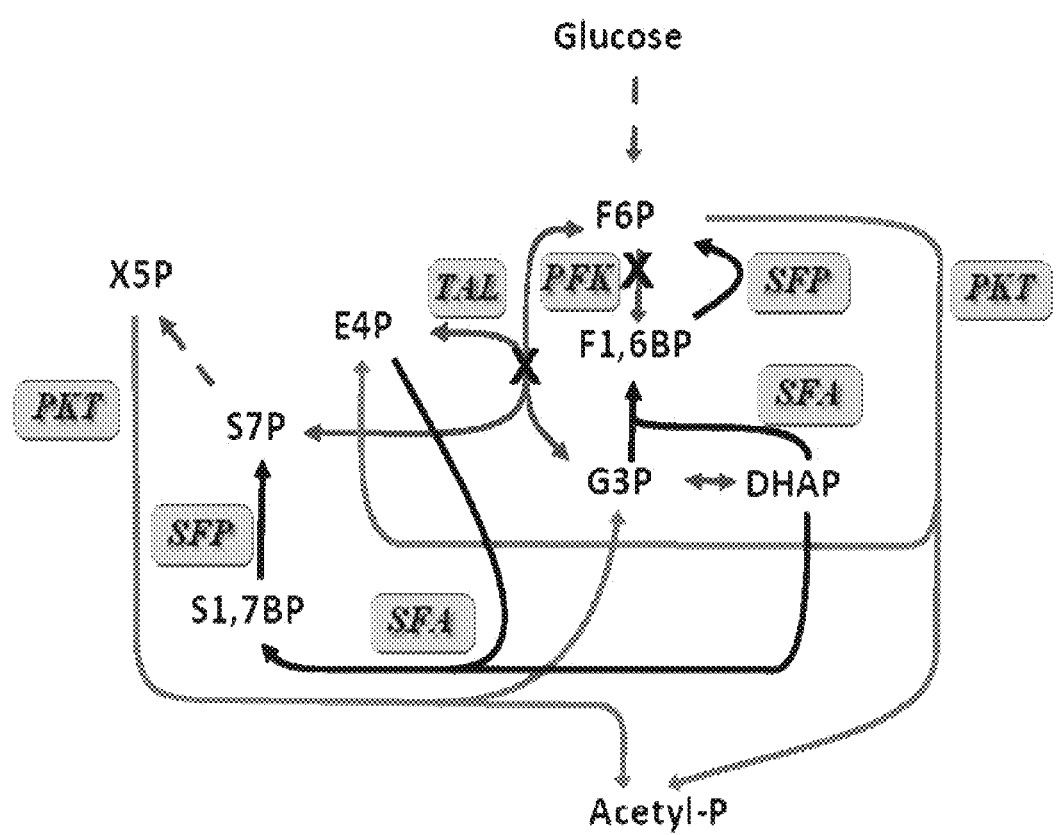
FIG. 5 depicts an engineered pathway in which erythrose 4 phosphate (E4P) and glucose-3 phosphate (G3P) generated in phosphoketolase-catalyzed reaction (PKT) are converted back to PKT substrates by sedoheptulose-1,7-bisphosphatase/fructose-1,6-bisphosphate aldolase (SFA) and sedoheptulose-1,7-bisphosphatase/fructose-1,6-bisphosphate phosphatase (SFP). Other abbreviations used in this figure indicate xylulose 5-phosphate (X5P), sedoheptulose-1,7-bisphosphate (S1,7BP), sedoheptulose-7-phosphate (S7P), fructose-1,6-bisphosphate (F1,6BP), fructose-6-phosphate (F6P), dihydroxyacetone phosphate (DHAP). X indicates the attenuated or deleted enzymatic reactions.

In other aspects, the host cells can be further engineered to increase intracellular acetyl-phosphate concentrations by introducing heterologous nucleic acids encoding sedoheptulose-1,7-bisphosphatase/fructose-1,6-bisphosphate aldolase and sedoheptulose-1,7-bisphosphatase/fructose-1,6-bisphosphate phosphatase. In certain embodiments, the host cells having these molecular manipulations can be combined with attenuated or deleted transaldolase (talB) and phosphofructokinase (pfkA and/or pfkB) genes, thereby allowing faster conversion of erythrose 4-phosphate, dihydroxyacetone phosphate, and glyceraldehyde 3-phosphate into sedoheptulose 7-phosphate and fructose 1-phosphate (see FIG. 5).

In other aspects, the introduction of 6-phosphogluconolactonase (PGL) into cells (such as various *E. coli* strains) which lack PGL can be used to improve production of mevalonate, isoprenoid precursors, isoprene, and isoprenoids. PGL may be introduced by introduction of the encoding gene using chromosomal integration or extra-chromosomal vehicles, such as plasmids.

In addition to the host cell (e.g., bacterial host cell) mutations for modulating various enzymatic pathways described herein that increases carbon flux towards mevalonate production, the host cells described herein comprise genes encoding phosphoketolase polypeptide, as well as other enzymes from the upper and lower MVA pathway, including but not limited to, the mvaE and mvaS gene products. Non-limiting examples of MVA pathway polypeptides include acetyl-CoA acetyltransferase (AA-CoA thiolase) polypeptides, 3-hydroxy-3-methylglutaryl-CoA synthase (HMG-CoA synthase) polypeptides, 3-hydroxy-3-methylglutaryl-CoA reductase (HMG-CoA reductase) polypeptides, mevalonate kinase (MVK) polypeptides, phosphomevalonate kinase (PMK) polypeptides, diphosphomevalonte decarboxylase (MVD) polypeptides, phosphomevalonate decarboxylase (PMDC) polypeptides, isopentenyl phosphate kinase (IPK) polypeptides, IDI polypeptides, and polypeptides (e.g., fusion polypeptides) having an activity of two or more MVA pathway polypeptides. MVA pathway polypeptides can include polypeptides, fragments of polypeptides, peptides, and fusions polypeptides that have at least one activity of an MVA pathway polypeptide. Exemplary MVA pathway nucleic acids include nucleic acids that encode a polypeptide, fragment of a polypeptide, peptide, or fusion polypeptide that has at least one activity of an MVA pathway polypeptide. Exemplary MVA pathway polypeptides and nucleic acids include naturally-occurring polypeptides and nucleic acids from any of the source organisms described herein.

Non-limiting examples of MVA pathway polypeptides which can be used are described in International Patent Application Publication No. WO2009/076676; WO2010/003007 and WO2010/148150

Exemplary Cell Culture Media

As used herein, the terms "minimal medium" or "minimal media" refer to growth media containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for bacterial growth; (2) various salts, which can vary among bacterial species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4$-$7H_2O$, 15 g $KH_2PO_4$, 2.5 g NaCl, and 5.0 g $NH_4Cl$ per liter); (2) 2 ml of 1 M $MgSO_4$ (sterile); (3) 20 ml of 20% (w/v) glucose (or other carbon source); and (4) 1001.11 of 1 M $CaCl_2$ (sterile). Each liter of TM3 minimal medium contains (1) 13.6 g $K_2HPO_4$; (2) 13.6 g $KH_2PO_4$; (3) 2 g $MgSO_4$*$7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4$*$H_2O$; (3) 10 g NaCl; (4) 1 g $FeSO_4$.$7H_2O$; (4) 1 g $CoCl_2$*$6H_2O$; (5) 1 g $ZnSO_4$.$7H_2O$; (6) 100 mg $CuSO_4$.$5H_2O$; (7) 100 mg $H_3BO_3$; and (8) 100 mg $NaMoO_4$*$2H_2O$; pH is adjusted to ~3.0.

An additional exemplary minimal media includes (1) potassium phosphate $K_2HPO_4$, (2) Magnesium Sulfate $MgSO_4$*$7H_2O$, (3) citric acid monohydrate $C_6H_8O_7$*$H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml. All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

In some aspects, the cells described herein are capable of using syngas as a source of energy and/or carbon. In some embodiments, the syngas includes at least carbon monoxide and hydrogen. In some embodiments, the syngas further additionally includes one or more of carbon dioxide, water, or nitrogen. In some embodiments, the molar ratio of hydrogen to carbon monoxide in the syngas is 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 3.0, 4.0, 5.0, or 10.0. In some embodiments, the syngas comprises 10, 20, 30, 40, 50, 60, 70, 80, or 90% by volume carbon monoxide. In some embodiments, the syngas comprises 10, 20, 30, 40, 50, 60, 70, 80, or 90% by volume hydrogen. In some embodiments, the syngas comprises 10, 20, 30, 40, 50, 60, 70, 80, or 90% by volume carbon dioxide. In some embodiments, the syngas comprises 10, 20, 30, 40, 50, 60, 70, 80, or 90% by volume water. In some embodiments, the syngas comprises 10, 20, 30, 40, 50, 60, 70, 80, or 90% by volume nitrogen.

Synthesis gas may be derived from natural or synthetic sources. The source from which the syngas is derived is referred to as a "feedstock." In some embodiments, the syngas is derived from biomass (e.g., wood, switch grass, agriculture waste, municipal waste) or carbohydrates (e.g., sugars). In other embodiments, the syngas is derived from coal, petroleum, kerogen, tar sands, oil shale, or natural gas. In other embodiments, the syngas is derived from rubber, such as from rubber tires.

Syngas can be derived from a feedstock by a variety of processes, including methane reforming, coal liquefaction, co-firing, fermentative reactions, enzymatic reactions, and biomass gasification. Biomass gasification is accomplished by subjecting biomass to partial oxidation in a reactor at temperatures above about 700° C. in the presence of less than a stoichiometric amount of oxygen. The oxygen is introduced into the bioreactor in the form of air, pure oxygen, or steam. Gasification can occur in three main steps: 1) initial heating to dry out any moisture embedded in the biomass; 2) pyrolysis, in which the biomass is heated to 300-500° C. in the absence of oxidizing agents to yield gas, tars, oils and solid char residue; and 3) gasification of solid char, tars and gas to yield the primary components of syngas. Co-firing is accomplished by gasification of a coal/biomass mixture. The composition of the syngas, such as the identity and molar ratios of the components of the syngas, can vary depending on the feedstock from which it is derived and the method by which the feedstock is converted to syngas.

Synthesis gas can contain impurities, the nature and amount of which vary according to both the feedstock and the process used in production. Fermentations may be tolerant to some impurities, but there remains the need to remove from the syngas materials such as tars and particulates that might foul the fermentor and associated equipment. It is also advisable to remove compounds that might contaminate the isoprene product such as volatile organic compounds, acid gases, methane, benzene, toluene, ethylbenzene, xylenes, $H_2S$, COS, $CS_2$, HCl, $O_3$, organosulfur compounds, ammonia, nitrogen oxides, nitrogen-containing organic compounds, and heavy metal vapors. Removal of impurities from syngas can be achieved by one of several means, including gas scrubbing, treatment with solid-phase adsorbents, and purification using gas-permeable membranes.

Exemplary Cell Culture Conditions

Materials and methods suitable for the maintenance and growth of the recombinant cells of the invention are described infra, e.g., in the Examples section. Other materials and methods suitable for the maintenance and growth of bacterial cultures are well known in the art. Exemplary techniques can be found in International Publication No. WO 2009/076676, U.S. Patent Publ. No. 2009/0203102, WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology*, Second Edition (1989) Sinauer Associates, Inc., Sunderland, Mass. In some aspects, the cells are cultured in a culture medium under conditions permitting the expression of phosphoketolase polypeptide, as well as other enzymes from the upper and lower MVA pathway, including but not limited to, the mvaE and mvaS gene products, isoprene synthase, DXP pathway (e.g., DXS), IDI, or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the recombinant cells (such as *E. coli* cells) comprise one or more heterologous nucleic acids encoding a phosphoketolase polypeptide, as well as enzymes from the upper, including but not limited to, the mvaE and mvaS gene products mvaE and mvaS polypeptides from *L. grayi*, *E. faecium*, *E. gallinarum*, *E. casseliflavus* and/or *E. faecalis* under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. Patent Publ. No. 2009/0203102, WO 2010/003007, US Publ. No. 2010/0048964, WO 2009/132220, US Publ. No. 2010/0003716. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the recombinant cells are grown in batch culture. The recombinant cells can also be grown in fed-batch culture or in continuous culture. Additionally, the recombinant cells can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

Exemplary Purification Methods

In some aspects, any of the methods described herein further include a step of recovering the compounds produced. In some aspects, any of the methods described herein further include a step of recovering the isoprene. In some aspects, the isoprene is recovered by absorption stripping (See, e.g., U.S. Publ. No. 2011/0178261). In some aspects, any of the methods described herein further include a step of recovering the heterologous polypeptide. In some aspects, any of the methods described herein further include a step of recovering the terpenoid or carotenoid.

Suitable purification methods are described in more detail in U.S. Patent Application Publication US2010/0196977 A1.

Throughout this specification, various patents, patent applications and other types of publications (e.g., journal articles) are referenced. The disclosure of all patents, patent applications, and publications cited herein are hereby incorporated by reference in their entirety for all purposes.

The invention can be further understood by reference to the following examples, which are provided by way of illustration and are not meant to be limiting.

EXAMPLES

Example 1

Cloning of the Gene Encoding Phosphoketolase Enzyme from *Bifidobacterium infantis*

Figure 6:
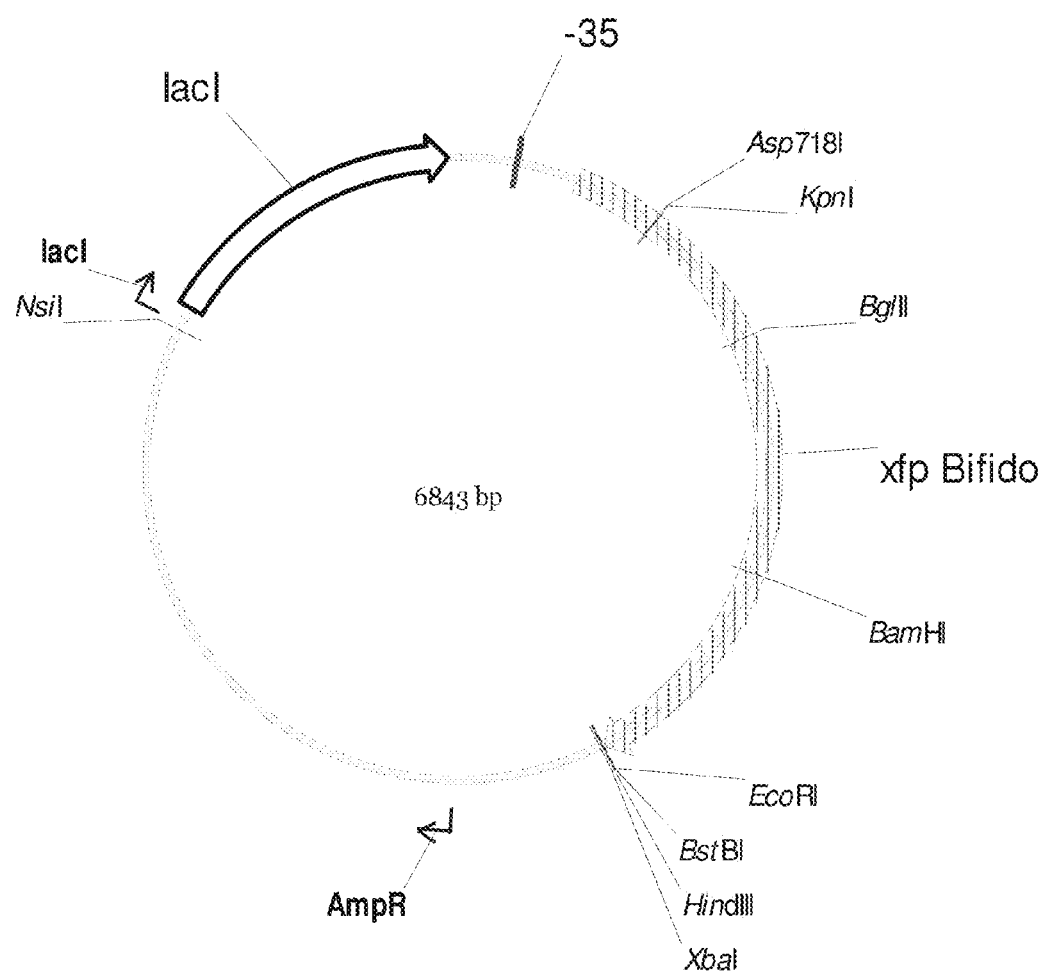
FIG. 6 depicts the plasmid map of pCMP1090, expressing *Bifidobacterium infantis* phosphoketolase.

Chromosomal DNA of *Bifidobacterium infantis* was obtained from ATCC (ATCC#15697D-5, ATCC, Manassas, Va.). The gene encoding phosphoketolase (PKL) enzyme was amplified using primers CMP283: 5'-ctgtatTCATGAcgagtc-ctgttattggcacc-3' (SEQ ID NO:30) and CMP284: 5'-ctctat-GAATTCTCACTCGTTGTCGCCAGCG-3' (SEQ ID NO:31), 100 ng DNA as template and the polymerase Herculase II Fusion according to the manufacturer (Agilent, Santa Clara, Calif.). After purification, the 2798 by fragment was digested with BspHI and EcoRI, and ligated with NcoI/EcoRI-digested pTrcHis2B (Invitrogen, Carlsbad, Calif.) to form plasmid pCMP1090 (SEQ ID NO: 15-FIG. 6).

Example 2

Cloning of Phosphoketolase Enzyme from *Lactobacillus reuteri* Strain F275

Figure 7:
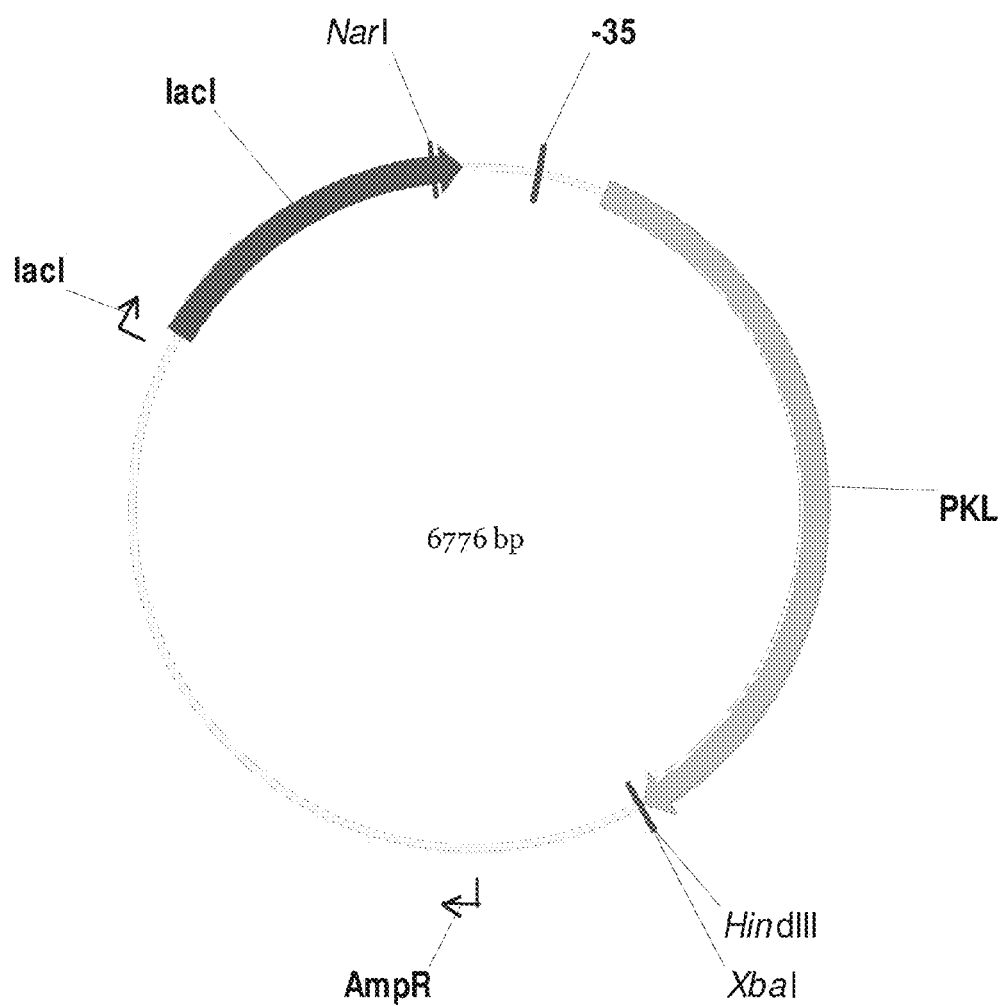
FIG. 7 depicts the plasmid map of pCMP1029, expressing *Lactobacillus reuteri* phosphoketolase.

Chromosomal DNA of *Lactobacillus reuteri* strain F275 was obtained from ATCC (ATCC#23272D-5, ATCC, Manassas, Va.). The gene encoding phosphoketolase (PKL) enzyme was amplified using primers CMP34: 5'-taaggaggaataaa-cATGGCAGTAGATTACGATTCCAAG-3' (SEQ ID NO:32) and CMP335: 5'-ttctagaaagcttcgttacttaagacccttccaagtccag-3' (SEQ ID NO:33), 100 ng DNA as template and the polymerase Herculase II Fusion according to the manufacturer (Agilent, Santa Clara, Calif.). After purification, the 2442 by fragment was assembled into NcoI/EcoRI-digested pTrcHis2B (Invitrogen, Carlsbad, Calif.) using the GENE-ART seamless cloning kit (Invitrogen, Carlsbad, Calif.) to form plasmid pCMP1029 (SEQ ID NO:16-FIG. 7).

Example 3

Construction of Strains CMP451, CMP674, CMP1015 and CMP1047 (BL21 GI1.2 gltA ldhA)

The promoter in front of the citrate synthase gene (gltA) in *E. coli* strain BL21 (Novagen) was previously replaced by a constitutive low expression promoter, namely GI1.2 (U.S. Pat. No. 7,371,558). Two wild-type promoters have been described for gltA (Wilde, R, and J. Guest. 1986. *J. Gen. Microbiol.* 132:3239-3251). The synthetic promoter was inserted just after the −35 region of the distal promoter. A PCR product was obtained using primers UpgltACm-F (5'-TATTTAATTTTTAATCATCTAATTTGA-CAATCATTCAACAAAGTTGTTACAATTAACCCT CACTAAAGGGCGG-3' (SEQ ID NO:34)) and DngltAl.xgiCm-R (5'-TCAACAGCTGTATCCCCGT-TGAGGGTGAGTTTTGCTTTTGTATCAGC-CATATATTCCACC AGCTATTTGTTAGTGAATAAAAGTGGT-TGAATTATTTGCTCAGGATGTGGCATHGTCAA GGGCTAATACGACTCACTATAGGGCTCG-3' (SEQ ID NO:35)), and plasmid FRT-gb2-Cm-FRT from Gene Bridges (Heidelberg, Germany) as a template. The PCR product was purified and used in a lambda red-mediated recombination as described by the manufacturer (Gene Bridges, Heidelberg, Germany). Several colonies were selected for further characterization. The promoter region was PCR-amplified using primers gltAPromSeqF: 5'-GGCAGTATAGGCTGTTCA-CAAAATC-3' (SEQ ID NO:36) and gltApromSeqR: 5'-CT-TGACCCAGCGTGCCTTTCAGC-3' (SEQ ID NO:37) and, as a template, DNA extracted by resuspending a colony in 30 uL H2O, heating at 95 C. for 4 min, spinning down, and using 2 uL of that material as a template in a 50 uL reaction. After observing the sequencing results of the PCR products obtained, a colony harboring the GI1.2 promoter (U.S. Pat. No. 7,371,558) was named CMP141.

Strain MD09-313 was built by transducing CMP258 (see U.S. patent application Ser. No. 12/978,324) with a P1 lysate from strain MCM521 (see U.S. patent application Ser. No. 12/978,324) and selecting for colonies on Luria-Bertani plates containing 20 ug/ml kanamycin. P1 lysates are prepared according to the method described in Ausubel, et al., *Current Protocols in Molecular Biology*, John Wiley and Sons, Inc. The kanamycin marker was removed using the protocol recommended by the manufacturer (Gene Bridges, Heidelberg, Germany) to form strain MD09-314.

A P1 lysate was made from strain CMP141 was used to transduce strain MD09-314, to form CMP440. The chloramphenicol marker was removed using the protocol recommended by the manufacturer (Gene Bridges, Heidelberg, Germany) to form strains CMP451.

A DNA fragment containing a chloramphenicol marker flanked by DNA homologous to the upstream and downstream regions of the λ attachment site attB was amplified by PCR using plasmid pKD3 (Datsenko, K., and Wanner, B. 2000. *PNAS* 97:6640-6645) as a template, and primers CMP171 (5'-AAAATTTTCATTCTGTGACAGAGAAAAAGTAGCCGAAGATGACGGTTTGTCACATGGA GTTGGCAGGATGTTTGATTACATGGGAATTAGCCATGGTCC-3' (SEQ ID NO:38)) and CMP172 (5'-GACCAGCCGCGTAACCTGGCAAAATCGGTTACGGTTGAGTAATAAATGGATGCCCTGC GTAAG CGG GGCATT TTTCTTGGTGTAGGCTGGAGCTGCTTCG-3' (SEQ ID NO:39)). The PCR product obtained was used in a recombineering reaction in BL21 (Novagen) as recommended by the manufacturer (Gene Bridges, Heidelberg, Germany) to integrate the PCR product at the λ attachment site attB. Strain CMP646 was thereby generated, selected on LB+5 ug/ml chloramphenicol. A P1 lysate of CMP646 was made and was used in a transduction reaction on strain CMP451, thereby removing the lower mevalonate pathway genes (encoding mevalonate kinase, phosphomevalonate kinase, diphosphomevalonate decarboxylase, and isopentenyl diphosphate isomerase) from the chromosome of that strain. The transduction reaction was plated on LB+ chloramphenicol 5 ug/ml and one colony for each transduction was picked and named CMP674.

TABLE 2

Description of *E. coli* strains

| Strain | Description | Parent |
|---|---|---|
| CMP141 | BL21 Cm-GI1.2 gltA | BL21 |
| CMP258 | BL21 pgl+ | BL21 |
| CMP374 | BL21 pgl + PL.2-mKKDyI ldhA::Kan | MD09-314 |
| CMP440 | BL21 pgl + PL.2 mKKDyI Cm-GI1.2 gltA | MD09-314 |
| CMP451 | BL21 pgl + PL.2 mKKDyI GI1.2 gltA | CMP440 |
| MCM521 | BL21 neo-PL.2-mKKDyI | U.S. patent application No.: 12/978,324 |
| CMP646 | BL21 attB:Cm (to restore LowerP) | BL21 (Novagen) |
| CMP674 | BL21 pgl + GI 1.2 gltA attB::Cm | CMP451 |
| CMP1015 | BL21 pgl + GI 1.2 gltA ldhA::Kan attB::Cm, | CMP674 |
| CMP1036 | BL21 pgl + GI 1.2 gltA attB::Cm, pTrcHis2B | CMP674 |
| CMP1038 | BL21 pgl + GI 1.2 gltA attB::Cm, pTrcPKL *Bifido* | CMP674 |
| CMP1040 | BL21 pgl + GI 1.2 gltA attB::Cm, pTrcPKL *L. reuteri* | CMP674 |
| CMP1047 | BL21 pgl + GI 1.2 gltA ldhA | CMP1015 |
| CMP1053 | BL21 pgl + GI 1.2 gltA ldhA, pTrcHis2B, pCLPtrcUpper*E. faecalis* | CMP1047 |
| CMP1055 | BL21 pgl + GI 1.2 gltA ldhA, pTrcPKL *Bifido*, pCLPtrcUpper*E. faecalis* | CMP1047 |
| CMP1057 | BL21 pgl + GI 1.2 gltA ldhA, pTrcPKL *L. reuteri*, pCLPtrcUpper*E. faecalis* | CMP1047 |

A DNA fragment containing the ldhA gene interrupted by a kanamycin marker was amplified by PCR using strain JW 1375 from the Keio collection (Baba et al. 2006. *Mol. Syst. Biol.* 2: 2006.0008) as a template, and primers ldhAseqR (5'-GGCTTACCGTTTACGCTTTCCAGC-3' (SEQ ID NO:40)) and ldhAseqF2 (5'-CTAATGCAATACGTGTCCCGAGC-3' (SEQ ID NO:41)). The PCR product obtained was used in a recombineering reaction as recommended by the manufacturer (Gene Bridges, Heidelberg, Germany) to integrate the PCR product at the ldhA locus in strain CMP674. That strain was named CMP1015. The chloramphenicol and kanamycin markers were looped out simultaneously by electroporating pCP20 (Datsenko and Wanner. 2000. *PNAS* 97:6640-6645) in the strain, selecting two colonies on LB+50 ug/ml carbenicillin at 30° C., then restreaking those colonies on an LB plate at 42° C. A $Cm^S$ and $Kan^S$ colony was selected from those plates and named CMP1047.

Example 4

Construction of Strains CMP1036, 1038 and 1040

Strain CMP674 was electroporated in the presence of plasmids pTrcHis2B, pCMP1090 (PKL from *Bifidobacterium infantis*) and pCMP1029 (PKL from *Lactobacillus reuteri*). Colonies were isolated on LB+ carbenicillin 50 ug/mL. One colony of each transformation was picked and was named CMP1036, CMP1038 and CMP1040 respectively.

Example 5

Measurement of Acetyl Phosphate in Strains CMP1036, 1038 and 1040

(i) Materials
TM3 Media Recipe (Per Liter Fermentation Media):
$K_2HPO_4$ 13.6 g, $KH_2PO_4$ 13.6 g, $MgSO_4 \cdot 7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotic are added after pH adjustment and sterilization.
1000× Trace Metal Solution (Per Liter Fermentation Media)
Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4.2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure
Cells were grown overnight in Luria-Bertani broth+ antibiotics. The day after, they were diluted to an OD600 of 0.05 in 20 mL TM3 medium containing 50 ug/mL carbenicillin (in a 250-mL baffled Erlenmeyer flask), and incubated at 34° C. and 200 rpm. After 2 h of growth, OD600 was measured and 200 uM IPTG was added. After 3.5 more hours, 1.5 ml sample was centrifuged, the supernatant was discarded and the pellet was resuspended in 100 uL dry-ice cold methanol.

(iii) Intracellular Acetyl-Phosphate Determination.
To extract acetyl-phosphate, 1.5 mL of *E. coli* cells grown to OD 0.57-2.26 was spun down by centrifugation and 100 μL of dry-ice cold methanol was added to the pellets. Methanol-quenched samples were stored at −20° C. for several days. Further sample processing included gentle cell re-suspension, 5-min centrifugation at −9° C. and aspiration of the supernatant into clean vials. The pellet was re-extracted twice with 75 μL of water containing 2% acetic acid. After each extraction, cell debris were pelleted by centrifugation at −9° C., the supernatants from all three extractions were pooled together and spiked with 1 μL of tributylamine. Mass spectrometric analysis of acetyl phosphate by LCMS was carried out using a Thermo Finnigan TSQ system (Thermo Electron Corporation, San Jose, Calif.). The system control, data acquisition, and mass spectral data evaluation were performed using XCalibur and LCQuan software (Thermo Electron Corp). A mobile phase gradient was applied to a Synergi MAX-RP 5 μM HPLC column (150×2 mm, Phenomenex) at a flow rate of 0.4 mL/min. The applied gradient profile was 99% A and 1% B at t=0-1 min; 80% A and 20% B at t=11 min; 75% B and 25% C at t=12-14 min; 99% A and 1% B at t=15-16 min, where solvent A was 15 mM tributylamine/10 mM acetic acid in water, solvent B was methanol, and solvent C was water. Mass detection of acetyl phosphate was carried out using electrospray ionization (ESI-MS/MS) in the negative mode (ESI spray voltage of 2.5-3.0 kV, ion transfer tube temperature 390° C.) with m/z value for the precursor ion of 138.9. Concentration of acetyl phosphate was determined based on the integrated intensity of peak generated by $PO_3^-$ product ion (m/z=79.0, collision energy 20 V, collision gas pressure 1.7 mTorr, Rt=13.2 min). Calibration curve obtained by injection of acetyl phosphate standard (Sigma-Aldrich) was used to calculate concentration of the metabolite in cell extracts. Intracellular concentration of acetyl phosphate was determined based on the assumption that in 1 mL of the culture at OD=200 the integrated volume of all cells is 50 Ml (FIG. 8).

(iv) Results

Figure 8:
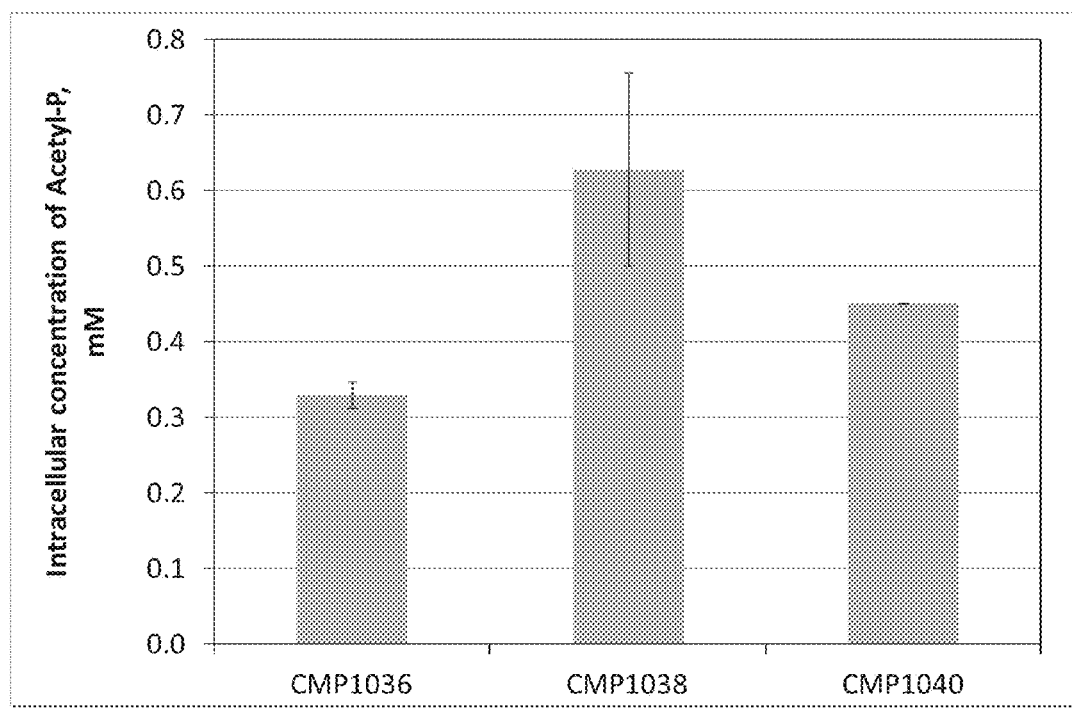
FIG. 8 depict the results of intracellular acetyl-phosphate (mM) in expressing phosphoketolase from *B. infantis* or *L. reuteri*, and the control strain.

Strains expressing phosphoketolase had higher intracellular concentrations of acetyl phosphate (CMP1040 and CMP1038) than the control strain not expressing phophoketolase (FIG. 8).

Example 6

Construction of Strains CMP1053, 1055 and 1057

Plasmids pTrcHis2B (Invitrogen, Carlsbad, Calif.), pCMP1090 (PKL from *Bifidobacterium infantis*) or pCMP1029 (PKL from *Lactobacillus reuteri*) were used to transform CMP1047 together with plasmid pMCM82 (expression vector MCM82 (U.S. Patent Application Publication No. US2010/0196977). Host CMP1047 was grown to mid-log in LB at 34 C. and prepared for electroporation by washing 2× in one culture volume of iced ddH2O and resuspended in one tenth culture volume of the same. 100 uL of cell suspension was combined with 1 uL of each plasmid DNA, moved to a 2 mm electroporation cuvette, electroporated at 25 uFD, 200 Ohms, 2.5 kV, and immediately quenched with 1 mL LB. Cells were recovered shaking at 34 C. for 1 hr and then transformants selected overnight on LB plates with 50 ug/mL spectinomycin+50 ug/mL carbenicillin at 34 C. One colony for each transformation was picked and named CMP1053, 1055 and 1057 respectively.

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehydes-3-phosphate dehydrogenase. The activity of glyceraldehydes 3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

Example 7

Production of Mevalonate by Strains CMP1053, 1055 and 1057

(i) Materials

TM3 Media Recipe (Per Liter Fermentation Media):
$K_2HPO_4$ 13.6 g, $KH_2PO_4$ 13.6 g, $MgSO_4.7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotics are added after pH adjustment and sterilization.

1000× Trace Metal Solution (Per Liter Fermentation Media)
Citric Acid*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4.7H_2O$ 1 g, $CuSO_4.5H_2O$ 100 mg, $H_3B O_3$ 100 mg, $NaMoO_4.2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+ antibiotics. The day after, they are diluted to an OD600 of 0.05 in 20 mL TM3 medium containing 50 ug/ml of spectinomycin and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. After 24 h, mevalonate is analyzed by HPLC. HPLC analysis was performed in the following way: 54 uL of 10% (w/v) H2SO4 was added to 300 uL of broth and the mixture was incubated on ice for 5 minutes. Next, the sample was centrifuged at 14,000×g for 5 minutes and the supernatant collected for HPLC analysis run under the following conditions: (1) BioRad-Aminex HPX-87H Ion Exclusion Column (300 mm×7.8 mm)(Catalog #125-0140)(BioRad, Hercules, Calif.); (2) column temperature=50° C.; (3) BioRad-Microguard Cation H guard column refill (30 mm×4.6 mm)(Catalog #125-0129)(Bio-Rad); (4) running buffer=0.01N H2SO4; (5) running buffer flow rate=0.6 ml/min; (6) approximate running pressure=~950 psi; (7) injection volume=20 microliters; (8) runtime=26 minutes.

Figure 9:
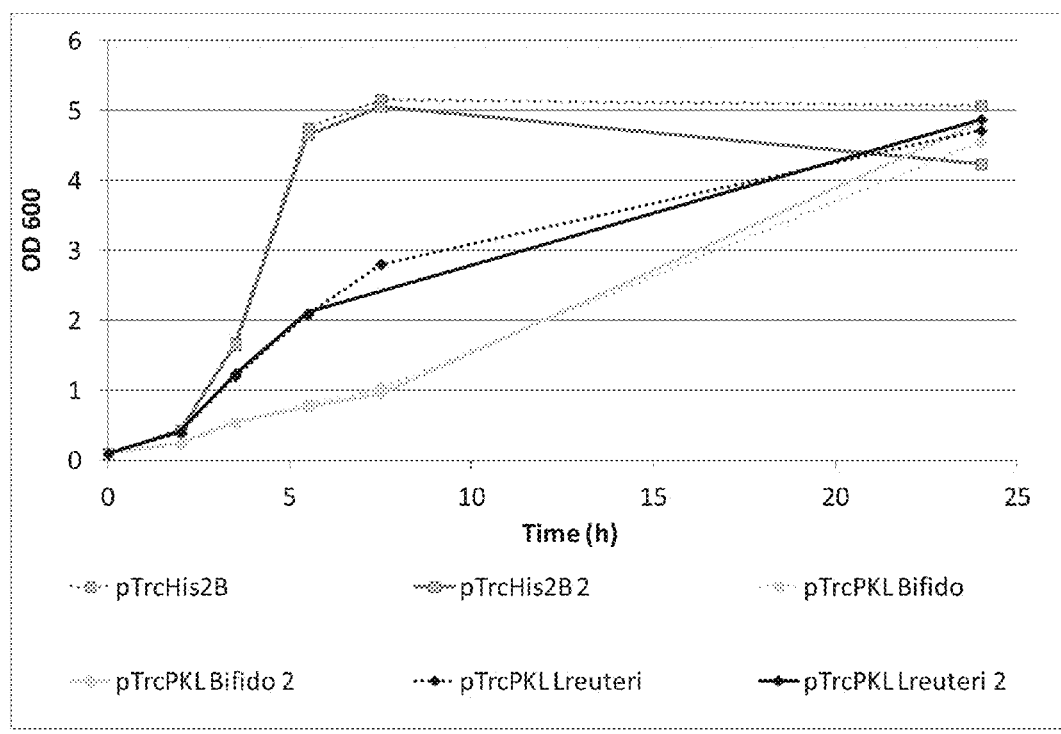
FIG. 9 depicts the Growth curve (measured as OD as a function of time) of the strains expressing phosphoketolase from *B. infantis* or *L. reuteri*, and the control strain.
Figure 10:
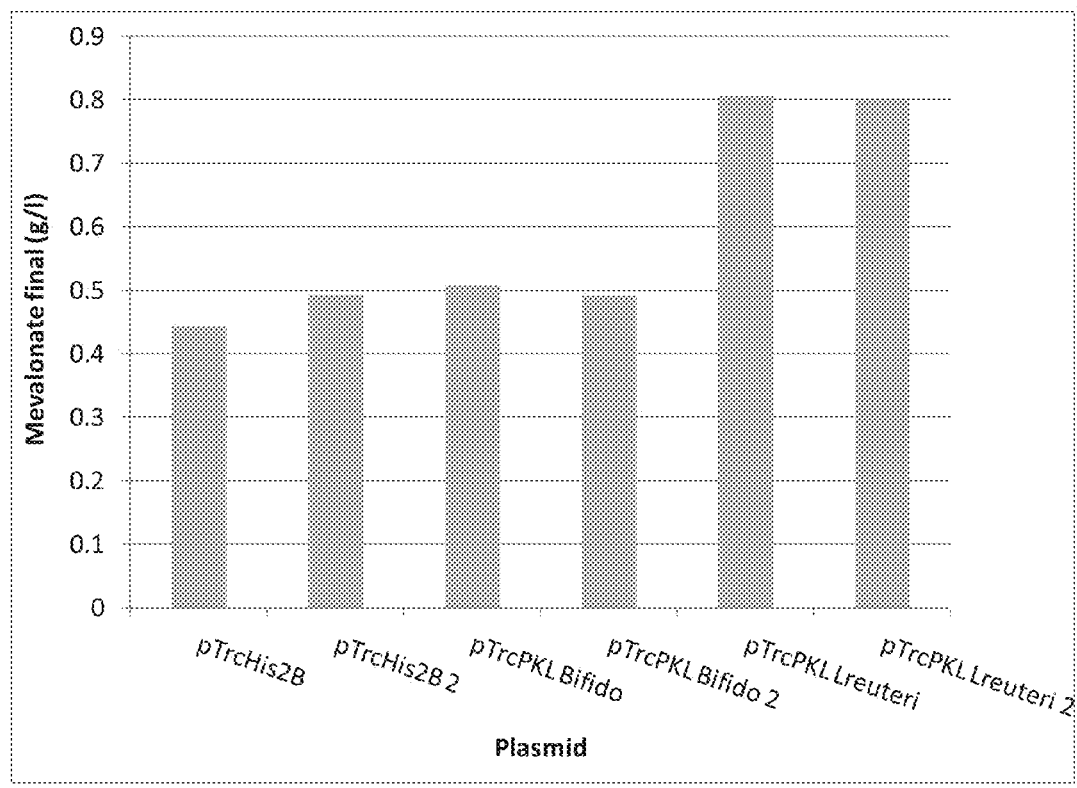
FIG. 10 depicts mevalonate concentration (g/L) in the shake flasks of strains expressing phosphoketolase from *B. infantis* or *L. reuteri*, and the control strain.

(iii) Results:

Strains expressing phosphoketolase grew slower than the control strain (FIG. 9). CMP1057 (expressing the *L. reuteri* phosphoketolase gene) produced more mevalonate than the strains containing the control empty plasmid or the phosphoketolase from *B. infantis* (FIG. 10).

Example 8

Construction of Strains Producing Isoprene and Expressing Phosphoketolase

A lower mevalonate pathway is introduced by transduction into CMP674 using a lysate from MCM521 (see Table 2). The kanamycin marker is looped out according to the manufacturer (Gene Bridges, Heidelberg, Germany). The lower pathway from MCM521 can be modified by changing the promoter upstream of the operon by modifying the rbs in front of each gene via the use of alternative genes. An expression plasmid expressing lacI, isoprene synthase and *M. mazei* mevalonate kinase, plasmid pMCM82 (expression vector MCM82 (U.S. Patent Application Publication No. US2010/ 0196977)) and plasmid pCMP1090 (PKL from *Bifidobacterium infantis*), pCMP1029 (PKL from *Lactobacillus reuteri*) or pTrcHis2B are electroporated (in two steps) into CMP1047. Colonies are selected on LB+ spectinomycin 50 ug/mL+ carbenicillin 50 ug/mL+ chloramphenicol 25 ug/mL.

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehyde-3-phosphate dehydrogenase. The activity of glyceraldehyde-3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

Example 9

Production of Isoprene by Strains Harboring a Plasmid Expressing the Upper Mevalonate Pathway, a Plasmid Expressing lacI, Isoprene Synthase and Mevalonate Kinase, and a Plasmid Expressing Phosphoketolase in Comparison to Cells Harboring a Plasmid Expressing the Upper Mevalonate Pathway, a Plasmid Expressing lacI, Isoprene Synthase and Mevalonate Kinase, and an Empty Plasmid (pTrcHis2B)

(i) Materials
TM3 Media Recipe (Per Liter Fermentation Media):
$K_2HPO_4$ 13.6 g, $KH_2PO_4$ 13.6 g, $MgSO_4 \cdot 7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotics are added after pH adjustment and sterilization.
1000× Trace Metal Solution (Per Liter Fermentation Media)
Citric Acid*$H_2O$ 40 g, $MnSO_4 \cdot H_2O$ 30 g, NaCl 10 g, $FeSO_4 \cdot 7H_2O$ 1 g, $CoCl_2 \cdot 6H_2O$ 1 g, $ZnSO_4 \cdot 7H_2O$ 1 g, $CuSO_4 \cdot 5H_2O$ 100 mg, $H_3BO_3$ 100 mg, $NaMoO_4 \cdot 2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure
Cells are grown overnight in Luria-Bertani broth+ antibiotics. The day after, they are diluted to an OD600 of 0.1 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. One hundred microliters of whole broth are placed in a sealed GC vial and incubated at 34° C. and 200 rpm for a fixed time of 30 minutes. Following a heat kill step, consisting of incubation at 70° C. for 7 minutes, the sample is loaded on the GC. The reported specific productivity is the amount of isoprene in ug/L read by the GC divided by the incubation time (30 min) and the measured OD600.

(iii) Results:
The strains expressing phosphoketolase grow more slowly than the control strain which does not express phosphoketolase. Strains expressing the phosphoketolase polypeptide display enhanced production of isoprene as compared to the strains containing the control empty plasmid (i.e., the strain that does not express phosphoketolase) due to the observance of increased specific productivity, yield, CPI and/or titer of isoprene in the strains expressing the phosphoketolase polypeptide.

Example 10

Construction of Strains Expressing Phosphoketolase and Producing Amorphadiene or Farnesene A lower mevalonate pathway is introduced by transduction into CMP674 using a lysate from MCM521 (see Table 2). The kanamycin marker is looped out according to the manufacturer (Gene Bridges, Heidelberg, Germany). The lower pathway from MCM521 can be modified by changing the promoter upstream of the operon by modifying the rbs in front of each gene via the use of alternative genes. Farnesyl diphosphate synthase (ispA) is overexpressed, either by altering the promoter and/or rbs on the chromosome, or by expressing it from a plasmid.

The expression plasmid expressing lacI, isoprene synthase and *M. mazei* mevalonate kinase from example 8 is modified to replace the gene coding for isoprene synthase by a codon-optimized gene coding for farnesene synthase or amorphadiene synthase. The following expression plasmids are electroporated (in two steps) into competent host cells: (i) the plasmid having lacI, farnesene synthase or amorphadiene synthase, and *M. mazei* mevalonate kinase, (ii) pMCM82 (expression vector MCM82 (U.S. Patent Application Publication No. US2010/0196977) and (iii) pCMP1090 (PKL from *Bifidobacterium infantis*), or pCMP1029 (PKL from *Lactobacillus reuteri*) or pTrcHis2B. Colonies are selected on LB+spectinomycin 50 ug/mL+carbenicillin 50 ug/mL+ chloramphenicol 25 ug/mL.

In other embodiments, any of the resultant strains described above can be further engineered to modulate the activity of the Entner-Doudoroff pathway. The gene coding for phosphogluconate dehydratase or aldolase can be attenuated or deleted. In other embodiments, any of the resultant strains described above may also be engineered to decrease or remove the activity of acetate kinase or citrate synthase. In other embodiments, any of the strains the resultant strain may also be engineered to decrease or remove the activity of phosphofructokinase. In other embodiments, any of the resultant strains described above may also be engineered to modulate the activity of glyceraldehyde-3-phosphate dehydrogenase. The activity of glyceraldehyde-3-phosphate dehydrogenase can be modulated by decreasing its activity. In other embodiments, the enzymes from the non-oxidative branch of the pentose phosphate pathway, such as transketolase, transaldolase, ribulose-5-phosphate-epimerase and (or) ribose-5-phosphate epimerase can be overexpressed.

Example 11

Production of Amorphadiene or Farnesene in Strains Containing a Plasmid Expressing Phosphoketolase in Comparison with the Control Strain (i) Materials TM3 Media Recipe (Per Liter Fermentation Media):
$K_2HPO_4$ 13.6 g, $KH_2PO_4$ 13.6 g, $MgSO_4 \cdot 7H_2O$ 2 g, citric acid monohydrate 2 g, ferric ammonium citrate 0.3 g, (NH$_4$)$_2$SO$_4$ 3.2 g, yeast extract 0.2 g, 1000× Trace Metals Solution 1 ml. All of the components are added together and dissolved in diH$_2$O. The pH is adjusted to 6.8 with ammonium hydroxide (30%) and brought to volume. Media is then filter-sterilized with a 0.22 micron filter. Glucose 10.0 g and antibiotics are added after sterilization and pH adjustment.

1000× Trace Metal Solution (Per Liter Fermentation Media):

Citric Acid*H$_2$O 40 g, MnSO$_4$*H$_2$O 30 g, NaCl 10 g, FeSO$_4$*7H$_2$O 1 g, CoCl$_2$*6H$_2$O 1 g, ZnSO$_4$*7H$_2$O 1 g, CuSO$_4$*5H$_2$O 100 mg, H$_3$BO$_3$ 100 mg, NaMoO$_4$*2H$_2$O 100 mg. Each component is dissolved one at a time in diH$_2$O. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+ antibiotics. The day after, they are diluted to an OD600 of 0.05 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. Prior to inoculation, an overlay of 20% (v/v) dodecane (Sigma-Aldrich) is added to each culture flask to trap the volatile sesquiterpene product as described previously (Newman et. al., 2006).

After 2 h of growth, OD600 is measured and 0.05-0.40 mM isopropyl β-D-1-thiogalactopyranoside (IPTG) is added. Samples are taken regularly during the course of the fermentation. At each timepoint, OD600 is measured. Also, amorphadiene or farnesene concentration in the organic layer is assayed by diluting the dodecane overlay into ethyl acetate. Dodecane/ethyl acetate extracts are analyzed by GC-MS methods as previously described (Martin et. al., *Nat. Biotechnol.* 2003, 21:96-802) by monitoring the molecular ion (204 m/z) and the 189 m/z fragment ion for amorphadiene or the molecular ion (204 m/z) for farnesene. Amorphadiene or farnesene samples of known concentration are injected to produce standard curves for amorphadiene or farnesene, respectively. The amount of amorphadiene or farnesene in samples is calculated using the amorphadiene or farnesene standard curves, respectively.

(iii) Results

The strains expressing the phosphoketolase polypeptide are compared to the strains containing an empty plasmid (i.e., lacking the phosphoketolase polypeptide) with the same backbone. The strains expressing the phosphoketolase polypeptide display enhanced production of amorphadiene or farnesene as compared to the strains containing the control empty plasmid (i.e., the strain that does not express phosphoketolase) due to the observance of increased specific productivity, yield, CPI and/or titer of amorphadiene or farnesene in the strains expressing the phosphoketolase polypeptide.

(iv) References

Newman, J. D., Marshal, J. L., Chang, M. C. Y., Nowroozi, F., Paradise, E. M., Pitera, D. J., Newman, K. L., Keasling, J. D., 2006. High-level production of amorpha-4,11-diene in a two-phase partitioning bioreactor of metabolically engineered *E. coli*. *Biotechnol. Bioeng.* 95, 684-691.

Martin, V. J., Pitera, D. J., Withers, S. T., Newman, J. D., Keasling, J. D., 2003. Engineering a mevalonate pathway in *E. coli* for production of terpenoids. *Nat. Biotechnol.* 21, 796-802.

Example 12

Production of Mevalonate (MVA) in Recombinant Host Cells Expressing Phosphoketolase at 15-L Scale Mevalonate production was evaluated in *E. coli* expressing a heterologous gene encoding a phosphoketolase polypeptide as well as genes from the mevalonate pathway and grown in fed-batch culture at the 15-L scale.

An MVA producing strain SHG0863 (CMP1053-HMB GI1.2gltA attB ldhA, pTrcHis2B, pCLPtrcUpperEfaecalis) was run in a standard MVA production process. The performance metrics (MVA productivity and MVA yield on glucose) are compared here to an experimental strain SHG0864 (CMP1057-HMB GI1.2gltA attB ldhA, pTrcPKL_Lreuteri, pCLPtrcUpperEfaecalis) that was run under the same conditions to determine yield improvement attributable to the expression of the phosphoketolase polypeptide.

Methods:

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter. Add 16.8 mls directly the tank media before sterilization, with no further addition.

This experiment was carried out to monitor mevalonate formation from glucose at the desired fermentation pH 7.0 and temperature 34° C. A frozen vial of the *E. coli* strain was thawed and inoculated into a flask with tryptone-yeast extract medium and the appropriate antibiotics. After the inoculum grew to optical density 1.0, measured at 550 nm (OD$_{550}$), 500 mL was used to inoculate a 15-L bioreactor and bring the initial tank volume to 5 L.

The batched media had glucose batched in at 9.7 g/L. Induction was achieved by adding isopropyl-beta-D-1-thiogalactopyranoside (IPTG). A shot of IPTG was added to the tank to bring the concentration to 250 uM when the cells were at an OD$_{550}$ of 6. A second shot of IPTG was added to the tank to bring the concentration to 500 uM when the cells were at an $OD_{550}$ of 100. Once the glucose was consumed by the culture, as signaled by a rise in pH, the glucose feed solution was fed to meet metabolic demands at rates less than or equal to 10 g/min. The fermentation was run long enough to determine the maximum mevalonate mass yield on glucose, a total of 48 hr elapsed fermentation time.

Analysis:

The mevalonate concentration in the fermentor broth was determined in broth samples taken at 4 hour intervals by an HPLC analysis. Mevalonate concentration in broth samples was determined by comparison of the refractive index response versus a previously generated calibration curve.

Figure 11:
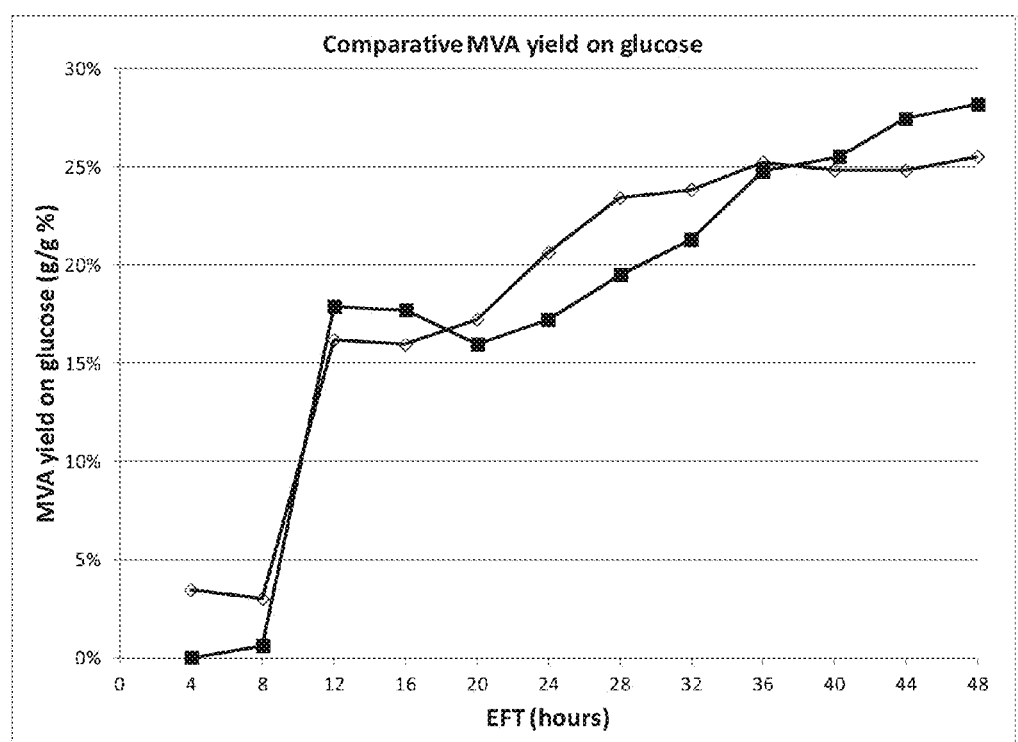
FIG. 11 depicts the yield of mevalonate on glucose achieved by the phosphoketolase expressing strain (closed black squares) compared the control strain (open diamonds) in the 15-L fermentation over time. Strains were run under the same conditions. Overall yield was calculated using the following formula: % wt Yield on glucose=Mevalonate total(t)/ [(Feed Wt(0)−Feed Wt(t)+83)*0.59)], where 0.59 is the wt % of glucose in the glucose feed solution and 83 is the grams of this feed batched into the fermentor at t=0.
Figure 12:
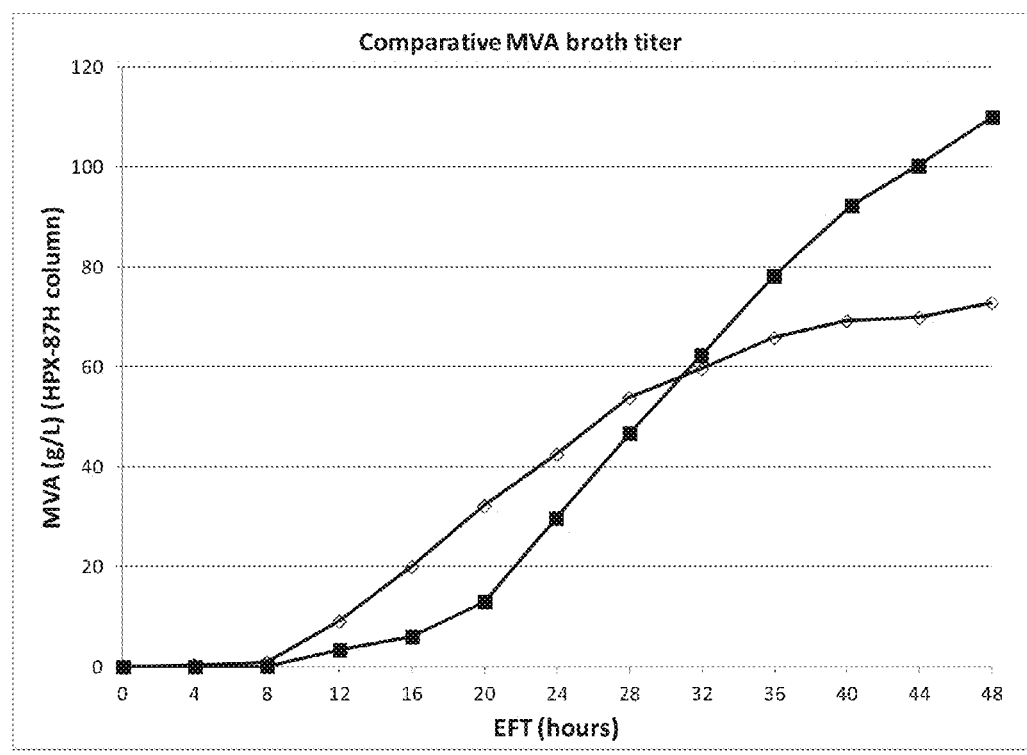
FIG. 12 depicts mevalonate titer achieved by the phosphoketolase expressing strain (closed black squares) compared the control strain (open diamonds) in the 15-L fermentation over time. Strains were run under the same conditions. Titer was calculated using the following formula.

HPLC Information
System: Waters Alliance 2695
Column: BioRad—Aminex HPX-87H Ion Exclusion Column 300 mm×7.8 mm Catalog #125-0140
Column Temperature: 50 C.
Guard column: BioRad—Microguard Cation H refill 30 mm×4.6 mm Catalog #125-0129
Running buffer: 0.01N $H_2SO_4$
Running buffer flow rate: 0.6 ml/min
Approximate running pressure: ~1100-1200 psi
Injection volume: 20 microliters
Detector: Refractive Index (Knauer K-2301)
Runtime: 26 minutes Results:

The fermentation with the phosphoketolase expressing strain (CMP1057) had higher a mevalonate yield on glucose than the empty plasmid control strain (CMP1053). See FIGS. 11-13 and Table 3 below. Additionally, the fermentation broth with the phosphoketolase expressing strain (CMP1057) had lower acetate accumulation in the fermentation broth as compared to the empty plasmid control strain (CMP1053). See FIG. 14.

TABLE 3

MVA Productivity Metrics

| Strain description/ Run Number | EFT (hrs) | Titer (g/L) | Volumetric Productivity (g/L/hr) | Overall % Yield of MVA on glucose (g/g) | CPI (gMVA/gDCW) |
|---|---|---|---|---|---|
| SHG0863 CMP1053 Control strain 20111003 | 48 | 72.8 | 1.52 | 25.5% | 2.40 |
| SHG0864 CMP1057 Phosphoketolase strain 20111004 | 48 | 109.9 | 2.29 | 28.2% | 2.94 |

Example 13

Production of Isoprene by *Saccharomyces cerevisiae* Expressing Phosphoketolase

Variations of the genetic constructs described above for expression of isoprene synthase, the upper MVA pathway, the lower MVA pathway and a phosphoketolase are prepared using a yeast expression system from Life Technologies (including competent, wild-type *S. cerevisiae* (INVScl (catalog number C810-00)) and the plasmid pYES2/CT (catalog number V8251-20).

The genes encoding the isoprene synthase, the upper MVA pathway, the lower MVA pathway and a phosphoketolase are first sub-cloned into the pYES2/CT vectors. The plasmids are then propagated in *E. coli* cells. The *S. cerevisiae* (INVScl) are then transformed with the purified plasmid DNA. Yeast strains harboring the plasmid are selected for and maintained on Minimal Medium with 2% glucose supplemented with the indicated selective marker. Isolated colonies harboring the plasmid are chosen for further experimentation.

The specific productivity of isoprene from the engineered yeast strains is determined. To induce expression of the genes encoded by the plasmid, cultures are grown overnight in liquid SC Minimal Medium supplemented with the selective marker. The cultures are then diluted to an $OD_{600}$ of approximately 0.2 and grown for 2-3 hours. A 100 μL sample of the broth is incubated in a 2 mL headspace vial at 34° C. for 30 minutes, followed by heat kill at 70° C. for 12 minutes. Levels of isoprene in the headspace are determined, for example, by flame ionization detector coupled to a gas chromatograph (Model G1562A, Agilent Technologies) (Mergen et al., *LC GC North America*, 28(7):540-543, 2010).

Example 14

Cloning of Phosphoketolase Enzyme from Various Diverse Bacteria

Chromosomal DNA of strain ATCC15697, *Bifidobacterium longum* subsp. *infantis* was obtained from ATCC (Manassas, Va.). The gene encoding *B. longhum* PKL (SEQ ID NO:3) was amplified by polymerase chain reaction (PCR) from the chromosomal DNA using primers CMP283: 5'-ctg-tatTCATGAcgagtcctgttattggcacc-3' (SEQ ID NO:42) and CMP284: 5'-ctctatGAATTCTCACTCGTTGTCGC-CAGCG-3' (SEQ ID NO:43), and the polymerase Herculase according to the manufacturer's protocol (Life Technologies, Carlsbad, Calif.). The PCR product was digested with EcoRI and BspHI restriction enzymes before purification. After purification, the approximately 2500 bp fragment was assembled into EcoRI/NcoI-digested pTrcHis2B (Invitrogen, Carlsbad, Calif.) using the GENEART seamless cloning kit (Invitrogen, Carlsbad, Calif.) to form plasmid pCMP1090 (SEQ ID NO:15, FIG. 6).

Chromosomal DNA of *Lactobacillus reuteri* strain F275 was obtained from ATCC (ATCC#23272D-5, ATCC, Manassas, Va.). The gene encoding *Lactobacillus reuteri* PKL (SEQ ID NO:1) was amplified using primers CMP34: 5'-taaggag-gaataaacATGGCAGTAGATTACGATTCCAAG-3' (SEQ ID NO:44) and CMP335: 5'-ttctagaaagcttcgttacttaagac-ccttccaagtccag-3' (SEQ ID NO:45), 100 ng DNA as template and the polymerase Herculase II Fusion according to the manufacturer (Agilent, Santa Clara, Calif.). After purification, the 2442 by fragment was assembled into NcoI/EcoRI-digested pTrcHis2B (Invitrogen, Carlsbad, Calif.) using the GENEART seamless cloning kit (Invitrogen, Carlsbad, Calif.) to form plasmid pCMP1029 (SEQ ID NO:16, FIG. 7).

The amino acid sequence of *Enterococcus gallinarum* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *E. gallinarum* PKL gene (SEQ ID NO:17) was then subcloned into a BspHI/SacI-digested pTrcHis2B vector (Life Technologies, Carlsbad, Calif.) to form plasmid pCMP1321.

Chromosomal DNA of strain ATCC27893, *Nostoc punctiforme* was obtained from ATCC (Manassas, Va.). The gene encoding *N. punctiforme* PKL (SEQ ID NO:18) was amplified by polymerase chain reaction (PCR) from the chromosomal DNA using primers NostocpTrcHis2BF: 5'-taaggag-gaataaaccatgacattagccagtcctctacaaac-3' (SEQ ID NO:46) and NostocpTrcHis2BR: 5'-TTCTAGAAAGCTTCGTTAAT-AGGGCCACTTCCAGTCACG-3' (SEQ ID NO:47), and the polymerase Herculase according to the manufacturer's protocol (Life Technologies, Carlsbad, Calif.). The PCR product was digested with EcoRI and BspHI restriction enzymes before purification. After purification, the approximately 2500 bp fragment was assembled into EcoRI/NcoI-digested pTrcHis2B (Invitrogen, Carlsbad, Calif.) using the GENE-ART seamless cloning kit (Invitrogen, Carlsbad, Calif.) to form plasmid pCMP1305.

Chromosomal DNA of strain ATCC BAA-98, *Rhodopseudomonas palustris* was obtained from ATCC (Manassas, Va.). The gene encoding *R. palustris* PKL (SEQ ID NO:19) was amplified by polymerase chain reaction (PCR) from the chromosomal DNA using primers RpalpTrcHis2BF: 5'-taaggaggaataaaccatgtccgacgtgttgtccaacgatc-3' (SEQ ID NO:48) and RpalpTrcHis2BR: 5'TTCTAGAAAGCTTCGT-CAGGCCGACCAGCGCCAG-3' (SEQ ID NO:49), and the polymerase Herculase according to the manufacturer's protocol (Life Technologies, Carlsbad, Calif.). The PCR product was digested with EcoRI and BspHI restriction enzymes before purification. After purification, the approximately 2500 bp fragment was assembled into EcoRI/NcoI-digested pTrcHis2B (Invitrogen, Carlsbad, Calif.) using the GENE-ART seamless cloning kit (Invitrogen, Carlsbad, Calif.) to form plasmid pCMP1306.

The amino acid sequence of *Pantoea* sp. PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *Pantoea* sp. PKL gene (SEQ ID NO:20) was then subcloned into a BspHI/SacI-digested pTrcHis2B vector (Life Technologies, Carlsbad, Calif.) to form plasmid pCMP1324.

The amino acid sequence of *Mucilaginibacter paludis* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *M. paludis* PKL gene (SEQ ID NO:21) was then subcloned into a BspHI/SacI-digested pTrcHis2B vector (Life Technologies, Carlsbad, Calif.) to form plasmid pCMP1323.

The amino acid sequence of *Thermobifida fusca* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *T. fusca* PKL gene (SEQ ID NO:22) was then subcloned into a BspHI/SacI-digested pTrcHis2B vector (Life Technologies, Carlsbad, Calif.) to form plasmid pCMP1326.

The amino acid sequence of *Bifidobacterium breve* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *B. breve* PKL gene (SEQ ID NO:23) was then subcloned into a BspHI/SacI-digested pTrcHis2B vector (Life Technologies, Carlsbad, Calif.) to form plasmid pCMP1322.

The amino acid sequence of *Rahnella aquatilis* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *R. aquatilis* PKL gene (SEQ ID NO:24) was then subcloned into a BspHI/SacI-digested pTrcHis2B vector (Life Technologies, Carlsbad, Calif.) to form plasmid pCMP1325.

The amino acid sequence of *Bifidobacterium animalis* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *B. animalis* PKL gene (SEQ ID NO:25) was then subcloned into a BspHI/SacI-digested pTrcHis2B vector (Life Technologies, Carlsbad, Calif.) to form plasmid pCMP1320.

The amino acid sequence of *Gardnerella vaginalis* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *G. vaginalis* PKL gene (SEQ ID NO:26) was then subcloned into a BspHI/SacI-digested pTrcHis2B vector (Life Technologies, Carlsbad, Calif.) to form plasmid pCMP1309.

The amino acid sequence of *Streptomyces avermitilis* PKL was obtained from GeneBank and was processed in GeneArt optimization software for optimized expression in *E. coli*. Two base pairs were added in front of the PKL gene to form a NcoI site and a SacI site was inserted just after the stop codon. The synthesized PKL gene was cloned into GeneArt kanamycin-resistant cloning plasmid. The *S. avermitilis* PKL gene (SEQ ID NO:27) was then subcloned into a BspHI/SacI-digested pTrcHis2B vector (Life Technologies, Carlsbad, Calif.) to form plasmid pEWL1362.

Chromosomal DNA of strain ATCC BAA-98, *Clostridium acetobutylicum* was obtained from ATCC (Manassas, Va.). The gene encoding *Clostridium acetobutylicum* PKL (SEQ ID NO:28) was amplified by polymerase chain reaction (PCR) from the chromosomal DNA using primers CacetpTrcHisBF: 5'-taaggaggaataaaccatgcaaag-tataataggaaaacataaggatgaagg-3' (SEQ ID NO:50) and CacetpTrcHisBR: 5'-ttctagaaagcttcgttatacatgc-cactgccaattagttatttc-3' (SEQ ID NO:51), and the polymerase Herculase according to the manufacturer's protocol (Life Technologies, Carlsbad, Calif.). The PCR product was digested with EcoRI and BspHI restriction enzymes before purification. After purification, the approximately 2500 by fragment was assembled into EcoRI/NcoI-digested pTrcHis2B (Invitrogen, Carlsbad, Calif.) using the GENE-ART seamless cloning kit (Invitrogen, Carlsbad, Calif.) to form plasmid pCMP1364.

The amino acid sequence of *Lactobacillus paraplantarum* PKL was obtained from GeneBank and Jeong et al., (J. Microbiol. Biotechnol. 2007, 17:822-829), and was processed in GeneArt optimization software for optimized expression in *E. coli*. The synthesized PKL gene was cloned into GeneArt kanamycin-resistant cloning plasmid. The *L. paraplantarum* PKL gene (SEQ ID NO:29) was then amplified using primers SML_NcoI_PhosphokLplantF (taaggagaataaacatgaccaccgattatagcagtcc) and v2SML_EcoRI_PhosphokLplantR (ttctagaaagcttcgTTA TTT CAG ACC TTT CCA CTG CC), and Herculase (Life Technologies, Carlsbad, Calif.) as polymerase according to the manufacter's protocol. The PCRs obtained was then assembled with an EcoRI/NcoI-digested pTrcHis2B plasmid (Life Technologies, Carlsbad, Calif.) using the GeneArt® seamless cloning and assembly kit (Life Technologies, Carlsbad, Calif.) to form plasmid pCMP1184.

Example 15

Construction of strains CMP1183, CMP1328, CMP 1366, CMP1182, CMP1308, CMP1309, CMP1331, CMP1330, CMP1333, CMP1329, CMP1184, and CMP1332

PKL expressing strains were constructed by transforming strain CMP1133 (BL21, Δpgl PL.2mKKDyl, GI1.2 gltA, yhfSFRTPyddVIspAyhfS, thiFRTtruncIspA) and selecting for colonies on Luria-Bertani plates containing 20 μg/ml kanamycin. The kanamycin marker was removed using the protocol recommended by the manufacturer (Gene Bridges, Heidelberg, Germany) to form the indicated strains (Table 4).

Example 16

Comparison of Expression, Solubility and Enzymatic Activity of Phosphoketolases Isolated from Various Diverse Bacteria Strains expressing pTrcPKL *B. longum* (strain CMP1183), pTrcPKL *E. gallinarum* (strain CMP1328), pTrcPKL *C. acetobutylicum* (strain CMP1328), pTrcPKL *L. reuteri* (strain CMP1182), pTrcPKL *N. punctiforme* (strain CMP1308), pTrcPKL *R. palustris* (CMP1309), pTrcPKL *Pantaoea* (CMP1331), pTrcPKL *M. paludis* (CMP1330), and pTrcPKL *T. fusca* (CMP1333) were grown in LB media, induced at $OD_{600}$~0.5 with 200 μM IPTG, and induced for 4 hours at a temperature of 30° C. or 34° C. Cells were harvested by centrifuging 4 ml culture broth at 3000 rpm for 10 minutes. Cell pellets were re-suspended in 2 ml of 50 mM MES, 50 mM NaCl pH6.0 with 0.1% DNAase and 0.5 mM AEBSF. The cell suspension was lysed using a french pressure cell at 14,000 psi (American Instrument Company). The lysate was then centrifuged at 15,000 RPM for 10 minutes at 4° C. in an Eppendorf 5804R centrifuge. The supernatant and pellet were separated. The pellets were resuspended in the lysis 50 mM MES, 50 mM NaCl pH6.0 buffer. Supernatent and pellet samples were analyzed by 4-12% SDS-PAGE gel electrophoresis. Solubility was assessed by comparison of soluble versus pellet (insoluble) phosphoketolase fractions.

Results showed that *B. longum* PKL, *E. gallinarum* PKL, *C. acetobutylicum* PKL, *L. reuteri* PKL, *N. punctiforme* PKL, *R. palustris* PKL, and *T. fusca* PKL had a solubility of greater than 70% at a temperature of 30° C. Solubility of *Pantaoea* PKL and *M. paludis* PKL increased to about 50% at a temperature of 34° C. (Table 5).

TABLE 5

Results of biochemical analysis

| Rank | Strain Description | Expression | Solubility (30° C./34° C.) |
|---|---|---|---|
| CMP1183 | *Bifidobacterium longum* | Strong | >90%/~75% |
| CMP1328 | *Enterococcus gallinarum* | Strong | >95% |

TABLE 4

Description of *E. coli* strains

| Strain Name | Genotype |
|---|---|
| CMP1183 | BL21, Δpgl PL.2mKKDyl, GI1.2gltA, yhfSFRTPyddVIspAyhfS, thiFRTtruncIspA, pCMP1090 (pTrcPKL *Bifidobacterium longum*) |
| CMP1328 | BL21, Δpgl PL.2mKKDyl, GI1.2gltA, yhfSFRTPyddVIspAyhfS, thiFRTtruncIspA, pCMP1321 (pTrcPKL *Enterococcus gallinarum*) |
| CMP1366 | BL21, Δpgl PL.2mKKDyl, GI1.2gltA, yhfSFRTPyddVIspAyhfS, thiFRTtruncIspA, pCMP1364 (pTrcPKL *Clostridium acetobutylicum*) |
| CMP1182 | BL21, Δpgl PL.2mKKDyl, GI1.2gltA, yhfSFRTPyddVIspAyhfS, thiFRTtruncIspA, pCMP1029 (pTrcPKL *Lactobacillus reuteri*) |
| CMP1308 | BL21, Δpgl PL.2mKKDyl, GI1.2gltA, yhfSFRTPyddVIspAyhfS, thiFRTtruncIspA, pCMP1305 (pTrcPKL *Nostoc punctiforme*) |
| CMP1309 | BL21, Δpgl PL.2mKKDyl, GI1.2gltA, yhfSFRTPyddVIspAyhfS, thiFRTtruncIspA, pCMP1306 (pTrcPKL *Rhodopseudomonas palustris*) |
| CMP1331 | BL21, Δpgl PL.2mKKDyl, GI1.2gltA, yhfSFRTPyddVIspAyhfS, thiFRTtruncIspA, pCMP1324 (pTrcPKL *Pantoea*) |
| CMP1330 | BL21, Δpgl PL.2mKKDyl, GI1.2gltA, yhfSFRTPyddVIspAyhfS, thiFRTtruncIspA, pCMP1323 (pTrcPKL *Mucilaginibacter paludis*) |
| CMP1333 | BL21, Δpgl PL.2mKKDyl, GI1.2gltA, yhfSFRTPyddVIspAyhfS, thiFRTtruncIspA, pCMP1326 (pTrcPKL *Thermobifida fusca*) |
| CMP1329 | BL21, Δpgl PL.2mKKDyl, GI1.2gltA, yhfSFRTPyddVIspAyhfS, thiFRTtruncIspA, pCMP1322 (pTrcPKL *Bifidobacterium breve*) |
| CMP1184 | BL21, Δpgl PL.2mKKDyl, GI1.2gltA, yhfSFRTPyddVIspAyhfS, thiFRTtruncIspA, pCMP1184 (pTrcPKL *Lactobacillus paraplantarum*) |
| CMP1332 | BL21, Δpgl PL.2mKKDyl, GI1.2gltA, yhfSFRTPyddVIspAyhfS, thiFRTtruncIspA, pCMP1325 (pTrcPKL *Rahnella aquatilus*) |

TABLE 5-continued

Results of biochemical analysis

| Rank | Strain Description | Expression | Solubility (30° C./34° C.) |
|---|---|---|---|
| CMP1366 | Clostridium acetobutylicum | Good | >80-90% |
| CMP1182 | Lactobacillus reuteri | Strong | >90%/<20% |
| CMP1308 | Nostoc punctiforme | Good | ~80%/<20% |
| CMP1309 | Rhodopseudomonas palustris | Good | ~80%/<20% |
| CMP1331 | Pantoea | Good | ~20%/~50% |
| CMP1330 | Mucilaginibacter paludis | Good | ~20%/~50% |
| CMP1333 | Thermobifida fusca | Good | ~80% |

Example 17

Kinetic Analysis of Phosphoketolase Isolated from *Bifidobacterium longum* and from *Enterococcus gallinarum*

Phosphoketolase (PKL) from *B. longum* was purified for use in subsequent kinetic experiments. PKL from *B. longum* was expressed in a BL21 strain (CMP1183) of a pTrc His2B plasmid. The cells were grown in Luria-Bertani medium with 50 µg/ml carbenecillin at 34° C. prior to induction. Following induction with 200 µM IPTG, cultures were transferred to a room temperature shaker for 5 hours. Cells were harvested by centrifugation at 10,000 rpm for 10 min, 4 C. Cell pellets were stored at −80 C. prior to purification. For purification, *B. longum* PKL cell pellet were resuspended in 20 mM HEPES pH 7.0, 60 mM NaCl, 0.5 mM AEBSF, 0.5 mM $MgCl_2$, 0.1 mg/ml DNaseI. Cells were lysed by repeated passage through the french pressure cell and clarified by ultracentrifugation at 50,000 rpm for 30 minutes. Clarified lysate containing PKL from *B. longum* was initially loaded onto a MonoQ 10/100GL column (GE Healthcare) equilibrated in 50 mM Tris, 50 mM NaCl, pH 7 and eluted with a gradient to 50 mM Tris, 1 M NaCl, pH 7. Resulting fractions were analyzed by SDS-PAGE. *B. longum* PKL was further purified using a Superdex 200 10/300GL equilibrated in 50 mM Tris, 50 mM NaCL, pH 7 and MonoQ 10/300 GL at pH 6.0 using a buffer gradient from 50 mM MES, 50 mM NaCl to 1M NaCl. *B. longum* PKL was quantitated using A280 and a molar extinction coefficient determined of 149550 (determined by Vector NTI) and also by gel densitometry method. Purification using ion exchange and gel filtration chromatography produced>95% apparent homogeneity of the PKL. Fractions containing *B. longum* PKL were pooled for use in assaying PKL activity by using the ferric hydroxamate assay.

Phosphoketolase (PKL) from *E. gallinarum* was purified for use in subsequent kinetic experiments. PKL from *E. gallinarum* was expressed in a BL21 strain (CMP1328) of a pTrc His2B plasmid. Cells were grown in LB medium with 50 ug/ml carbenecillin at 37 C. prior to induction. Following induction with 200 uM IPTG, cultures were transferred to a 30 C. shaker for 5 hours. Cells were harvested by centrifugation at 10,000 rpm for 10 min, 4 C. Cell pellets were stored at −80 C. prior to purification. For purification, *E. gallinarum* PKL cell pellets were resuspended in 50 mM MES pH 6.0, 50 mM NaCL, 0.5 mM AEBSF, 0.1 mg/ml DNaseI. Cells were lysed by repeated passage through a French press and clarified by ultracentrifugation at 50,000 rpm for 60 min. Clarified lysate containing PKL from *E. gallinarum* was loaded onto a DEAE HiTrap FF column equilibrated in 50 mM MES, 50 mM NaCl, pH 6 and eluted with a gradient to 50 mM MES, 1M NaCl, pH 6. The resulting fractions were analyzed by SDS-PAGE. Fractions containing PKL were pooled and desalted using a G25 desalting column into 50 mM MES, 50 mM NaCL pH 6.0. Further purification was achieved using a MonoQ 10/100 GL column equilibrated in 50 mM MES, 50 mM NaCL, pH 6 with a salt gradient to 1M NaCl. Fractions containing PKL were pooled and analyzed by SDS PAGE, quantitation was achieved using A280 a molar extinction coefficient of 136980 determined by Vector NTI. Purification using ion exchange and gel filtration chromatography produced>95% apparent homogeneity of the PKL. Fractions containing *E. gallinarum* PKL were pooled for use in assaying PKL activity by using the ferric hydroxamate assay.

Pooled fractions containing either *B. longum* PKL or *E. gallinarum* PKL were assayed for PKL activity using ferric hydroxamate assay. The catalytic activities of the PKLs were measured using a scaled down version of hydroxamate assay described in L. Meile et. al., *Bacteriol.*, 2001, 183:2929-2936 and Frey et. al., *Bioorganic Chem.*, 2008, 36:121-127, which are incorporated herein in there entirety by reference. The assays were performed in a 96-well plate (Costar catalog #9017) format, at 37° C. Each 300 µl reaction contained 1 mM TPP, 10 mM potassium phosphate pH 6.0, 50 mM MES pH 6, 10 mM $MgCl_2$, 5 mM F6P and PKL at concentration of 250 nM. Time points were taken at various intervals. In order to stop the reaction 60 µl of the reaction mixture was mixed with 60 µl of 2M hydroxylamine at pH 6.5, incubated for 10 min at room temperature. Addition of 40 µl of 15% TCA, 40 µl of 4M HCl, and 40 µl of 5% $FeCl_3$ in 0.1 M HCl was used to precipitate the protein and allow AcP detection. The samples were then centrifuged at 3000 rpm for 10 min. A 200 µl sample of supernatant was transferred to a microtiter plate and a plate reader was used to measure A505. An AcP standard curve ranging between 12.5 and 0.2 mM was generated for quantitation. The Michaelis constant, $K_M$ for PKL from *B. longum* and *E. gallinarum* were determined at a saturating concentration of Pi (20 mM) and with F6P concentrations ranging from 0.3 mM to 20 mM. The reaction was initiated with the addition of 250 nM (7 µg) of purified *B. longum* or 500 nM (4 µg) of *E. gallinarum* PKL. Absorbance changes associated with the amount of AcP formed were monitored at 505 nm and plotted against time to determine the rate of the PKL reactions.

Kinetic parameters were evaluated for *B. longum* and *E. gallinarum* PKL with respect to F6P at saturating concentrations of Pi, and for *E. gallinarum* PKL with respect to X5P at saturating concentrations of Pi. The reaction rates were fit to the Michaelis-Menten equation in order to calculate the kinetic constants (Table 6, FIG. 43 and FIG. 44). *B. longum* PKL had a greater $K_M$ for F6P substrate of 21.16 mM, where as *E. gallinarum* PKL had a $K_M$ of 2.86 mM for F6P substrate and of 5.81 mM for X5P substrate. The $k_{cat}$ of *B. longum* PKL was 16.6 $s^{-1}$, and $k_{cat}$ of *E. gallinarum* PKL was 1.4 s−1 with respect to F6P and 4.4 $s^{-1}$ with respect to X5P.

TABLE 6

Summary of kinetic parameters

| Enzyme | Temp | Enzyme (µM) | Enzyme (mg) | Substrate | Time measured | Km (mM) | Vmax (µM/sec) | kcat (sec-1) |
|---|---|---|---|---|---|---|---|---|
| *B. longum* PKL | 37° C. | 0.25 | 6.94E-03 | F6P | 60 | 21.16 | 4.41 | 16.6 |
| *E. gallinarum* PKL | 37° C. | 0.5 | 4.01E-03 | F6P | 30 | 2.86 | 0.71 | 1.4 |
| *E. gallinarum* PKL | 37° C. | 0.5 | 4.01E-03 | X5P | 30 | 5.81 | 2.18 | 4.4 |

Example 18

Phosphoketolase Isolated from *Bifidobacterium longum* has Sedoheptulose-7-Phosphate Catalytic Activity Cells expressing fructose 6-phosphate (positive control), ribose 5-phosphate (negative control), or sedoheptulose 7-phosphate alone or with *B. longum* phosphoketolase were grown and assayed for metabolite production by LC-MS detection.

Analysis of metabolite detection by LC-MS indicated that in cells only expressing fructose 6-phosphate (F6P), ribose 5-phosphate (R5P), or sedoheptulose 7-phosphate (S7P), metabolites F6P, R5P, or S7P, respectively, were primarily detected (FIG. 45). Cells co-expressing R5P with *B. longum* phosphoketolase showed that it was primarily retained as R5P with some AcP production. In contrast, cells co-expressing F6P with *B. longum* phosphoketolase showed that F6P detection disappeared and the formation of AcP was detected (FIG. 45). Similarly, cells co-expressing S7P with *B. longum* phosphoketolase showed that S7P detection disappeared and the formation of AcP was detected (FIG. 45).

Example 19

Production of Mevalonate (MVA) in Recombinant Host Cells Expressing Phosphoketolase at Small Scale Melavonate (MVA) producing *E. coli* strains were constructed by expressing phosphoketolase from *Bifidobacterium longum, Enterococcus gallinarum, Clostridium acetubutylicum, Nostoc, Rhodopseudomonas palustris, Pantoea*, or *Thermobifida fusca* in addition to genes that encode thiolase, HMG-CoA synthase and HMG-CoA reductase (Table 7). An MVA—producing strain that did not express a phosphoketolase was used as control (Table 7). The phosphoketolase expressing strains were screened for phosphoketolase expression and mevalonic acid yield when grown in glucose as compared to a control strain not expressing phosphoketolase in a small scale experiment.

(i) Materials

Modified TM3 Media Recipe Without Yeast Extract and $MgSO_4$ (Per Liter Fermentation Medium):

$K_2HPO_4$ 13.6 g, $KH_2PO_4$ 13.6 g, citric acid monohydrate 2 g, ferric ammonium citrate 0.3 g, $(NH_4)_2SO_4$ 3.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotic are added after pH adjustment and sterilization.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

(ii) Experimental Procedure

Growth Rate Measurement

Shake tubes containing 3 ml LB media, with appropriate antibiotics, were inoculated with glycerol culture stocks. Cultures were incubated for approximately 15 hours at 30° C., 220 rpm. Supplemented TM3 media was prepared by combining TM3 media (without $MgSO_4$ and yeast extract), 1% Glucose, 8 mM $MgSO_4$, 0.02% yeast extract and appropriate antibiotics. 2 mL of supplemented TM3 were inoculated in each well of a 48-well sterile block to a final $OD_{600}$ of 0.2. Blocks were sealed with Breathe Easier membranes and incubated for 2 hours at 34° C., 600 rpm. After 2 hours of growth, the $OD_{600}$ was measured in the micro-titer plate and cells were induced with various concentrations of IPTG. $OD_{600}$ reading was taken every hour after the IPTG induction for 4 hrs. $OD_{600}$ was measurements were performed using a SpectraMax Plus190 (Molecular Devices). Cells were grown overnight and the $OD_{600}$ was measured.

Glucose Measurement

Glucose samples were collected by centrifuging 300 µl of cell culture in the 96-well conical bottom plate and centrifuged for 10 min at 4° C., 3000 rpm. The supernatant was

TABLE 7

MVA-producing strains expressing phophoketolase

| Strain name | Genotype |
| --- | --- |
| CHL875 | BL21, GI1.2-gltA, yhfS-PyddV-ispA, pgl-, attB-, pTrcHis2B (empty plasmid), pCHL416 (constitutive pCL Upper *E. gallinarum* Upper MVA) |
| EWL1319 | BL21, GI1.2-gltA, yhfS-PyddV-ispA, pgl-, attB-, pCMP1090 (pTrc *B. longum* PKL), pCHL416 (constitutive pCL Upper *E. gallinarum* Upper MVA) |
| EWL1341 | BL21, GI1.2-gltA, yhfS-PyddV-ispA, pgl-, attB-, pCMP1321 (pTrc *E. gallinarum* PKL), pCHL416 (constitutive pCL Upper *E. gallinarum* Upper MVA) |
| EWL1344 | BL21, GI1.2-gltA, yhfS-PyddV-ispA, pgl-, attB-, pCMP1305 (pTrc *N. punctiforme* PKL), pCHL416 (constitutive pCL Upper *E. gallinarum* Upper MVA) |
| EWL1347 | BL21, GI1.2-gltA, yhfS-PyddV-ispA, pgl-, attB-, pCMP1306 (pTrc *R. palustris* PKL), pCHL416 (constitutive pCL Upper *E. gallinarum* Upper MVA) |
| EWL1350 | BL21, GI1.2-gltA, yhfS-PyddV-ispA, pgl-, attB-, pCMP1324 (pTrc *Pantoea* PKL), pCHL416 (constitutive pCL Upper *E. gallinarum* Upper MVA) |
| EWL1353 | BL21, GI1.2-gltA, yhfS-PyddV-ispA, pgl-, attB-, pCMP1326 (pTrc *Thermobifida fusca* PKL), pCHL416 (constitutive pCL Upper *E. gallinarum* Upper MVA) |
| EWL1359 | BL21, GI1.2-gltA, yhfS-PyddV-ispA, pgl-, attB-, pCMP1364 (pTrc *C. acetobutylicum* PKL), pCHL416 (constitutive pCL Upper *E. gallinarum* Upper MVA) | diluted 10-fold in DI water and the glucose concentration was measured using a Glucose oxidase assay kit purchased from Pointe Scientific.

Mevalonate Measurement

Mevalonate samples were processed by combining and incubating 34 µl of 10% sulfuric acid and 300 µl of cell culture on ice for 10 min. After 10 minutes at 4° C. the mixture was centrifuged for 10 min at 4° C., 3000 rpm. 250 µl of supernatant was collected in the 96-well conical bottom plate and sealed with Zone-Free™ Films plate sealer for mevalonate measurement in HPLC. Mevalonate yield was determined by calculating amount of total mevalonate made for the amount for glucose utilized.

Protein Expression Analysis

A 50 µl sample of 4 hrs post induction whole broth cell culture was boiled for 5 minutes at 95° C. with 50 µl of 2×SDS sample buffer and 10 µl of sample was loaded in the 4-12% Bis-Tris gels for expression analysis. Purified phosphoketolase enzyme and pre-stained standard were added in each gel. Gels were stained with SimplylBlue Coomassie® G-250 stain and destained with deionized water.

Phosphoketolase Expression and Solubility Analysis

Cells were harvested by centrifuging 4 ml culture broth at 3000 rpm for 10 minutes. Cell pellets were re-suspended in 2 ml of 100 mM Tris, 100 mM NaCl pH7.6 with 0.1% DNAase and 0.5 mM AEBSF. The cell suspension was lysed using a french pressure cell at 14,000 psi (American Instrument Company). The lysate was then centrifuged at 15,000 RPM for 10 minutes at 4° C. in an Eppendorf 5804R centrifuge. The supernatant and pellet were separated. The pellets were resuspended in the lysis buffer. Gel samples were prepared for both pellet and supernatant to perform electrophoresis. Using the iBlot® Dry Blotting System, proteins were transferred into a nitrocellulose membrane followed by immune-detection with rabbit *Bifido longum* phosphoketoalse anti-serum as a primary antibody at 1:10,000 dilution and Alexa Fluor 488 goat anti-rabbit IgG as a detection antibody at 2 µg/ml concentration according to the manufacturers protocol. Protein bands were detected using a Storm 860 Molecular Imager (Molecular Dynamics) using the blue fluorescence scanner screen and protein concentration was calculated using ImageQuant software.

(iii) Results

Analysis of MVA produced from engineered *E. coli* strains expressing *B. longum* PKL (EWL1319), *E. gallinarum* PKL (EWL1341), *Nostoc* PKL (EWL1344), *R. palustris* PKL (EWL1347), *Pantoea* PKL (EWL1350), or *T. fusca* PKL (EWL1353) demonstrated that increasing mevalonate yield correlated with increasing IPTG induction (FIG. 46). Analysis of protein expression in whole cell lysates prepared from engineered strains expressing PKL showed that protein expression was induced by IPTG (FIG. 47A-D). These findings show that increased melvanolate yield was a result of increasing phosphoketolase protein expression. Increased mevalonate yield was also observed in strains expressing *B. longum* PKL (EWL1319), *E. gallinarum* PKL (EWL1341), or *C. acetobutylicum* PKL (EWL1359) as compared to the MVA producing control strain not expressing PKL (CHL875). The increased mevalonate yield in strains expressing *B. longum* PKL (FIG. 48A), *gallinarum* PKL (FIG. 49A), or *C. acetobutylicum* PKL (FIG. 50A) correlated with increased IPTG induction. The maximum mevalonate yield of *B. longum* PKL, *E. gallinarum* PKL, and *C. acetobutylicum* strains expressing phosphoketolase demonstrated an increased yield as compared to maximum mevalonate yield produced by the control strain CHL875. Analysis of protein expression in cell lysates prepared from engineered strains expressing PKL confirmed that *B. longum* PKL (FIGS. 48B and C), *gallinarum* PKL (FIG. 49B), or *C. acetobutylicum* PKL (FIG. 50B) expression was induced by IPTG. Further analysis of the supernatant and pellet fraction isolated from strains expressing *B. longum* PKL showed that the phosphoketolase was primarily in the soluble fraction (FIG. 48B) as compared to the insoluble fraction (FIG. 48C). These results are consistent with the conclusion that increased mevalonate yield was a result of increasing phosphoketolase expression.

Example 20

Production of Mevalonate (MVA) in Recombinant Host Cells Expressing Phosphoketolase at 15-L Scale Mevalonate (MVA) producing strains expressing phosphoketolase from *Enterococcus gallinarum* (strain EWL1341) and *Clostridium acetobutylicum* (strain EWL1359) were compared to an MVA producing strain not expressing phosphoketolase (strain CHL875) in a 15 Liter scale experiment. Cumulative MVA yield on glucose, instantaneous yield on glucose, volumetric productivity of MVA, specific MVA productivity and cell performance index (CPI) were measured and analyzed.

(i) Materials

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H$_3$BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Experimental Procedure

Mevalonate (MVA) production from a modified *E. coli* (BL21) host (CMP1133) expressing introduced genes from the mevalonate pathway and PKL isolated from either *E. gallinarum* (strain EWL1341) or *C. acetobutylicum* (strain EWL1359) was evaluated by growing the strains in fed-batch culture at the 15-L scale (Table 9). MVA production was compared to a modified *E. coli* (BL21) host (CMP1133) that expressed introduced genes from the mevalonate pathway but did not express a PKL (strain CHL875) to determine if any yield improvement can be attributed to the use of a phosphoketolase.

TABLE 9

List of strains assayed for MVA production

| Strain Name | Host | MVA plasmid | PKL plasmid |
|---|---|---|---|
| CHL875 (Control) | BL21, Δpgl PL.2mKKDyI, GI1.2gltA, yhfSFRTPyddVIspAyhfS, thiFRTtruncIspA (MD12-778) | pCHL416 (pCL-PL(1.6) Upper E. gallinarum) | pTrcHis2B (empty vector) |
| EWL1341 | BL21, Δpgl PL.2mKKDyI, GI1.2gltA, yhfSFRTPyddVIspAyhfS, thiFRTtruncIspA (MD12-778) | pCHL416 (pCL-PL(1.6) Upper E. gallinarum) | pCMP1321 (pTrc PKL_gallinarum) |
| EWL1359 | BL21, Δpgl PL.2mKKDyI, GI1.2gltA, yhfSFRTPyddVIspAyhfS, thiFRTtruncIspA (MD12-778) | pCHL416 (pCL-PL(1.6) Upper E. gallinarum) | pCMP1364 (pTrc PKL_acetobutylicum) |

Mevalonate (MVA) formation from glucose at the desired fermentation pH (7.0) and temperature (34° C.) was determined. To start each experiment, the appropriate frozen vial of the E. coli (BL21) strain was thawed and inoculated into a flask with tryptone-yeast extract (LB) medium and the appropriate antibiotics. After the inoculum grew to an optical density of approximately 1.0, measured at 550 nm ($OD_{550}$), 500 mL was used to inoculate a 15-L bioreactor and bring the initial tank volume to 5 L.

Mevalonate producing strains were run in several production process conditions (Table 10). The batched media had glucose batched in at 9.7 g/L. Induction was achieved by adding isopropyl-beta-D-1-thiogalactopyranoside (IPTG). A shot of IPTG was added to the tank to bring the concentration to a specified level when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum cumulative mevalonate mass yield on glucose, a total of 60 to 64 hrs elapsed fermentation time.

The performance metrics of a control strain, (CHL875) were compared to experimental strains, EWL1341, EWL1359. The relevant performance metrics were cumulative MVA yield on glucose, instantaneous MVA yield on glucose, volumetric productivity of MVA, specific MVA productivity and cell performance index. The experimental strains (with phosphoketolase) were run in the same conditions as the control (no phosphketolase expression) to determine if any yield improvement can be attributed to the use of the phosphoketolase enzyme.

Overall yield was calculated using the following formula:

$$\% \, wt \text{ Yield on glucose} = MVA \text{ total}(t)/[(\text{Feed } Wt(0) - \text{Feed } Wt(t) + 83.5)*0.59)],$$

where 0.59 is the wt % of glucose in the glucose feed solution and 83.5 is the grams of this feed batched into the fermentor at t=0. Each feed had its weight % measured independently.

CPI was calculated using the following formula:

$$CPI = \text{total grams } MVA/\text{total grams dry cell weight}$$

Oxygen, Nitrogen, and Carbon Dioxide levels in the offgas were determined independently by two mass spectrometers, an iSCAN (Hamilton Sundstrand), and a Hiden HPR20 (Hiden Analytical) mass spectrometer. Dissolved Oxygen in the fermentation broth is measured by sanitary, sterilizable probe with an optical sensor provided Hamilton Company. The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration.

HPLC Information
System: Waters Alliance 2695
Column: BioRad—Aminex HPX-87H Ion Exclusion Column 300 mm×7.8 mm Catalog #125-0140
Column Temperature: 50 C.
Guard column: BioRad—Microguard Cation H refill 30 mm×4.6 mm Catalog #125-0129
Running buffer: $0.01N \, H_2SO_4$
Running buffer flow rate: 0.6 ml/min
Approximate running pressure: ~1100-1200 psi
Injection volume: 20 microliters
Detector: Refractive Index (Knauer K-2301)
Runtime: 26 minutes

TABLE 10

Production process conditions

| Run Number | Strain Used | Target IPTG concentration upon addition (if any) (uM) |
|---|---|---|
| 20120821 | CHL875 | 0 |
| 20120976 | CHL875 | 0 |
| 20120977 | EWL1341 | 0 |
| 20120978 | EWL1341 | 50 |
| 20120979 | EWL1341 | 100 |
| 20121056 | EWL1359 | 0 |
| 20121057 | EWL1359 | 100 |
| 20121058 | EWL1359 | 400 |
| 20121059 | CHL875 | 100 (not expected to have an effect due to empty PKL vector) |

(iii) Results

The strain expressing the C. acetobutylicum phosphoketolase (EWL1359, runs 20121056, 201201057, 20121058) achieved a higher cumulative % yield of MVA on glucose than the strain expressing no phosphoketolase (CHL875, run 20120821, 20120976, 20121059) (Table 11 and FIG. 51). The MVA yield increase was noted when at least 100 μM IPTG was added to the tank (20121057 and 20121058).

The strain expressing the E. gallinarum phosphoketolase (EWL1341, runs 20120977, 201200978, 20120979) achieved a higher cumulative % yield of MVA on glucose than the strain expressing no phosphoketolase (CHL875, runs 20120821, 20120976, 20121059) (Table 11 and FIG. 52). The MVA yield increase was noted when at least 50 μM IPTG was added to the tank (20120978 and 20120979).

achieved a slightly higher cell performance index (g MVA/g dry cell weight) than the strain expressing no phosphoketolase (CHL875, run 20121059, induced at 100 μM IPTG).

TABLE 11

MVA Productivity Metrics

| Strain Name/ Run Number/ μM IPTG | Max Cumulative % Yield of MVA on glucose (g/g %) | Overall MVA Volumetric Productivity at time of max overall MVA yield (g/L/hr) | Max Optical Density | CPI (Total g MVA/total gDCW) at time of max overall MVA yield | Peak Specific Productivity (mg MVA/ L/hr/OD) | Peak MVA Titer (gram MVA/Liter tank broth) |
|---|---|---|---|---|---|---|
| CHL875/ 20120821/ 0 | 28.9 | 1.92 | 115.6 | 3.7 | 54.4 | 109.0 |
| CHL875/ 20120976/ 0 | 29.8 | 1.84 | 106.1 | 3.7 | 58.0 | 107.9 |
| EWL1341/ 20120977/ 0 | 30.1 | 1.84 | 105.5 | 4.1 | 64.8 | 109.7 |
| EWL1341/ 20120978/ 50 | 33.7 | 1.86 | 100.3 | 4.5 | 67.7 | 114.3 |
| EWL1341/ 20120979/ 100 | 34.6 | 1.75 | 95.3 | 4.4 | 74.6 | 107.0 |
| EWL1359/ 20121056/ 0 | 31.8 | 1.81 | 101.0 | 3.6 | 59.6 | 105.0 |
| EWL1359/ 20121057/ 100 | 32.8 | 1.83 | 99.4 | 3.9 | 68.2 | 109.2 |
| EWL1359/ 20121058/ 400 | 34.6 | 1.39 | 71.1 | 4.3 | 64.5 | 89.9 |
| CHL875/ 20121059/ 100 | 31.3 | 1.91 | 102.4 | 3.9 | 63.2 | 112.4 |

The MVA yield in all cases correlated with the amount of IPTG added (FIG. 53). For a direct comparison, in runs where 100 uM IPTG was added, both strains expressing phosphoketolase (20120979 and 20121057) achieved a significantly higher cumulative % yield of MVA on glucose than the strain expressing no phosphoketolase (CHL875, run 201201059) (Table 12 and FIG. 53). The cumulative MVA yield (in both cases where phosphoketolase was expressed) correlated well with the phosphoketolase activity measured in the respective runs (Table 12 and FIG. 54).

TABLE 12

MVA yield/Phosphoketolase Activity

| Strain Name | Run Number | μM IPTG | Max Cumulative % Yield of MVA on glucose (g/g %) | Phosphoketolase activity (mmol AcetylP/ L/hr/OD) |
|---|---|---|---|---|
| CHL875 | 20120821 | 0 | 28.9 | Not measured |
| CHL875 | 20120976 | 0 | 29.8 | Not measured |
| EWL1341 | 20120977 | 0 | 30.1 | 0.751 |
| EWL1341 | 20120978 | 50 | 33.7 | 1.114 |
| EWL1341 | 20120979 | 100 | 34.6 | 1.511 |
| EWL1359 | 20121056 | 0 | 31.8 | 0.123 |
| EWL1359 | 20121057 | 100 | 32.8 | 0.481 |
| EWL1359 | 20121058 | 400 | 34.6 | 0.685 |
| CHL875 | 20121059 | 100 | 31.3 | Not measured |

The strain expressing the C. acetobutylicum phosphoketolase (EWL1359, run 20121057, induced at 100 μM IPTG)

When induced with 400 μM IPTG (EWL1359, run 20121058), the CPI was higher than the control (CHL875, run 20121059, induced at 100 μM IPTG) (FIG. 55).

The strain expressing the E. gallinarum phosphoketolase (EWL1341, run 20120978 and 20120979, induced at 50 μM IPTG and 100 μM, respectively) achieved a higher cell performance index (g MVA/g dry cell weight) than the strain expressing no phosphoketolase (CHL875, run 20120976, no IPTG given). When no IPTG was added (EWL1341, run 20120977), the CPI was only slightly higher than the control (CHL875, run 20120976, no IPTG given) (FIG. 56).

Example 21

Production of Isoprene in Recombinant Host Cells Expressing Phosphoketolase at Small Scale Isoprene producing E. coli strains were constructed that expressed phosphoketolase from Bifidobacterium longum, Enterococcus gallinarum or Clostridium acetobutylicum. Isoprene producing strains that did not express a phophoketolase were used as controls (Table 13). The phosphoketolase expressing strains were screened for phosphoketolase expression and isoprene yield when grown in glucose as compared to a control strain not expressing phosphoketolase in a small scale experiment.

Isoprene producing strains were made in a modified E. coli (BL21) host (MCM2065) expressing B. longum PKL were made by introducing plasmid pEWL1418 (FIG. 57) to produce strain EWL1427 (Table 13). For production of strains expressing *E. gallinarum* PKL, plasmid pEWL1421 (FIG. 58) or pEWL1438 (FIG. 59) was introduced into a modified *E. coli* (BL21) host (MCM2065) to generate strain EWL1430 and strain EWL1449, respectively (Table 13). For production of strains expressing *C. acetobutylicum* PKL, plasmid pEWL1436 (FIG. 60) and plasmid pEWL1440 (FIG. 61) were used to produce strain EWL1446 and strain EWL1452, respectively (Table 13).

(ii) Experimental Procedure

Growth Rate Measurement

Shake tubes containing 3 ml LB media, with appropriate antibiotics, were inoculated with glycerol culture stocks. Cultures were incubated for approximately 15 hours at 30° C., 220 rpm. Supplemented TM3 media was prepared by combining TM3 media (without $MgSO_4$ and yeast extract), 1% Glucose, 8 mM $MgSO_4$, 0.02% yeast extract and appropriate antibiotics. 2 mL of supplemented TM3 were inoculated in

TABLE 13

Isoprene-producing strains expressing phophoketolase

| Strain name | Genotype |
|---|---|
| MCM2158 (Control) | BL21, Δpgl PL.2mKKDyl, GI1.2gltA, yhfSFRTPyddVIspAyhfS, thiFRTtruncIspA, bMVK + pTrc *P. alba*(MEA variant) – MVKdel + pMCM1225 (inducible pCL *E. gal* Upper MVA) |
| EWL1427 | BL21, Δpgl PL.2mKKDyl, GI1.2gltA, yhfSFRTPyddVIspAyhfS, thiFRTtruncIspA, bMVK + pTrc *P. alba*(MEA variant) – *B. longum* PKL + pMCM1225 (inducible pCL *E. gal* Upper MVA) |
| EWL1430 | BL21, Δpgl PL.2mKKDyl, GI1.2gltA, yhfSFRTPyddVIspAyhfS, thiFRTtruncIspA, bMVK + pTrc *P. alba*(MEA variant) – *E. gallinarum* PKL + pMCM1225 (inducible pCL *E. gal* Upper MVA) |
| EWL1446 | BL21, Δpgl PL.2mKKDyl, GI1.2gltA, yhfSFRTPyddVIspAyhfS, thiFRTtruncIspA, bMVK, + pTrc *P. alba*(MEA variant) – *C. acetobutylicum* PKL + pMCM1225 (inducible pCL *E. gal* Upper MVA) |
| DW719 (Control) | BL21, Δpgl PL.2mKKDyl, GI1.2gltA, yhfSFRTPyddVIspAyhfS, thiFRTtruncIspA, pTrc *P. alba*(MEA variant) – mMVK + pMCM1225 (inducible pCL *E. gal* Upper MVA) |
| EWL1449 | BL21, Δpgl PL.2mKKDyl, GI1.2gltA, yhfSFRTPyddVIspAyhfS, thiFRTtruncIspA, pTrc *P. alba*(MEA variant) – mMVK – *E. gallinarum* PKL + pMCM1225 (inducible pCL *E. gal* Upper MVA) |
| EWL1452 | BL21, Δpgl PL.2mKKDyl, GI1.2gltA, yhfSFRTPyddVIspAyhfS, thiFRTtruncIspA, pTrc *P. alba*(MEA variant) – mMVK – *C. acetobutylicum* PKL + pMCM1225 (inducible pCL *E. gal* Upper MVA) | bMVK indicates *M. burtonii* mevalonate kinase
mMVK indicates *M. mazei* mevalonate kinase (i) Materials TM3 Media Recipe (Per Liter Fermentation Medium):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotic are added after pH adjustment and sterilization.

Modified TM3 Media Recipe without Yeast Extract and $MgSO_4$ (Per Liter Fermentation Medium):

$K_2HPO_4$ 13.6 g, $KH_2PO_4$ 13.6 g, citric acid monohydrate 2 g, ferric ammonium citrate 0.3 g, $(NH_4)_2SO_4$ 3.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotic are added after pH adjustment and sterilization.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, $H_3BO3$ 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

each well of a 48-well sterile block to a final $OD_{600}$ of 0.2. Blocks were sealed with Breathe Easier membranes and incubated for 2 hours at 34° C., 600 rpm. After 2 hours of growth, the $OD_{600}$ was measured in the micro-titer plate and cells were induced with various concentrations of IPTG. $OD_{600}$ reading was taken every hour after the IPTG induction for 4 hrs. $OD_{600}$ was measurements were performed using a SpectraMax Plus190 (Molecular Devices). Cells were grown overnight and the $OD_{600}$ was measured.

Glucose Measurement

Glucose samples were collected by centrifuging 300 μl of cell culture in the 96-well conical bottom plate and centrifuged for 10 min at 4° C., 3000 rpm. The supernatant was diluted 10-fold in DI water and the glucose concentration was measured using a Glucose oxidase assay kit purchased from Pointe Scientific.

Isoprene Specific Productivity Measurement

A 100 μl of isoprene sample was collected in a 96-well glass block every hour after IPTG induction for 4 hours. The glass block was sealed with aluminum foil and incubated at 34° C. while shaking at 450 rpm, for 30 minutes using a Thermomixer. After 30 minutes, the block was kept at 70° C. water bath for 2 minutes and levels of isoprene in the headspace measurement were determined using gas chromatography-mass spectrometry.

Protein Expression Analysis

A 50 μl sample of 4 hrs post induction whole broth cell culture was boiled for 5 minutes at 95° C. with 50 μl of 2×SDS sample buffer and 10 μl of sample was loaded in the 4-12%

Bis-Tris gels for expression analysis. Purified phosphoketolase enzyme and pre-stained standard were added in each gel. Gels were stained with SimplyBlue Coomassie® G-250 stain and destained with deionized water.

(iii) Results

Analysis of isoprene produced from glucose by engineered *E. coli* strains expressing *B. longum* PKL in the presence of *M. burtonii* mevalonate kinase expression (strain EWL1427), *E. gallinarum* PKL in the presence of *M. burtonii* mevalonate kinase expression (strain EWL1430), or *C. acetobutylicum* PKL in the presence of *M. burtonii* mevalonate kinase expression (strain EWL1446) demonstrated that increasing isoprene yield correlated with increasing IPTG induction as compared to a control strain that did not express a PKL (strain MCM2158) (FIGS. 62A and B). Analysis of protein expression in whole cell lysates prepared from engineered strains expressing PKL showed that protein expression was induced by IPTG (FIGS. 63A and B). These findings indicate that increased isoprene yield was a result of increasing phosphoketolase protein expression.

Analysis of isoprene produced from glucose by engineered *E. coli* strains expressing *E. gallinarum* PKL in the presence of *M. mazei* mevalonate kinase expression (strain EWL1449) or *C. acetobutylicum* PKL in the presence of *M. mazei* mevalonate kinase expression (strain EWL1452) demonstrated that increasing isoprene yield correlated with increasing IPTG induction as compared to a control strain that did not express a PKL (strain DW719) (FIG. 64A). Analysis of protein expression in whole cell lysates prepared from engineered strains expressing PKL showed that protein expression was induced by IPTG (FIG. 64B). These findings indicate that increased isoprene yield was a result of increasing phosphoketolase protein expression.

Overall these results demonstrated the production of isoprene from glucose in strains that express PKL genes isolated from different bacteria such as *B. longum*, *E. gallinarum*, and *C. acetobutylicum* in the presence of different mevalonate kinase genes.

Example 22

Production of Isoprene in Recombinant Host Cells Expressing Phosphoketolase at 15-L Scale Isoprene producing strains expressing phosphoketolase from *B. longum* (strain EWL1427) or *E. gallinarum* (strain EWL1430) were compared to an isoprene producing strain not expressing phosphoketolase (strain MCM2158) in a 15 Liter scale experiment for production of isoprene. Cumulative isoprene yield on glucose, instantaneous isoprene yield on glucose and cell performance index (CPI) were measured and analyzed.

(i) Materials

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H$_3$BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Experimental Procedure

Isoprene production from a modified *E. coli* (BL21) host (MCM2065) expressing introduced genes from the mevalonate pathway and PKL isolated from either *B. longum* (strain EWL1427) or *E. gallinarum* (strain EWL1430) was evaluated by growing the strains in fed-batch culture at the 15-L scale (Table 14). Isoprene production was compared to a modified *E. coli* (BL21) host (MCM2065) that expressed introduced genes from the mevalonate pathway but did not express a PKL (strain MCM2158) to determine if any yield improvement could be attributed to the use of a phosphoketolase.

TABLE 14

List of isoprene producing strains

| Strain Name | Host | Upper pathway MVA plasmid | Isoprene synthase/ PKL plasmid | Run numbers |
| --- | --- | --- | --- | --- |
| MCM2158 (Control) | BL21, Δpgl PL.2mKKDyl, GI1.2gltA, yhfSFRTPyddVIsp AyhfS, thiFRTtruncIspA, bMVK (MCM2065) | inducible *E. gallinarum* Upper (pMCM1225 Spec 50) | pTrc*P. alba*(MEA variant) minusMVK/no PKL gene on this plasmid | 20121134 |

TABLE 14-continued

List of isoprene producing strains

| Strain Name | Host | Upper pathway MVA plasmid | Isoprene synthase/ PKL plasmid | Run numbers |
|---|---|---|---|---|
| EWL1427 | BL21, Δpgl PL.2mKKDyI, GI1.2gltA, yhfSFRTPyddVIsp AyhfS, thiFRTtruncIspA, bMVK (MCM2065) | pMCM1225 inducible E. gallinarum Upper (pMCM1225 Spec 50) | pTrc P. alba(MEA variant) minusMVK + B. longum PKL (pEWL1418 Carb50) | 20121135 |
| EWL1430 | BL21, Δpgl PL.2mKKDyI, GI1.2gltA, yhfSFRTPyddVIsp AyhfS, thiFRTtruncIspA, bMVK (MCM2065) | pMCM1225 inducible E. gallinarum Upper (pMCM1225 Spec 50) | pTrc P. alba(MEA variant) minusMVK + E. gal PKL (pEWL1421 Carb50) | 20121136 | bMVK indicates *M. burtonii* mevalonate kinase

Isoprene producing strains were run in a standard production process (Table 15). Isoprene production from glucose was monitored at the fermentation pH 7.0 and temperature of 34° C. To initiate the experiment, a frozen vial of the *E. coli* (BL21) strain was thawed and inoculated into a flask with tryptone-yeast extract (LB) medium and the appropriate antibiotics. After the inoculum grew to an optical density of approximately 1.0, measured at 550 nm ($OD_{550}$), 500 mL was used to inoculate a 15-L bioreactor and bring the initial tank volume to 5 L. The batched media had glucose batched in at 9.7 g/L. Induction was achieved by adding isopropyl-beta-D-1-thiogalactopyranoside (IPTG). A shot of IPTG was added to the tank to bring the concentration to a specified level when the cells were at an $OD_{550}$ of 6. Once the glucose was consumed by the culture, as signaled by a rise in pH, the glucose feed solution was fed to meet metabolic demands at rates less than or equal to 10 g/min. The fermentation was run long enough to determine the maximum cumulative isoprene mass yield on glucose for a total of 60 to 64 hrs elapsed fermentation time.

TABLE 15

Production process conditions

| Run Number | Strain Used | Target IPTG concentration upon tank addition (μM) | Target IPTG concentration in feed bottle (μM) |
|---|---|---|---|
| 20121134 | MCM2158 | 100 | 100 |
| 20121135 | EWL1427 | 100 | 100 |
| 20121136 | EWL1430 | 100 | 100 |

The performance metrics of a control strain, (MCM2158) were compared to experimental strains, EWL1427 and EWL1430. The performance metrics were cumulative isoprene yield on glucose, instantaneous isoprene yield on glucose and cell performance index (CPI). The experimental strains (with phosphoketolase) were run in the same conditions as the control (no phosphketolase expression).

Overall isoprene yield was calculated using the following formula:

% wt Yield on glucose=Isoprene total($t$)/[(Feed $Wt(0)$–Feed $Wt(t)$+83.5)*0.59)], where 0.59 is the wt % of glucose in the glucose feed solution and 83.5 is the grams of this feed batched into the fermentor at t=0. Each feed had its weight % measured independently.

Isoprene Instantaneous yield was calculated using the following formula:

Isoprene Inst. yield(g/g %)=Isoprene produced($t_1$–$t_0$)/ consumed glucose($t_1$–$t_0$)*100

CPI was calculated using the following formula:

*CPI*=total grams Isoprene/total grams dry cell weight

Isoprene, Oxygen, Nitrogen, and Carbon Dioxide levels in the off-gas were determined independently by two mass spectrometers, an iSCAN (Hamilton Sundstrand), and a Hiden HPR20 (Hiden Analytical) mass spectrometer. Dissolved Oxygen in the fermentation broth is measured by sanitary, sterilizable probe with an optical sensor provided Hamilton Company. The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration.
HPLC Information
System: Waters Alliance 2695
Column: BioRad—Aminex HPX-87H Ion Exclusion Column 300 mm×7.8 mm Catalog #125-0140
Column Temperature: 50 C.
Guard column: BioRad—Microguard Cation H refill 30 mm×4.6 mm Catalog #125-0129
Running buffer: $0.01NH_2SO_4$
Running buffer flow rate: 0.6 ml/min
Approximate running pressure: ~1100-1200 psi
Injection volume: 20 microliters
Detector: Refractive Index (Knauer K-2301)
Runtime: 26 minutes
   (iii) Results
The strain expressing the *E. gallinarum* phosphoketolase (EWL1430, 20121136) achieved a higher cumulative % yield of isoprene on glucose than the strain expressing no phosphoketolase (MCM2158, 20121134) (Table 16 and FIG. 65). The strain expressing the *E. gallinarum* phosphoketolase (EWL1430, 20121136) achieved a higher instantaneous % yield of isoprene on glucose than the strain expressing no phosphoketolase (MCM2158, 20121134) (Table 16 and FIG. 66) and maintained the high yield for a longer period of time resulting in a higher cumulative yield (Table 16 and FIG. 65). Though the strain expressing the *B. longum* phosphketolase (EWL1427, 20121135) had a higher peak instantaneous yield late in the run (FIG. 66), this strain took longer to attain the peak yield and in the end finished with approximately about the same cumulative yield of isoprene on glucose as the control strain (MCM2158, 20121134) (Table 16 and FIG. 65)

The strain expressing the *E. gallinarum* phosphoketolase (EWL1430, 20121136) achieved a slightly higher CPI than the strain expressing no phosphoketolase (MCM2158, 20121134) (FIG. 67). The strain expressing the *B. longum* phosphketolase (EWL1427, 20121135) had a CPI that was slightly lower than the strain expressing no phosphoketolase (MCM2158, 20121134) (FIG. 67). The time of peak cumulative yield (60 hrs EFT) was the time point where the CPI was compared.

Example 23

In Vitro Specific Activity Analysis of Phosphoketolase in Recombinant Host Cells Grown Expressing Cells Grown at 14 L Scale Strains expressing phosphoketolase (PKL) from *E. gallinarum* (Table 19 and Table 21), *C. acetobutylicum* (Table 20), or *B. longum* (Table 21) were assayed in kinetic experiments. For preparation of the samples, cell pellets were obtained from one mL of culture during the course of 14 L fermentation runs and stored at −80° C. Pellet samples were resuspended and normalized to OD(600)=20 in 50 mM MES, pH 6 with 1 mg/ml lysozyme, 0.2 mg/ml DNaseI and 0.5 mM AEBSF. OD normalized cell pellets were lysed by repeated passage through a French Pressure Mini Cell at 700 psi set to medium ratio. Lysed samples were then clarified by centrifugation at 14,000 rpm for 10 min at 4° C. Activity assays and protein measurements were preformed on the soluble lysate fraction. Total protein was determined by Bradford Bio Rad method using a standard curve prepared by titrating BSA at concentrations ranging between 0.5 and 0.05 mg/ml.

The catalytic activities of the PKLs were measured using a scaled down version of hydroxamate assay described in L. Meile et. al., *Bacteriol.*, 2001, 183:2929-2936 and Frey et. al., *Bioorganic Chem.*, 2008, 36:121-127, which are incorporated in their entirety herein by reference. The assays were performed in a 96-well plate (Costar catalog #9017) format, at 37° C. In the standard assay, the reaction mixture consisted of 5 mM F6P, 1 mM TPP, 10 mM potassium phosphate, 50 mM MES buffer at pH 6, and 10 mM $MgCl_2$, 20 mM sodium fluoride, 8 mM iodoacetomide and 1 mM DTT. The reaction is started with the addition of F6P and stopped after 30 minutes of incubation. Total reaction volume is usually 300 ul (smaller amounts where used when necessary). AcP was used as a standard curve with concentrations ranging between 15-0.23 mM. In order to stop the reaction, 60 μl of the reaction mixture was mixed with 60 μl of 2M hydroxylamine at pH 6.5, incubated for 10 min at room temperature. Addition of 40 μl of 15% TCA, 40 μl of 4M HCl, and 40 μl of 5% $FeCl_3$ in 0.1 M HCl was used to precipitate the protein and allow AcP detection. The samples were then centrifuged at 3000 rpm for 10 min. 200 μl of the supernatant was transferred to a microtiter plate in order to measure the rates of AcP formation at absorbance of 505 nm.

MVA Productivity Metrics

| Strain Name/ Run Number/ [IPTG] in batch (μM) | Max Cumulative % Yield of isoprene on glucose (g/g %) | Overall Isoprene Volumetric Productivity at time of max overall isoprene yield (g/L/hr) | Max Optical Density | CPI (Total g isoprene/ total gDCW) at time of max overall isoprene yield | Peak Specific Productivity (mg isoprene/ L/hr/OD) | Peak Instantaneous yield of isoprene on glucose (g/g %) | Peak isoprene Titer (gram isoprene/ average volume of tank broth in Liters) |
|---|---|---|---|---|---|---|---|
| MCM2158/ 20121134/ 100 | 16.3 | 2.21 | 103.6 | 2.5 | 41.1 | 19.9 | 123.6 |
| EWL1427/ 20121135/ 100 | 16.2 | 1.53 | 123.9 | 2.2 | 26.6 | 21.9 | 85.4 |
| EWL1430/ 20121136/ 100 | 17.4 | 1.94 | 105.8 | 2.6 | 39.2 | 21.4 | 108.8 |

TABLE 17

Summary of Isoprene yield

| Strain Name | Run Number | [IPTG] (μM) | Max Cumulative % Yield of isoprene on glucose (g/g %) |
|---|---|---|---|
| MCM2158 | 20121134 | 100 | 16.3 |
| EWL1427 | 20121135 | 100 | 16.2 |
| EWL1430 | 20121136 | 100 | 17.4 |

TABLE 18

Summary of PKL specific productivities in units of AcP formation and specific activity of PKL from *B. longum* and *E. gallinarum*.

| Fermentation Run | Strain | IPTG induction (μM) | EFT (h) | Specific Productivity of AcP (mmol/ L/h/OD) | PKL Specific Activity (μmol/ mg/min) |
|---|---|---|---|---|---|
| F20121134 | MCM2158 | 100 | 24 | 0.06 | 5.9E−03 |
| F20121135 | EWL1427 | 100 | 24 | 7.30 | 7.1E−01 |
|  |  |  | 36 | 9.41 | 8.7E−01 |
|  |  |  | 48 | 10.01 | 8.1E−01 |
| F20121136 | EWL1430 | 100 | 24 | 0.98 | 8.0E−02 |
|  |  |  | 36 | 1.09 | 1.0E−01 |
|  |  |  | 48 | 1.13 | 9.9E−02 |

TABLE 19

14 L scale runs with *E. gallinarum* PKL expressed in a constitutive mevalonate background

| Fermentation run | Strain | Description | IPTG induction (μM) |
|---|---|---|---|
| 20120977 | EWL1341 | BL21, Δpgl PL.2mKKDyl, GI1.2gltA, yhfSFRTPyddVIspAyhfS, thiFRTtruncIspA, attB-pCHL416 (constitutive PL.6-*E. gallinarum* upper), pCMP1321 (pTrc PKL_*E. gallinarum*) | 0 |
| 20120978 | EWL1341 | BL21, Δpgl PL.2mKKDyl, GI1.2gltA, yhfSFRTPyddVIspAyhfS, thiFRTtruncIspA, attB-pCHL416 (constitutive PL.6-*E. gallinarum* upper), pCMP1321 (pTrc PKL_*E. gallinarum*) | 50 |
| 20120979 | EWL1341 | BL21, Δpgl PL.2mKKDyl, GI1.2gltA, yhfSFRTPyddVIspAyhfS, thiFRTtruncIspA, attB-pCHL416 (constitutive PL.6-*E. gallinarum* upper), pCMP1321 (pTrc PKL_*E. gallinarum*) | 100 |

TABLE 20

14 L scale runs with *C. acetobutylicum* PKL expressed in a constitutive upper pathway strain

| Fermentation run | Strain | Description | IPTG induction (μM) |
|---|---|---|---|
| 20121056 | EWL1359 | BL21, Δpgl PL.2mKKDyl, GI1.2gltA, yhfSFRTPyddVIspAyhfS, thiFRTtruncIspA, attB-pCHL416 (constitutive PL.6-*E. gallinarum* upper), pCMP1364 (pTrc PKL_*C. acetobutylicum*) | 0 |
| 20121057 | EWL1359 | BL21, Δpgl PL.2mKKDyl, GI1.2gltA, yhfSFRTPyddVIspAyhfS, thiFRTtruncIspA, attB-pCHL416 (constitutive PL.6-*E. gallinarum* upper), pCMP1364 (pTrc PKL_*C. acetobutylicum*) | 100 |
| 20121058 | EWL1359 | BL21, Δpgl PL.2mKKDyl, GI1.2gltA, yhfSFRTPyddVIspAyhfS, thiFRTtruncIspA, attB-pCHL416 (constitutive PL.6-*E. gallinarum* upper), pCMP1364 (pTrc PKL_*C. acetobutylicum*) | 400 |

TABLE 21

14 L scale runs with *E. gallinarum* PKL or *B. longum* PKL expressed in a strain with a full mevalonate pathway and isoprene synthase

| Fermentation run | Strain | Description | IPTG induction (μM) |
|---|---|---|---|
| 20121134 | MCM2158 | BL21, Δpgl PL.2mKKDyl, GI1.2gltA, yhfSFRTPyddVIspAyhfS, thiFRTtruncIspA, FRT-MVK(*burtonii*) + pTrc*P. alba* (MEA variant) - MVKdel2 + pCL-Ptrc-Upper_E gallinarum) | 100 |
| 20121135 | EWL1427 | BL21, Δpgl PL.2mKKDyl, GI1.2gltA, yhfSFRTPyddVIspAyhfS, thiFRTtruncIspA, bMVK + pEWL1418 (pTrc *P. alba* IspS MEA variant) - *B. longum* PKL) + pMCM1225) | 100 |
| 20121136 | EWL1430 | BL21, Δpgl PL.2mKKDyl, GI1.2gltA, yhfSFRTPyddVIspAyhfS, thiFRTtruncIspA, bMVK + pEWL1421 (pTrc *P. alba* IspS MEA variant) - *E. gallinarum* PKL) + pMCM1225 | 100 |

In vitro specific productivities of AcP formation for EWL1341 strain harboring *E. gallinarum* PKL ranged from 0.75 to 1.77 mmol/L/h/OD depending on the level of induction (Table 22 and FIG. 68A). Furthermore, in vitro specific activities of AcP formation for EWL1341 strain harboring *E. gallinarum* PKL ranged from 7.1E-02 and 1.1E-01 μmmol/mg/min depending on the level of induction (Table 22 and FIG. 68B).

TABLE 22

Summary of *E. gallinarum* PKL specific productivities in units of AcP formation and specific activity of *E. gallinarum* PKL.

| Fermentation Run | Strain | IPTG induction (μM) | EFT (h) | Specific Productivity of AcP (mmol/L/h/OD) | PKL Specific Activity (μmol/mg/min) |
|---|---|---|---|---|---|
| F20120977 | EWL1341 | 0 | 24 | 0.88 | 8.8E-02 |
|  |  |  | 36 | 0.75 | 7.1E-02 |
| F20120978 | EWL1341 | 50 | 24 | 1.27 | 9.0E-02 |
|  |  |  | 36 | 1.11 | 7.6E-02 |
| F20120979 | EWL1341 | 100 | 24 | 1.77 | 1.1E-01 |
|  |  |  | 36 | 1.51 | 8.0E-02 |

In vitro specific productivities of AcP formation for EWL1359 strain harboring *C. acetobutylicum* PKL ranged from 0.12 to 0.74 mmol/L/h/OD depending on the level of induction (Table 23 and FIG. 69A). Furthermore, in vitro specific activities of AcP formation for EWL1359 strain harboring *C. acetobutylicum* PKL ranged from 1.1E-02 and 7.6E-02 μmol/mg/min depending on the level of induction (Table 23 and FIG. 69B).

TABLE 23

Summary of C. acetobutylicum PKL specific productivities in units of AcP formation and specific activity of C. acetobutylicum PKL.

| Fermentation Run | Strain | IPTG induction (µM) | EFT (h) | Specific Productivity of AcP (mmol/L/h/OD) | PKL Specific Activity (µmol/mg/min) |
|---|---|---|---|---|---|
| F20121056 | EWL1359 | 0 | 24 | 0.15 | 1.4E−02 |
|  |  |  | 36 | 0.12 | 1.2E−02 |
|  |  |  | 48 | 0.10 | 1.1E−02 |
| F20121057 | EWL1359 | 100 | 24 | 0.48 | 4.3E−02 |
|  |  |  | 36 | 0.40 | 3.5E−02 |
|  |  |  | 48 | 0.36 | 3.3E−02 |
| F20121058 | EWL1359 | 400 | 24 | 0.74 | 7.6E−02 |
|  |  |  | 36 | 0.69 | 6.8E−02 |
|  |  |  | 48 | 0.62 | 6.5E−02 |

In vitro specific productivities of AcP formation for EWL1427 strain harboring B. longum PKL and induced with 100 µM IPTG ranged from 7.30 to 10.01 mmol/L/h/OD (Table 23 and FIG. 70). In vitro specific productivities of AcP formation for EWL1430 strain harboring E. gallinarum PKL ranged from 0.98 to 1.13 mmol/L/h/OD when induced with 100 µM IPTG and from 1.30 to 1.38 mmol/L/h/OD when induced with 200 µM IPTG (Table 24 and FIG. 70).

In vitro specific activities of AcP formation for EWL1427 strain harboring B. longum PKL and induced with 100 µM IPTG ranged from 7.1E−01 to 8.7E−01 µmol/mg/min (Table 23 and FIG. 71). In vitro specific productivities of AcP formation for EWL1430 strain harboring E. gallinarum PKL ranged from 8.0E−02 to 1.0E−01 µmol/mg/min when induced with 100 µM IPTG and from 1.1E−01 to 1.2E−01 µmol/mg/min when induced with 200 µM IPTG (Table 24 and FIG. 71).

Overall, these findings indicate that phophoketolase activity was present in all strains.

TABLE 24

Summary of PKL specific productivities in units of AcP formation and specific activity of PKL from B. longum and E. gallinarum.

| Fermentation Run | Strain | IPTG induction (µM) | EFT (h) | Specific Productivity of AcP (mmol/L/h/OD) | PKL specific Activity (µmol/mg/min) |
|---|---|---|---|---|---|
| F20121134 | MCM2158 | 100 | 24 | 0.06 | 5.9E−03 |
| F20121135 | EWL1427 | 100 | 24 | 7.30 | 7.1E−01 |
|  |  |  | 36 | 9.41 | 8.7E−01 |
|  |  |  | 48 | 10.01 | 8.1E−01 |
| F20121136 | EWL1430 | 100 | 24 | 0.98 | 8.0E−02 |
|  |  |  | 36 | 1.09 | 1.0E−01 |
|  |  |  | 48 | 1.13 | 9.9E−02 |

Example 24

Construction of Phosphoketolase-Expressing Strains Harboring Host Mutations for Producing Isoprene Isoprene-producing strains comprising an active phosphoketolase polypeptide as described above can be further engineered to increase the activity of one or more of the following genes including ribose-5-phosphate isomerase (rpiA and/or rpiB), D-ribulose-5-phosphate 3-epimerase (rpe), transketolase (tktA and/or tktB), transaldolase B (tal B), phosphoenolpyruvate synthetase (ppsA), phosphate acetyltransferase (pta and/or eutD) to improve carbon flux through the phosphoketolase pathway (FIG. 72). In certain aspects, the activity of the following genes rpiA, rpiB, rpe, tktA, tktB, tal B, ppsA, eutD, and/or pta can be increased by altering the promoter and/or rbs on the chromosome, or by expressing it from a plasmid. In one embodiment the activity of ribose-5-phosphate isomerase (rpiA and/or rpiB) is increased by altering the promoter and/or rbs on the chromosome, or by expressing it from a plasmid. In another embodiment the activity of D-ribulose-5-phosphate 3-epimerase (rpe) is increased by altering the promoter and/or rbs on the chromosome, or by expressing it from a plasmid. In another embodiment the activity of transketolase (tktA and/or tktB) is increased by altering the promoter and/or rbs on the chromosome, or by expressing it from a plasmid. In yet another embodiment the activity of transaldolase B (tal B) is increased by altering the promoter and/or rbs on the chromosome, or by expressing it from a plasmid. In another embodiment the activity of phosphoenolpyruvate synthetase (ppsA) is increased by altering the promoter and/or rbs on the chromosome, or by expressing it from a plasmid. In still other embodiments the activity of phosphate acetyltransferase (pta and/or eutD) is increased by altering the promoter and/or rbs on the chromosome, or by expressing it from a plasmid. In certain aspects, isozymes of the following genes rpiA, rpiB, rpe, tktA, tktB, tal B, ppsA, eutD, and/or pta can be increased by altering the promoter and/or rbs on the chromosome, or by expressing it from a plasmid.

These strains can be further engineered to decrease the activity of one or more of the following genes including glucose-6-phosphate dehydrogenase (zwf), 6-phosphofructokinase-1 (pfkA and/or pfkB), fructose bisphosphate aldolase (Tba, fbaA, fbaB, and/or fbaC), glyceraldehyde-3-phosphate dehydrogenase (gapA and/or gapB), acetate kinase (ackA), citrate synthase (gltA), transketolase (tktA and/or tktB), EI (ptsI), EIICB$^{Glc}$ (ptsG), EIIA$^{Glc}$ (crr), and/or HPr (ptsH) to increase carbon flux into the phosphoketolase pathway (FIG. 73). In one embodiment, a zwf gene encoding glucose-6-phosphate dehydrogenase is downregulated. In another embodiment, a pfkA gene encoding 6-phosphofructokinase-1 A is downregulated. In another embodiment, a gapA gene encoding glyceraldehyde-3-phosphate dehydrogenase A is downregulated. In another embodiment, a fba gene encoding fructose bisphosphate aldolase is downregulated. In yet another embodiment, a gltA gene encoding citrate synthase is downregulated. In an embodiment ackA gene encoding acetate kinase is downregulated. In another embodiment, a ptsI gene encoding EI is downregulated. In an embodiment, a ptsH gene encoding HPr is downregulated. In another embodiment, a ptsG gene encoding EIICB$^{Glc}$ is downregulated. In a yet another embodiment, a crr gene encoding EIIA$^{Glc}$ is downregulated. The pts operon encodes genes of the phosphotransferase system. In some embodiments, the strains can be engineered to decrease activity of the phosphotransferase system (PTS) to increase carbon flux into the phosphoketolase pathway. In some embodiments, the PTS is downregulated by downregulation of the pts operon. In certain aspects, the PTS is downregulated and a glucose transport pathway is upregulated. A glucose transport pathway includes, but is not limited to, galactose (galP) and glucokinase (glk) genes. In some embodiments, the pts operon is downregulated, the galactose (galP) gene is upregulated, and the glucokinase (glk) gene is upregulated. In certain aspects, isozymes of proteins encoded by the following genes zwf, pfkA, fba, gapA, ackA, gltA, tktA, ptsG, ptsH, ptsI, and/or crr can be downregulated to increase carbon flux into the phosphoketolase pathway. In some embodiments, the pfkB gene is downregulated. In some embodiments, the glyceraldehyde-3-phosphate dehydrogenase B (gapB) gene is downregulated. In some embodiments, the transketolase B (tktB) gene is downregulated.

Example 25

Production of Isoprene by Phosphoketolase-Expressing Strains Harboring Host Mutations at Small Scale (i) Materials TM3 Media Recipe (Per Liter Fermentation Media):

$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is filter-sterilized with a 0.22 micron filter. Glucose 10.0 g and antibiotics are added after pH adjustment and sterilization.

1000× Trace Metal Solution (Per Liter Fermentation Media)

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4.2H_2O$ 100 mg. Each component is dissolved one at a time in $diH_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+ antibiotics. The day after, they are diluted to an OD600 of 0.1 in 20 mL TM3 medium containing 50 ug/ml of spectinomycin, 25 ug/mL chloramphenicol and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. One hundred microliters of whole broth are placed in a sealed GC vial and incubated at 34° C. and 200 rpm for a fixed time of 30 minutes. Following a heat kill step, consisting of incubation at 70° C. for 7 minutes, the sample is loaded on the GC. The reported specific productivity is the amount of isoprene in ug/L read by the GC divided by the incubation time (30 min) and the measured OD600.

Example 26

Production of Isoprene by Phosphoketolase-Expressing Strains Harboring Host Mutations at 15-L Scale (i) Materials Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di H2O, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Analysis

Isoprene, Oxygen, Nitrogen, and Carbon Dioxide levels in the off-gas are determined independently by two mass spectrometers, an iSCAN (Hamilton Sundstrand), and a Hiden HPR20 (Hiden Analytical) mass spectrometer.

Dissolved Oxygen in the fermentation broth is measured by sanitary, sterilizable probe with an optical sensor provided Hamilton Company.

The citrate, glucose, acetate, and mevalonate concentrations in the fermentor broth is determined in broth samples taken at 4 hour intervals by an HPLC analysis. Concentration in broth samples are determined by comparison of the refractive index response versus a previously generated calibration curve using standard of a known concentration.

---

What is claimed is:

1. Recombinant microbial cells capable of producing isoprene from a carbon source, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding a polypeptide having isoprene synthase activity, wherein culturing of said recombinant cells in a suitable media provides for the production of isoprene, wherein the production of isoprene occurs without an increase in intracellular acetyl-CoA, and wherein the production of isoprene is increased relative to cells that do not comprise the one or more heterologous nucleic acids encoding a polypeptide having phosphoketolase activity.

2. The cells of claim 1, wherein the one or more heterologous nucleic acids encoding a polypeptide having phosphoketolase activity is capable of synthesizing glyceraldehyde 3-phosphate and acetyl phosphate from xylulose 5-phosphate.

3. The cells of claim 1, wherein the one or more heterologous nucleic acids encoding a polypeptide having phosphoketolase activity is capable of synthesizing erythrose 4-phosphate and acetyl phosphate from fructose 6-phosphate.

4. The cells of claim 1, wherein the heterologous nucleic acid encoding a polypeptide having phosphoketolase activity is a phosphoketolase polypeptide from an organism selected from the group consisting of: *Bifidobacterium longum, Enterococcus galliniarum, Clostridium acetobutylicum, Nostoc punctiforme, Rhodopseudomonas palustris, Pantoea, Mucilaginibacter paludis, Thermobifida fusca, Bifidobacterium breve, Rahnella aquatili, Bifidobacterium animalis, Gardnerella vaginalis, Streptomyces avermitilis, Lactobacillus plantarum*, and *Lactobacillus reuteri*.

5. The cells of claim 1, wherein the heterologous nucleic acid encoding a polypeptide having phosphoketolase activity is a phosphoketolase polypeptide from an organism selected from the group consisting of: *Bifidobacterium longum, Enterococcus galliniarum*, and *Clostridium acetobutylicum*.

6. The cells of claim 1, wherein the polypeptide having isoprene synthase activity is a plant isoprene synthase polypeptide.

7. The cells of claim 1, wherein the polypeptide having isoprene synthase activity is a polypeptide from *Pueraria* or *Populus* or a hybrid of *Populus alba*×*Populus tremula*.

8. The cells of claim 1, wherein the polypeptide having isoprene synthase activity is from an organism selected from the group consisting of *Pueraria montana, Pueraria lobata, Populus tremuloides, Populus alba, Populus nigra*, and *Populus trichocarpa*.

9. The cells of claim 1, wherein one or more polypeptides of the complete MVA pathway is selected from (a) (i) an acetyl-CoA acetyltransferase polypeptide that condenses two molecules of acetyl-CoA to form acetoacetyl-CoA or (ii) an acetoacetyl-CoA synthase polypeptide that utilizes acetyl-CoA and malonyl-CoA to form acetoacetyl-CoA; (b) a 3-hydroxy-3-methylglutaryl-CoA synthase polypeptide that condenses acetoacetyl-CoA with acetyl-CoA to form HMG-CoA; (c) a 3-hydroxy-3-methylglutaryl-CoA reductase polypeptide that converts HMG-CoA to mevalonate; (d) a mevalonate kinase polypeptide that phosphorylates mevalonate to mevalonate 5-phosphate; (e) a phosphomevalonate kinase polypeptide that converts mevalonate 5-phosphate to mevalonate 5-pyrophosphate; and (f) a diphosphomevalonte decarboxylase polypeptide that converts mevalonate 5-pyrophosphate to isopentenyl pyrophosphate.

10. The cells of claim 9, wherein the recombinant cells further comprise one or more nucleic acids encoding one or more 1-deoxy-D-xylulose 5-phosphate (DXP) pathway polypeptides.

11. The cells of claim 1, wherein the one or more nucleic acids is placed under control of an inducible promoter or a constitutive promoter.

12. The cells of claim 1, wherein the one or more nucleic acids is cloned into one or more multicopy plasmids.

13. The cells of claim 1, wherein the one or more nucleic acids is integrated into a chromosome of the cells.

14. The cells of claim 1, wherein the recombinant cells are gram-positive bacterial cells, gram-negative bacterial cells, fungal cells, filamentous fungal cells, algal cells or yeast cells.

15. The cells of claim 1, wherein the recombinant cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae, Aspergillus niger, Saccharomyces cerevisieae* and *Yarrowia lipolytica*.

16. Recombinant microbial cells capable of producing isoprenoid precursors from a carbon source, wherein the cells comprise one or more heterologous nucleic acids encoding a polypeptide having phosphoketolase activity and one or more nucleic acids encoding one or more polypeptides of the complete MVA pathway, wherein culturing of said recombinant cells in a suitable media provides for the production of isoprenoid precursors, wherein the production of isoprenoid precursors occurs without an increase in intracellular acetyl-CoA, and wherein the production of isoprenoid precursors is increased relative to cells that do not comprise the one or more heterologous nucleic acids encoding a polypeptide having phosphoketolase activity.

17. The cells of claim 16, wherein the polypeptide having phosphoketolase activity is capable of synthesizing glyceraldehyde 3-phosphate and acetyl phosphate from xylulose 5-phosphate.

18. The cells of claim 16, wherein the polypeptide having phosphoketolase activity is capable of synthesizing erythrose 4-phosphate and acetyl phosphate from fructose 6-phosphate.

19. The cells of claim 16 wherein the heterologous nucleic acid encoding a polypeptide having phosphoketolase activity is a phosphoketolase polypeptide from an organism selected from the group consisting of: *Bifidobacterium longum, Enterococcus gallinarum, Clostridium acetobutylicum, Nostoc punctiforme, Rhodopseudomonas palustris, Pantoea, Mucilaginibacter paludis, Thermobifida fusca, Bifidobacterium breve, Rahnella aquatili, Bifidobacterium animalis, Gardnerella vaginalis, Streptomyces avermitilis, Lactobacillus plantarum*, and *Lactobacillus reuteri*.

20. The cells of claim 16, wherein the heterologous nucleic acid encoding a polypeptide having phosphoketolase activity is a phosphoketolase polypeptide from an organism selected from the group consisting of: *Bifidobacterium longum, Enterococcus gallinarum*, and *Clostridium acetobutylicum*.

21. The cells of claim 16, wherein one or more polypeptides of the complete MVA pathway is selected from (a)-(i) an acetyl-CoA acetyltransferase polypeptide that condenses two molecules of acetyl-CoA to form acetoacetyl-CoA or (ii) an acetoacetyl-CoA synthase polypeptide that utilizes acetyl-CoA and malonyl-CoA to form acetoacetyl-CoA; (b) a 3-hydroxy-3-methylglutaryl-CoA synthase polypeptide that condenses acetoacetyl-CoA with acetyl-CoA to form HMG-CoA; (c) a 3-hydroxy-3-methylglutaryl-CoA reductase polypeptide that converts HMG-CoA to mevalonate; (d) a mevalonate kinase polypeptide that phosphorylates mevalonate to mevalonate 5-phosphate; (e) a phosphomevalonate kinase polypeptide that converts mevalonate 5-phosphate to mevalonate 5-pyrophosphate; and (f) a diphosphomevalonte decarboxylase polypeptide that converts mevalonate 5-pyrophosphate to isopentenyl pyrophosphate.

22. The cells of claim 16, wherein the one or more nucleic acids is placed under control of an inducible promoter or a constitutive promoter.

23. The cells of claim 16, wherein the one or more nucleic acids is cloned into one or more multicopy plasmids.

24. The cells of claim 16, wherein the one or more nucleic acids is integrated into a chromosome of the cells.

25. The cells of claim 16, wherein the recombinant cells are gram-positive bacterial cells, gram-negative bacterial cells, fungal cells, filamentous fungal cells, algal cells or yeast cells.

26. The cells of claim 16, wherein the recombinant cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae, Aspergillus niger, Saccharomyces cerevisieae* and *Yarrowia lipolytica*.

27. Recombinant microbial cells capable of producing of an isoprenoid from a carbon source, wherein the cells comprise one or more heterologous nucleic acids encoding a polypeptide having phosphoketolase activity and (i) one or more nucleic acids encoding one or more polypeptides of the complete MVA pathway and (ii) a heterologous nucleic acid encoding a polyprenyl pyrophosphate synthase polypeptide, wherein culturing of said recombinant cells in a suitable media provides for the production of the isoprenoid, wherein the production the isoprenoid occurs without an increase in intracellular acetyl-CoA, and wherein the production of the isoprenoid is increased relative to cells that do not comprise the one or more heterologous nucleic acids encoding a polypeptide having phosphoketolase activity.

28. The cells of claim 27, wherein the polypeptide having phosphoketolase activity is capable of synthesizing glyceraldehyde 3-phosphate and acetyl phosphate from xylulose 5-phosphate.

29. The cells of claim 27, wherein the polypeptide having phosphoketolase activity is capable of synthesizing erythrose 4-phosphate and acetyl phosphate from fructose 6-phosphate.

30. The cells of claim 27, wherein the polypeptide having phosphoketolase activity is a phosphoketolase polypeptide from an organism selected from the group consisting of: *Bifidobacterium longum, Enterococcus gallinarum, Clostridium acetobutylicum, Nostoc punctiforme, Rhodopseudomonas palustris, Pantoea, Mucilaginibacter paludis, Thermobifida fusca, Bifidobacterium breve, Rahnella aquatili, Bifidobacterium animalis, Gardnerella vaginalis, Streptomyces avermitilis, Lactobacillus plantarum*, and *Lactobacillus reuteri*.

31. The cells of claim 27, wherein the polypeptide having phosphoketolase activity is a phosphoketolase polypeptide from an organism selected from the group consisting of: *Bifidobacterium longum, Enterococcus gallinarum*, and *Clostridium acetobutylicum*.

32. The cells of claim 27, wherein the isoprenoid is selected from the group consisting of a monoterpene, diterpene, triterpene, tetraterpene, sequiterpene, and polyterpene.

33. The cells of claim 27, wherein the isoprenoid is a sesquiterpene.

34. The cells of claim 27, wherein the isoprenoid is selected from the group consisting of abietadiene, amorphadiene, carene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

35. The cells of claim 27, wherein one or more polypeptides of the complete MVA pathway is selected from (a) (i) an acetyl-CoA acetyltransferase polypeptide that condenses two molecules of acetyl-CoA to form acetoacetyl-CoA or (ii) an acetoacetyl-CoA synthase polypeptide that utilizes acetyl-CoA and malonyl-CoA to form acetoacetyl-CoA; (b) a 3-hydroxy-3-methylglutaryl-CoA synthase polypeptide that condenses acetoacetyl-CoA with acetyl-CoA to form HMG-CoA; (c) a 3-hydroxy-3-methylglutaryl-CoA reductase polypeptide that converts HMG-CoA to mevalonate; (d) a mevalonate kinase polypeptide that phosphorylates mevalonate to mevalonate 5-phosphate; (e) a phosphomevalonate kinase polypeptide that converts mevalonate 5-phosphate to mevalonate 5-pyrophosphate; and (f) a diphosphomevalonte decarboxylase polypeptide that converts mevalonate 5-pyrophosphate to isopentenyl pyrophosphate.

36. The cells of claim 27, wherein the one or more nucleic acids is placed under control of an inducible promoter or a constitutive promoter.

37. The cells of claim 27, wherein the one or more nucleic acids is cloned into one or more multicopy plasmids.

38. The cells of claim 27, wherein the one or more nucleic acids is integrated into a chromosome of the cells.

39. The cells of claim 27, wherein the recombinant host cells are gram-positive bacterial cells, gram-negative bacterial cells, fungal cells, filamentous fungal cells, algal cells or yeast cells.

40. The cells of claim 27, wherein the recombinant host cells are selected from the group consisting of *Bacillus subtilis, Streptomyces lividans, Streptomyces coelicolor, Streptomyces griseus, Escherichia coli, Pantoea citrea, Trichoderma reesei, Aspergillus oryzae, Aspergillus niger, Saccharomyces cerevisieae* and *Yarrowia lipolytica*.

41. The cells of claim 1, wherein the recombinant cells are further engineered to disrupt the expression of the acetate kinase gene or delete the acetate kinase gene.

42. The cells of claim 16, wherein the recombinant cells are further engineered to disrupt the expression of the acetate kinase gene or delete the acetate kinase gene.

43. The cells of claim 27, wherein the recombinant cells are further engineered to disrupt the expression of the acetate kinase gene or delete the acetate kinase gene.

44. The cells of claim 1, wherein the recombinant cells are further engineered to overexpress the phosphate acetyltransferase gene.

45. The cells of claim 16, wherein the recombinant cells are further engineered to overexpress the phosphate acetyltransferase gene.

46. The cells of claim 27, wherein the recombinant cells are further engineered to overexpress the phosphate acetyltransferase gene.

47. The cells of claim 1, wherein the production of isoprene is increased by at least 5% relative to cells that do not comprise the one or more heterologous nucleic acids encoding a polypeptide having phosphoketolase activity.

48. The cells of claim 1, wherein the production of isoprene is increased by at least 10% relative to cells that do not comprise the one or more heterologous nucleic acids encoding a polypeptide having phosphoketolase activity.

49. The cells of claim 16, wherein the production of isoprenoid precursors is increased by at least 5% relative to cells that do not comprise the one or more heterologous nucleic acids encoding a polypeptide having phosphoketolase activity.

50. The cells of claim 16, wherein the production of isoprenoid precursors is increased by at least 10% relative to cells that do not comprise the one or more heterologous nucleic acids encoding a polypeptide having phosphoketolase activity.

51. The cells of claim 27, wherein the production of the isoprenoid is increased by at least 5% relative to cells that do not comprise the one or more heterologous nucleic acids encoding a polypeptide having phosphoketolase activity.

52. The cells of claim 27, wherein the production of the isoprenoid is increased by at least 10% relative to cells that do not comprise the one or more heterologous nucleic acids encoding a polypeptide having phosphoketolase activity.

* * * * *